(12) United States Patent
Iino et al.

(10) Patent No.: US 7,754,743 B2
(45) Date of Patent: Jul. 13, 2010

(54) HETEROARYLCARBAMOYLBENZENE DERIVATIVES

(75) Inventors: Tomoharu Iino, Tsukuba (JP); Noriaki Hashimoto, Tsukuba (JP); Hiroshi Nakashima, Noda (JP); Keiji Takahashi, Tsukuba (JP); Teruyuki Nishimura, Ushiku (JP); Jun-ichi Eiki, Tsuchiura (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/231,856

(22) Filed: Sep. 5, 2008

(65) Prior Publication Data

US 2009/0018056 A1    Jan. 15, 2009

Related U.S. Application Data

(62) Division of application No. 10/546,962, filed as application No. PCT/JP2004/002284 on Feb. 26, 2004, now Pat. No. 7,432,287.

(30) Foreign Application Priority Data

| Feb. 26, 2003 | (JP) | ............................. 2003-049466 |
| Nov. 28, 2003 | (JP) | ............................. 2003-400882 |
| Feb. 6, 2004 | (JP) | ............................. 2004-031298 |

(51) Int. Cl.
*A61K 31/44* (2006.01)
*A61K 31/425* (2006.01)
*C07D 417/12* (2006.01)

(52) U.S. Cl. ..................... 514/342; 514/371; 546/270.7; 548/195

(58) Field of Classification Search ................. 514/342, 514/371; 546/270.7; 548/195
See application file for complete search history.

(56) References Cited

U.S. PATENT DOCUMENTS

| 5,429,942 | A | 7/1995 | Kock et al. |
| 7,524,957 | B2 | 4/2009 | Boyd et al. |
| 2005/0080106 | A1 | 4/2005 | Boyd et al. |

FOREIGN PATENT DOCUMENTS

| EP | 1 529 530 B1 | 5/2005 |
| EP | 1 568 367 B1 | 8/2005 |
| EP | 1 420 784 B1 | 4/2006 |
| EP | 1 661 563 A1 | 5/2006 |
| EP | 1 661 567 A1 | 5/2006 |
| EP | 1 661 568 A1 | 5/2006 |
| EP | 1 661 569 A1 | 5/2006 |
| EP | 1 669 068 A1 | 6/2006 |
| EP | 1 669 069 A1 | 6/2006 |
| EP | 1 674 097 A1 | 6/2006 |
| EP | 1 529 530 B1 | 8/2006 |
| EP | 1 695 705 A1 | 8/2006 |

(Continued)

OTHER PUBLICATIONS

Papanikolaou S. et al. Biotechnological valorisation for raw glycerol discharged after bio-diesel . . . Biomass and Bioenergy 23(2008) 60-71.

(Continued)

*Primary Examiner*—Joseph R Kosack
(74) *Attorney, Agent, or Firm*—Richard C. Billups; John C. Todaro

(57) ABSTRACT

Compounds having glucokinase activating effects and being useful as treatments for diabetes, which are represented by the following formula (I):

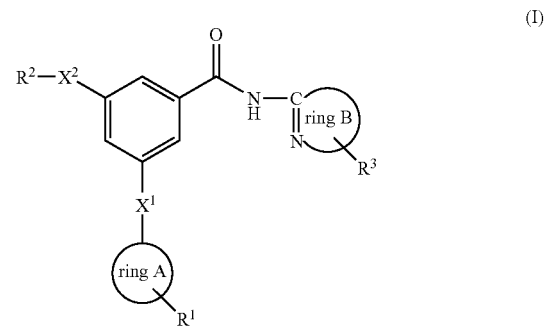

[wherein $X^1$ represents oxygen, etc., $X^2$ represents oxygen, etc., $R^1$ represents a group on Ring A such as alkylsulfonyl, etc., $R^2$ represents C3-7 cyclic alkyl optionally substituted with a halogen, etc., $R^3$ represents a substituent on Ring B such as lower alkyl, etc., formula (II):
[Chemical Formula 1]

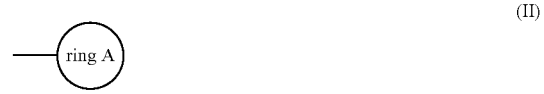

represents 6- to 10-membered aryl, etc., and formula (III):
[Formula 1]

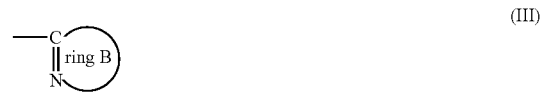

represents monocyclic or bicyclic heteroaryl optionally having on Ring B a substituent represented by $R^3$ above, wherein the carbon atom of Ring B which is bonded to the nitrogen atom of the amide group of formula (I) forms a C=N bond with the nitrogen atom of the ring],
as well as their pharmaceutically acceptable salts.

15 Claims, No Drawings

FOREIGN PATENT DOCUMENTS

| | | |
|---|---|---|
| EP | 1 568 367 B1 | 4/2007 |
| EP | 1 674 097 A1 | 6/2009 |
| GB | 2331748 A * | 6/1999 |
| SE | 0101764-8 | 8/2001 |
| SE | 0102764-8 | 8/2001 |
| WO | WO 03/000267 A1 | 1/2003 |
| WO | WO 03/015774 | 2/2003 |
| WO | WO 03/015774 A1 | 2/2003 |
| WO | WO 2005/054200 A1 | 6/2005 |
| WO | WO 2005/080359 A1 | 9/2005 |
| WO | WO 2005/080360 A1 | 9/2005 |

OTHER PUBLICATIONS

Chi, Z. et al. A laboratory study of producting docosahexaenoic acid from biodiesel-waste glycerol . . . Process Biochrmistry 42 (2007): 1537-1545.

Madigan M.T. et al. Biology of Microorganisms. Prentice Hall, inv. Upper Saddle River, NJ 2000; pp. 407-409.

Anonymous. Make your own biodiesel, ch. Deacidigying WVO. http://journeyforever.org/biodiesel_make2.html#deacid. Feb. 28, 2008.

U.S. Appl. No. 12/024,561—AstraZeneca AB—Filed Feb. 1, 2008.

* cited by examiner

HETEROARYLCARBAMOYLBENZENE DERIVATIVES

CROSS-REFERENCE TO RELATED APPLICATIONS

This application is a divisional application of U.S. Ser. No. 10/546,962, filed Aug. 25, 2005 now U.S. Pat. No. 7,432,287, which is a U.S. National Phase application under 35 U.S.C. §371 of PCT Application No. PCT/JP2004/002284, filed Feb. 26, 2004, which claims priority under 35 U.S.C. 119 from Japanese patent application Nos. IP 2003-49466, filed Feb. 26, 2003, JP 2003-400882, filed Nov. 28, 2003, and JP 2004-31298, filed Feb. 6, 2004.

TECHNICAL FIELD

The present invention relates to glucokinase activators comprising heteroarylcarbamoylbenzene derivatives as active ingredients. The invention further relates to novel heteroarylcarbamoylbenzene derivatives.

SUMMARY OF THE INVENTION

Glucokinase (GK) (ATP:D-hexose 6-phosphotransferase, EC2.7.1.1) is one of the four types of mammalian hexokinases (hexokinase IV). Hexokinases are enzymes in the first step of the glycolysis pathway which catalyze the reaction from glucose to glucose-6-phosphate. Expression of glucokinase is largely localized in the liver and pancreatic beta cells, and it plays an important role in glucose metabolism throughout the body by controlling the rate limiting step of glucose metabolism in these cells. The glucokinase types expressed in the liver and pancreatic beta cells differ in the sequence of the 15 N-terminal amino acids due to a difference in splicing, but their enzymatic properties are identical. The enzyme activities of the three hexokinases (I, II, III) other than glucokinase become saturated at a glucose concentration of below 1 mM, whereas the Km of glucokinase for glucose is 8 mM, or close to the physiological glucose level. Thus, glucokinase-mediated intracellular glucose metabolism is accelerated in response to glucose level changes by postprandial glucose level increase (10-15 mM) from normal glucose (5 mM).

The theory that glucokinase acts as a glucose sensor for pancreatic beta cells and the liver has been advocated for about 10 years (for example, Garfinkel D. et al., Computer modeling identifies glucokinase as glucose sensor of pancreatic beta cells, American Journal Physiology, Vol. 247 (3Pt2) 1984, p 527-536).

Recent results in glucokinase gene-manipulated mice have confirmed that glucokinase does in fact play an important role in systemic glucose homeostasis. Mice lacking a functional glucokinase gene die shortly after birth (for example, Grupe A. et al., Transgenic knockouts reveal a critical requirement for pancreatic beta cell glucokinase in maintaining glucose homeostasis, Cell, Vol. 83, 1995, p 69-78), while healthy and diabetic mice overexpressing glucokinase have lower blood glucose levels (for example, Ferre T. et al., Correction of diabetic alterations by glucokinase, Proceedings of the National Academy of Sciences of the U.S.A., Vol. 93, 1996, p 7225-7230). With glucose level increase, the reactions of pancreatic beta cells and the liver, while differing, both act toward lowering blood glucose. Pancreatic beta cells secrete more insulin, while the liver takes up glucose and stores it as glycogen while also reducing glucose release.

Such variation in glucokinase enzyme activity is important for liver and pancreatic beta cell-mediated glucose homeostasis in mammals. A mutant form of the glucokinase gene is expressed in a type of diabetes which occurs in youth, known as MODY2 (maturity-onset diabetes of the young), and the reduced glucokinase activity has been shown to be responsible for blood glucose increase (for example, Vionnet N. et al., Nonsense mutation in the glucokinase gene causes early-onset non-insulin-dependent diabetes mellitus, Nature Genetics, Vol. 356, 1992, p 721-722).

On the other hand, families have been found having a mutation which increases glucokinase activity, and such individuals exhibit hypoglycemic symptoms (for example, Glaser B. et al., Familial hyperinsulinism caused by an activating glucokinase mutation, New England Journal Medicine, Vol. 338, 1998, p 226-230).

This suggests that in humans as well, glucokinase functions as a glucose sensor and thus plays an important role in glucose homeostasis. Glucose regulation utilizing a glucokinase sensor system should be possible to achieve in type II diabetic patients. Since glucokinase activators should have effects of accelerating insulin secretion by pancreatic beta cells and of promoting glucose uptake and inhibiting glucose release by the liver, they are potentially useful as therapeutic agents for type II diabetic patients.

In recent years it has been demonstrated that pancreatic beta cell glucokinase is expressed locally in rat brain, and particularly in the ventromedial hypothalamus (VMH). Approximately 20% of VMH neurons are known as "glucose-responsive neurons", and these have long been considered to play an important role in body weight control. Administration of glucose into rat brain reduces feeding consumption, but inhibiting glucose metabolism by intracerebral administration of the glucose analog glucosamine produces hyperphagia. Electrophysiological experiments have indicated that glucose-responsive neurons are activated in response to physiological glucose level changes (5-20 mM) but that their activation is inhibited with glucose metabolism inhibition by glucosamine or the like. The glucose level-detecting system in the VMH is believed to be based on a glucokinase-mediated mechanism similar to that for insulin secretion by pancreatic beta cells. Consequently, substances which activate glucokinase in the VMH in addition to pancreatic beta cells not only exhibit a glucose rectifying effect but can also potentially rectify obesity, which is a problem for most type II diabetic patients.

This indicates that compounds having glucokinase-activating effects are useful as therapeutic and/or prophylactic agents for diabetes, as therapeutic and/or prophylactic agents for diabetes complications such as retinopathy, nephropathy, neuropathy, ischemic cardiopathy, arteriosclerosis and the like, and as therapeutic and/or prophylactic agents for obesity.

The compound represented by the following formula (IV), having substituents at the 3- and 5-positions of the same benzene ring as the heteroarylcarbamoylbenzene derivatives (I) of the invention, has been described.

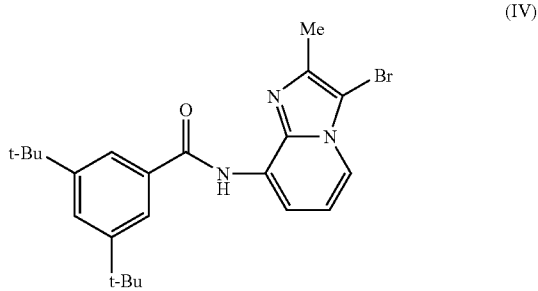

(IV)

This compound has tert-butyl groups at both the 3- and 5-positions of the heteroarylcarbamoylbenzene ring, and does not have alkyl groups at the 3- and 5-positions as according to the compounds of the invention. It also has imidazo-[1,2-a]pyridine bonded to the nitrogen atom of the carbamoyl group, but the relative positional relationship between the N of the pyridine ring of the imidazo-[1,2-a]pyridyl group and the carbamoyl group differs from the relative positional relationship between the carbamoyl group and the nitrogen atom of the heteroaryl group in the compounds of the invention (for example, Japanese Laid-Open Publication of International Application No. 11-505524).

The compound represented by the following formula (V), having two substituents on the benzene ring of a heteroarylcarbamoylbenzene derivative, has also been described (for example, Japanese Laid-Open Publication of International Application No. 2001-526255).

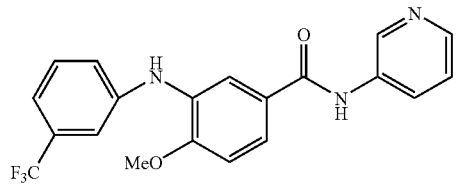

(V)

Although the compound described in the aforementioned Patent document 2 partially matches the structure of the compounds of the invention in that one of the two substituents is trifluoromethylphenylamino, trifluoromethylphenylamino being included in the $X^1$-(Ring A)-$R^1$ of the compounds of the invention, and in that it contains a pyridine ring as the group bonded to the nitrogen atom of the carbamoyl group, in the compounds of the invention the nitrogen atom of the pyridine ring bonded to the nitrogen atom of the carbamoyl group is adjacent to the carbon atom of the pyridine ring which is bonded to the nitrogen atom of the carbamoyl group, whereas the compound described in the aforementioned Patent document 2 differs in that the nitrogen atom is bonded via another carbon atom lying between it and the carbon atom of the pyridine ring which is bonded to the nitrogen atom of the carbamoyl group, and also in that the bonding position of the methoxy group is different from the bonding position of the compounds of the invention.

The compound represented by the following formula (VI) has also been described (for example, Japanese Laid-Open Publication of International Application No. 2002-509536).

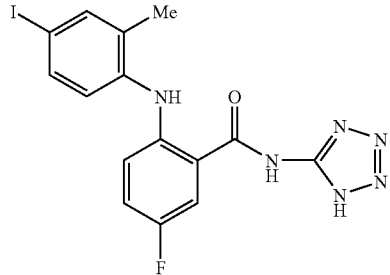

(VI)

Although the compound described in the aforementioned Patent document 3 matches the structure of the compounds of the invention in that one of the two substituents on the benzene ring is 2-methyl-4-iodo-phenylamino and in that a nitrogen atom is adjacent to the carbon atom bonded to the nitrogen atom of the carbamoyl group, it differs in that the positional relationship between the 2-methyl-4-iodo-phenylamino group and the carbamoyl group is different from the positional relationship in the compounds of the invention, and in that it has a fluoro group as the other of the two substituents on the benzene ring while the compounds of the invention contain no halogen atoms as substituents on the benzene ring.

DISCLOSURE OF THE INVENTION

As a result of diligent research directed toward developing novel diabetes drugs having novel drug effects which also exceed the drug effects of existing diabetes drugs, due to action differing from that of the existing drugs, the present inventors have found that compounds represented by formula (I) shown below have glucokinase-activating effects, and the invention has been completed on the basis of this finding. Specifically, the present invention relates to the following.

(1) Compounds represented by the following formula (I):

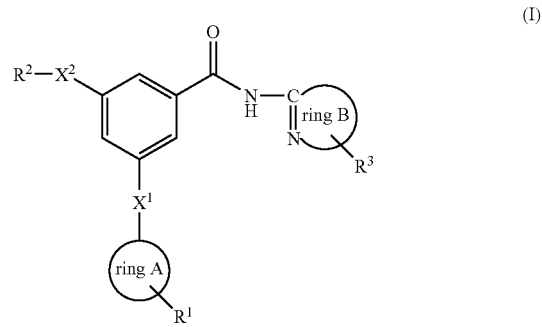

(I)

[wherein $X^1$ represents oxygen, sulfur or NH, $X^2$ represents oxygen, sulfur or $CH_2$, $R^1$ represents 1 or 2 substituents optionally present on Ring A which are selected from the group consisting of alkylsulfonyl, alkanoyl, lower alkyl, hydroxyalkyl, hydroxy, alkylcarbamoyl, alkylsulfamoyl, dialkylsulfamoyl, alkylthio, alkoxy, dialkylcarbamoyl, alkoxycarbonylamino, alkoxycarbonyl, halogen atoms, alkanoylaminoalkyl, alkoxycarbonylaminoalkyl, alkylsulfonylaminoalkyl, cyano and trifluoromethyl, $R^2$ represents a C3-7 cyclic alkyl group (wherein one of the constituent carbon atoms of the ring (except for the carbon atom, among the constituent carbon atoms of the ring, which is bonded to $X^2$) is optionally replaced with oxygen, NH, N-alkanoyl or CONH), a straight-chain or branched lower alkyl group or a lower alkenyl group, optionally having a substituent selected from the group consisting of halogen atoms, carboxyl, alkoxycarbonyl, hydroxy, amino (where the amino may be further substituted with 1 or 2 alkanoyl or lower alkyl groups), alkoxy and N-alkylcarbamoyl, $R^3$ represents 1 or 2 substituents optionally present on Ring B which are selected from the group consisting of lower alkyl, alkoxy, alkylamino, lower dialkylamino, halogen atoms, trifluoromethyl, hydroxyalkyl (wherein the hydrogen of the hydroxy in the hydroxyalkyl group may be replaced with lower alkyl), aminoalkyl, alkanoyl, carboxyl, alkoxycarbonyl and cyano, the following formula (II):

(II)

represents a 6- to 10-membered aryl group or 5- to 7-membered heteroaryl group optionally having on the ring 1 or 2 substituents represented by $R^1$ above, and the following formula (III):

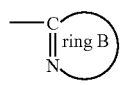

represents a monocyclic or bicyclic heteroaryl group optionally having on the ring 1 or 2 substituents represented by $R^3$ above, wherein the carbon atom of Ring B which is bonded to the nitrogen atom of the amide group of formula (I) forms a C=N bond with the nitrogen atom of the ring], and their pharmaceutically acceptable salts;

(2) Compounds according to (1) above, wherein $X^1$ is O or S, and $X^2$ is O or $CH_2$;

(3) Compounds according to (2) above, wherein Ring A is a phenyl group or a 5- to 6-membered heteroaryl group;

(4) Compounds according to (2) above wherein Ring A is a phenyl group;

(5) Compounds according to (2) above wherein Ring A is a 5- to 6-membered heteroaryl group;

(6) Compounds according to any one of (4) to (5) above, wherein $R^1$ is hydrogen, alkylsulfonyl, alkanoyl, hydroxyalkyl, alkylcarbamoyl, alkylsulfamoyl, dialkylsulfamoyl, dialkylcarbamoyl, alkoxycarbonylamino, halogen atoms, alkanoylaminoalkyl, alkylsulfonylaminoalkyl or alkoxycarbonylaminoalkyl;

(7) Compounds according to (4) above, wherein $R^1$ is alkylsulfonyl, alkanoyl, hydroxyalkyl, alkanoylaminoalkyl, alkylsulfonylaminoalkyl or alkoxycarbonylaminoalkyl;

(8) Compounds according to (4) above, wherein $R^1$ is alkylsulfonyl, alkanoyl or hydroxyalkyl;

(9) Compounds according to any one of (3) to (8) above, wherein formula (III) represents a monocyclic or bicyclic heteroaryl group (provided that the heteroaryl group is not 5-alkoxycarbonyl-pyridin-2-yl or 5-carboxyl-pyridin-2-yl) optionally having on the ring 1 or 2 substituents represented by $R^3$ above, wherein the carbon atom of Ring B which is bonded to the nitrogen atom of the amide group of formula (I) forms a C=N bond with the nitrogen atom of Ring B;

(10) Compounds according to (7) above, wherein Ring B has at least one hetero atom in the ring selected from the group consisting of nitrogen, sulfur and oxygen atoms, in addition to the nitrogen atom forming the C=N group together with the carbon atom in the ring which is bonded to the nitrogen atom of the amide group in formula (I);

(11) Compounds according to any one of (1) to (10) above, wherein $R^2$ is a C3-7 cyclic alkyl group (wherein one of the constituent carbon atoms of the ring is optionally replaced with oxygen, NH or N-alkanoyl), a straight-chain or branched lower alkyl group or a lower alkenyl group, optionally substituted with a halogen atom, carboxyl, alkoxycarbonyl, hydroxy, amino (where the amino may be further substituted with 1 or 2 lower alkyl groups), alkoxy, N-alkylcarbamoyl or alkanoylamino;

(12) Compounds according to any one of (1) to (11) above, wherein Ring B is thiazolyl, imidazolyl, isothiazolyl, thiadiazolyl, triazolyl, oxazolyl, isoxazolyl, pyrazinyl, pyridazinyl, pyrazolyl, pyrimidinyl, pyridothiazolyl or benzothiazolyl;

(13) Compounds according to any one of (1) to (12) above, wherein $R^3$ is lower alkyl, alkoxy, a halogen, hydroxyalkyl (wherein the hydrogen of the hydroxy in the hydroxyalkyl group may be replaced with lower alkyl), aminoalkyl or alkanoyl;

(14) Compounds according to any one of (1) to (12) above, wherein $R^3$ is lower alkyl or hydroxyalkyl (wherein the hydrogen of the hydroxy in the hydroxyalkyl group may be replaced with lower alkyl);

(15) Compounds represented by formula (I):

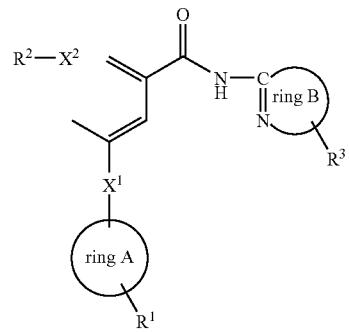

[wherein the symbols have the same definitions specified above], which are 5-isopropoxy-3-(4-methanesulfonylphenoxy)-N-(4-methylthiazol-2-yl)-benzamide, 5-(2-hydroxy-1-methyl-ethoxy)-3-(4-methanesulfonylphenoxy)-N-thiazol-2-yl-benzamide, 5-ethoxy-3-(4-methanesulfonylphenoxy)-N-(4-methoxymethyl-thiazol-2-yl)benzamide, 5-cyclopentyloxy-3-(4-methanesulfonylphenoxy)-N-thiazol-2-yl-benzamide, 3-(4-methanesulfonylphenoxy)-5-(tetrahydrofuran-3-yloxy)-N-thiazol-2-yl-benzamide, 3-(4-methanesulfonylphenoxy)-5-(2-methoxy-1-methyl-ethoxy)-N-thiazol-2-yl-benzamide, 3-(4-methanesulfonylphenoxy)-5-(2-methoxy-1-methoxymethyl-ethoxy)-N-thiazol-2-yl-benzamide, 3-(2-fluoro-4-methanesulfonylphenoxy)-5-isopropoxy-N-thiazol-2-yl-benzamide, 3-(4-methanesulfonylphenoxy)-5-(1-methoxymethyl-propoxy)-N-(4-methyl-thiazol-2-yl)-benzamide, 5-isopropoxy-3-(4-methanesulfonylphenoxy)-N-pyrazol-3-yl-benzamide, 5-isopropoxy-3-(4-methanesulfonylphenoxy)-N-pyrazin-2-yl-benzamide, 3-(4-methanesulfonylphenoxy)-5-(3-methoxy-1-methyl-propoxy)-N-thiazol-2-yl-benzamide, 5-(3-hydroxy-1-methyl-propoxy)-3-(4-methanesulfonylphenoxy)-N-thiazol-2-yl-benzamide, 5-isopropoxy-3-(4-methanesulfonylphenoxy)-N-pyrimidin-4-yl-benzamide, 5-isopropoxy-3-(4-methanesulfonylphenoxy)-N-(pyrimidin-2-yl)-benzamide, N-(4-hydroxymethyl-thiazol-2-yl)-5-isopropoxy-3-(4-methanesulfonylphenoxy)-benzamide, N-(isooxazol-3-yl)-3-(4-methanesulfonylphenoxy)-5-(1-methoxymethyl-propoxy)-benzamide, 3-(4-methanesulfonylphenoxy)-5-(1-methoxymethyl-propoxy)-N-[1,3,4]thiadiazol-2-yl-benzamide, 5-(1-hydroxymethyl-propoxy)-3-(4-methanesulfonylphenoxy)-N-(4-methyl-thiazol-2-yl)-benzamide, N-(4-hydroxymethyl-thiazol-2-yl)-3-(4-methanesulfonylphenoxy)-5-(1-methoxymethyl-propoxy)-benzamide, 5-(2-amino-1-methyl-ethoxy)-3-(4-methanesulfonylphenoxy)-N-thiazol-2-yl-benzamide, 5-(2-dimethylamino-1-methyl-ethoxy)-3-(4-methanesulfonylphenoxy)-N-thiazol-2-yl-benzamide, 5-(2-hydroxy-propoxy)-3-(4-methanesulfonylphenoxy)-N-(4-methyl-thiazol-2-yl)-benzamide, 3-(4-methanesulfonylphenoxy)-5-(2-methoxy-propoxy)-N-(4-methyl-thiazol-2-yl)-benzamide, 5-isopropoxy-3-(4- methanesulfonylphenoxy)-N-(thiazolo[5,4-b]pyridin-2-yl)-benzamide, 5-(2-hydroxymethyl-allyl)-3-(4-methanesulfonylphenoxy)-N-thiazol-2-yl-benzamide, 5-(2-hydroxy-1-methyl-ethoxy)-3-(4-methanesulfonylphenoxy)-N-thiazolo[5,4-b]pyridin-2-yl-benzamide, 5-(3-hydroxy-2-methyl-propyl)-3-(4-methanesulfonylphenoxy)-N-thiazol-2-yl-benzamide, 3-(4-methanesulfonylphenoxy)-N-(4-methyl-thiazol-2-yl)-5-(piperidin-4-yl-oxy)-benzamide hydrochloride, 5-(1-acetyl-piperidin-4-yloxy)-3-(4-methanesulfonylphenoxy)-N-(4-methyl-thiazol-2-yl)-benzamide, 2-[3-(4-methanesulfonylphenoxy)-5-(4-methyl-thiazol-2-yl-carbamoyl)-phenoxy]propionic acid, 5-(3-hydroxy-1-methyl-propoxy)-3-(4-methanesulfonylphenoxy)-N-thiazol-2-yl-benzamide, 3-(4-methanesulfonylphenoxy)-5-(1-methylcarbamoyl-ethoxy)-N-(4-methyl-thiazol-2-yl)-benzamide, 5-(2-acetylamino-1-methyl-ethoxy)-3-(4-methanesulfonylphenoxy)-N-thiazol-2-yl-benzamide, N-[4-(1-hydroxy-ethyl)-thiazol-2-yl]-5-isopropoxy-3-(4-methanesulfonylphenoxy)-benzamide, 5-(2-hydroxy-1-methyl-ethoxy)-3-(4-methanesulfonylphenoxy)-N-pyridin-2-yl-benzamide, 5-(2-hydroxy-ethoxy)-3-(4-methanesulfonylphenoxy)-N-thiazol-2-yl-benzamide, 5-(2-hydroxy-cyclopentyloxy)-3-(4-methanesulfonylphenoxy)-N-thiazol-2-yl-benzamide, N-(4-acetyl-thiazol-2-yl)-5-(2-hydroxy-1-methyl-ethoxy)-3-(4-methanesulfonylphenoxy)-benzamide, 5-(2-hydroxy-1-methyl-ethoxy)-N-(4-hydroxymethyl-thiazol-2-yl)-3-(4-methanesulfonylphenoxy)-benzamide, N-[4-(1-hydroxy-ethyl)-thiazol-2-yl]-5-(2-hydroxy-1-methyl-ethoxy)-3-(4-methanesulfonylphenoxy)-benzamide, 3-(3-fluoro-4-methanesulfonylphenoxy)-5-(2-hydroxy-1-methyl-ethoxy)-N-thiazol-2-yl-benzamide, 5-(2-hydroxy-1-methyl-ethoxy)-3-(4-methanesulfonylphenoxy)-N-(5-methyl-thiazol-2-yl)benzamide, 5-(2-hydroxy-1-methyl-ethoxy)-3-(4-methanesulfonylphenoxy)-N-([1,2,4]thiadiazol-5-yl)-benzamide, N-(4-hydroxymethyl-thiazol-2-yl)-3-(4-methanesulfonylphenoxy)-5-(2-methoxy-1-methyl-ethoxy)-benzamide, 5-(2-hydroxy-1-methyl-ethoxy)-3-(4-methanesulfonylphenoxy)-N-(5-methoxycarbonyl-pyridin-2-yl)-benzamide, 6-[5-isopropoxy-3-(4-methanesulfonylphenoxy)-benzoylamino]nicotinic acid, 5-(2-hydroxy-1-methyl-propoxy)-3-(4-methanesulfonylphenoxy)-N-thiazol-2-yl-benzamide, 5-(2-hydroxy-1-methyl-ethoxy)-N-(isoxazol-3-yl)-3-(4-methanesulfonylphenoxy)-benzamide, N-(5-hydroxymethyl-thiazol-2-yl)-5-isopropoxy-3-(4-methanesulfonylphenoxy)-benzamide, N-[4-(1-hydroxy-ethyl)-thiazol-2-yl]-3-(4-methanesulfonylphenoxy)-5-(2-methoxy-1-methyl-ethoxy)-benzamide, N-(4-hydroxymethyl-thiazol-2-yl)-3-(4-methanesulfonylphenoxy)-5-(tetrahydrofuran-3-yl-oxy)-benzamide, 5-(2-hydroxy-1-methyl-ethoxy)-3-(4-methanesulfonylphenoxy)-N-(2-methylthiazol-4-yl)-benzamide, 5-(2-hydroxy-1-methyl-ethoxy)-3-(4-methanesulfonylphenoxy)-N-(4-methoxymethyl-thiazol-2-yl)-benzamide, N-[4-(1-hydroxy-ethyl)-thiazol-2-yl]-3-(4-methanesulfonylphenoxy)-5-(2-methoxy-1-methyl-ethoxy)-benzamide, N-[4-(1-hydroxy-ethyl)-thiazol-2-yl]-3-(4-methanesulfonylphenoxy)-5-(tetrahydrofuran-3-yl-oxy)-benzamide, N-[4-(1-hydroxy-ethyl)-thiazol-2-yl]-3-(4-methanesulfonylphenoxy)-5-(tetrahydrofuran-3-yl-oxy)-benzamide, N-(2,5-dimethylthiazol-4-yl)-5-(2-hydroxy-1-methyl-ethoxy)-3-(4-methanesulfonylphenoxy)-benzamide, 5-isopropoxy-3-(4-methoxycarbonylaminomethylphenoxy)-N-thiazol-2-yl-benzamide, 5-isopropoxy-3-(4-methylcarbamoyl-phenoxy)-N-thiazol-2-yl-benzamide, 3-(4-dimethylcarbamoyl-phenoxy)-5-isopropoxy-N-thiazol-2-yl-benzamide, 5-isopropoxy-3-(4-methylcarbonylaminomethyl-phenoxy)-N-thiazol-2-yl-benzamide, 5-isopropoxy-3-(4-methanesulfonylaminomethyl-phenoxy)-N-thiazol-2-yl-benzamide, 3-[4-(1-hydroxy-propyl)-phenoxy]-5-isopropoxy-N-thiazol-2-yl-benzamide, 6-[3-isopropoxy-5-(thiazol-2-ylcarbamoyl)-phenoxy]-nicotinic acid methyl ester, 3-(5-hydroxymethyl-pyridin-2-yl-oxy)-5-isopropoxy-N-thiazol-2-yl-benzamide, 5-isopropoxy-3-(5-methanesulfonylpyridin-2-yl)-N-thiazol-2-yl-benzamide, 3-(5-acetyl-pyridin-2-yl-oxy)-5-isopropoxy-N-thiazol-2-yl-benzamide, 5-isopropoxy-3-(5-methoxycarbonyl-pyrazin-2-yl-oxy)-N-thiazol-2-yl-benzamide, 3-(5-cyano-pyridin-2-yl-oxy)-5-isopropoxy-N-thiazol-2-yl-benzamide, 5-isopropoxy-3-(2-oxo-1,2-dihydro-pyridin-4-yl-oxy)-N-thiazol-2-yl-benzamide, 5-isopropoxy-3-(2-oxo-1,2-dihydro-pyridin-3-yl-oxy)-N-thiazol-2-yl-benzamide, 5-isopropoxy-3-(2-oxo-1,2-dihydro-pyridin-3-yl-oxy)-N-thiazolo[5,4-b]pyridin-2-yl-benzamide, 5-isopropoxy-3-([1,3,4]thiadiazol-2-ylsulfanyl)-N-thiazolo[5,4-b]-pyridine-2-yl-benzamide, 5-isopropoxy-3-(4-methyl-[1,2,4]triazol-3-ylsulfanyl)-N-thiazol-2-yl-benzamide, 5-isopropoxy-3-thiazol-2-ylsulfanyl-N-thiazol-2-yl-benzamide, 5-isopropoxy-3-(4H-[1,2,4]triazol-3-ylsulfanyl)-N-thiazol-2-yl-benzamide, 5-isopropoxy-3-([1,3,4]thiadiazol-2-ylsulfanyl)-N-thiazol-2-yl-benzamide, 5-isopropoxy-3-(5-methylsulfanyl-[1,3,4]thiadiazol-2-ylsulfanyl)-N-thiazol-2-yl-benzamide, 5-isopropoxy-3-(5-methyl-[1,3,4]thiadiazol-2-ylsulfanyl)-N-thiazol-2-yl-benzamide, 5-(tetrahydrofuran-3-yl-oxy)-N-thiazol-2-yl-3-(4H-[1,2,4]triazol-3-ylsulfanyl)-benzamide, 5-(2-hydroxy-1-methyl-ethoxy)-N-(4-methyl-thiazol-2-yl)-3-([1,3,4]thiadiazol-2-ylsulfanyl)-benzamide, 5-(3-hydroxy-1-methyl-propoxy)-N-(4-methyl-thiazol-2-yl)-3-([1,3,4]thiadiazol-2-ylsulfanyl)-benzamide, 5-(2-hydroxy-1-methyl-ethoxy)-3-([1,3,4]thiadiazol-2-ylsulfanyl)-N-thiazol-2-yl-benzamide, 5-(2-hydroxy-1-methyl-ethoxy)-3-(4-methanesulfonylphenylsulfanyl)-N-thiazol-2-yl-benzamide, 3-(3-fluoro-phenylthio)-5-(2-hydroxy-1-methyl-ethoxy)-N-thiazol-2-yl-benzamide, 5-(2-hydroxy-1-methyl-ethoxy)-3-(pyridin-4-ylsulfanyl)-N-thiazol-2-yl-benzamide, 5-(2-hydroxy-1-methyl-ethoxy)-3-(6-methyl-pyridin-3-ylsulfanyl)-N-thiazol-2-yl-benzamide, 5-(2-hydroxy-1-methyl-ethoxy)-3-(4-methanesulfonylphenoxy)-N-(3-methyl-[1,2,4]-thiadiazol-5-yl)-benzamide, N-[3-hydroxymethyl-1,2,4-thiadiazol-5-yl]-3-(4-methanesulfonylphenoxy)-5-(2-methoxy-1-methyl-ethoxy)benzamide, 5-(3-hydroxy-1-methylethoxy)-3-(4-methanesulfonylphenoxy)-N-[5-methyl-1,2,4-thiadiazol-3-yl]benzamide, 5-(hydroxy-1-methylethoxy)-3-(4-methanesulfonylphenoxy)-N-(3-methoxy-1,2,4-thiadiazol-5-yl)benzamide, 5-(2-hydroxy-1-methyl-ethoxy)-3-(4-methanesulfonylphenoxy)-N-(1,2,5-thiadiazol-3-yl)benzamide, 5-(2-hydroxy-1-methyl-ethoxy)-3-(4-methanesulfonylphenoxy)-N-(4-trifluoromethyl-thiazol-2-yl)benzamide, 5-(2-hydroxy-1-methyl-ethoxy)-3-(4-methanesulfonylphenoxy)-N-(4,5,6,7-tetrahydrobenzothiazol-2-yl)benzamide, 5-(2-hydroxy-1-methyl-ethoxy)-3-(4-methanesulfonylphenoxy)-N-(pyridazin-3-yl)-benzamide, 5-(2-hydroxy-1-methyl-ethoxy)-N-(3-isopropyl-[1,2,4]-triazol-5-yl)-3-(4-methanesulfonylphenoxy)benzamide, 5-(2-hydroxy-1-methyl-ethoxy)-3-(4-methanesulfonylphenoxy)-N-(3-methyl-[1,2,4]-oxadiazol-5-yl)benzamide, 5-(2-hydroxy-1-methyl-ethoxy)-N-[4-(1-hydroxy-1-methyl-ethyl)-thiazol-2-yl]-3-(4-methanesulfonylphenoxy)benzamide, N-(4-cyano-thiazol-2-yl)-5-(2-hydroxy-1-methyl-ethoxy)-3-(4-methanesulfonylphenoxy)benzamide, 5-(2-hydroxy-1-methyl-ethoxy)-3-(4-methanesulfonylphenoxy)-N-(1-methyl-1H-pyrazol-3-yl)benzamide, 5-(1-hydroxymethylpropoxy)-3-(4-methanesulfonylphenoxy)-N-(pyridin-2-yl)benzamide, 5-(2-hydroxy-1-methyl-ethoxy)-3-(4-methanesulfonylphenoxy)-N-(5-methyl-isothiazol-3-yl)benzamide, 5-(3-hydroxy-cyclopentyloxy)-3-(4-methanesulfonylphenoxy)-N-(thiazol-2-yl)benzamide, 5-(2-hydroxy-1-methyl-ethoxy)-3-(4-methanesulfonylphenoxy)-N-(5-methoxy-thiazol-2-yl)benzamide, 5-(1-hydroxymethyl-2-methyl-propoxy)-3-(4-methanesulfonylphenoxy)-N-(thiazol-2-yl)benzamide, 5-(2-hydroxy-1-methyl-ethoxy)-3-(4-methanesulfonylphenoxy)-N-(1H-[1,2,3]triazol-4-yl)benzamide, N-(1-acetyl-1H-pyrazol-3-yl)-5-(2-hydroxy-1-methyl-ethoxy)-3-(4-methanesulfonylphenoxy)benzamide, 5-(2-hydroxy-1-methyl-ethoxy)-3-(4-methanesulfonylphenoxy)-N-(pyrazol-3-yl)benzamide, N-(5,6-dihydro-4H-cyclopentathiazol-2-yl)-5-(2-hydroxy-1-methyl-ethoxy)-3-(4-methanesulfonylphenoxy)benzamide, 5-(1-hydroxymethyl-propoxy)-3-(4-methanesulfonylphenoxy)-N-(1-methyl-1H-pyrazol-3-yl)benzamide, 5-(2-hydroxy-1-methyl-ethoxy)-3-(4-methanesulfonylphenoxy)-N-(thieno[3,2-d]thiazol-2-yl)benzamide, 3-(3-fluoro-4-methanesulfonylphenoxy)-5-(2-hydroxy-1-methyl-ethoxy)-N-(1-methyl-1H-pyrazol-3-yl)benzamide, 3-(4-methanesulfonylphenoxy)-5-(2-methoxy-1-methyl-ethoxy)-N-(pyrazol-3-yl)benzamide, 3-(4-cyano-phenoxy)-5-(2-hydroxy-1-methyl-ethoxy)-N-(1-methyl-1H-pyrazol-3-yl)benzamide, 3-(4-ethylsulfonylphenoxy)-5-(2-hydroxy-1-methyl-ethoxy)-N-(1-methyl-1H-pyrazol-3-yl)benzamide, 3-(6-ethanesulfonylpyridin-3-yloxy)-5-(2-hydroxy-1-methyl-ethoxy)-N-(1-methyl-1H-pyrazol-3-yl)benzamide, 5-(3-hydroxy-1-methyl-propoxy)-3-(4-methanesulfonylphenoxy)-N-(1-methyl-1H-pyrazol-3-yl)benzamide, 3-(4-ethanesulfonylphenoxy)-5-(2-hydroxy-1-methyl-ethoxy)-N-(isoxazol-3-yl)benzamide, 5-(2-hydroxy-1-methyl-ethoxy)-3-(4-isopropylsulfonylphenoxy)-N-(1-methyl-1H-pyrazol-3-yl)benzamide, 5-(2-hydroxy-1-methyl-ethoxy)-N-(4-hydroxy-4-methyl-4,5,6,6a-tetrahydro-3 aH-cyclopentathiazol-2-yl)-3-(4-methanesulfonylphenoxy)benzamide, 3-(4-dimethylcarbamoyl-phenoxy)-5-(2-hydroxy-1-methyl-ethoxy)-N-(1-methyl-1H-pyrazol-3-yl)benzamide, 3-(4-acetylphenoxy)-5-(2-hydroxy-1-methyl-ethoxy)-N-(1-methyl-1H-pyrazol-3-yl)benzamide, 5-(2-hydroxy-1-methyl-ethoxy)-N-(1-methyl-1H-pyrazol-3-yl)-3-(1,3,4-thiadiazol-2-ylsulfanyl)benzamide, N-(1-ethyl-1H-pyrazol-3-yl)-5-(2-hydroxy-1-methyl-ethoxy)-3-(4-methanesulfonylphenoxy)benzamide, 5-(2-hydroxy-1-methyl-ethoxy)-3-(6-methanesulfonylpyridin-3-yloxy)-N-(1-methyl-1H-pyrazol-3-yl)benzamide, 5-(2-hydroxy-1-methyl-ethoxy)-3-(4-methoxycarbonylaminomethyl-phenoxy)-N-(3-methyl-1,2,4-thiadiazol-5-yl)benzamide, 5-(1-hydroxymethyl-propoxy)-3-(6-methanesulfonylpyridin-3-yloxy)-N-(1-methyl-1H-pyrazol-3-yl)benzamide, 3-(6-methanesulfonylpyridin-3-yloxy)-5-(1-methoxymethyl-propoxy)-N-(1-methyl-1H-pyrazol-3-yl)benzamide, 5-isopropoxy-3-(6-methanesulfonylpyridin-3-yloxy)-N-(1-methyl-1H-pyrazol-3-yl)benzamide, 5-(2-fluoro-1-fluoromethyl-ethoxy)-3-(6-methanesulfonylpyridin-3-yloxy)-N-(1-methyl-1H-pyrazol-3-yl)benzamide, 3-(6-ethanesulfonylpyridin-3-yloxy)-5-(2-hydroxy-1-methyl-ethoxy)-N-(isoxazol-3-yl)benzamide, 5-(2-hydroxy-1-methyl-ethoxy)-3-(4-methanesulfonylphenylsulfanyl)-N-(1-methyl-1H-pyrazol-3-yl)benzamide, 5-cyclopropyloxy-3-(4-methanesulfonylphenoxy)-N-(1-methyl-1H-pyrazol-3-yl)benzamide, 3-(6-methanesulfonylpyridin-3-yloxy)-5-(1-methoxymethyl-propoxy)-N-(pyrazol-3-yl)benzamide, 5-(2-fluoro-1-fluoromethyl-ethoxy)-3-(4-methanesulfonylphenoxy)-N-(1-methyl-1H-pyrazol-3-yl)benzamide, 3-(6-ethanesulfonylpyridin-3-yloxy)-5-(1-hydroxymethyl-propoxy)-N-(1-methyl-1H-pyrazol-3-yl)benzamide, 5-(6-ethanesulfonylpyridin-3-yloxy)-3-(2-methoxy-1-methyl-ethoxy)-N-(1-methyl-1H-pyrazol-3-yl)benzamide, 2-[3-(4-methanesulfonylphenoxy)-5-(1-methyl-1H-pyrazol-3-ylcarbamoyl)-phenoxy]propionic acid tert-butyl ester, 3-(6-ethanesulfonylpyridin-3-yloxy)-5-(2-methoxy-1-methyl-ethoxy)-N-(pyrazol-3-yl)-benzamide, 3-(6-methanesulfonylpyridin-3-yloxy)-N-(1-methyl-1H-pyrazol-3-yl)-5-(tetrahydrofuran-3-yl)benzamide, N-(1-ethyl-1H-pyrazol-3-yl)-5-(2-hydroxy-1-methyl-ethoxy)-3-(6-methanesulfonylpyridin-3-yloxy)benzamide, 5-(2-fluoro-1-fluoromethyl-ethoxy)-3-(6-methanesulfonylpyridin-3-yloxy)-N-(pyrazol-3-yl)benzamide, 3-(6-methanesulfonylpyridin-3-yloxy)-5-(2-methoxy-1-methyl-ethoxy)-N-(1-methyl-1H-pyrazol-3-yl)benzamide, 3-(6-ethanesulfonylpyridin-3-yloxy)-5-(2-fluoro-1-fluoromethyl-ethoxy)-N-(1-methyl-1H-pyrazol-3-yl)benzamide, 2-[3-(4-methanesulfonylphenoxy)-5-(1-methyl-1H-pyrazol-3-ylcarbamoyl)-phenoxy]propionic acid, 3-(6-ethanesulfonylpyridin-3-yloxy)-5-isopropoxy-N-(pyrazol-3-yl)benzamide, 3-(6-ethanesulfonylpyridin-3-yloxy)-5-isopropoxy-N-(1-methyl-1H-pyrazol-3-yl)benzamide, 3-(6-ethanesulfonylpyridin-3-yloxy)-5-(2-hydroxy-1-methyl-ethoxy)-N-(pyrazol-3-yl)benzamide, 3-(6-ethanesulfonylpyridin-3-yloxy)-5-(2-hydroxy-1-methyl-ethoxy)-N-(pyridin-2-yl)benzamide, 3-(6-ethanesulfonylpyridin-3-yloxy)-5-(2-hydroxy-1-methyl-ethoxy)-N-thiazol-2-yl-benzamide-5-(2-fluoro-1-methyl-ethoxy)-3-(6-methanesulfonylpyridin-3-yloxy)-N-(1-methyl-1H-pyrazol-3-yl)benzamide, 5-(2-chloro-1-methyl-ethoxy)-3-(6-ethanesulfonylpyridin-3-yloxy)-N-(1-methyl-1H-pyrazol-3-yl)benzamide, 5-(2-fluoro-1-fluoromethyl-ethoxy)-N-(isoxazol-3-yl)-3-(6-methanesulfonylpyridin-3-yloxy)benzamide, 5-(2-fluoro-1-fluoromethyl-ethoxy)-3-(6-methanesulfonylpyridin-3-yloxy)-N-(pyridin-2-yl)benzamide, 5-(2-fluoro-1-fluoromethyl-ethoxy)-3-(6-methanesulfonylpyridin-3-yloxy)-N-(3-methyl-[1,2,4]-thiadiazol-5-yl)benzamide, 3-(4-dimethylsulfamoylphenoxy)-5-(2-hydroxy-1-methyl-ethoxy)-N-(1-methyl-1H-pyrazol-3-yl)benzamide, 5-(2-hydroxy-1-methyl-ethoxy)-3-(3-methanesulfonylphenoxy)-N-(1-methyl-1H-pyrazol-3-yl)benzamide, 5-(2-hydroxy-1-methyl-ethoxy)-3-(6-isopropylsulfonylpyridin-3-yloxy)-N-(1-methyl-1H-pyrazol-3-yl)benzamide, 3-(3-chloro-4-methanesulfonylphenoxy)-5-(2-hydroxy-1-methyl-ethoxy)-N-(1-methyl-1H-pyrazol-3-yl)benzamide, 5-(2-hydroxy-1-methyl-ethoxy)-N-(1-methyl-1H-pyrazol-3-yl)-3-(pyridin-3-yloxy)benzamide, 5-(2-fluoro-1-fluoromethyl-ethoxy)-N-(1-methyl-1H-pyrazol-3-yl)-3-(pyridin-3-yloxy)benzamide, 5-(2-hydroxy-1-methyl-ethoxy)-N-(1-methyl-1H-pyrazol-3-yl)-3-(pyridin-4-yloxy)benzamide, 5-(2-fluoro-1-fluoromethyl-ethoxy)-N-(1-methyl-1H-pyrazol-3-yl)-3-(pyridin-4-yloxy)benzamide, 2-[3-(6-ethanesulfonylpyridin-3-yloxy)-5-(1-methyl-1H-pyrazol-3-ylcarbamoyl)-phenoxy]propionic acid, 5-(2-fluoro-1-fluoromethyl-ethoxy)-3-(3-fluoro-4-methanesulfonylphenoxy)-N-(1-methyl-1H-pyrazol-3-yl)benzamide, or their pharmaceutically acceptable salts;

(16) The compound 5-(2-hydroxy-1-methyl-ethoxy)-3-(4-methanesulfonyl-phenoxy)-N-thiazol-2-yl-benzamide or a pharmaceutically acceptable salt thereof;

(17) The compound N-(4-hydroxymethyl-thiazol-2-yl)-3-(4-methanesulfonylphenoxy)-5-(1-methoxymethyl-propoxy)-benzamide or a pharmaceutically acceptable salt thereof;

(18) The compound 5-(2-hydroxy-1-methyl-ethoxy)-3-(4-methanesulfonyl-phenoxy)-N-pyridin-2-yl-benzamide or a pharmaceutically acceptable salt thereof;

(19) The compound 5-(2-hydroxy-1-methyl-ethoxy)-3-(4-methanesulfonyl-phenoxy)-N-(2-methylthiazol-4-yl)-benzamide or a pharmaceutically acceptable salt thereof;

(20) The compound 5-(2-hydroxy-1-methyl-ethoxy)-3-([1,3,4]thiadiazol-2-ylsulfanyl)-N-thiazol-2-yl-benzamide or a pharmaceutically acceptable salt thereof;

(21) The compound 5-(2-hydroxy-1-methyl-ethoxy)-3-(4-methanesulfonyl-phenoxy)-N-(3-methyl-[1,2,4]-thiadiazol-5-yl)-benzamide or a pharmaceutically acceptable salt thereof;

(22) The compound 5-(2-hydroxy-1-methyl-ethoxy)-3-(4-methanesulfonyl-phenoxy)-N-(1-methyl-1H-pyrazol-3-yl)benzamide or a pharmaceutically acceptable salt thereof;

(23) The compound 3-(3-fluoro-4-methanesulfonylphenoxy)-5-(2-hydroxy-1-methyl-ethoxy)-N-(1-methyl-1H-pyrazol-3-yl)benzamide or a pharmaceutically acceptable salt thereof;

(24) The compound 3-(6-ethanesulfonylpyridin-3-yloxy)-5-(2-hydroxy-1-methyl-ethoxy)-N-(1-methyl-1H-pyrazol-3-yl)benzamide or a pharmaceutically acceptable salt thereof;

(25) The compound 3-(6-ethanesulfonyl-pyridin-3-yloxy)-5-isopropoxy-N-(1-methyl-1H-pyrazol-3-yl)benzamide or a pharmaceutically acceptable salt thereof;

(26) The compound 5-(2-fluoro-1-fluoromethyl-ethoxy)-3-(6-methanesulfonyl-pyridin-3-yloxy)-N-(1-methyl-1H-pyrazol-3-yl)benzamide or a pharmaceutically acceptable salt thereof;

(27) The compound 3-(6-ethanesulfonyl-pyridin-3-yloxy)-5-(2-hydroxy-1-methyl-ethoxy)-N-(isoxazol-3-yl)benzamide or a pharmaceutically acceptable salt thereof;

(28) The compound 5-(2-fluoro-1-fluoromethyl-ethoxy)-3-(6-methanesulfonyl-pyridin-3-yloxy)-N-(pyrazol-3-yl)benzamide or a pharmaceutically acceptable salt thereof;

(29) Pharmaceutical compositions comprising the following (1) to (3), which are used to treat, prevent or delay onset of type II diabetes.

(1) A compound represented by formula (I), (2) 1, 2 or more compounds selected from the group consisting of the following (a) to (g):

(a) other glucokinase activators
(b) bisguanides
(c) PPAR agonists
(d) insulin
(e) somatostatin
(f) α-glucosidase inhibitors, and
(g) insulin secretagogues, (3) a pharmaceutically acceptable carrier.

(30) Glucokinase activators comprising compounds according to any one of (1) to (28) above as active ingredients;

(31) Drugs for treatment and/or prevention of diabetes which comprise compounds according to any one of (1) to (28) above; and

(32) Drugs for treatment and/or prevention of obesity which comprise compounds according to any one of (1) to (28) above.

The meanings of the terms used throughout the present specification will now be explained, and the compounds of the invention will then be explained in greater detail.

An "aryl" group is a C6-14 hydrocarbon aryl group, examples of which include phenyl, naphthyl, biphenyl and anthryl.

A "lower alkyl" group is preferably a C1-6 straight-chain or branched alkyl group, examples of which include methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl and 1-ethyl-2-methylpropyl.

A "lower alkenyl" group is a C1-6 straight-chain or branched lower alkenyl group, examples of which include vinyl, allyl, 1-butenyl, 2-butenyl and 1-pentenyl.

An "alkoxy" group is a group wherein the hydrogen of hydroxyl has been substituted with the aforementioned lower alkyl group, and examples thereof include methoxy, ethoxy, propoxy, isopropoxy, butoxy, sec-butoxy, tert-butoxy, pentyloxy, isopentyloxy, hexyloxy and isohexyloxy.

A "heteroaryl" group is a 5- to 7-membered monocyclic group having in the heteroaryl group 1 to 3 hetero atoms selected from the group consisting of oxygen, sulfur and nitrogen atoms, or a bicyclic heteroaryl group comprising such a monocyclic heteroaryl group fused with a benzene ring or pyridine ring, and examples thereof include furyl, thienyl, pyrrolyl, imidazolyl, triazolyl, thiazolyl, thiadiazolyl, isothiazolyl, oxazolyl, isoxazolyl, pyridyl, pyrimidinyl, pyridazinyl, pyrazolyl, pyrazinyl, quinolyl, isoquinolyl, quinazolinyl, quinolidinyl, quinoxalinyl, cinnolinyl, benzimidazolyl, imidazopyridyl, benzofuranyl, naphthylidinyl, 1,2-benzoisoxazolyl, benzooxazolyl, benzothiazolyl, oxazolopyridyl, pyridothiazolyl, isothiazolopyridyl and benzothienyl.

A "halogen atom" is, for example, fluorine, chlorine, bromine, iodine, or the like.

A "hydroxyalkyl" group is a group wherein one hydrogen of the aforementioned lower alkyl group is substituted with hydroxy, and examples thereof include hydroxymethyl, hydroxyethyl, 1-hydroxypropyl, 1-hydroxyethyl, 2-hydroxypropyl and 2-hydroxy-1-methyl-ethyl.

An "alkylcarbamoyl" group is a carbamoyl group monosubstituted with the aforementioned lower alkyl, and examples thereof include methylcarbamoyl, ethylcarbamoyl, propylcarbamoyl, isopropylcarbamoyl, butylcarbamoyl, sec-butylcarbamoyl and tert-butylcarbamoyl.

A "dialkylcarbamoyl" group is a carbamoyl group disubstituted with identical or different lower alkyl groups, and examples of "dialkylcarbamoyl" groups include dimethylcarbamoyl, diethylcarbamoyl, ethylmethylcarbamoyl, dipropylcarbamoyl, methylpropylcarbamoyl and diisopropylcarbamoyl.

An "alkylamino" group is an amino group monosubstituted with the aforementioned lower alkyl group, and examples thereof include methylamino, ethylamino, propylamino, isopropylamino, butylamino, sec-butylamino and tert-butylamino.

A "dialkylamino" group is an amino group disubstituted with identical or different lower alkyl groups, and examples thereof include dimethylamino, diethylamino, dipropylamino, methylpropylamino and diisopropylamino.

An "aminoalkyl" group is a group wherein one hydrogen of the aforementioned alkyl group is substituted with an amino group, and examples thereof include aminomethyl, aminoethyl and aminopropyl.

An "alkanoyl" group is a group wherein the aforementioned alkyl group is bonded with a carbonyl group, and examples thereof include methylcarbonyl, ethylcarbonyl, propylcarbonyl and isopropylcarbonyl.

An "alkanoylamino" group is a group wherein the aforementioned alkanoyl group is bonded with an amino group, and examples thereof include methylcarbonylamino, ethylcarbonylamino and isopropylcarbonylamino.

An "alkanoylaminoalkyl" group is a group wherein one hydrogen of the aforementioned alkyl group is substituted with the aforementioned alkanoylamino group, and examples thereof include acetylaminomethyl, ethylcarbonylaminomethyl, methylcarbonylaminoethyl and isopropylcarbonylaminomethyl.

An "alkylthio" group is a group wherein the aforementioned alkyl group is bonded with a sulfur atom, and examples thereof include methylthio, ethylthio, propylthio and isopropylthio.

An "alkylsulfonyl" group is a group wherein the aforementioned alkyl group is bonded with a sulfonyl group, and examples thereof include methylsulfonyl, ethylsulfonyl, propylsulfonyl and isopropylsulfonyl.

An "alkylsulfonylamino" group is a group wherein one hydrogen of an amino group is monosubstituted with the aforementioned alkylsulfonyl group, and examples thereof include methylsulfonylamino, ethylsulfonylamino, propylsulfonylamino and isopropylsulfonylamino.

An "alkoxycarbonyl" group is a group wherein the hydrogen of a carboxyl group is substituted with the aforementioned alkyl group, and examples thereof include methoxycarbonyl, ethoxycarbonyl, propylcarbonyl and isopropylcarbonyl.

An "alkoxycarbonylamino" group is a group wherein one hydrogen of an amino group is substituted with the aforementioned alkoxycarbonyl group, and examples thereof include methoxycarbonylamino, ethoxycarbonylamino, propylcarbonylamino and isopropylcarbonylamino.

An "alkoxycarbonylaminoalkyl" group is a group wherein one hydrogen of the aforementioned alkyl group is substituted with the aforementioned alkoxycarbonylamino group, and examples thereof include methoxycarbonylaminomethyl, ethoxycarbonylaminomethyl and isopropylcarbonylaminoethyl.

An "alkylsulfamoyl" group is a group wherein one hydrogen of the $NH_2$ of a sulfamoyl group is substituted with the aforementioned lower alkyl group, and examples thereof include methylsulfamoyl, ethylsulfamoyl and isopropylsulfamoyl.

A "dialkylsulfamoyl" group is a group wherein the two hydrogens of $NH_2$ of a sulfamoyl group are substituted with identical or different lower alkyl groups, and examples thereof include dimethylsulfamoyl, diethylsulfamoyl, ethylmethylsulfamoyl and diisopropylsulfamoyl.

For a more detailed disclosure of the compounds represented by formula (I) above of the present invention, each of the symbols used in formula (I) will be explained using specific examples.

Formula (II):

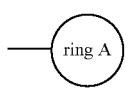

(II)

represents a 6- to 10-membered aryl group or 5- to 7-membered heteroaryl group optionally having on the ring 1 or 2 substituents represented by $R^1$ above.

As examples of "6- to 10-membered aryl" groups represented by Ring A there may be mentioned phenyl and naphthyl, among which phenyl is preferred.

As "5- to 7-membered heteroaryl" groups represented by Ring A there may be mentioned the "5- to 7-membered heteroaryl" groups for the "heteroaryl" groups defined above, and 5- to 6-membered heteroaryl groups are preferred.

As examples of "5- to 7-membered heteroaryl" groups represented by Ring A there are preferred furyl, thienyl, pyrrolyl, imidazolyl, triazolyl, pyrazolyl, thiazolyl, thiadiazolyl, isothiazolyl, oxazolyl, isoxazolyl, pyridyl, pyrimidinyl, pyridazinyl and pyrazinyl, among which triazolyl, thiazolyl, thiadiazolyl, pyridyl and pyrazinyl are more preferred, and triazolyl, thiadiazolyl and pyridyl are even more preferred.

Preferred as Ring A are thiadiazolyl, phenyl and pyridyl, with phenyl and pyridyl being more preferred.

Ring A optionally has on the ring 1 or 2 substituents represented by $R^1$. Here, $R^1$ represents a group selected from among alkylsulfonyl, alkanoyl, alkyl, hydroxyalkyl, hydroxy, alkylcarbamoyl, alkylsulfamoyl, dialkylsulfamoyl, alkylthio, alkoxy, dialkylcarbamoyl, alkoxycarbonylamino, halogen atoms, cyano, alkoxycarbonyl, alkanoylaminoalkyl, alkylsulfonylaminoalkyl, alkoxycarbonylaminoalkyl and trifluoromethyl, and when Ring A has two such substituents, the substituents may be the same or different.

As groups for $R^1$ there are preferred alkylsulfonyl, alkanoyl, hydroxyalkyl, alkylcarbamoyl, alkylsulfamoyl, dialkylsulfamoyl, dialkylcarbamoyl, alkoxycarbonylamino, halogen atoms, alkanoylaminoalkyl, alkylsulfonylaminoalkyl and alkoxycarbonylaminoalkyl, with alkylsulfonyl, alkanoyl, hydroxyalkyl, halogen atoms, alkanoylaminoalkyl, alkylsulfonylaminoalkyl and alkoxycarbonylaminoalkyl being more preferred, alkylsulfonyl, alkanoyl, halogen atoms and hydroxyalkyl being even more preferred, and alkylsulfonyl being especially preferred.

When Ring A has an $R^1$ group on the ring, the position at which $R^1$ is bonded on Ring A is not particularly restricted, and may be any bondable position.

When Ring A is phenyl, the bonding position of $R^1$ on the phenyl group is preferably the para position with respect to the bond between $X^1$ and the phenyl group.

$X^1$ represents O, S or NH, among which O or S is preferred, and O is more preferred.

Thus, as specific examples of —$X^1$-Ring A-$R^1$ when $X^1$ is O and Ring A is phenyl, there may be mentioned 4-(1-hydroxyethyl)-phenoxy, 4-(1-hydroxypropyl)-phenoxy, 4-methanesulfonylphenoxy, 4-methylcarbonyl-phenoxy, 4-methylcarbamoyl-phenoxy, 4-ethylcarbonyl-phenoxy, 4-dimethylcarbamoyl-phenoxy, 4-methylcarbonylaminomethyl-phenoxy, 4-methanesulfonylaminomethyl-phenoxy, 4-methoxycarbonylaminomethyl-phenoxy, 2-fluoro-phenoxy, 4-methoxycarbonyl-phenoxy, 4-hydroxymethyl-phenoxy, 4-methanesulfonyl-2-fluoro-phenoxy, 4-cyano-phenoxy, 4-methyl-phenyloxy, 4-trifluoromethyl-phenyloxy, 3-fluoro-4-methanesulfonylphenoxy, 4-dimethylsulfamoylphenoxy, 3-chloro-4-methanesulfonylphenoxy and 3-methanesulfonylphenoxy, among which 4-(1-hydroxyethyl)-phenoxy, 4-(1-hydroxypropyl)-phenoxy, 4-methanesulfonylphenoxy, 4-methylcarbonyl-phenoxy, 4-methylcarbamoyl-phenoxy, 4-ethylcarbonyl-phenoxy, 4-dimethylcarbamoyl-phenoxy, 4-methylcarbonylaminomethyl-phenoxy, 4-methanesulfonylaminomethyl-phenoxy, 4-methoxycarbonylaminomethyl-phenoxy, 4-hydroxymethyl-phenoxy, 4-methanesulfonyl-2-fluoro-phenoxy, 3-fluoro-4-methanesulfonylphenoxy, 4-dimethylsulfamoylphenoxy and 3-chloro-4-methanesulfonylphenoxy are preferred, 4-(1-hydroxyethyl)-phenoxy, 4-(1-hydroxypropyl)-phenoxy, 4-methanesulfonylphenoxy, 4-methylcarbonyl-phenoxy, 4-ethylcarbonyl-phenoxy, 4-methylcarbonylaminomethyl-phenoxy, 4-methanesulfonylaminomethylphenoxy, 4-methoxycarbonylaminomethyl-phenoxy, 4-hydroxymethyl-phenoxy, 3-fluoro-4-methanesulfonylphenoxy, 4-dimethylsulfamoylphenoxy and 3-chloro-4-methanesulfonylphenoxy are more preferred, 4-(1-hydroxyethyl)-phenoxy, 4-(1-hydroxypropyl)-phenoxy, 4-methanesulfonylphenoxy, 4-methylcarbonyl-phenoxy, 4-ethylcarbonyl-phenoxy, 4-hydroxymethyl-phenoxy and 3-fluoro-4-methanesulfonylphenoxy are even more preferred, and 4-methanesulfonylphenoxy is especially preferred.

As specific examples of —$X^1$-Ring A-$R^1$— when $X^1$ is S and Ring A is phenyl, there may be mentioned 4-fluorophenylsulfanyl, 4-methyl-phenylsulfanyl, 4-trifluoromethylphenylsulfanyl, 4-(1-hydroxyethyl)-phenylsulfanyl, 4-methanesulfonylphenylsulfanyl, 4-methylcarbonyl-phenylsulfanyl, 4-ethylcarbonyl-phenylsulfanyl, 4-methylcarbamoyl-phenylsulfanyl, 4-dimethylcarbamoyl-phenylsulfanyl, 4-methylcarbonylaminomethyl-phenylsulfanyl, 4-methylsulfonylaminomethyl-phenylsulfanyl, 4-methoxycarbonyl-phenylsulfanyl, 4-methoxycarbonyl-aminomethyl-phenylsulfanyl, 4-hydroxymethyl-phenylsulfanyl and 4-cyano-phenylsulfanyl, among which 4-fluoro-phenylsulfanyl, 4-(1-hydroxyethyl)-phenylsulfanyl, 4-methanesulfonylphenylsulfanyl, 4-methylcarbonyl-phenylsulfanyl, 4-ethylcarbonyl-phenylsulfanyl, 4-methylcarbamoyl-phenylsulfanyl, 4-dimethylcarbamoyl-phenylsulfanyl, 4-methylcarbonylaminomethyl-phenylsulfanyl, 4-methylsulfonylaminomethyl-phenylsulfanyl, 4-methoxycarbonyl-aminomethyl-phenylsulfanyl and 4-hydroxymethyl-phenylsulfanyl are preferred, 4-(1-hydroxyethyl)-phenylsulfanyl, 4-methanesulfonylphenylsulfanyl, 4-methylcarbonyl-phenylsulfanyl, 4-ethylcarbonyl-phenylsulfanyl, 4-methylcarbonylaminomethyl-phenylsulfanyl, 4-methylsulfonylaminomethyl-phenylsulfanyl, 4-methoxycarbonyl-aminomethyl-phenylsulfanyl and 4-hydroxymethyl-phenylsulfanyl are more preferred, 4-(1-hydroxyethyl)-phenylsulfanyl, 4-methanesulfonylphenylsulfanyl, 4-methylcarbonyl-phenylsulfanyl, 4-ethylcarbonyl-phenylsulfanyl and 4-hydroxymethyl-phenylsulfanyl are even more preferred, and 4-methanesulfonylphenylsulfanyl is especially preferred.

As specific examples of —$X^1$-Ring A-$R^1$— when $X^1$ is S and Ring A is a 5- to 7-membered heteroaryl group, there may be mentioned 5-cyano-pyridin-2-ylsulfanyl, 5-bromo-pyridin-2-ylsulfanyl, 5-methoxycarbonyl-pyridin-2-ylsulfanyl, 5-hydroxymethyl-pyridin-2-ylsulfanyl, 5-methanesulfonylpyridin-2-ylsulfanyl, 5-methyl-pyridin-2-ylsulfanyl, 5-trifluoromethyl-pyridin-2-ylsulfanyl, pyridine-2-ylsulfanyl, pyridin-4-ylsulfanyl, 6-methyl-pyridin-3-ylsulfanyl, [1,3,4]thiadiazol-2-ylsulfanyl, 5-methylthio-[1,3,4]thiadiazol-2-ylsulfanyl, 5-methanesulfonyl[1,3,4]thiadiazol-2-ylsulfanyl, [1,2,4]-triazol-3-ylsulfanyl, furan-3-ylsulfanyl, thiophen-3-ylsulfanyl, pyrrol-3-ylsulfanyl, imidazol-2-ylsulfanyl, thiazol-2-ylsulfanyl, oxazol-2-ylsulfanyl, isoxazol-3-ylsulfanyl, pyrazin-2-ylsulfanyl, pyrimidin-2-ylsulfanyl, pyridazin-3-ylsulfanyl and 3H-pyrazol-3-ylsulfanyl, among which 5-bromo-pyridin-2-ylsulfanyl, 5-hydroxymethyl-pyridin-2-ylsulfanyl, 5-methanesulfonylpyridin-2-ylsulfanyl, pyridine-2-ylsulfanyl, pyridin-4-ylsulfanyl, [1,3,4]thiadiazol-2-ylsulfanyl, 5-methanesulfonyl[1,3,4]thiadiazol-2-ylsulfanyl, [1,2,4]-triazol-3-ylsulfanyl, furan-3-ylsulfanyl, thiophen-3-ylsulfanyl, pyrrol-3-ylsulfanyl, imidazol-2-ylsulfanyl, thiazol-2-ylsulfanyl, oxazol-2-ylsulfanyl, isoxazol-3-ylsulfanyl, pyrazin-2-ylsulfanyl, pyrimidin-2-ylsulfanyl, pyridazin-3-ylsulfanyl and 3H-pyrazol-3-ylsulfanyl are preferred, 5-hydroxymethyl-pyridin-2-ylsulfanyl, 5-methanesulfonylpyridin-2-ylsulfanyl, pyridine-2-ylsulfanyl, pyridin-4-ylsulfanyl, [1,3,4]thiadiazol-2-ylsulfanyl, 5-methanesulfonyl[1,3,4]thiadiazol-2-ylsulfanyl, [1,2,4]-triazol-3-ylsulfanyl, thiazol-2-ylsulfanyl and pyrazin-2-ylsulfanyl are more preferred, 5-hydroxymethyl-pyridin-2-ylsulfanyl, 5-methanesulfonylpyridin-2-ylsulfanyl, pyridine-2-ylsulfanyl, pyridin-4-ylsulfanyl, [1,3,4]thiadiazol-2-ylsulfanyl, 5-methanesulfonyl[1,3,4]thiadiazol-2-ylsulfanyl, [1,2,4]-triazol-3-ylsulfanyl and thiazol-2-ylsulfanyl are even more preferred, and pyridine-2-ylsulfanyl, pyridin-4-ylsulfanyl, [1,3,4]thiadiazol-2-ylsulfanyl, [1,2,4]-triazol-3-ylsulfanyl and thiazol-2-ylsulfanyl are especially preferred.

As specific examples of —$X^1$-Ring A-$R^1$ when $X^1$ is O and Ring A is a 5- to 7-membered heteroaryl group, there may be mentioned pyrimidin-4-yloxy, pyridazin-3-yloxy, pyrazin-2-yloxy, pyridin-2-yloxy, 2-hydroxy-pyridin-3-yloxy, 2-hydroxy-pyridin-4-yloxy, 5-hydroxymethyl-pyridin-2-yloxy, 5-methylcarbonyl-pyridin-2-yloxy, 5-(1-hydroxyethyl)-pyridin-2-yloxy, 5-methoxycarbonylaminomethyl-pyridin-2-yloxy, 5-methanesulfonylpyridin-2-yloxy, 5-methoxycarbonyl-pyridin-2-yloxy, 5-cyano-pyridin-2-yloxy, 5-bromo-pyridine-2-yloxy, 5-dimethylcarbamoyl-pyridin-2-yloxy, 5-methoxycarbonyl-pyridin-2-yloxy, 5-methylcarbonylaminomethyl-pyridin-2-yloxy, 5-trifluoromethyl-pyridin-2-yloxy, 5-methylcarbonyl-imidazol-2-yloxy, 6-hydroxymethyl-pyrimidin-2-yloxy, 6-methylcarbonyl-pyrimidin-2-yloxy, 6-methanesulfonylpyrimidin-2-yloxy, 6-hydroxymethyl-pyridazin-3-yloxy, 6-methylcarbonyl-pyridazin-3-yloxy, 6-methanesulfonylpyridazin-3-yloxy, 5-hydroxymethyl-pyrazin-2-yloxy, 5-methylcarbonyl-pyrazin-2-yloxy, 5-methanesulfonylpyrazin-2-yloxy, 6-ethanesulfonylpyridin-3-yloxy, 6-methanesulfonylpyridin-3-yloxy, pyridin-3-yloxy, pyridin-4-yloxy and 6-isopropylsulfonylpyridin-3-yloxy, among which pyrimidin-4-yloxy, pyridazin-3-yloxy, pyrazin-2-yloxy, pyridin-2-yloxy, 2-hydroxy-pyridin-3-yloxy, 2-hydroxy-pyridin-4-yloxy, 5-hydroxymethyl-pyridin-2-yloxy, 5-methylcarbonyl-pyridin-2-yloxy, 5-(1-hydroxyethyl)-pyridin-2-yloxy, 5-methoxycarbonylaminomethyl-pyridin-2-yloxy, 5-methanesulfonylpyridin-2-yloxy, 5-bromo-pyridine-2-yloxy, 5-dimethylcarbamoyl-pyridin-2-yloxy, 5-methylcarbonylaminomethyl-pyridin-2-yloxy, 5-methylcarbonyl-imidazol-2-yloxy, 6-hydroxymethyl-pyrimidin-2-yloxy, 6-methylcarbonyl-pyrimidin-2-yloxy, 6-methanesulfonylpyrimidin-2-yloxy, 6-hydroxymethyl-pyridazin-3-yloxy, 6-methylcarbonyl-pyridazin-3-yloxy, 6-methanesulfonylpyridazin-3-yloxy, 5-hydroxymethyl-pyrazin-2-yloxy, 5-methylcarbonyl-pyrazin-2-yloxy, 5-methanesulfonylpyrazin-2-yloxy, 6-ethanesulfonylpyridin-3-yloxy, 6-methanesulfonylpyridin-3-yloxy, pyridin-3-yloxy and pyridin-4-yloxy are preferred, pyrazin-2-yloxy, pyridin-2-yloxy, 2-hydroxy-pyridin-3-yloxy, 2-hydroxy-pyridin-4-yloxy, 5-hydroxymethyl-pyridin-2-yloxy, 5-methylcarbonyl-pyridin-2-yloxy, 5-(1-hydroxyethyl)-pyridin-2-yloxy, 5-methoxycarbonylaminomethyl-pyridin-2-yloxy, 5-methanesulfonylpyridin-2-yloxy, 5-methylcarbonylaminomethyl-pyridin-2-yloxy, 5-hydroxymethyl-pyrazin-2-yloxy, 5-methylcarbonyl-pyrazin-2-yloxy, 5-methanesulfonylpyrazin-2-yloxy, 6-ethanesulfonylpyridin-3-yloxy and 6-methanesulfonylpyridin-3-yloxy are more preferred, and 2-hydroxy-pyridin-3-yloxy, 2-hydroxy-pyridin-4-yloxy, 5-hydroxymethyl-pyridin-2-yloxy, 5-methylcarbonyl-pyridin-2-yloxy, 5-(1-hydroxyethyl)-pyridin-2-yloxy or 5-methanesulfonylpyridin-2-yloxy, 6-methanesulfonylpyridin-3-yloxy and 6-ethanesulfonylpyridin-3-yloxy are especially preferred.

$X^2$ represents O, S or $CH_2$, among which O and $CH_2$ are preferred, and O is more preferred.

$R^2$ represents a C3-7 cyclic alkyl group, a straight-chain or branched lower alkyl group or a lower alkenyl group, optionally having 1 or 2 substituents selected from the group consisting of halogen atoms, carboxyl, alkoxycarbonyl, hydroxy, amino (where the amino may be further substituted with 1 or 2 alkanoyl or lower alkyl groups), alkoxy and N-alkylcarbamoyl.

As "halogen atoms" represented by $R^2$ there may be mentioned the same ones referred to above. Chlorine and fluorine are preferred.

An "alkoxycarbonyl" group represented by $R^2$ is a carbonyl group having an alkoxy group as defined above, and as examples there may be mentioned methoxycarbonyl, ethoxycarbonyl, propyloxycarbonyl, isopropyloxycarbonyl and tert-butyloxycarbonyl.

As examples of the "C3-7 cyclic alkyl group" represented by $R^2$ there may be mentioned cyclopropyl, cyclobutyl, cyclopentyl, cyclohexyl and cycloheptyl, among which cyclopentyl or cyclohexyl are preferred, and cyclopentyl is more preferred.

When $R^2$ is a C3-7 cyclic alkyl group, any one of the carbon atoms forming the ring, other than the carbon atom bonding with $X^2$, may be replaced with oxygen, NH, N-alkanoyl or CONH.

As groups wherein "a carbon atom forming the C3-7 cyclic alkyl group (other than the carbon atom bonding with $X^2$) is replaced with oxygen, NH, N-alkanoyl or CONH", there are preferred groups wherein the carbon atom is replaced with oxygen, NH or N-alkanoyl, and more preferably groups wherein it is replaced with oxygen or N-alkanoyl. More specifically, $R^2$ is preferably, for example, tetrahydrofuranyl, tetrahydropyranyl, pyrrolidinyl, piperidinyl or N-acetylpiperidinyl, and even more preferably tetrahydrofuranyl, tetrahydropyranyl or N-acetylpiperidinyl.

A "straight-chain or branched lower alkyl group" represented by $R^2$ is a lower alkyl having the same meaning as defined above. As lower alkyl groups there are preferred ethyl, propyl, isopropyl, butyl, isobutyl and sec-butyl, with propyl, isopropyl, isobutyl and sec-butyl being more preferred.

As a "lower alkenyl group" represented by $R^2$ there may be mentioned the same ones as defined above, among which propenyl, isopropenyl and isobutenyl are preferred, and isopropenyl is more preferred.

$R^2$ is preferably a C3-7 cyclic alkyl group, a straight-chain or branched lower alkyl group, or a group wherein a carbon atom forming the C3-7 cyclic alkyl group (other than the carbon atom bonding with $X^2$) is replaced with oxygen, NH, N-alkanoyl or CONH, and it is more preferably a straight-chain or branched lower alkyl group or a group wherein a carbon atom forming the C3-7 cyclic alkyl group (other than the carbon atom bonding with $X^2$) is replaced with oxygen, NH, N-alkanoyl or CONH.

Therefore, as examples of —$X^2$—$R^2$ there may be mentioned propyl, isobutyl, sec-butyl, 3-methoxy-2-methyl-propyl, 2-methoxymethyl-butyl, 4-hydroxy-2-methyl-butyl, 2-hydroxymethyl-butyl, 3-hydroxy-butyl, 3-methoxybutyl, 3-hydroxy-2-methyl-propyl, 3-hydroxy-butyl, 3-methylcarbamoyl-propyl, 3-acetylamino-2-methyl-propyl, 2-hydroxymethyl-3-propenyl, 2-methyl-2-propenyl, ethoxy, isopropoxy, 2-methoxy-1-methyl-ethoxy, 1-methoxymethyl-propoxy, 3-hydroxy-1-methyl-propoxy, 1-hydroxymethyl-propoxy, 2-amino-1-ethoxy, 2-hydroxy-propoxy, 2-methoxypropoxy, 2-hydroxy-1-methyl-ethoxy, 2-hydroxy-ethoxy, 2-dimethylamino-1-methyl-ethoxy, 1-carboxy-ethoxy, 2-methylcarbamoyl-ethoxy, 2-acetylamino-1-methyl-ethoxy, cyclopentyloxy, cyclohexyloxy, cycloheptyloxy, 2-hydroxy-cyclopentyloxy, tetrahydrofuran-3-yloxy, tetrahydrofuran-2-yloxy, tetrahydrofuran-4-yloxy, piperidin-4-yloxy, piperidin-3-yloxy, pyrrolidin-3-yloxy, pyrrolidin-2-yloxy, 1-acetyl-piperidin-4-yloxy, 1-acetyl-piperidin-3-yloxy, 3-allyloxy, 3-isopropenyloxy, 1-methyl-allyloxy, 2-fluoro-1-fluoromethyl-ethoxy, 2-fluoro-1-methyl-ethoxy and 2-chloro-1-methyl-ethoxy, among which ethoxy, isopropoxy, 2-methoxy-1-methyl-ethoxy, 1-methoxymethyl-propoxy, 3-hydroxy-1-methyl-propoxy, 1-hydroxymethyl-propoxy, 2-hydroxy-propoxy, 2-methoxypropoxy, 2-hydroxy-1-methyl-ethoxy, 2-hydroxy-ethoxy, 2-methylcarbamoyl-ethoxy, 2-acetylamino-1-methyl-ethoxy, cyclopentyloxy, cyclohexyloxy, 2-hydroxy-cyclopentyloxy, tetrahydrofuran-3-yloxy, tetrahydrofuran-2-yloxy, tetrahydropyran-3-yloxy, tetrahydrofuran-4-yloxy, piperidin-4-yloxy, piperidin-3-yloxy, pyrrolidin-3-yloxy, pyrrolidin-2-yloxy, 1-acetyl-piperidin-4-yloxy, 1-acetyl-piperidin-3-yloxy, 3-isopropenyloxy, 1-methyl-allyloxy, butyl, isobutyl, s-butyl, 3-methoxy-2-methyl-propyl, 2-methoxymethyl-butyl, 4-hydroxy-2-methyl-butyl, 2-hydroxymethyl-butyl, 3-hydroxy-butyl, 3-methoxybutyl, 3-hydroxy-2-methyl-propyl, 3-hydroxy-butyl, 3-methylcarbamoyl-propyl, 3-acetylamino-2-methyl-propyl, 2-hydroxymethyl-3-propenyl, 2-methyl-2-propenyl, 2-fluoro-1-fluoromethyl-ethoxy, 2-fluoro-1-methyl-ethoxy and 2-chloro-1-methyl-ethoxy are preferred, 2-methoxy-1-methyl-ethoxy, 1-methoxymethyl-propoxy, 3-hydroxy-1-methyl-propoxy, 1-hydroxymethyl-propoxy, 2-hydroxy-propoxy, 2-methoxypropoxy, 2-hydroxy-1-methyl-ethoxy, 2-hydroxy-ethoxy, 2-methylcarbamoyl-ethoxy, 2-acetylamino-1-methyl-ethoxy, cyclopentyloxy, cyclohexyloxy, 2-hydroxy-cyclopentyloxy, tetrahydrofuran-3-yloxy, tetrahydropyran-3-yloxy, 1-acetyl-piperidin-4-yloxy, 1-acetyl-piperidin-3-yloxy, 3-isopropenyloxy, 3-methoxy-2-methyl-propyl, 2-methoxymethyl-butyl, 4-hydroxy-2-methyl-butyl, 2-hydroxymethyl-butyl, 3-hydroxy-butyl, 3-methoxybutyl, 3-hydroxy-2-methyl-propyl, 3-hydroxy-butyl, 3-methylcarbamoyl-propyl, 3-acetylamino-2-methyl-propyl, 2-hydroxymethyl-3-propenyl, 2-methyl-2-propenyl, 2-fluoro-1-fluoromethyl-ethoxy and 2-fluoro-1-methyl-ethoxy are more preferred, and 2-methoxy-1-methyl-ethoxy, 1-methoxymethyl-propoxy, 3-hydroxy-1-methyl-propoxy, 1-hydroxymethyl-propoxy, 2-hydroxy-1-methyl-ethoxy, 2-acetylamino-1-methyl-ethoxy, 2-hydroxy-cyclopentyloxy, tetrahydrofuran-3-yloxy, 1-acetyl-piperidin-4-yloxy, 3-methoxy-2-methyl-propyl, 2-methoxymethyl-butyl, 4-hydroxy-2-methyl-butyl, 2-hydroxymethyl-butyl, 3-hydroxy-2-methyl-propyl, 3-acetylamino-2-methyl-propyl, 2-hydroxymethyl-3-propenyl and 2-fluoro-1-fluoromethyl-ethoxy are especially preferred.

Ring B is a group represented by the aforementioned formula (III):

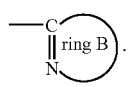

(III)

which is a monocyclic or bicyclic heteroaryl group wherein the carbon atom of Ring B which is bonded to the nitrogen atom of the amide group of formula (I) forms a C=N bond with the nitrogen atom of the ring.

Here, a "heteroaryl" group represented by Ring B is a "heteroaryl" group represented by formula (III) and as defined above, wherein the carbon atom of Ring B which is bonded to the amide group in formula (I) forms a C=N bond with the nitrogen atom. The double bond of C=N in Ring B is only a formal representation, and it is sufficient if Ring B is a heteroaryl group.

Preferred examples of Ring B are those wherein the heteroaryl group does not include a 5-alkoxycarbonyl-pyridin-2-yl or 5-carboxyl-pyridin-2-yl group, and more preferred are monocyclic or bicyclic heteroaryl groups having at least one hetero atom in Ring B selected from the group consisting of nitrogen, sulfur and oxygen atoms, in addition to the nitrogen atom forming the C=N group together with the carbon atom in the ring which is bonded to the nitrogen atom of the amide group in formula (I) above.

Ring B is a monocyclic or bicyclic heteroaryl group having at least one hetero atom in Ring B selected from the group consisting of nitrogen, sulfur and oxygen atoms, in addition to the nitrogen atom forming the C=N group together with the carbon atom in Ring B which is bonded to the nitrogen atom of the amide group in formula (I) above, and when Ring B is a thiazole group, the substituent at the 5-position of the thiazole group is most preferably not isopropyl.

When Ring B is a monocycle, the number of atoms forming the monocycle is preferably 5 or 6, and more preferably 5. When Ring B is a bicycle, it is preferably a 9- to 10-membered bicycle which is a 5- or 6-membered monocycle fused with a benzene ring or pyridine ring, and it is more preferably a 9-membered bicycle which is a 5-membered monocycle fused with a pyridine ring.

As specific examples for Ring B there may be mentioned thiazolyl, imidazolyl, isothiazolyl, thiadiazolyl, triazolyl, oxazolyl, isoxazolyl, pyrazinyl, pyridyl, pyridazinyl, pyrazolyl, pyrimidinyl, pyridothiazolyl and benzothiazolyl, among which thiazolyl, thiadiazolyl, isoxazolyl, pyrazinyl, pyridyl, pyridothiazolyl and pyrazolyl are preferred, and thiazolyl, thiadiazolyl, isoxazolyl, pyridothiazolyl or pyrazolyl are more preferred.

Ring B may have 1 or 2 substituents represented by $R^3$. Here, $R^3$ represents a group selected from among lower alkyl, alkoxy, alkylamino, lower dialkylamino, halogen atoms, trifluoromethyl, hydroxyalkyl (wherein the hydrogen of the hydroxy in the hydroxyalkyl group may be substituted with lower alkyl), aminoalkyl, alkanoyl, carboxyl, alkoxycarbonyl and cyano.

When Ring B has two $R^3$ substituents in the ring, they may be identical or different.

The bonding position of $R^3$ on Ring B may be any bondable position on Ring B, with no particular restrictions, regardless of whether Ring B is a 5- to 7-membered monocyclic heteroaryl group or a 9- to 11-membered bicyclic heteroaryl group.

Among these, $R^3$ is preferably lower alkyl, alkoxy, a halogen, hydroxyalkyl (where the hydrogen of the hydroxy in the hydroxyalkyl group may be substituted with lower alkyl), aminoalkyl or alkanoyl, and it is more preferably lower alkyl, hydroxyalkyl (where the hydrogen of the hydroxy in the hydroxyalkyl group may be substituted with lower alkyl) or alkanoyl.

As specific examples for $R^3$ there may be mentioned methyl, ethyl, propyl, isopropyl, butyl, methoxy, ethoxy, propoxy, isopropoxy, butoxy, chlorine, fluorine, bromine, hydroxymethyl, hydroxyethyl, methoxymethyl, ethoxyethyl, methoxyethyl, methoxycarbonyl, ethoxycarbonyl, propoxycarbonyl, aminomethyl, aminoethyl, aminopropyl, methylcarbonyl, ethylcarbonyl and propylcarbonyl, among which methyl, ethyl, chlorine, fluorine, hydroxymethyl, hydroxyethyl, methoxymethyl, methoxyethyl, methoxycarbonyl, ethoxycarbonyl, aminomethyl, aminoethyl, methylcarbonyl and ethylcarbonyl are preferred, and methyl, hydroxymethyl, methoxymethyl and methylcarbonyl are more preferred.

Therefore, as specific examples of groups represented by the following formula (VII):

[wherein the symbols have the same definitions specified above] there are preferred thiazol-2-yl, 4-methyl-thiazol-2-yl, 4-hydroxymethyl-thiazol-2-yl, 4-methoxycarbonyl-thiazol-2-yl, 4-methoxymethyl-thiazol-2-yl, 4-aminomethyl-thiazol-2-yl, 4-cyano-thiazol-2-yl, 4-cyano-thiazol-2-yl, 4-fluoro-thiazol-2-yl, imidazol-2-yl, 4-methyl-imidazol-2-yl, 4-methoxycarbonyl-imidazol-2-yl, isothiazol-3-yl, 4-hydroxymethyl-isothiazol-3-yl, [1,3,4]thiadiazol-2-yl, 5-acetyl-[1,3,4]thiadiazol-2-yl, [1,2,4]triazol-2-yl, 5-hydroxymethyl-[1,2,4]triazol-3-yl, pyrazin-2-yl, pyridin-2-yl, 4-methyl-pyridin-2-yl, 4-methoxymethyl-imidazol-2-yl, 4-acetyl-imidazol-2-yl, 5-hydroxymethyl-imidazol-2-yl, 5-methyl-[1,3,4]thiadiazol-2-yl, 5-fluoro-[1,3,4]thiadiazol-2-yl, 5-methyl-[1,2,4]triazol-2-yl, 5-acetyl-[1,2,4]triazol-3-yl, isoxazol-3-yl, 4-methoxymethyl-isoxazol-2-yl, 5-methyl-isoxazol-3-yl, 5-hydroxymethyl-isoxazol-3-yl, 5-methoxymethyl-isoxazol-3-yl, 5-methylcarbonyl-isoxazol-3-yl, 5-chloro-isoxazol-3-yl, 5-aminomethyl-isoxazol-3-yl, pyrazol-3-yl, 4-methyl-1H-pyrazol-3-yl, 6-methyl-pyridazin-3-yl, thiazol-4-yl, 2-methyl-thiazol-4-yl, isoxazol-3-yl, thiazolo[5,4-b]pyridin-2-yl, 3-methyl-[1,2,4]thiadiazolyl-5-yl and 1-methyl-1H-pyrazol-3-yl.

Thus, as more specific examples of compounds represented by formula (I) according to the present invention:

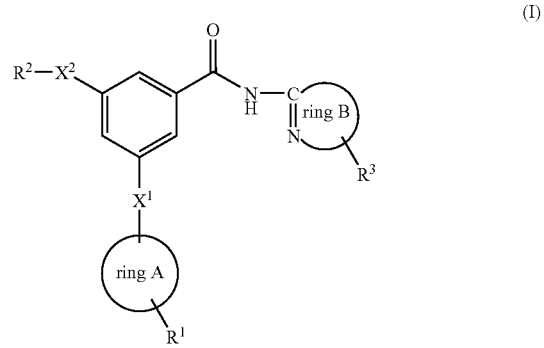

[wherein the symbols have the same definitions specified above] there may be mentioned 5-isopropoxy-3-(4-methanesulfonylphenoxy)-N-(4-methylthiazol-2-yl)-benzamide, 5-(2-hydroxy-1-methyl-ethoxy)-3-(4-methanesulfonylphenoxy)-N-thiazol-2-yl-benzamide, 5-ethoxy-3-(4-methanesulfonylphenoxy)-N-(4-methoxymethyl-thiazol-2-yl)benzamide, 5-cyclopentyloxy-3-(4-methanesulfonylphenoxy)-N-thiazol-2-yl-benzamide, 3-(4-methanesulfonylphenoxy)-5-(tetrahydrofuran-3-yloxy)-N-thiazol-2-yl-benzamide, 3-(4-methanesulfonylphenoxy)-5-(2-methoxy-1-methyl-ethoxy)-N-thiazol-2-yl-benzamide, 3-(4-methanesulfonylphenoxy)-5-(2-methoxy-1-methoxymethyl-ethoxy)-N-thiazol-2-yl-benzamide, 3-(2-fluoro-4-methanesulfonylphenoxy)-5-isopropoxy-N-thiazol-2-yl-benzamide, 3-(4- methanesulfonylphenoxy)-5-(1-methoxymethyl-propoxy)-N-(4-methyl-thiazol-2-yl)-benzamide, 5-isopropoxy-3-(4-methanesulfonylphenoxy)-N-pyrazol-3-yl-benzamide, 5-isopropoxy-3-(4-methanesulfonylphenoxy)-N-pyrazin-2-yl-benzamide, 3-(4-methanesulfonylphenoxy)-5-(3-methoxy-1-methyl-propoxy)-N-thiazol-2-yl-benzamide, 5-(3-hydroxy-1-methyl-propoxy)-3-(4-methanesulfonylphenoxy)-N-thiazol-2-yl-benzamide, 5-isopropoxy-3-(4-methanesulfonylphenoxy)-N-pyrimidin-4-yl-benzamide, 5-isopropoxy-3-(4-methanesulfonylphenoxy)-N-(pyrimidin-2-yl)-benzamide, N-(4-hydroxymethyl-thiazol-2-yl)-5-isopropoxy-3-(4-methanesulfonylphenoxy)-benzamide, N-(isooxazol-3-yl)-3-(4-methanesulfonylphenoxy)-5-(1-methoxymethyl-propoxy)-benzamide, 3-(4-methanesulfonylphenoxy)-5-(1-methoxymethyl-propoxy)-N-[1,3,4]thiadiazol-2-yl-benzamide, 5-(1-hydroxymethyl-propoxy)-3-(4-methanesulfonylphenoxy)-N-(4-methyl-thiazol-2-yl)-benzamide, N-(4-hydroxymethyl-thiazol-2-yl)-3-(4-methanesulfonylphenoxy)-5-(1-methoxymethyl-propoxy)-benzamide, 5-(2-amino-1-methyl-ethoxy)-3-(4-methanesulfonylphenoxy)-N-thiazol-2-yl-benzamide, 5-(2-dimethylamino-1-methyl-ethoxy)-3-(4-methanesulfonylphenoxy)-N-thiazol-2-yl-benzamide, 5-(2-hydroxy-propoxy)-3-(4-methanesulfonylphenoxy)-N-(4-methyl-thiazol-2-yl)-benzamide, 3-(4-methanesulfonylphenoxy)-5-(2-methoxy-propoxy)-N-(4-methyl-thiazol-2-yl)-benzamide, 5-isopropoxy-3-(4-methanesulfonylphenoxy)-N-(thiazolo[5,4-b]pyridin-2-yl)-benzamide, 5-(2-hydroxymethyl-allyl)-3-(4-methanesulfonylphenoxy)-N-thiazol-2-yl-benzamide, 5-(2-hydroxy-1-methyl-ethoxy)-3-(4-methanesulfonylphenoxy)-N-thiazolo[5,4-b]pyridin-2-yl-benzamide, 5-(3-hydroxy-2-methyl-propyl)-3-(4-methanesulfonylphenoxy)-N-thiazol-2-yl-benzamide, 3-(4-methanesulfonylphenoxy)-N-(4-methyl-thiazol-2-yl)-5-(piperidin-4-yl-oxy)-benzamide hydrochloride, 5-(1-acetyl-piperidin-4-yloxy)-3-(4-methanesulfonylphenoxy)-N-(4-methyl-thiazol-2-yl)-benzamide, 2-[3-(4-methanesulfonylphenoxy)-5-(4-methyl-thiazol-2-yl-carbamoyl)-phenoxy]propionic acid, 5-(3-hydroxy-1-methyl-propoxy)-3-(4-methanesulfonylphenoxy)-N-thiazol-2-yl-benzamide, 3-(4-methanesulfonylphenoxy)-5-(1-methylcarbamoyl-ethoxy)-N-(4-methyl-thiazol-2-yl)-benzamide, 5-(2-acetylamino-1-methyl-ethoxy)-3-(4-methanesulfonylphenoxy)-N-thiazol-2-yl-benzamide, N-[4-(1-hydroxy-ethyl)-thiazol-2-yl]-5-isopropoxy-3-(4-methanesulfonylphenoxy)-benzamide, 5-(2-hydroxy-1-methyl-ethoxy)-3-(4-methanesulfonylphenoxy)-N-pyridin-2-yl-benzamide, 5-(2-hydroxy-ethoxy)-3-(4-methanesulfonylphenoxy)-N-thiazol-2-yl-benzamide, 5-(2-hydroxy-cyclopentyloxy)-3-(4-methanesulfonylphenoxy)-N-thiazol-2-yl-benzamide, N-(4-acetyl-thiazol-2-yl)-5-(2-hydroxy-1-methyl-ethoxy)-3-(4-methanesulfonylphenoxy)-benzamide, 5-(2-hydroxy-1-methyl-ethoxy)-N-(4-hydroxymethyl-thiazol-2-yl)-3-(4-methanesulfonylphenoxy)-benzamide, N-[4-(1-hydroxy-ethyl)-thiazol-2-yl]-5-(2-hydroxy-1-methyl-ethoxy)-3-(4-methanesulfonylphenoxy)-benzamide, 3-(3-fluoro-4-methanesulfonylphenoxy)-5-(2-hydroxy-1-methyl-ethoxy)-N-thiazol-2-yl-benzamide, 5-(2-hydroxy-1-methyl-ethoxy)-3-(4-methanesulfonylphenoxy)-N-(5-methyl-thiazol-2-yl)benzamide, 5-(2-hydroxy-1-methyl-ethoxy)-3-(4-methanesulfonylphenoxy)-N-([1,2,4]thiadiazol-5-yl)-benzamide, N-(4-hydroxymethyl-thiazol-2-yl)-3-(4-methanesulfonylphenoxy)-5-(2-methoxy-1-methyl-ethoxy)-benzamide, 5-(2-hydroxy-1-methyl-ethoxy)-3-(4-methanesulfonylphenoxy)-N-(5-methoxycarbonyl-pyridin-2-yl)-benzamide, 6-[5-isopropoxy-3-(4-methanesulfonylphenoxy)-benzoylamino]nicotinic acid, 5-(2-hydroxy-1-methyl-propoxy)-3-(4-methanesulfonylphenoxy)-N-thiazol-2-yl-benzamide, 5-(2-hydroxy-1-methyl-ethoxy)-N-(isoxazol-3-yl)-3-(4-methanesulfonylphenoxy)-benzamide, N-(5-hydroxymethyl-thiazol-2-yl)-5-isopropoxy-3-(4-methanesulfonylphenoxy)-benzamide, N-[4-(1-hydroxy-ethyl)-thiazol-2-yl]-3-(4-methanesulfonylphenoxy)-5-(2-methoxy-1-methyl-ethoxy)-benzamide, N-(4-hydroxymethyl-thiazol-2-yl)-3-(4-methanesulfonylphenoxy)-5-(tetrahydrofuran-3-yl-oxy)-benzamide, 5-(2-hydroxy-1-methyl-ethoxy)-3-(4-methanesulfonylphenoxy)-N-(2-methylthiazol-4-yl)-benzamide, 5-(2-hydroxy-1-methyl-ethoxy)-3-(4-methanesulfonylphenoxy)-N-(4-methoxymethyl-thiazol-2-yl)-benzamide, N-[4-(1-hydroxy-ethyl)-thiazol-2-yl]-3-(4-methanesulfonylphenoxy)-5-(2-methoxy-1-methyl-ethoxy)-benzamide, N-[4-(1-hydroxy-ethyl)-thiazol-2-yl]-3-(4-methanesulfonylphenoxy)-5-(tetrahydrofuran-3-yl-oxy)-benzamide, N-[4-(1-hydroxy-ethyl)-thiazol-2-yl]-3-(4-methanesulfonylphenoxy)-5-(tetrahydrofuran-3-yl-oxy)-benzamide, N-(2,5-dimethylthiazol-4-yl)-5-(2-hydroxy-1-methyl-ethoxy)-3-(4-methanesulfonylphenoxy)-benzamide, 5-isopropoxy-3-(4-methoxycarbonylaminomethylphenoxy)-N-thiazol-2-yl-benzamide, 5-isopropoxy-3-(4-methylcarbamoyl-phenoxy)-N-thiazol-2-yl-benzamide, 3-(4-dimethylcarbamoyl-phenoxy)-5-isopropoxy-N-thiazol-2-yl-benzamide, 5-isopropoxy-3-(4-methylcarbonylaminomethyl-phenoxy)-N-thiazol-2-yl-benzamide, 5-isopropoxy-3-(4-methanesulfonylaminomethyl-phenoxy)-N-thiazol-2-yl-benzamide, 3-[4-(1-hydroxy-propyl)-phenoxy]-5-isopropoxy-N-thiazol-2-yl-benzamide, 6-[3-isopropoxy-5-(thiazol-2-ylcarbamoyl)-phenoxy]-nicotinic acid methyl ester, 3-(5-hydroxymethyl-pyridin-2-yl-oxy)-5-isopropoxy-N-thiazol-2-yl-benzamide, 5-isopropoxy-3-(5-methanesulfonylpyridin-2-yl)-N-thiazol-2-yl-benzamide, 3-(5-acetyl-pyridin-2-yl-oxy)-5-isopropoxy-N-thiazol-2-yl-benzamide, 5-isopropoxy-3-(5-methoxycarbonyl-pyrazin-2-yl-oxy)-N-thiazol-2-yl-benzamide, 3-(5-cyano-pyridin-2-yl-oxy)-5-isopropoxy-N-thiazol-2-yl-benzamide, 5-isopropoxy-3-(2-oxo-1,2-dihydro-pyridin-4-yl-oxy)-N-thiazol-2-yl-benzamide, 5-isopropoxy-3-(2-oxo-1,2-dihydro-pyridin-3-yl-oxy)-N-thiazol-2-yl-benzamide, 5-isopropoxy-3-(2-oxo-1,2-dihydro-pyridin-3-yl-oxy)-N-thiazolo[5,4-b]pyridin-2-yl-benzamide, 5-isopropoxy-3-([1,3,4]thiadiazol-2-ylsulfanyl)-N-thiazolo[5,4-b]-pyridine-2-yl-benzamide, 5-isopropoxy-3-(4-methyl-[1,2,4]triazol-3-ylsulfanyl)-N-thiazol-2-yl-benzamide, 5-isopropoxy-3-thiazol-2-ylsulfanyl-N-thiazol-2-yl-benzamide, 5-isopropoxy-3-(4H-[1,2,4]triazol-3-ylsulfanyl)-N-thiazol-2-yl-benzamide, 5-isopropoxy-3-([1,3,4]thiadiazol-2-ylsulfanyl)-N-thiazol-2-yl-benzamide, 5-isopropoxy-3-(5-methylsulfanyl-[1,3,4]thiadiazol-2-ylsulfanyl)-N-thiazol-2-yl-benzamide, 5-isopropoxy-3-(5-methyl-[1,3,4]thiadiazol-2-ylsulfanyl)-N-thiazol-2-yl-benzamide, 5-(tetrahydrofuran-3-yl-oxy)-N-thiazol-2-yl-3-(4H-[1,2,4]triazol-3-ylsulfanyl)-benzamide, 5-(2-hydroxy-1-methyl-ethoxy)-N-(4-methyl-thiazol-2-yl)-3-([1,3,4]thiadiazol-2-ylsulfanyl)-benzamide, 5-(3-hydroxy-1-methyl-propoxy)-N-(4-methyl-thiazol-2-yl)-3-([1,3,4]thiadiazol-2-ylsulfanyl)-benzamide, 5-(2-hydroxy-1-methyl-ethoxy)-3-([1,3,4]thiadiazol-2-ylsulfanyl)-N-thiazol-2-yl-benzamide, 5-(2-hydroxy-1-methyl-ethoxy)-3-(4-methanesulfonylphenylsulfanyl)-N-thiazol-2-yl-benzamide, 3-(3-fluoro-phenylthio)-5-(2-hydroxy-1-methyl-ethoxy)-N-thiazol-2-yl-benzamide, 5-(2-hydroxy-1-methyl-ethoxy)-3-(pyridin-4-ylsulfanyl)-N-thiazol-2-yl-benzamide, 5-(2-hydroxy-1-methyl-ethoxy)-3-(6-methyl-pyridin-3-ylsulfanyl)-N-thiazol-2-yl-benzamide, 5-(2- hydroxy-1-methyl-ethoxy)-3-(4-methanesulfonylphenoxy)-N-(3-methyl-[1,2,4]-thiadiazol-5-yl)-benzamide, N-[3-hydroxymethyl-1,2,4-thiadiazol-5-yl]-3-(4-methanesulfonyl-1-methyl-ethoxy)-5-(2-methoxy-1-methyl-ethoxy)benzamide, 5-(3-hydroxy-1-methylethoxy)-3-(4-methanesulfonylphenoxy)-N-[5-methyl-1,2,4-thiadiazol-3-yl]benzamide, 5-(hydroxy-1-methylethoxy)-3-(4-methanesulfonylphenoxy)-N-(3-methoxy-1,2,4-thiadiazol-5-yl)benzamide, 5-(2-hydroxy-1-methyl-ethoxy)-3-(4-methanesulfonylphenoxy)-N-(1,2,5-thiadiazol-3-yl)benzamide, 5-(2-hydroxy-1-methyl-ethoxy)-3-(4-methanesulfonylphenoxy)-N-(4-trifluoromethyl-thiazol-2-yl)benzamide, 5-(2-hydroxy-1-methyl-ethoxy)-3-(4-methanesulfonylphenoxy)-N-(4,5,6,7-tetrahydrobenzothiazol-2-yl)benzamide, 5-(2-hydroxy-1-methyl-ethoxy)-3-(4-methanesulfonylphenoxy)-N-(pyridazin-3-yl)-benzamide, 5-(2-hydroxy-1-methyl-ethoxy)-N-(3-isopropyl-[1,2,4]-triazol-5-yl)-3-(4-methanesulfonylphenoxy)benzamide, 5-(2-hydroxy-1-methyl-ethoxy)-3-(4-methanesulfonylphenoxy)-N-(3-methyl-[1,2,4]-oxadiazol-5-yl)benzamide, 5-(2-hydroxy-1-methyl-ethoxy)-N-[4-(1-hydroxy-1-methyl-ethyl)-thiazol-2-yl]-3-(4-methanesulfonylphenoxy)benzamide, N-(4-cyano-thiazol-2-yl)-5-(2-hydroxy-1-methyl-ethoxy)-3-(4-methanesulfonylphenoxy)benzamide, 5-(2-hydroxy-1-methyl-ethoxy)-3-(4-methanesulfonylphenoxy)-N-(1-methyl-1H-pyrazol-3-yl)benzamide, 5-(1-hydroxymethyl-propoxy)-3-(4-methanesulfonylphenoxy)-N-(pyridin-2-yl)benzamide, 5-(2-hydroxy-1-methyl-ethoxy)-3-(4-methanesulfonylphenoxy)-N-(5-methyl-isothiazol-3-yl)benzamide, 5-(3-hydroxy-cyclopentyloxy)-3-(4-methanesulfonylphenoxy)-N-(thiazol-2-yl)benzamide, 5-(2-hydroxy-1-methyl-ethoxy)-3-(4-methanesulfonylphenoxy)-N-(5-methoxy-thiazol-2-yl)benzamide, 5-(1-hydroxymethyl-2-methyl-propoxy)-3-(4-methanesulfonylphenoxy)-N-(thiazol-2-yl)benzamide, 5-(2-hydroxy-1-methyl-ethoxy)-3-(4-methanesulfonylphenoxy)-N-(1H-[1,2,3]triazol-4-yl)benzamide, N-(1-acetyl-1H-pyrazol-3-yl)-5-(2-hydroxy-1-methyl-ethoxy)-3-(4-methanesulfonylphenoxy)benzamide, 5-(2-hydroxy-1-methyl-ethoxy)-3-(4-methanesulfonylphenoxy)-N-(pyrazol-3-yl)benzamide, N-(5,6-dihydro-4H-cyclopentathiazol-2-yl)-5-(2-hydroxy-1-methyl-ethoxy)-3-(4-methanesulfonylphenoxy)benzamide, 5-(1-hydroxymethyl-propoxy)-3-(4-methanesulfonylphenoxy)-N-(1-methyl-1H-pyrazol-3-yl)benzamide, 5-(2-hydroxy-1-methyl-ethoxy)-3-(4-methanesulfonylphenoxy)-N-(thieno[3,2-d]thiazol-2-yl)benzamide, 3-(3-fluoro-4-methanesulfonylphenoxy)-5-(2-hydroxy-1-methyl-ethoxy)-N-(1-methyl-1H-pyrazol-3-yl)benzamide, 3-(4-methanesulfonylphenoxy)-5-(2-methoxy-1-methyl-ethoxy)-N-(pyrazol-3-yl)benzamide, 3-(4-cyanophenoxy)-5-(2-hydroxy-1-methyl-ethoxy)-N-(1-methyl-1H-pyrazol-3-yl)benzamide, 3-(4-ethylsulfonylphenoxy)-5-(2-hydroxy-1-methyl-ethoxy)-N-(1-methyl-1H-pyrazol-3-yl)benzamide, 3-(6-ethanesulfonylpyridin-3-yloxy)-5-(2-hydroxy-1-methyl-ethoxy)-N-(1-methyl-1H-pyrazol-3-yl)benzamide, 5-(3-hydroxy-1-methyl-propoxy)-3-(4-methanesulfonylphenoxy)-N-(1-methyl-1H-pyrazol-3-yl)benzamide, 3-(4-ethanesulfonylphenoxy)-5-(2-hydroxy-1-methyl-ethoxy)-N-(isoxazol-3-yl)benzamide, 5-(2-hydroxy-1-methyl-ethoxy)-3-(4-isopropylsulfonylphenoxy)-N-(1-methyl-1H-pyrazol-3-yl)benzamide, 5-(2-hydroxy-1-methyl-ethoxy)-N-(4-hydroxy-4-methyl-4,5,6,6a-tetrahydro-3aH-cyclopentathiazol-2-yl)-3-(4-methanesulfonylphenoxy)benzamide, 3-(4-dimethylcarbamoyl-phenoxy)-5-(2-hydroxy-1-methyl-ethoxy)-N-(1-methyl-1H-pyrazol-3-yl)benzamide, 3-(4-acetylphenoxy)-5-(2-hydroxy-1-methyl-ethoxy)-N-(1-methyl-1H-pyrazol-3-yl)benzamide, 5-(2-hydroxy-1-methyl-ethoxy)-N-(1-methyl-1H-pyrazol-3-yl)-3-(1,3,4-thiadiazol-2-ylsulfanyl)benzamide, N-(1-ethyl-1H-pyrazol-3-yl)-5-(2-hydroxy-1-methyl-ethoxy)-3-(4-methanesulfonylphenoxy)benzamide, 5-(2-hydroxy-1-methyl-ethoxy)-3-(6-methanesulfonylpyridin-3-yloxy)-N-(1-methyl-1H-pyrazol-3-yl)benzamide, 5-(2-hydroxy-1-methyl-ethoxy)-3-(4-methoxycarbonylaminomethyl-phenoxy)-N-(3-methyl-1,2,4-thiadiazol-5-yl)benzamide, 5-(1-hydroxymethyl-propoxy)-3-(6-methanesulfonylpyridin-3-yloxy)-N-(1-methyl-1H-pyrazol-3-yl)benzamide, 3-(6-methanesulfonylpyridin-3-yloxy)-5-(1-methoxymethyl-propoxy)-N-(1-methyl-1H-pyrazol-3-yl)benzamide, 5-isopropoxy-3-(6-methanesulfonylpyridin-3-yloxy)-N-(1-methyl-1H-pyrazol-3-yl)benzamide, 5-(2-fluoro-1-fluoromethyl-ethoxy)-3-(6-methanesulfonylpyridin-3-yloxy)-N-(1-methyl-1H-pyrazol-3-yl)benzamide, 3-(6-ethanesulfonylpyridin-3-yloxy)-5-(2-hydroxy-1-methyl-ethoxy)-N-(isoxazol-3-yl)benzamide, 5-(2-hydroxy-1-methyl-ethoxy)-3-(4-methanesulfonylphenylsulfanyl)-N-(1-methyl-1H-pyrazol-3-yl)benzamide, 5-cyclopropyloxy-3-(4-methanesulfonylphenoxy)-N-(1-methyl-1H-pyrazol-3-yl)benzamide, 3-(6-methanesulfonylpyridin-3-yloxy)-5-(1-methoxymethyl-propoxy)-N-(pyrazol-3-yl)benzamide, 5-(2-fluoro-1-fluoromethyl-ethoxy)-3-(4-methanesulfonylphenoxy)-N-(1-methyl-1H-pyrazol-3-yl)benzamide, 3-(6-ethanesulfonylpyridin-3-yloxy)-5-(1-hydroxymethyl-propoxy)-N-(1-methyl-1H-pyrazol-3-yl)benzamide, 5-(6-ethanesulfonylpyridin-3-yloxy)-3-(2-methoxy-1-methyl-ethoxy)-N-(1-methyl-1H-pyrazol-3-yl)benzamide, 2-[3-(4-methanesulfonylphenoxy)-5-(1-methyl-1H-pyrazol-3-ylcarbamoyl)-phenoxy]propionic acid-tert-butyl ester, 3-(6-ethanesulfonylpyridin-3-yloxy)-5-(2-methoxy-1-methyl-ethoxy)-N-(pyrazol-3-yl)-benzamide, 3-(6-methanesulfonylpyridin-3-yloxy)-N-(1-methyl-1H-pyrazol-3-yl)-5-(tetrahydrofuran-3-yl)benzamide, N-(1-ethyl-1H-pyrazol-3-yl)-5-(2-hydroxy-1-methyl-ethoxy)-3-(6-methanesulfonylpyridin-3-yloxy)benzamide, 5-(2-fluoro-1-fluoromethyl-ethoxy)-3-(6-methanesulfonylpyridin-3-yloxy)-N-(pyrazol-3-yl)benzamide, 3-(6-methanesulfonylpyridin-3-yloxy)-5-(2-methoxy-1-methyl-ethoxy)-N-(1-methyl-1H-pyrazol-3-yl)benzamide, 3-(6-ethanesulfonylpyridin-3-yloxy)-5-(2-fluoro-1-fluoromethyl-ethoxy)-N-(1-methyl-1H-pyrazol-3-yl)benzamide, 2-[3-(4-methanesulfonylphenoxy)-5-(1-methyl-1H-pyrazol-3-ylcarbamoyl)-phenoxy]propionic acid, 3-(6-ethanesulfonylpyridin-3-yloxy)-5-isopropoxy-N-(pyrazol-3-yl)benzamide, 3-(6-ethanesulfonylpyridin-3-yloxy)-5-isopropoxy-N-(1-methyl-1H-pyrazol-3-yl)benzamide, 3-(6-ethanesulfonylpyridin-3-yloxy)-5-(2-hydroxy-1-methyl-ethoxy)-N-(pyrazol-3-yl)benzamide, 3-(6-ethanesulfonylpyridin-3-yloxy)-5-(2-hydroxy-1-methyl-ethoxy)-N-(pyridin-2-yl)benzamide, 3-(6-ethanesulfonylpyridin-3-yloxy)-5-(2-hydroxy-1-methyl-ethoxy)-N-thiazol-2-yl-benzamide-5-(2-fluoro-1-methyl-ethoxy)-3-(6-methanesulfonylpyridin-3-yloxy)-N-(1-methyl-1H-pyrazol-3-yl)benzamide, 5-(2-chloro-1-methyl-ethoxy)-3-(6-ethanesulfonylpyridin-3-yloxy)-N-(1-methyl-1H-pyrazol-3-yl)benzamide, 5-(2-fluoro-1-fluoromethyl-ethoxy)-N-(isoxazol-3-yl)-3-(6-methanesulfonylpyridin-3-yloxy)benzamide, 5-(2-fluoro-1-fluoromethyl-ethoxy)-3-(6-methanesulfonylpyridin-3-yloxy)-N-(pyridin-2-yl)benzamide, 5-(2-fluoro-1-fluoromethyl-ethoxy)-3-(6-methanesulfonylpyridin-3-yloxy)-N-(3-methyl-[1,2,4]thiadiazol-5-yl)benzamide, 3-(4-dimethylsulfamoylphenoxy)-5-(2-hydroxy-1-methylethoxy)-N-(1-methyl-1H-pyrazol-3-yl)benzamide, 5-(2-hydroxy-1-methyl-ethoxy)-3-(3-methanesulfonylphenoxy)-N-(1-methyl-1H-pyrazol-3-yl)benzamide, 5-(2-hydroxy-1-methyl-ethoxy)-3-(6-isopropylsulfonylpyridin-3-yloxy)-N-(1-methyl-1H-pyrazol-3-yl)benzamide, 3-(3-chloro-4-methanesulfonylphenoxy)-5-(2-hydroxy-1-methyl-ethoxy)-N-(1-methyl-1H-pyrazol-3-yl)benzamide, 5-(2-hydroxy-1-methyl-ethoxy)-N-(1-methyl-1H-pyrazol-3-yl)-3-(pyridin-3-yloxy)benzamide, 5-(2-fluoro-1-fluoromethyl-ethoxy)-N-(1-methyl-1H-pyrazol-3-yl)-3-(pyridin-3-yloxy)benzamide, 5-(2-hydroxy-1-methyl-ethoxy)-N-(1-methyl-1H-pyrazol-3-yl)-3-(pyridin-4-yloxy)benzamide, 5-(2-fluoro-1-fluoromethyl-ethoxy)-N-(1-methyl-1H-pyrazol-3-yl)-3-(pyridin-4-yloxy)benzamide, 2-[3-(6-ethanesulfonylpyridin-3-yloxy)-5-(1-methyl-1H-pyrazol-3-ylcarbamoyl)-phenoxy] propionic acid and 5-(2-fluoro-1-fluoromethyl-ethoxy)-3-(3-fluoro-4-methanesulfonylphenoxy)-N-(1-methyl-1H-pyrazol-3-yl)benzamide, among which examples of preferred compounds include 5-isopropoxy-3-(4-methanesulfonylphenoxy)-N-(4-methylthiazol-2-yl)-benzamide, 5-(2-hydroxy-1-methyl-ethoxy)-3-(4-methanesulfonylphenoxy)-N-thiazol-2-yl-benzamide, 5-ethoxy-3-(4-methanesulfonylphenoxy)-N-(4-methoxymethyl-thiazol-2-yl)benzamide, 5-cyclopentyloxy-3-(4-methanesulfonylphenoxy)-N-thiazol-2-yl-benzamide, 3-(4-methanesulfonylphenoxy)-5-(tetrahydrofuran-3-yloxy)-N-thiazol-2-yl-benzamide, 3-(4-methanesulfonylphenoxy)-5-(2-methoxy-1-methyl-ethoxy)-N-thiazol-2-yl-benzamide, 3-(4-methanesulfonylphenoxy)-5-(2-methoxy-1-methoxymethyl-ethoxy)-N-thiazol-2-yl-benzamide, 3-(2-fluoro-4-methanesulfonylphenoxy)-5-isopropoxy-N-thiazol-2-yl-benzamide, 3-(4-methanesulfonylphenoxy)-5-(1-methoxymethyl-propoxy)-N-(4-methyl-thiazol-2-yl)-benzamide, 3-(4-methanesulfonylphenoxy)-5-(3-methoxy-1-methyl-propoxy)-N-thiazol-2-yl-benzamide, 5-(3-hydroxy-1-methyl-propoxy)-3-(4-methanesulfonylphenoxy)-N-thiazol-2-yl-benzamide, N-(4-hydroxymethyl-thiazol-2-yl)-5-isopropoxy-3-(4-methanesulfonylphenoxy)-benzamide, N-(isooxazol-3-yl)-3-(4-methanesulfonylphenoxy)-5-(1-methoxymethyl-propoxy)-benzamide, 3-(4-methanesulfonylphenoxy)-5-(1-methoxymethyl-propoxy)-N-[1,3,4]thiadiazol-2-yl-benzamide, 5-(1-hydroxymethyl-propoxy)-3-(4-methanesulfonylphenoxy)-N-(4-methyl-thiazol-2-yl)-benzamide, N-(4-hydroxymethyl-thiazol-2-yl)-3-(4-methanesulfonylphenoxy)-5-(1-methoxymethyl-propoxy)-benzamide, 5-(2-amino-1-methyl-ethoxy)-3-(4-methanesulfonylphenoxy)-N-thiazol-2-yl-benzamide, 5-(2-hydroxy-propoxy)-3-(4-methanesulfonylphenoxy)-N-(4-methyl-thiazol-2-yl)-benzamide, 3-(4-methanesulfonylphenoxy)-5-(2-methoxy-propoxy)-N-(4-methyl-thiazol-2-yl)-benzamide, 5-isopropoxy-3-(4-methanesulfonylphenoxy)-N-(thiazolo[5,4-b]pyridin-2-yl)-benzamide, 5-(2-hydroxymethyl-allyl)-3-(4-methanesulfonylphenoxy)-N-thiazol-2-yl-benzamide, 5-(2-hydroxy-1-methyl-ethoxy)-3-(4-methanesulfonylphenoxy)-N-thiazolo[5,4-b]pyridin-2-yl-benzamide, 5-(3-hydroxy-2-methyl-propyl)-3-(4-methanesulfonylphenoxy)-N-thiazol-2-yl-benzamide, 5-(1-acetyl-piperidin-4-yloxy)-3-(4-methanesulfonylphenoxy)-N-(4-methyl-thiazol-2-yl)-benzamide, 2-[3-(4-methanesulfonylphenoxy)-5-(4-methyl-thiazol-2-yl-carbamoyl)-phenoxy]propionic acid, 5-(3-hydroxy-1-methyl-propoxy)-3-(4-methanesulfonylphenoxy)-N-thiazol-2-yl-benzamide, 5-(2-acetylamino-1-methyl-ethoxy)-3-(4-methanesulfonylphenoxy)-N-thiazol-2-yl-benzamide, N-[4-(1-hydroxy-ethyl)-thiazol-2-yl]-5-isopropoxy-3-(4-methanesulfonylphenoxy)-benzamide, 5-(2-hydroxy-1-methyl-ethoxy)-3-(4-methanesulfonylphenoxy)-N-pyridin-2-yl-benzamide, 5-(2-hydroxy-ethoxy)-3-(4-methanesulfonylphenoxy)-N-thiazol-2-yl-benzamide, 5-(2-hydroxy-cyclopentyloxy)-3-(4-methanesulfonylphenoxy)-N-thiazol-2-yl-benzamide, N-(4-acetyl-thiazol-2-yl)-5-(2-hydroxy-1-methyl-ethoxy)-3-(4-methanesulfonylphenoxy)-benzamide, 5-(2-hydroxy-1-methyl-ethoxy)-N-(4-hydroxymethyl-thiazol-2-yl)-3-(4-methanesulfonylphenoxy)-benzamide, N-[4-(1-hydroxy-ethyl)-thiazol-2-yl]-5-(2-hydroxy-1-methyl-ethoxy)-3-(4-methanesulfonylphenoxy)-benzamide, 3-(3-fluoro-4-methanesulfonylphenoxy)-5-(2-hydroxy-1-methyl-ethoxy)-N-thiazol-2-yl-benzamide, 5-(2-hydroxy-1-methyl-ethoxy)-3-(4-methanesulfonylphenoxy)-N-(5-methyl-thiazol-2-yl) benzamide, 5-(2-hydroxy-1-methyl-ethoxy)-3-(4-methanesulfonylphenoxy)-N-([1,2,4]thiadiazol-5-yl)-benzamide, N-(4-hydroxymethyl-thiazol-2-yl)-3-(4-methanesulfonylphenoxy)-5-(2-methoxy-1-methyl-ethoxy)-benzamide, 5-(2-hydroxy-1-methyl-ethoxy)-3-(4-methanesulfonylphenoxy)-N-(5-methoxycarbony-pyridin-2-yl)-benzamide, 6-[5-isopropoxy-3-(4-methanesulfonylphenoxy)-benzoylamino]nicotinic acid, 5-(2-hydroxy-1-methyl-propoxy)-3-(4-methanesulfonylphenoxy)-N-thiazol-2-yl-benzamide, 5-(2-hydroxy-1-methyl-ethoxy)-N-(isoxazol-3-yl)-3-(4-methanesulfonylphenoxy)-benzamide, N-(5-hydroxymethyl-thiazol-2-yl)-5-isopropoxy-3-(4-methanesulfonylphenoxy)-benzamide, N-[4-(1-hydroxy-ethyl)-thiazol-2-yl]-3-(4-methanesulfonylphenoxy)-5-(2-methoxy-1-methyl-ethoxy)-benzamide, N-(4-hydroxymethyl-thiazol-2-yl)-3-(4-methanesulfonylphenoxy)-5-(tetrahydrofuran-3-yl-oxy)-benzamide, 5-(2-hydroxy-1-methyl-ethoxy)-3-(4-methanesulfonylphenoxy)-N-(2-methylthiazol-4-yl)-benzamide, 5-(2-hydroxy-1-methyl-ethoxy)-3-(4-methanesulfonylphenoxy)-N-(4-methoxymethyl-thiazol-2-yl)-benzamide, N-[4-(1-hydroxy-ethyl)-thiazol-2-yl]-3-(4-methanesulfonylphenoxy)-5-(2-methoxy-1-methyl-ethoxy)-benzamide, N-[4-(1-hydroxy-ethyl)-thiazol-2-yl]-3-(4-methanesulfonylphenoxy)-5-(tetrahydrofuran-3-yl-oxy)-benzamide, N-[4-(1-hydroxy-ethyl)-thiazol-2-yl]-3-(4-methanesulfonyphenoxy)-5-(tetrahydrofuran-3-yl-oxy)-benzamide, N-(2,5-dimethylthiazol-4-yl)-5-(2-hydroxy-1-methyl-ethoxy)-3-(4-methanesulfonylphenoxy)-benzamide, 5-isopropoxy-3-(4-methoxycarbonylaminomethylphenoxy)-N-thiazol-2-yl-benzamide, 5-isopropoxy-3-(4-methylcarbamoyl-phenoxy)-N-thiazol-2-yl-benzamide, 5-isopropoxy-3-(4-methylcarbonylaminomethyl-phenoxy)-N-thiazol-2-yl-benzamide, 5-isopropoxy-3-(4-methanesulfonylaminomethyl-phenoxy)-N-thiazol-2-yl-benzamide, 3-[4-(1-hydroxy-propyl)-phenoxy]-5-isopropoxy-N-thiazol-2-yl-benzamide, 6-[3-isopropoxy-5-(thiazol-2-ylcarbamoyl)-phenoxy]-nicotinic acid methyl ester, 3-(5-hydroxymethyl-pyridin-2-yl-oxy)-5-isopropoxy-N-thiazol-2-yl-benzamide, 5-isopropoxy-3-(5-methanesulfonylpyridin-2-yl)-N-thiazol-2-yl-benzamide, 3-(5-acetyl-pyridin-2-yl-oxy)-5-isopropoxy-N-thiazol-2-yl-benzamide, 5-isopropoxy-3-(5-methoxycarbonyl-pyrazin-2-yl-oxy)-N-thiazol-2-yl-benzamide, 3-(5-cyano-pyridin-2-yl-oxy)-5-isopropoxy-N-thiazol-2-yl-benzamide, 5-isopropoxy-3-(2-oxo-1,2-dihydro-pyridin-4-yl-oxy)-N-thiazol-2-yl-benzamide, 5-isopropoxy-3-(2-oxo-1,2-dihydro-pyridin-3-yl-oxy)-N-thiazol-2-yl-benzamide, 5-isopropoxy-3-(2-oxo-1,2-dihydro-pyridin-3-yl-oxy)-N-thiazolo[5,4-b]pyridin-2-yl-benzamide, 5-isopropoxy-3-([1,3,4]thiadiazol-2-ylsulfanyl)-N-thiazolo[5,4-b]-pyridin-2-yl-benzamide, 5-isopropoxy-3-(4-methyl-[1,2,4]triazol-3-ylsulfanyl)-N-thiazol-2-yl-benzamide, 5-isopropoxy-3-thiazol-2-ylsulfanyl-N-thiazol-2-yl-benzamide, 5-isopropoxy-3-(4H-[1,2,4]triazol-3-ylsulfanyl)-N-thiazol-2-yl-benzamide, 5-isopropoxy-3-([1,3,4]thiadiazol-2-ylsulfanyl)-N-thiazol-2-yl-benzamide, 5-isopropoxy-3-(5-methylsulfanyl-[1,3,4]thiadiazol-2-ylsulfanyl)-N-thiazol-2-yl-benzamide, 5-isopropoxy-3-(5-methyl-[1,3,4]thiadiazol-2-ylsulfanyl)-N-thiazol-2-yl-benzamide, 5-(tetrahydrofuran-3-yl-oxy)-N-thiazol-2-yl-3-(4H-[1,2,4]triazol-3-ylsulfanyl)-benzamide, 5-(2-hydroxy-1-methyl-ethoxy)-N-(4-methyl-thiazol-2-yl)-3-([1,3,4]thiadiazol-2-ylsulfanyl)-benzamide, 5-(3-hydroxy-1-methyl-propoxy)-N-(4-methyl-thiazol-2-yl)-3-([1,3,4]thiadiazol-2-ylsulfanyl)-benzamide, 5-(2-hydroxy-1-methyl-ethoxy)-3-([1,3,4]thiadiazol-2-ylsulfanyl)-N-thiazol-2-yl-benzamide, 5-(2-hydroxy-1-methyl-ethoxy)-3-(4-methanesulfonylphenylsulfanyl)-N-thiazol-2-yl-benzamide, 3-(3-fluoro-phenylthio)-5-(2-hydroxy-1-methyl-ethoxy)-N-thiazol-2-yl-benzamide, 5-(2-hydroxy-1-methyl-ethoxy)-3-(pyridin-4-ylsulfanyl)-N-thiazol-2-yl-benzamide, 5-(2-hydroxy-1-methyl-ethoxy)-3-(6-methyl-pyridin-3-ylsulfanyl)-N-thiazol-2-yl-benzamide, 5-(2-hydroxy-1-methyl-ethoxy)-3-(4-methanesulfonylphenoxy)-N-(3-methyl-[1,2,4]-thiadiazol-5-yl)-benzamide, N-[3-hydroxymethyl-1,2,4-thiadiazol-5-yl]-3-(4-methanesulfonylphenoxy)-5-(2-methoxy-1-methyl-ethoxy) benzamide, 5-(hydroxy-1-methylethoxy)-3-(4-methanesulfonylphenoxy)-N-(3-methoxy-1,2,4-thiadiazol-5-yl)benzamide, 5-(2-hydroxy-1-methyl-ethoxy)-3-(4-methanesulfonylphenoxy)-N-(1,2,5-thiadiazol-3-yl) benzamide, 5-(2-hydroxy-1-methyl-ethoxy)-N-(3-isopropyl-[1,2,4]-triazol-5-yl)-3-(4-methanesulfonylphenoxy)benzamide, 5-(2-hydroxy-1-methyl-ethoxy)-N-[4-(1-hydroxy-1-methyl-ethyl)-thiazol-2-yl]-3-(4-methanesulfonylphenoxy)benzamide, N-(4-cyano-thiazol-2-yl)-5-(2-hydroxy-1-methyl-ethoxy)-3-(4-methanesulfonylphenoxy)benzamide, 5-(2-hydroxy-1-methyl-ethoxy)-3-(4-methanesulfonylphenoxy)-N-(1-methyl-1H-pyrazol-3-yl)benzamide, 5-(1-hydroxymethyl-propoxy)-3-(4-methanesulfonylphenoxy)-N-(pyridin-2-yl)benzamide, 5-(2-hydroxy-1-methyl-ethoxy)-3-(4-methanesulfonylphenoxy)-N-(5-methyl-isothiazol-3-yl)benzamide, 5-(3-hydroxy-cyclopentyloxy)-3-(4-methanesulfonylphenoxy)-N-(thiazol-2-yl)benzamide, 5-(2-hydroxy-1-methyl-ethoxy)-3-(4-methanesulfonylphenoxy)-N-(5-methoxy-thiazol-2-yl)benzamide, 5-(1-hydroxymethyl-2-methyl-propoxy)-3-(4-methanesulfonylphenoxy)-N-(thiazol-2-yl)benzamide, 5-(2-hydroxy-1-methyl-ethoxy)-3-(4-methanesulfonylphenoxy)-N-(1H-[1,2,3]triazol-4-yl)benzamide, N-(1-acetyl-1H-pyrazol-3-yl)-5-(2-hydroxy-1-methyl-ethoxy)-3-(4-methanesulfonylphenoxy)benzamide, 5-(2-hydroxy-1-methyl-ethoxy)-3-(4-methanesulfonylphenoxy)-N-(pyrazol-3-yl)benzamide, N-(5,6-dihydro-4H-cyclopentathiazol-2-yl)-5-(2-hydroxy-1-methyl-ethoxy)-3-(4-methanesulfonylphenoxy)benzamide, 5-(1-hydroxymethyl-propoxy)-3-(4-methanesulfonylphenoxy)-N-(1-methyl-1H-pyrazol-3-yl)benzamide, 5-(2-hydroxy-1-methyl-ethoxy)-3-(4-methanesulfonylphenoxy)-N-(thieno[3,2-d]thiazol-2-yl)benzamide, 3-(3-fluoro-4-methanesulfonylphenoxy)-5-(2-hydroxy-1-methyl-ethoxy)-N-(1-methyl-1H-pyrazol-3-yl)benzamide, 3-(4-methanesulfonylphenoxy)-5-(2-methoxy-1-methyl-ethoxy)-N-(pyrazol-3-yl)benzamide, 3-(4-cyanophenoxy)-5-(2-hydroxy-1-methyl-ethoxy)-N-(1-methyl-1H-pyrazol-3-yl)benzamide, 3-(4-ethylsulfonylphenoxy)-5-(2-hydroxy-1-methyl-ethoxy)-N-(1-methyl-1H-pyrazol-3-yl) benzamide, 3-(6-ethanesulfonylpyridin-3-yloxy)-5-(2-hydroxy-1-methyl-ethoxy)-N-(1-methyl-1H-pyrazol-3-yl)benzamide, 5-(3-hydroxy-1-methyl-propoxy)-3-(4-methanesulfonylphenoxy)-N-(1-methyl-1H-pyrazol-3-yl)benzamide, 3-(4-ethanesulfonylphenoxy)-5-(2-hydroxy-1-methyl-ethoxy)-N-(isoxazol-3-yl)benzamide, 5-(2-hydroxy-1-methyl-ethoxy)-3-(4-isopropylsulfonylphenoxy)-N-(1-methyl-1H-pyrazol-3-yl)benzamide, 5-(2-hydroxy-1-methyl-ethoxy)-N-(4-hydroxy-4-methyl-4,5,6,6a-tetrahydro-3 aH-cyclopentathiazol-2-yl)-3-(4-methanesulfonylphenoxy)benzamide, 3-(4-acetylphenoxy)-5-(2-hydroxy-1-methyl-ethoxy)-N-(1-methyl-1H-pyrazol-3-yl)benzamide, N-(1-ethyl-1H-pyrazol-3-yl)-5-(2-hydroxy-1-methyl-ethoxy)-3-(4-methanesulfonylphenoxy)benzamide, 5-(2-hydroxy-1-methyl-ethoxy)-3-(6-methanesulfonylpyridin-3-yloxy)-N-(1-methyl-1H-pyrazol-3-yl)benzamide, 5-(2-hydroxy-1-methyl-ethoxy)-3-(4-methoxycarbonylaminomethyl-phenoxy)-N-(3-methyl-1,2,4-thiadiazol-5-yl)benzamide, 5-(1-hydroxymethyl-propoxy)-3-(6-methanesulfonylpyridin-3-yloxy)-N-(1-methyl-1H-pyrazol-3-yl)benzamide, 3-(6-methanesulfonylpyridin-3-yloxy)-5-(1-methoxymethyl-propoxy)-N-(1-methyl-1H-pyrazol-3-yl)benzamide, 5-isopropoxy-3-(6-methanesulfonylpyridin-3-yloxy)-N-(1-methyl-1H-pyrazol-3-yl)benzamide, 5-(2-fluoro-1-fluoromethyl-ethoxy)-3-(6-methanesulfonylpyridin-3-yloxy)-N-(1-methyl-1H-pyrazol-3-yl)benzamide, 3-(6-ethanesulfonylpyridin-3-yloxy)-5-(2-hydroxy-1-methyl-ethoxy)-N-(isoxazol-3-yl)benzamide, 3-(6-methanesulfonylpyridin-3-yloxy)-5-(1-methoxymethyl-propoxy)-N-(pyrazol-3-yl)benzamide, 5-(2-fluoro-1-fluoromethyl-ethoxy)-3-(4-methanesulfonylphenoxy)-N-(1-methyl-1H-pyrazol-3-yl)benzamide, 3-(6-ethanesulfonylpyridin-3-yloxy)-5-(1-hydroxymethyl-propoxy)-N-(1-methyl-1H-pyrazol-3-yl)benzamide, 5-(6-ethanesulfonylpyridin-3-yloxy)-3-(2-methoxy-1-methyl-ethoxy)-N-(1-methyl-1H-pyrazol-3-yl)benzamide, 3-(6-ethanesulfonylpyridin-3-yloxy)-5-(2-methoxy-1-methyl-ethoxy)-N-(pyrazol-3-yl)-benzamide, 3-(6-methanesulfonylpyridin-3-yloxy)-N-(1-methyl-1H-pyrazol-3-yl)-5-(tetrahydrofuran-3-yl)benzamide, N-(1-ethyl-1H-pyrazol-3-yl)-5-(2-hydroxy-1-methyl-ethoxy)-3-(6-methanesulfonylpyridin-3-yloxy)benzamide, 5-(2-fluoro-1-fluoromethyl-ethoxy)-3-(6-methanesulfonylpyridin-3-yloxy)-N-(pyrazol-3-yl)benzamide, 3-(6-methanesulfonylpyridin-3-yloxy)-5-(2-methoxy-1-methyl-ethoxy)-N-(1-methyl-1H-pyrazol-3-yl)benzamide, 3-(6-ethanesulfonylpyridin-3-yloxy)-5-(2-fluoro-1-fluoromethyl-ethoxy)-N-(1-methyl-1H-pyrazol-3-yl) benzamide, 3-(6-ethanesulfonylpyridin-3-yloxy)-5-isopropoxy-N-(pyrazol-3-yl)benzamide, 3-(6-ethanesulfonylpyridin-3-yloxy)-5-isopropoxy-N-(1-methyl-1H-pyrazol-3-yl)benzamide, 3-(6-ethanesulfonylpyridin-3-yloxy)-5-(2-hydroxy-1-methyl-ethoxy)-N-(pyrazol-3-yl) benzamide, 3-(6-ethanesulfonylpyridin-3-yloxy)-5-(2-hydroxy-1-methyl-ethoxy)-N-(pyridin-2-yl)benzamide, 3-(6-ethanesulfonylpyridin-3-yloxy)-5-(2-hydroxy-1-methyl-ethoxy)-N-thiazol-2-yl-benzamide5-(2-fluoro-1-methyl-ethoxy)-3-(6-methanesulfonylpyridin-3-yloxy)-N-(1-methyl-1H-pyrazol-3-yl)benzamide, 5-(2-chloro-1-methyl-ethoxy)-3-(6-methanesulfonylpyridin-3-yloxy)-N-(1-methyl-1H-pyrazol-3-yl)benzamide, 5-(2-fluoro-1-fluoromethyl-ethoxy)-N-(isoxazol-3-yl)-3-(6-methanesulfonylpyridin-3-yloxy)benzamide, 5-(2-fluoro-1-fluoromethyl-ethoxy)-3-(6-methanesulfonylpyridin-3-yloxy)-N-(pyridin-2-yl)benzamide, 5-(2-fluoro-1-fluoromethyl-ethoxy)-3-(6-methanesulfonylpyridin-3-yloxy)-N-(3-methyl-[1,2,4]-thiadiazol-5-yl)benzamide, 3-(4-dimethylsulfamoylphenoxy)-5-(2-hydroxy-1-methyl-ethoxy)-N-(1-methyl-1H-pyrazol-3-yl)benzamide, 3-(3- chloro-4-methanesulfonylphenoxy)-5-(2-hydroxy-1-methyl-ethoxy)-N-(1-methyl-1H-pyrazol-3-yl)benzamide, 5-(2-hydroxy-1-methyl-ethoxy)-N-(1-methyl-1H-pyrazol-3-yl)-3-(pyridin-3-yloxy)benzamide, 5-(2-fluoro-1-fluoromethyl-ethoxy)-N-(1-methyl-1H-pyrazol-3-yl)-3-(pyridin-3-yloxy)benzamide, 5-(2-hydroxy-1-methyl-ethoxy)-N-(1-methyl-1H-pyrazol-3-yl)-3-(pyridin-4-yloxy)benzamide, 5-(2-fluoro-1-fluoromethyl-ethoxy)-N-(1-methyl-1H-pyrazol-3-yl)-3-(pyridin-4-yloxy)benzamide and 5-(2-fluoro-1-fluoromethyl-ethoxy)-3-(3-fluoro-4-methanesulfonylphenoxy)-N-(1-methyl-1H-pyrazol-3-yl)benzamide, examples of more preferred compounds include 5-isopropoxy-3-(4-methanesulfonylphenoxy)-N-(4-methylthiazol-2-yl)-benzamide, 5-(2-hydroxy-1-methyl-ethoxy)-3-(4-methanesulfonylphenoxy)-N-thiazol-2-yl-benzamide, 3-(4-methanesulfonylphenoxy)-5-(tetrahydrofuran-3-yloxy)-N-thiazol-2-yl-benzamide, 3-(4-methanesulfonylphenoxy)-5-(2-methoxy-1-methyl-ethoxy)-N-thiazol-2-yl-benzamide, 3-(4-methanesulfonylphenoxy)-5-(2-methoxy-1-methoxymethyl-ethoxy)-N-thiazol-2-yl-benzamide, 3-(2-fluoro-4-methanesulfonylphenoxy)-5-isopropoxy-N-thiazol-2-yl-benzamide, 3-(4-methanesulfonylphenoxy)-5-(1-methoxymethyl-propoxy)-N-(4-methyl-thiazol-2-yl)-benzamide, 3-(4-methanesulfonylphenoxy)-5-(3-methoxy-1-methyl-propoxy)-N-thiazol-2-yl-benzamide, N-(4-hydroxymethyl-thiazol-2-yl)-5-isopropoxy-3-(4-methanesulfonylphenoxy)-benzamide, N-(isooxazol-3-yl)-3-(4-methanesulfonylphenoxy)-5-(1-methoxymethyl-propoxy)-benzamide, 3-(4-methanesulfonylphenoxy)-5-(1-methoxymethyl-propoxy)-N-[1,3,4]thiadiazol-2-yl-benzamide, 5-(1-hydroxymethyl-propoxy)-3-(4-methanesulfonylphenoxy)-N-(4-methyl-thiazol-2-yl)-benzamide, N-(4-hydroxymethyl-thiazol-2-yl)-3-(4-methanesulfonylphenoxy)-5-(1-methoxymethyl-propoxy)-benzamide, 5-isopropoxy-3-(4-methanesulfonylphenoxy)-N-(thiazolo[5,4-b]pyridin-2-yl)-benzamide, 5-(2-hydroxy-1-methyl-ethoxy)-3-(4-methanesulfonylphenoxy)-N-thiazolo[5,4-b]pyridin-2-yl-benzamide, 5-(3-hydroxy-2-methyl-propyl)-3-(4-methanesulfonylphenoxy)-N-thiazol-2-yl-benzamide, 5-(3-hydroxy-1-methyl-propoxy)-3-(4-methanesulfonylphenoxy)-N-thiazol-2-yl-benzamide, 5-(2-acetylamino-1-methyl-ethoxy)-3-(4-methanesulfonylphenoxy)-N-thiazol-2-yl-benzamide, N-[4-(1-hydroxy-ethyl)-thiazol-2-yl]-5-isopropoxy-3-(4-methanesulfonylphenoxy)-benzamide, 5-(2-hydroxy-1-methyl-ethoxy)-3-(4-methanesulfonylphenoxy)-N-pyridin-2-yl-benzamide, 5-(2-hydroxy-ethoxy)-3-(4-methanesulfonylphenoxy)-N-thiazol-2-yl-benzamide, 5-(2-hydroxy-cyclopentyloxy)-3-(4-methanesulfonylphenoxy)-N-thiazol-2-yl-benzamide, N-(4-acetyl-thiazol-2-yl)-5-(2-hydroxy-1-methyl-ethoxy)-3-(4-methanesulfonylphenoxy)-benzamide, 5-(2-hydroxy-1-methyl-ethoxy)-N-(4-hydroxymethyl-thiazol-2-yl)-3-(4-methanesulfonylphenoxy)-benzamide, N-[4-(1-hydroxy-ethyl)-thiazol-2-yl]-5-(2-hydroxy-1-methyl-ethoxy)-3-(4-methanesulfonylphenoxy)-benzamide, 3-(3-fluoro-4-methanesulfonylphenoxy)-5-(2-hydroxy-1-methyl-ethoxy)-N-thiazol-2-yl-benzamide, 5-(2-hydroxy-1-methyl-ethoxy)-3-(4-methanesulfonylphenoxy)-N-([1,2,4]thiadiazol-5-yl)-benzamide, N-(4-hydroxymethyl-thiazol-2-yl)-3-(4-methanesulfonylphenoxy)-5-(2-methoxy-1-methyl-ethoxy)-benzamide, 6-[5-isopropoxy-3-(4-methanesulfonylphenoxy)-benzoylamino]nicotinic acid, 5-(2-hydroxy-1-methyl-ethoxy)-N-(isoxazol-3-yl)-3-(4-methanesulfonylphenoxy)-benzamide, N-(5-hydroxymethyl-thiazol-2-yl)-5-isopropoxy-3-(4-methanesulfonylphenoxy)-benzamide, N-[4-(1-hydroxy-ethyl)-thiazol-2-yl]-3-(4-methanesulfonylphenoxy)-5-(2-methoxy-1-methyl-ethoxy)-benzamide, N-(4-hydroxymethyl-thiazol-2-yl)-3-(4-methanesulfonylphenoxy)-5-(tetrahydrofuran-3-yl-oxy)-benzamide, 5-(2-hydroxy-1-methyl-ethoxy)-3-(4-methanesulfonylphenoxy)-N-(2-methylthiazol-4-yl)-benzamide, 5-(2-hydroxy-1-methyl-ethoxy)-3-(4-methanesulfonylphenoxy)-N-(4-methoxymethyl-thiazol-2-yl)-benzamide, N-[4-(1-hydroxy-ethyl)-thiazol-2-yl]-3-(4-methanesulfonylphenoxy)-5-(2-methoxy-1-methyl-ethoxy)-benzamide, N-[4-(1-hydroxy-ethyl)-thiazol-2-yl]-3-(4-methanesulfonylphenoxy)-5-(tetrahydrofuran-3-yl-oxy)-benzamide, N-[4-(1-hydroxy-ethyl)-thiazol-2-yl]-3-(4-methanesulfonylphenoxy)-5-(tetrahydrofuran-3-yl-oxy)-benzamide, N-(2,5-dimethylthiazol-4-yl)-5-(2-hydroxy-1-methyl-ethoxy)-3-(4-methanesulfonylphenoxy)-benzamide, 3-(5-acetyl-pyridin-2-yl-oxy)-5-isopropoxy-N-thiazol-2-yl-benzamide, 5-isopropoxy-3-(2-oxo-1,2-dihydro-pyridin-4-yl-oxy)-N-thiazol-2-yl-benzamide, 5-isopropoxy-3-(2-oxo-1,2-dihydro-pyridin-3-yl-oxy)-N-thiazol-2-yl-benzamide, 5-isopropoxy-3-(2-oxo-1,2-dihydro-pyridin-3-yl-oxy)-N-thiazolo[5,4-b]pyridin-2-yl-benzamide, 5-isopropoxy-3-([1,3,4]thiadiazol-2-ylsulfanyl)-N-thiazolo[5,4-b]-pyridine-2-yl-benzamide, 5-isopropoxy-3-thiazol-2-ylsulfanyl-N-thiazol-2-yl-benzamide, 5-isopropoxy-3-([1,3,4]thiadiazol-2-ylsulfanyl)-N-thiazol-2-yl-benzamide, 5-isopropoxy-3-(5-methyl-([1,3,4]thiadiazol-2-ylsulfanyl)-N-thiazol-2-yl-benzamide, 5-(2-hydroxy-1-methyl-ethoxy)-N-(4-methyl-thiazol-2-yl)-3-([1,3,4]thiadiazol-2-ylsulfanyl)-benzamide, 5-(3-hydroxy-1-methyl-propoxy)-N-(4-methyl-thiazol-2-yl)-3-([1,3,4]thiadiazol-2-ylsulfanyl)-benzamide, 5-(2-hydroxy-1-methyl-ethoxy)-3-([1,3,4]thiadiazol-2-ylsulfanyl)-N-thiazol-2-yl-benzamide, 5-(2-hydroxy-1-methyl-ethoxy)-3-(4-methanesulfonylphenylsulfanyl)-N-thiazol-2-yl-benzamide, 3-(3-fluoro-phenylthio)-5-(2-hydroxy-1-methyl-ethoxy)-N-thiazol-2-yl-benzamide, 5-(2-hydroxy-1-methyl-ethoxy)-3-(pyridin-4-ylsulfanyl)-N-thiazol-2-yl-benzamide, 5-(2-hydroxy-1-methyl-ethoxy)-3-(6-methyl-pyridin-3-ylsulfanyl)-N-thiazol-2-yl-benzamide, 5-(2-hydroxy-1-methyl-ethoxy)-3-(4-methanesulfonylphenoxy)-N-(3-methyl-[1,2,4]-thiadiazol-5-yl)-benzamide, 5-(hydroxy-1-methylethoxy)-3-(4-methanesulfonylphenoxy)-N-(3-methoxy-1,2,4-thiadiazol-5-yl)benzamide, 5-(2-hydroxy-1-methyl-ethoxy)-N-(3-isopropyl-[1,2,4]-triazol-5-yl)-3-(4-methanesulfonylphenoxy)benzamide, 5-(2-hydroxy-1-methyl-ethoxy)-N-[4-(1-hydroxy-1-methyl-ethyl)-thiazol-2-yl]-3-(4-methanesulfonylphenoxy)benzamide, 5-(2-hydroxy-1-methyl-ethoxy)-3-(4-methanesulfonylphenoxy)-N-(1-methyl-1H-pyrazol-3-yl)benzamide, 5-(1-hydroxymethyl-propoxy)-3-(4-methanesulfonylphenoxy)-N-(pyridin-2-yl)benzamide, 5-(1-hydroxymethyl-2-methyl-propoxy)-3-(4-methanesulfonylphenoxy)-N-(thiazol-2-yl)benzamide, 5-(2-hydroxy-1-methyl-ethoxy)-3-(4-methanesulfonylphenoxy)-N-(pyrazol-3-yl)benzamide, N-(5,6-dihydro-4H-cyclopentathiazol-2-yl)-5-(2-hydroxy-1-methyl-ethoxy)-3-(4-methanesulfonylphenoxy)benzamide, 5-(1-hydroxymethyl-propoxy)-3-(4-methanesulfonylphenoxy)-N-(1-methyl-1H-pyrazol-3-yl)benzamide, 3-(3-fluoro-4-methanesulfonylphenoxy)-5-(2-hydroxy-1-methyl-ethoxy)-N-(1-methyl-1H-pyrazol-3-yl)benzamide, 3-(4-methanesulfonylphenoxy)-5-(2-methoxy-1-methyl-ethoxy)-N-(pyrazol-3-yl)benzamide, 3-(4-ethylsulfonylphenoxy)-5-(2-hydroxy-1-methyl-ethoxy)-N-(1-methyl-1H-pyrazol-3-yl)benzamide, 3-(6-ethanesulfonylpyridin-3-yloxy)-5-(2-hydroxy-1-methyl-ethoxy)-N-(1-methyl-1H-pyrazol-3-yl)benzamide, 3-(4-ethanesulfonylphenoxy)-5-(2-hydroxy-1-methyl-ethoxy)-N-(isoxazol-3-yl)benzamide, 5-(2-hydroxy- 1-methyl-ethoxy)-3-(4-isopropylsulfonylphenoxy)-N-(1-methyl-1H-pyrazol-3-yl)benzamide, 5-(2-hydroxy-1-methyl-ethoxy)-N-(4-hydroxy-4-methyl-4,5,6,6a-tetrahydro-3 aH-cyclopentathiazol-2-yl)-3-(4-methanesulfonylphenoxy) benzamide, 3-(4-acetylphenoxy)-5-(2-hydroxy-1-methyl-ethoxy)-N-(1-methyl-1H-pyrazol-3-yl)benzamide, 5-(2-hydroxy-1-methyl-ethoxy)-3-(6-methanesulfonylpyridin-3-yloxy)-N-(1-methyl-1H-pyrazol-3-yl)benzamide, 5-(2-hydroxy-1-methyl-ethoxy)-3-(4-methoxycarbonylaminomethyl-phenoxy)-N-(3-methyl-1,2,4-thiadiazol-5-yl)benzamide, 5-(1-hydroxymethyl-propoxy)-3-(6-methanesulfonylpyridin-3-yloxy)-N-(1-methyl-1H-pyrazol-3-yl)benzamide, 3-(6-methanesulfonylpyridin-3-yloxy)-5-(1-methoxymethyl-propoxy)-N-(1-methyl-1H-pyrazol-3-yl)benzamide, 5-isopropoxy-3-(6-methanesulfonylpyridin-3-yloxy)-N-(1-methyl-1H-pyrazol-3-yl)benzamide, 5-(2-fluoro-1-fluoromethyl-ethoxy)-3-(6-methanesulfonylpyridin-3-yloxy)-N-(1-methyl-1H-pyrazol-3-yl)benzamide, 3-(6-ethanesulfonylpyridin-3-yloxy)-5-(2-hydroxy-1-methyl-ethoxy)-N-(isoxazol-3-yl)benzamide, 3-(6-methanesulfonylpyridin-3-yloxy)-5-(1-methoxymethyl-propoxy)-N-(pyrazol-3-yl)benzamide, 3-(6-ethanesulfonylpyridin-3-yloxy)-5-(1-hydroxymethyl-propoxy)-N-(1-methyl-1H-pyrazol-3-yl)benzamide, 5-(6-ethanesulfonylpyridin-3-yloxy)-3-(2-methoxy-1-methyl-ethoxy)-N-(1-methyl-1H-pyrazol-3-yl)benzamide, 3-(6-ethanesulfonylpyridin-3-yloxy)-5-(2-methoxy-1-methyl-ethoxy)-N-(pyrazol-3-yl)-benzamide, N-(1-ethyl-1H-pyrazol-3-yl)-5-(2-hydroxy-1-methyl-ethoxy)-3-(6-methanesulfonylpyridin-3-yloxy)benzamide, 5-(2-fluoro-1-fluoromethyl-ethoxy)-3-(6-methanesulfonylpyridin-3-yloxy)-N-(pyrazol-3-yl)benzamide, 3-(6-methanesulfonylpyridin-3-yloxy)-5-(2-methoxy-1-methyl-ethoxy)-N-(1-methyl-1H-pyrazol-3-yl)benzamide, 3-(6-ethanesulfonylpyridin-3-yloxy)-5-isopropoxy-N-(pyrazol-3-yl)benzamide, 3-(6-ethanesulfonylpyridin-3-yloxy)-5-isopropoxy-N-(1-methyl-1H-pyrazol-3-yl)benzamide, 3-(6-ethanesulfonylpyridin-3-yloxy)-5-(2-hydroxy-1-methyl-ethoxy)-N-(pyrazol-3-yl)benzamide, 3-(6-ethanesulfonylpyridin-3-yloxy)-5-(2-hydroxy-1-methyl-ethoxy)-N-thiazol-2-yl-benzamide5-(2-fluoro-1-methyl-ethoxy)-3-(6-methanesulfonylpyridin-3-yloxy)-N-(1-methyl-1H-pyrazol-3-yl)benzamide, 5-(2-fluoro-1-fluoromethyl-ethoxy)-3-(6-methanesulfonylpyridin-3-yloxy)-N-(3-methyl-[1,2,4]-thiadiazol-5-yl)benzamide, 3-(4-dimethylsulfamoylphenoxy)-5-(2-hydroxy-1-methyl-ethoxy)-N-(1-methyl-1H-pyrazol-3-yl)benzamide and 3-(3-chloro-4-methanesulfonylphenoxy)-5-(2-hydroxy-1-methyl-ethoxy)-N-(1-methyl-1H-pyrazol-3-yl)benzamide, and examples of particularly preferred compounds include 5-(2-hydroxy-1-methyl-ethoxy)-3-(4-methanesulfonylphenoxy)-N-thiazol-2-yl-benzamide, 3-(4-methanesulfonylphenoxy)-5-(tetrahydrofuran-3-yloxy)-N-thiazol-2-yl-benzamide, 3-(4-methanesulfonylphenoxy)-5-(2-methoxy-1-methyl-ethoxy)-N-thiazol-2-yl-benzamide, 3-(4-methanesulfonylphenoxy)-5-(1-methoxymethyl-propoxy)-N-(4-methyl-thiazol-2-yl)-benzamide, N-(4-hydroxymethyl-thiazol-2-yl)-5-isopropoxy-3-(4-methanesulfonylphenoxy)-benzamide, N-(isooxazol-3-yl)-3-(4-methanesulfonylphenoxy)-5-(1-methoxymethyl-propoxy)-benzamide, 3-(4-methanesulfonylphenoxy)-5-(1-methoxymethyl-propoxy)-N-[1,3,4]thiadiazol-2-yl-benzamide, 5-(1-hydroxymethyl-propoxy)-3-(4-methanesulfonylphenoxy)-N-(4-methyl-thiazol-2-yl)-benzamide, N-(4-hydroxymethyl-thiazol-2-yl)-3-(4-methanesulfonylphenoxy)-5-(1-methoxymethyl-propoxy)-benzamide, 5-isopropoxy-3-(4-methanesulfonylphenoxy)-N-(thiazolo[5,4-b]pyridin-2-yl)-benzamide, 5-(2-hydroxy-1-methyl-ethoxy)-3-(4-methanesulfonylphenoxy)-N-thiazolo[5,4-b]pyridin-2-yl-benzamide, N-[4-(1-hydroxy-ethyl)-thiazol-2-yl]-5-isopropoxy-3-(4-methanesulfonylphenoxy)-benzamide, 5-(2-hydroxy-1-methyl-ethoxy)-3-(4-methanesulfonylphenoxy)-N-pyridin-2-yl-benzamide, 5-(2-hydroxy-cyclopentyloxy)-3-(4-methanesulfonylphenoxy)-N-thiazol-2-yl-benzamide, 5-(2-hydroxy-1-methyl-ethoxy)-N-(4-hydroxymethyl-thiazol-2-yl)-3-(4-methanesulfonylphenoxy)-benzamide, N-[4-(1-hydroxy-ethyl)-thiazol-2-yl]-5-(2-hydroxy-1-methyl-ethoxy)-3-(4-methanesulfonylphenoxy)-benzamide, 5-(2-hydroxy-1-methyl-ethoxy)-3-(4-methanesulfonylphenoxy)-N-([1,2,4]thiadiazol-5-yl)-benzamide, N-(4-hydroxymethyl-thiazol-2-yl)-3-(4-methanesulfonylphenoxy)-5-(2-methoxy-1-methyl-ethoxy)-benzamide, N-[4-(1-hydroxy-ethyl)-thiazol-2-yl]-3-(4-methanesulfonylphenoxy)-5-(2-methoxy-1-methyl-ethoxy)-benzamide, N-(4-hydroxymethyl-thiazol-2-yl)-3-(4-methanesulfonylphenoxy)-5-(tetrahydrofuran-3-yl-oxy)-benzamide, 5-(2-hydroxy-1-methyl-ethoxy)-3-(4-methanesulfonylphenoxy)-N-(2-methylthiazol-4-yl)-benzamide, 5-(2-hydroxy-1-methyl-ethoxy)-3-(4-methanesulfonylphenoxy)-N-(4-methoxymethyl-thiazol-2-yl)-benzamide, N-[4-(1-hydroxy-ethyl)-thiazol-2-yl]-3-(4-methanesulfonylphenoxy)-5-(2-methoxy-1-methyl-ethoxy)-benzamide, N-[4-(1-hydroxy-ethyl)-thiazol-2-yl]-3-(4-methanesulfonylphenoxy)-5-(tetrahydrofuran-3-yl-oxy)-benzamide, N-[4-(1-hydroxy-ethyl)-thiazol-2-yl]-3-(4-methanesulfonylphenoxy)-5-(tetrahydrofuran-3-yl-oxy)-benzamide, N-(2,5-dimethylthiazol-4-yl)-5-(2-hydroxy-1-methyl-ethoxy)-3-(4-methanesulfonylphenoxy)-benzamide, 5-isopropoxy-3-([1,3,4]thiadiazol-2-ylsulfanyl)-N-thiazolo[5,4-b]-pyridine-2-yl-benzamide, 5-(2-hydroxy-1-methyl-ethoxy)-3-([1,3,4]thiadiazol-2-ylsulfanyl)-N-thiazol-2-yl-benzamide, 5-(2-hydroxy-1-methyl-ethoxy)-3-(4-methanesulfonylphenoxy)-N-(3-methyl-[1,2,4]-thiadiazol-5-yl)-benzamide, 5-(2-hydroxy-1-methyl-ethoxy)-3-(4-methanesulfonylphenoxy)-N-(1-methyl-1H-pyrazol-3-yl)benzamide, 5-(1-hydroxymethyl-propoxy)-3-(4-methanesulfonylphenoxy)-N-(1-methyl-1H-pyrazol-3-yl)benzamide, 3-(3-fluoro-4-methanesulfonylphenoxy)-5-(2-hydroxy-1-methyl-ethoxy)-N-(1-methyl-1H-pyrazol-3-yl)benzamide, 3-(6-ethanesulfonylpyridin-3-yloxy)-5-(2-hydroxy-1-methyl-ethoxy)-N-(1-methyl-1H-pyrazol-3-yl)benzamide, 5-(2-hydroxy-1-methyl-ethoxy)-3-(6-methanesulfonylpyridin-3-yloxy)-N-(1-methyl-1H-pyrazol-3-yl)benzamide, 5-(2-fluoro-1-fluoromethyl-ethoxy)-3-(6-methanesulfonylpyridin-3-yloxy)-N-(1-methyl-1H-pyrazol-3-yl)benzamide, 3-(6-ethanesulfonylpyridin-3-yloxy)-5-(2-hydroxy-1-methyl-ethoxy)-N-(isoxazol-3-yl)benzamide, 5-(2-fluoro-1-fluoromethyl-ethoxy)-3-(6-methanesulfonylpyridin-3-yloxy)-N-(pyrazol-3-yl)benzamide, 3-(6-ethanesulfonylpyridin-3-yloxy)-5-isopropoxy-N-(1-methyl-1H-pyrazol-3-yl)benzamide.

The heteroarylcarbamoylbenzene derivatives of the present invention may also be used as pharmaceutically acceptable salts. Such salts may be acid addition salts or base addition salts.

Depending on the manner of the substituents, the compounds of the invention may also exist as stereoisomers or tautomers, including optical isomers, diastereomers and geometric isomers. All such isomers are, needless to mention, included in the compounds of the invention. Any desired mixtures of such isomers are also, needless to mention, included in the compounds of the invention.

Since the compounds of the invention have glucokinase-activating effects, they are useful as therapeutic and/or prophylactic agents for diabetes, and also as therapeutic and/or prophylactic agents for diabetes complications.

Here, "diabetes complications" refers to conditions which occur in association with diabetes, and examples of such diabetes complications include diabetic nephropathy, diabetic retinopathy, diabetic neuropathy and diabetic arteriosclerosis.

The compounds of the invention may be applied for either insulin-dependent diabetes mellitus (IDDM) or non-insulin-dependent diabetes mellitus (NIDDM).

Insulin-dependent diabetes mellitus (IDDM) is considered to be caused by reduction in insulin secretion and insulin resistance in the skeletal muscle due to genetic factors, while non-insulin-dependent diabetes mellitus (NIDDM) is considered to be predominantly an adult onset form, with increasing insulin resistance associated with obesity. Diabetes is therefore classified as type I (IDDM) or type II (NIDDM), depending on the cause.

The compounds of the invention are believed to be useful not only for type I diabetes, but also for type II diabetes for which adequate blood glucose level reduction has not been possible using conventional diabetes drugs.

In type II diabetes, the degree of postprandial hyperglycemia continues for a notably more prolonged period than in healthy persons, and the compounds of the invention are also useful against this type II diabetes.

PREFERRED MODE OF THE INVENTION

Processes for production of compounds of the invention will now be explained.

Compound (I) of the present invention may be easily produced using publicly known reaction means, or by carrying out a publicly known method. A compound (I) of the present invention may also be produced by a synthesis method in an ordinary liquid phase, as well as by a method employing a solid phase such as, for example, combinatorial synthesis or parallel synthesis methods, which have undergone rapid development in recent years.

The compounds of the invention are preferably produced by the following scheme, for example.

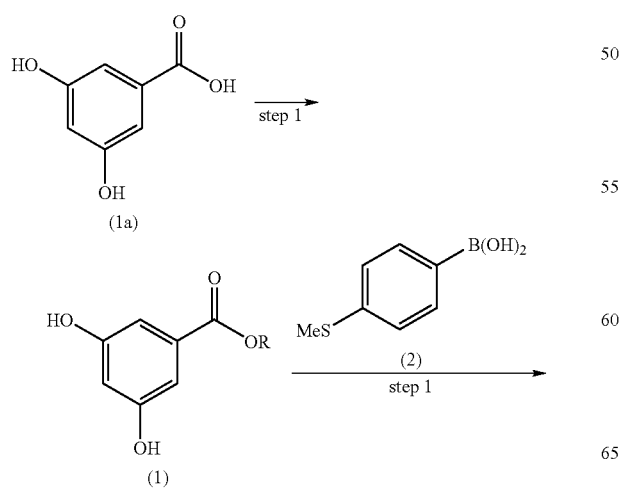

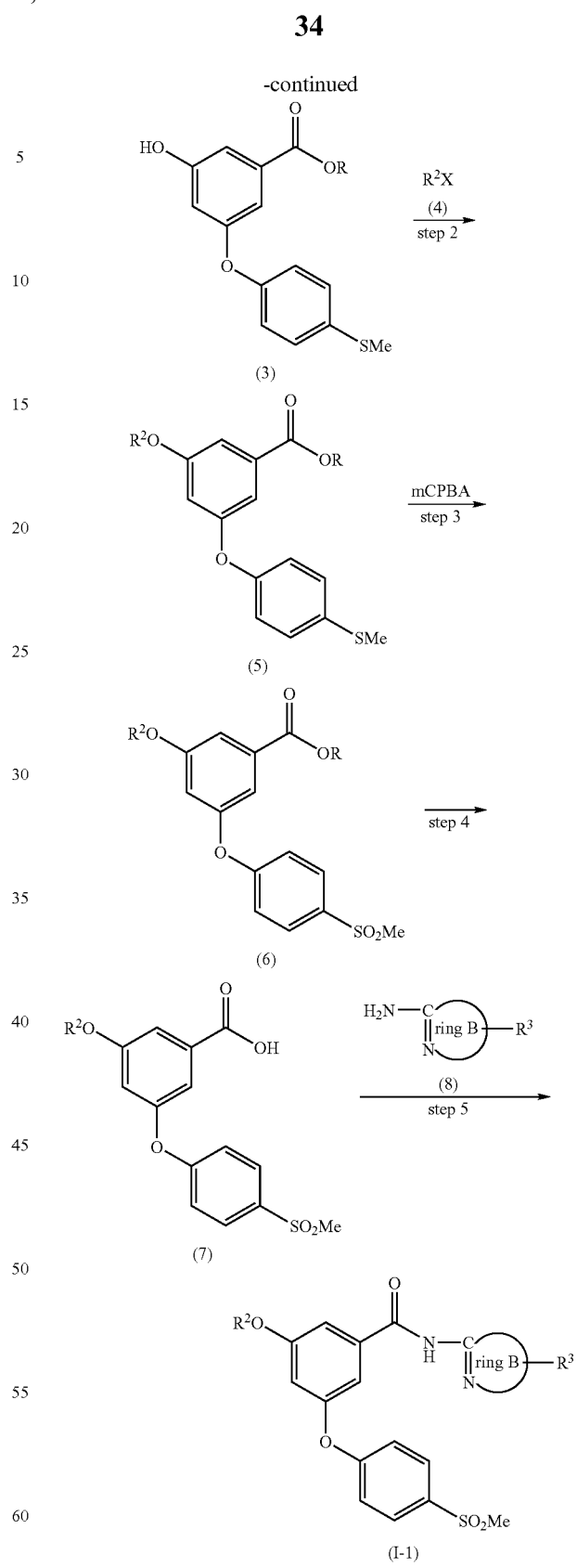

[wherein R represents lower alkyl, X represents a halogen atom, and the other symbols have the same definitions specified above].

(Step 1-1) This step introduces a protective group at the carboxyl group of 3,5-dihydrobenzoic acid (1a) to produce compound (1).

The protective group R for the carboxyl group of compound (1) functions as a protective group for the carboxyl group through Steps 1 to 3 and it may be any group so long as it can be easily removed in Step 4. As examples there may be mentioned straight-chain or branched lower alkyl groups such as methyl, ethyl and tert-butyl, halogenated lower alkyl groups such as 2-ethyl iodide and 2,2,2-trichloroethyl, lower alkenyl groups such as allyl, 2-propenyl and 2-methyl-2-propenyl, or aralkyl groups such as benzyl and PMB.

The method of introducing and removing the protective group R for the carboxyl group may be a method described in the relevant literature (for example, Protective Groups in Organic Synthesis, T. W. Green, 2nd printing, John Wiley & Sons, 1991), a corresponding method, or a combination thereof with an ordinary method.

Compound (1) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 1) In this step, compound (1) and p-methylthiophenylboric acid (2) are reacted in the presence of copper acetate and a base to produce a 5-hydroxy-3-(4-methylthiophenoxy) benzoic acid ester (3).

The amount of p-methylthiophenylboric acid (2) used will usually be from 1 to 10 equivalents, and preferably from 1 to 2.5 equivalents, with respect to 1 equivalent of compound (1).

Copper nitrate may be used instead of copper acetate, but copper acetate is preferred.

The amount of copper acetate or copper nitrate used will usually be from 0.1 to 5 equivalents, and preferably from 1 to 1.5 equivalents.

As examples of bases to be used there may be mentioned triethylamine, diisopropylethylamine, and the like, among which triethylamine is preferred.

The amount of base used will usually be from 0 to 10 equivalents, and preferably from 4 to 6 equivalents.

The reaction temperature will usually be from 0° C. to the reflux temperature of the reaction solvent, and preferably from 15 to 30° C.

The reaction time in this step will usually be from 2 to 48 hours, and preferably 12 hours.

The reaction solvent used in this step may be any one which does not impede the reaction, and as examples there may be mentioned methylene chloride, acetonitrile, toluene and the like, among which methylene chloride is preferred.

Compound (3) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification.

(Step 2) In this step, compound (3) obtained in Step 1 above and an alkyl halide (4) are reacted in the presence of a base to produce compound (5).

As compound (4) there may be used any compound which allows the reaction of this step to proceed uninhibited to produce compound (5), and as examples there may be mentioned ethyl iodide, 2-propyl bromide, cyclopentyl bromide, 2-bromoethanol and the like, among which 2-propyl bromide and cyclopentyl bromide, for example, are preferred, and 2-propyl bromide is more preferred.

The amount of compound (4) used will usually be from 0.5 to 10 equivalents, and preferably from 1 to 3 equivalents, with respect to 1 equivalent of compound (3).

As examples of bases to be used there may be mentioned potassium carbonate, diisopropylamine and the like, among which potassium carbonate is preferred.

The amount of the base used will usually be from 1 to 10 equivalents, and preferably from 1.5 to 3 equivalents.

The reaction temperature will usually be from 0° C. to the reflux temperature of the reaction solvent, and preferably from 25 to 40° C.

The reaction time will usually be from 1 to 12 hours, and preferably from 4 to 8 hours.

The reaction solvent used in this step may be any one which does not impede the reaction, but N,N-dimethylformamide is preferred.

Compound (5) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 3) In this step, compound (5) obtained in Step 2 above is reacted with mCPBA to produce compound (6). The oxidation reaction conducted in this step may be according to a method described in the relevant literature (for example, Brown. D. et al., Simple pyrimidines. X. The formation and reactivity of 2-, 4-, and 5-pyrimidinyl sulfones and sulfoxides, Journal of the Chemical Society [Section]C: Organic, Vol. 7, 1967, p 568-572), a corresponding method, or a combination thereof with an ordinary method.

The amount of mCPBA used will usually be from 2 to 10 equivalents, and preferably from 3 to 4 equivalents, with respect to 1 equivalent of compound (5).

The reaction time will usually be from 10 minutes to 12 hours, and preferably from 30 minutes to 1 hour.

The reaction temperature will usually be from −78 to 15° C., and preferably from 0 to 10° C.

The reaction solvent used may be any one which does not impede the reaction, and as examples there may be mentioned methylene chloride, chloroform and the like, among which chloroform is preferred.

Compound (6) obtained in this manner may be isolated and purified by publicly known separation and purification means such as, for example, concentration, concentration under reduced pressure, crystallization, reprecipitation, solvent extraction or chromatography, or it may be supplied to the subsequent step without isolation and purification.

(Step 4) In this step, the protective group R for the carboxyl group of compound (6) obtained in Step 3 above is removed to produce compound (7).

The method of removing the carboxyl protective group R may be a method described in the relevant literature (for example, Protective Groups in Organic Synthesis, T. W. Green, 2nd printing, John Wiley & Sons, 1991), a corresponding method, or a combination thereof with an ordinary method.

Compound (7) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 5) In this step, compound (7) obtained in Step 4 above is reacted with an amino compound represented by the following formula (8):

(8)

[wherein the symbols have the same definitions specified above]

to produce compound (I-1).

This reaction may be accomplished by conducting an ordinary amide-forming reaction by a method described in the relevant literature (for example, Peptide Gosei no Kiso to Jikken, Izumiya, N. et al., Maruzen Publ., 1983, Comprehensive Organic Synthesis, Vol. 6, Pergamon Press, 1991), a corresponding method, or a combination thereof with an ordinary method, using, specifically, a condensation agent which is well known to those skilled in the art, or it may be carried out by an ester-activating method, mixed acid anhydride method, acid chloride method, carbodiimide method, etc. available to those skilled in the art. As examples of such amide-forming reagents there may be mentioned thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphorylazide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazo-1-yl-oxy-tris(dimethylamino)phosphonium hexafluorophosphate and the like, among which thionyl chloride, 1-ethyl-3-(3-dimethylaminopropyl)carbodiimide hydrochloride, N,N-dicyclohexylcarbodi imide and benzotriazo-1-yl-oxy-tris(dimethylamino)phosphonium hexafluorophosphate, for example, are preferred. For an amide-forming reaction, a base and condensation aid may be used together with the aforementioned amide-forming reagent.

As examples of bases to be used there may be mentioned tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-azabicyclo[4.3.0]non-5-ene (DBN) and aromatic amines such as pyridine, 4-dimethylaminopyridine, picoline, lutidine, quinoline and isoquinoline, among which tertiary aliphatic amines, for example, are preferred, and triethylamine and N,N-diisopropylethylamine, for example, are particularly preferred.

As examples of condensation aids to be used there may be mentioned N-hydroxybenzotriazole hydrate, N-hydroxysuccinimide, N-hydroxy-5-norbornane-2,3-dicarboxylmide and 3-hydroxy-3,4-dihydro-4-oxo-1,2,3-benzotriazole, among which N-hydroxybenzotriazole, for example, is preferred.

The amount of compound (8) used will differ depending on the types of compounds and solvent used and the other reaction conditions, but will usually be from 0.1 to 10 equivalents, and preferably from 0.5 to 3 equivalents, with respect to 1 equivalent of the carboxylic acid derivative (7) or its reactive derivative.

The amount of amide-forming reagent used will differ depending on the types of compounds and solvent used and the other reaction conditions, but will usually be from 1 to 10 equivalents, and preferably from 1 to 3 equivalents with respect to 1 equivalent of the carboxylic acid compound (7) or its reactive derivative.

The amount of condensation agent used will also differ depending on the types of compounds and solvent used and the other reaction conditions, but will usually be from 1 to 10 equivalents, and preferably from 1 to 3 equivalents, with respect to 1 equivalent of the carboxylic acid compound (7) or its reactive derivative.

The amount of base used will also differ depending on the types of compounds and solvent used and the other reaction conditions, but will usually be from 1 to 10 equivalents, and preferably from 1 to 5 equivalents.

The reaction solvent used for this step may be, for example, an inert solvent, and is not particularly restricted so long as it does not impede the reaction, but as specific examples there may be mentioned methylene chloride, chloroform, 1,2-dichloroethane, N,N-dimethylformamide, acetic acid ethyl ester, acetic acid methyl ester, acetonitrile, benzene, xylene, toluene, 1,4-dioxane, tetrahydrofuran, dimethoxyethane or mixtures thereof, among which methylene chloride, chloroform, 1,2-dichloroethane, acetonitrile, N,N-dimethylformamide and the like are preferred from the standpoint of ensuring a suitable reaction temperature.

The reaction temperature in this step will usually be from −78° C. to the boiling point of the solvent, and preferably from 0 to 30° C.

The reaction time in this step will usually be from 0.5 to 96 hours, and preferably from 3 to 24 hours.

The base, amide-forming reagent and condensation agent used for this step may each be a single type or a combination of more than one type.

When substituent $R^3$ on Ring B of compound (I-1) produced in this step has a protective group, the protective group may be removed if necessary. The removal of the protective group may be accomplished by a method described in the relevant literature (for example, Protective Groups in Organic Synthesis, T. W. Green, 2nd printing, John Wiley & Sons, 1991), a corresponding method, or a combination thereof with an ordinary method.

Compound (I-1) of the present invention obtained in this manner may be isolated and purified by publicly known separation and purification means such as, for example, concentration, concentration under reduced pressure, crystallization, solvent extraction, reprecipitation or chromatography.

Compound (5) produced in Step 3 above may also be produced by the following method.

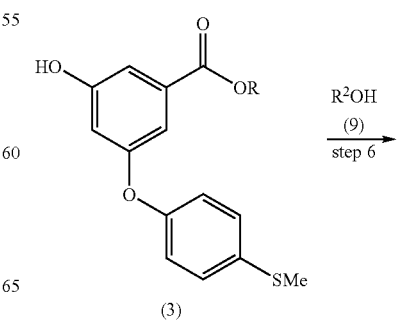

-continued

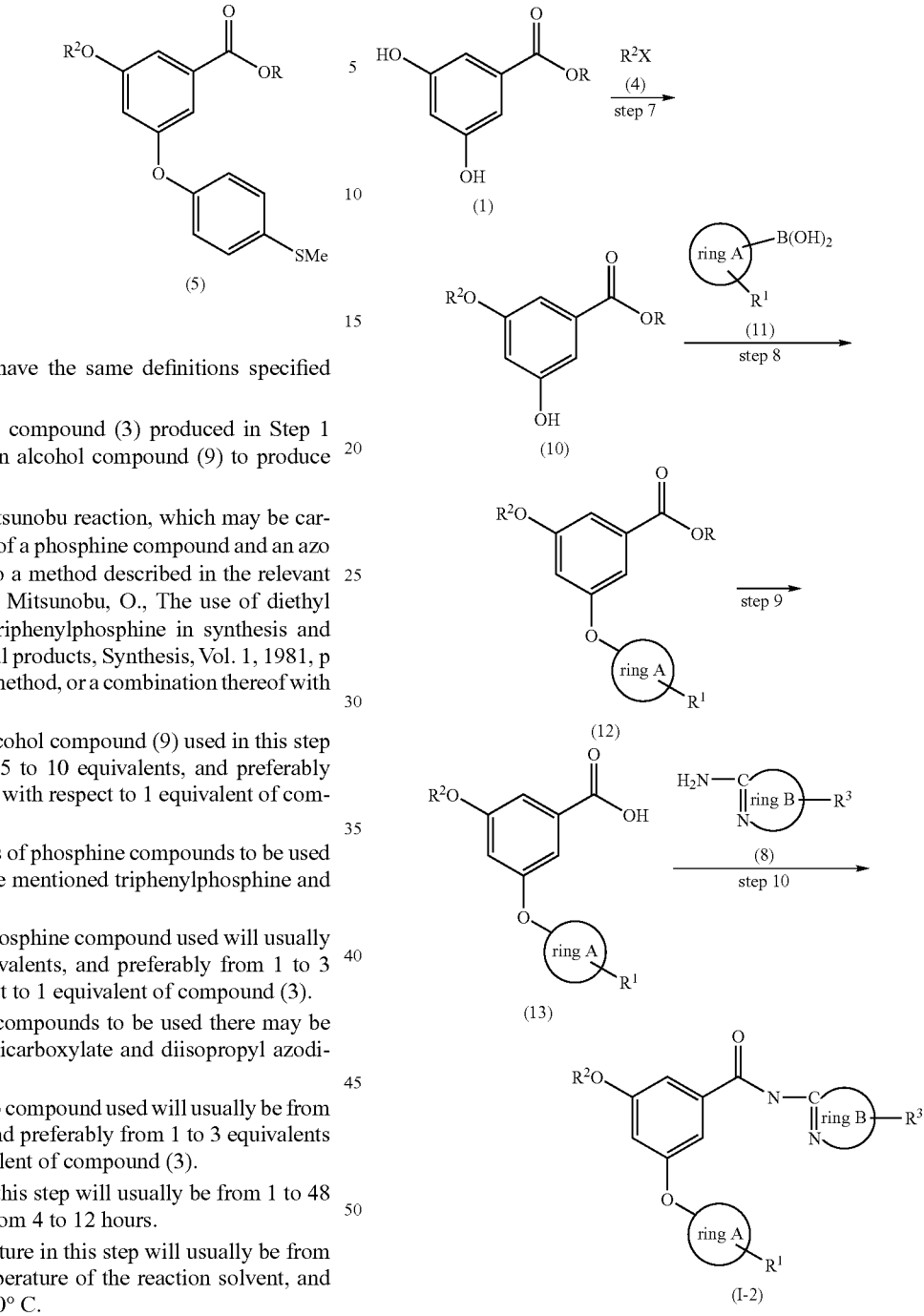

[wherein the symbols have the same definitions specified above]

(Step 6) In this step, compound (3) produced in Step 1 above is reacted with an alcohol compound (9) to produce compound (5).

This reaction is a Mitsunobu reaction, which may be carried out in the presence of a phosphine compound and an azo compound, according to a method described in the relevant literature (for example, Mitsunobu, O., The use of diethyl azodicarboxylate and triphenylphosphine in synthesis and transformation of natural products, Synthesis, Vol. 1, 1981, p 1-28), a corresponding method, or a combination thereof with an ordinary method.

The amount of the alcohol compound (9) used in this step will usually be from 0.5 to 10 equivalents, and preferably from 1 to 3 equivalents, with respect to 1 equivalent of compound (3).

As ordinary examples of phosphine compounds to be used in this step there may be mentioned triphenylphosphine and triethylphosphine.

The amount of the phosphine compound used will usually be from 0.5 to 10 equivalents, and preferably from 1 to 3 equivalents, with respect to 1 equivalent of compound (3).

As examples of azo compounds to be used there may be mentioned diethyl azodicarboxylate and diisopropyl azodicarboxylate.

The amount of the azo compound used will usually be from 0.5 to 10 equivalents, and preferably from 1 to 3 equivalents with respect to 1 equivalent of compound (3).

The reaction time in this step will usually be from 1 to 48 hours, and preferably from 4 to 12 hours.

The reaction temperature in this step will usually be from 0° C. to the reflux temperature of the reaction solvent, and preferably from 15 to 30° C.

The reaction solvent used in this step is not particularly restricted so long as it does not impede the reaction, and as specific examples there may be mentioned tetrahydrofuran and toluene.

Compound (I-1) obtained in this manner may be isolated and purified by publicly known separation and purification means such as, for example, concentration, concentration under reduced pressure, reprecipitation, solvent extraction, crystallization or chromatography, or it may be supplied to the subsequent step without isolation and purification.

Compound (I-2) of the present invention may be produced by the following scheme.

[wherein the symbols have the same definitions specified above]

(Step 7) In this step, compound (I) obtained in the previous step is reacted with compound (4) to produce compound (10).

This step may be carried out by the same method as in Step 2 above.

The number of equivalents of the alkyl halide compound (4) with respect to compound (1), and the reaction conditions such as the reaction temperature, reaction time, etc. may be according to the method of Step 2 above, a corresponding method, or a combination thereof with an ordinary method.

(Step 8) In this step, compound (10) obtained in Step 7 above is reacted with a boric acid derivative represented by the following formula (II):

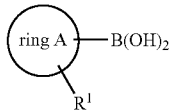

(11)

[wherein the symbols have the same definitions specified above]

to produce compound (12).

When $R^1$ requires a protective group, the necessary protective group may be introduced according to the type of $R^1$ group. The protecting group for $R^1$ may be any group which functions as a protective group for $R^1$ from Step 8 to Step 10 and which can be easily removed thereafter to yield compound (I-2) of the present invention.

The method of introducing and removing the protective group for $R^1$ may be a method described in the relevant literature (for example, Protective Groups in Organic Synthesis, T. W. Green, 2nd printing, John Wiley & Sons, 1991), a corresponding method, or a combination thereof with an ordinary method.

Substituent $R^{11}$ on Ring A may be converted to $R^1$.

The conversion from substituent $R^{11}$ on Ring A to $R^1$ may be carried out by a method described in the relevant literature (for example, Comprehensive Organic Synthesis, Vol. 6, Pergamon Press, 1991; Comprehensive Organic Transformations, Richard L. et al., VCH Publishers, 1988), a corresponding method, or a combination thereof with an ordinary method.

As examples of groups for $R^{11}$ there may be mentioned formyl, halogen atoms and alkoxycarbonyl.

When $R^{11}$ is a formyl group, for example, the formyl group may be reduced to convert it to hydroxymethyl. The reaction for conversion of formyl to hydroxymethyl may be a reaction whereby a compound having a formyl group is reacted with sodium borohydride to produce a compound having hydroxymethyl as $R^1$.

Alternatively, a compound having hydroxymethyl as $R^1$ may be subjected to azidation followed by reduction reaction for conversion to aminomethyl.

Conversion reaction from an alkoxycarbonyl group to an alkylcarbamoyl group may also be accomplished by hydrolyzing a compound having an alkoxycarbonyl group and then subjecting it to an amide-forming reaction with an alkylamine to produce a compound having an alkylcarbamoyl group as $R^1$.

As examples of boric acid derivatives represented by formula (II) above there may be mentioned 4-bromo-phenylboric acid, 4-fluoro-phenylboric acid, 4-methyl-phenylboric acid, 4-methoxy-phenylboric acid, 4-trifluoromethyl-phenylboric acid, 4-hydroxymethyl-phenylboric acid, 4-acetyl-phenylboric acid, 4-cyano-phenylboric acid, 4-methoxycarbonyl-phenylboric acid, 4-carboxy-phenylboric acid, 4-formyl-phenylboric acid, 4-aminomethyl-phenylboric acid and 4-carbamoyl-phenylboric acid.

When the phenylboric acid derivative represented by formula (11) has $R^{11}$ as a substituent on Ring A, $R^{11}$ may have a protective group.

The method of introducing the protective group may be a method described in the relevant literature (for example, Protective Groups in Organic Synthesis, T. W. Green, 2nd printing, John Wiley & Sons, 1991), a corresponding method, or a combination thereof with an ordinary method.

The compound obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 9) In this step, the protective group R for the carboxyl group of compound (12) obtained in Step 8 above is removed. This step may be carried out under the same reaction conditions as in Step 4, by a method described in the relevant literature (for example, Protective Groups in Organic Synthesis, T. W. Green, 2nd printing, John Wiley & Sons, 1991), a corresponding method, or a combination thereof with an ordinary method.

Compound (13) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 10) In this step, compound (13) obtained in Step 9 above is reacted with an amino compound (8) to produce compound (I-2) of the present invention. This step may be carried out under the same reaction conditions as in Step 5.

Compound (I-2) of the present invention which is obtained in this manner may be isolated and purified by publicly known separation and purification means such as, for example, concentration, concentration under reduced pressure, solvent extraction, crystallization, reprecipitation or chromatography.

Compound (I-3) of the present invention may be produced by the following scheme.

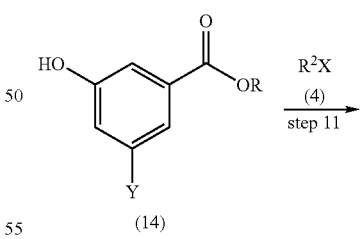

(14)

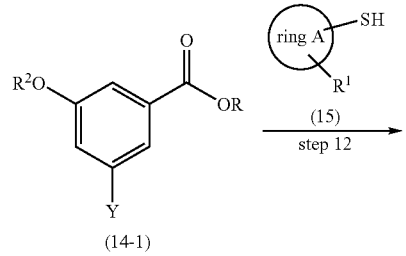

(14-1)

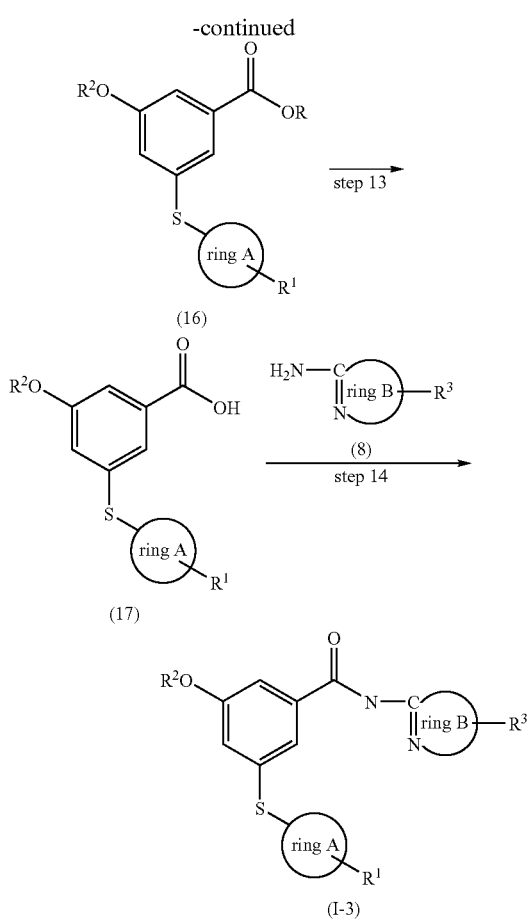

[wherein Y represents a halogen atom, and the other symbols have the same definitions specified above]

(Step 11) In this step, compound (14) is reacted with compound (4) above to produce compound (14-1). The number of equivalents of compound (4) used with respect to 1 equivalent of the phenol derivative (14), and the reaction conditions such as the reaction temperature, reaction time, etc. in this step may be according to the method of Step 7 above.

Compound (14-1) obtained in this manner may be isolated and purified by publicly known separation and purification means such as, for example, concentration, concentration under reduced pressure, solvent extraction, reprecipitation, crystallization or chromatography, or it may be supplied to the subsequent step without isolation and purification.

(Step 12) In this step, compound (14-1) obtained in Step 11 above is reacted with compound (15) to produce compound (16).

This reaction may be carried out by reacting compound (14-1) and a mercapto derivative (15) in the presence of a base, hydroquinone and copper bromide.

As bases to be used in this step there may be mentioned potassium carbonate, cesium carbonate, sodium hydride and the like, among which potassium carbonate and sodium hydride are preferred.

The amount of the base used in this step will usually be from 0.5 to 20 equivalents, and preferably from 3 to 10 equivalents, with respect to 1 equivalent of compound (14-1).

The amount of hydroquinone used in this step will usually be from 0.1 to 10 equivalents, and preferably from 0.2 to 1.5 equivalents, with respect to 1 equivalent of compound (14-1).

The amount of copper bromide used in this step will usually be from 0.1 to 10 equivalents, and preferably from 0.2 to 2 equivalents, with respect to 1 equivalent of compound (14-1).

The reaction temperature will usually be from 25° C. to the reflux temperature of the reaction solvent, and preferably from 50° C. to the reflux temperature of the reaction solvent.

The reaction time will usually be from 10 minutes to 24 hours, and preferably from 15 minutes to 3 hours.

The reaction solvent used in this step is not particularly restricted so long as it does not impede the reaction, but a specific preferred example is N,N-dimethylformamide.

Compound (16) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 13) In this step, the protective group for the carboxyl group of compound (16) obtained in Step 12 above is removed to produce compound (17).

This step may be carried out according to the same method as in Step 4 or 9, or by a method described in the relevant literature (for example, Protective Groups in Organic Synthesis, T. W. Green, 2nd printing, John Wiley & Sons, 1991), a corresponding method, or a combination thereof with an ordinary method.

Compound (17) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 14) In this step, compound (17) obtained in Step 13 above is reacted with compound (8) to produce compound (I-3) of the present invention.

This reaction is an amide bond-forming reaction, and the reaction conditions including the reaction temperature and reaction solvent may be the same as in Step 5 or Step 10 above.

Compound (I-3) of the present invention which is obtained in this manner may be isolated and purified by publicly known separation and purification means such as, for example, concentration, concentration under reduced pressure, solvent extraction, crystallization, reprecipitation or chromatography.

Compound (I-4) of the present invention may be produced according to the following scheme.

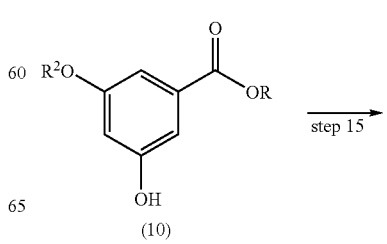

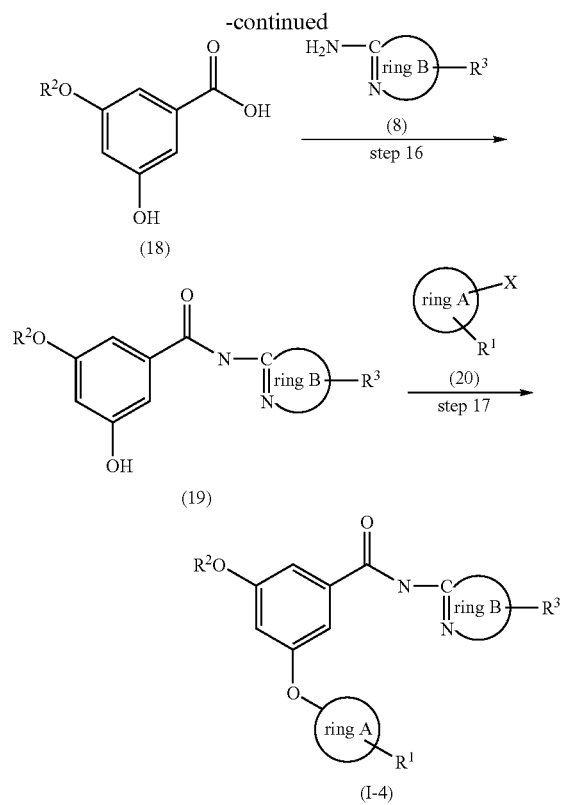

[wherein Ring A represents a pyridine ring, pyrazine ring, pyrimidine ring or pyridazine ring, and the other symbols have the same definitions specified above]

in the presence of a base to produce compound (I-4) of the present invention.

The amount of the halogen compound (20) used in this step will usually be from 0.5 to 10 equivalents, and preferably from 1 to 3 equivalents, with respect to 1 equivalent of compound (19).

As bases to be used in this step there may be mentioned potassium carbonate, cesium carbonate, sodium hydride and the like, with potassium carbonate being preferred among these.

The amount of the base to be used in this step will usually be from 0.5 to 20 equivalents, and preferably from 1 to 10 equivalents, with respect to 1 equivalent of compound (19).

The reaction temperature will generally be from 25° C. to the reflux temperature of the reaction solvent, and it is preferably from 50° C. to the reflux temperature of the reaction solvent.

The reaction time will usually be from 1 to 48 hours, and preferably from 1 to 24 hours.

The reaction solvent used in this step is not particularly restricted so long as it does not impede the reaction, but a specific preferred example is N,N-dimethylformamide.

When $R^1$ requires a protective group, the necessary protective group may be introduced according to the type of $R^1$ group. The protecting group for $R^1$ may be any group which functions as a protective group for $R^1$ in Step 17 and which can be easily removed thereafter.

The method of introducing and removing the protective group for $R^1$ may be a method described in the relevant literature (for example, Protective Groups in Organic Synthesis, T. W. Green, 2nd printing, John Wiley & Sons, 1991), a corresponding method, or a combination thereof with an ordinary method.

Substituent $R^{11}$ on Ring A may also be converted to R.

Conversion of substituent $R^{11}$ on Ring A to R' may be carried out by a method described in the relevant literature (for example, Comprehensive Organic Synthesis, Vol. 6, Pergamon Press, 1991; Comprehensive Organic Transformations, Richard L. et al., VCH Publishers, 1988), a corresponding method, or a combination thereof with an ordinary method.

As examples for $R^{11}$ there may be mentioned halogen atoms and alkoxycarbonyl.

When $R^{11}$ is, for example, alkoxycarbonyl, the alkoxycarbonyl may be reduced for conversion to hydroxymethyl.

The reaction for conversion of an alkoxycarbonyl to hydroxymethyl may be reaction between a compound having an alkoxycarbonyl group and lithium aluminum hydride to produce a compound having hydroxymethyl as $R^1$.

Alternatively, a compound having hydroxymethyl as $R^1$ may be subjected to azidation followed by reduction reaction for conversion to aminomethyl.

[wherein the symbols have the same definitions specified above]

(Step 15) In this step, the protective group for the carboxyl group of compound (10) obtained in Step 7 above is removed. This step is carried out under the same reaction conditions as in Step 4 above, or according to a method described in the relevant literature (for example, Protective Groups in Organic Synthesis, T. W. Green, 2nd printing, John Wiley & Sons, 1991), a corresponding method, or a combination thereof with an ordinary method.

Compound (18) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 16) In this step, compound (18) obtained in Step 15 above is reacted with compound (8) to produce compound (19). This reaction is an amide bond-forming reaction, and the reaction conditions including the reaction temperature and reaction solvent may be the same as in Step 5 or Step 10 above.

Compound (19) of the present invention which is obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 17) In this step, compound (19) obtained in Step 16 above is reacted with a halogen compound represented by the following formula (20):

When the halogen compound (20) represented by the formula shown above has $R^{11}$ as a substituent on Ring A, $R^{11}$ may also have a protective group.

The method of introducing the protective group may be a method described in the relevant literature (for example, Protective Groups in Organic Synthesis, T. W. Green, 2nd printing, John Wiley & Sons, 1991), a corresponding method, or a combination thereof with an ordinary method.

Compound (I-4) obtained in this manner may be isolated and purified by publicly known separation and purification means such as, for example, concentration, concentration under reduced pressure, solvent extraction, crystallization, reprecipitation or chromatography.

Compound (I-5) of the present invention may be produced by the following scheme.

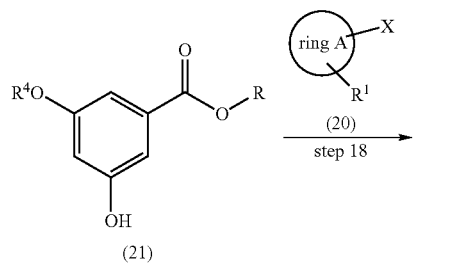

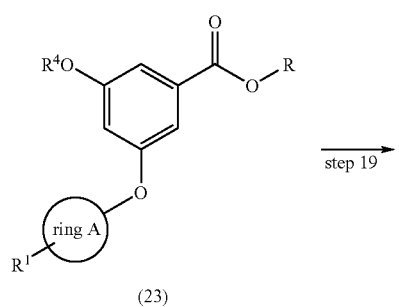

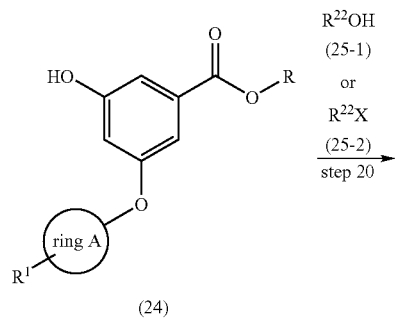

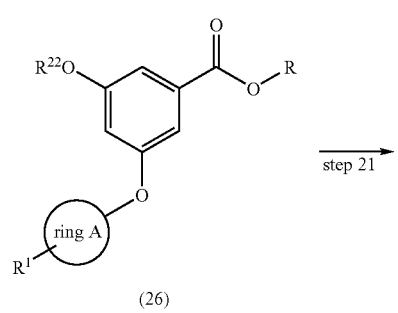

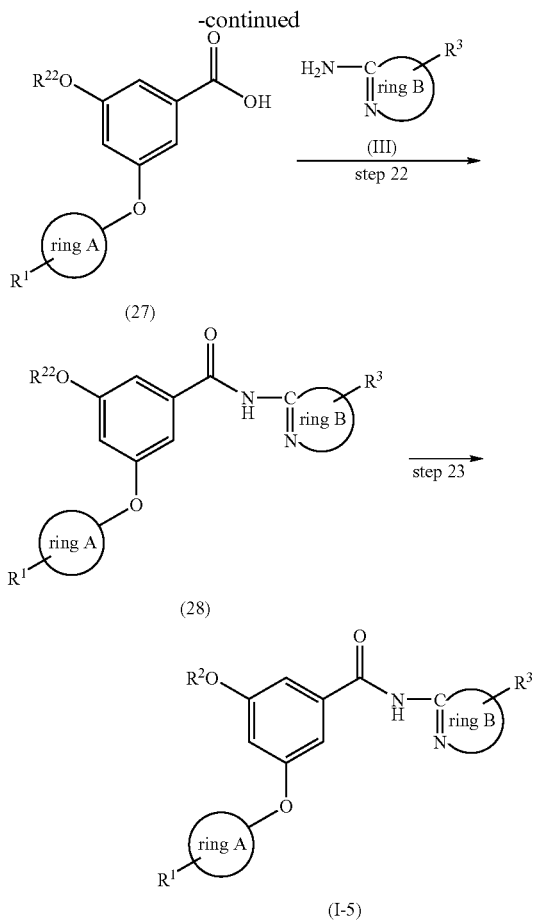

[wherein $R^{22}$ represents $R^2$ optionally having a substituent, and the other symbols have the same definitions specified above]

(Step 18) In this step, compound (21) is reacted with a halogen compound represented by formula (20) below:

[wherein $R^4$ represents a protective group for hydroxy, and the other symbols have the same definitions specified above]

in the presence of a base, to produce compound (23).

The method of introducing the protective group $R^4$ for the hydroxy group of compound (21) used in this step may be a method described in the aforementioned literature (for example, Protective Groups in Organic Synthesis, T. W. Green, 2nd printing, John Wiley & Sons, 1991), a corresponding method, or a combination thereof with an ordinary method.

This step may be carried out by the same method as in Step 17 above, a corresponding method, or a combination thereof with an ordinary method.

As examples of specific groups for $R^4$ there may be mentioned methoxymethyl, benzyl, 4-methoxy-benzyl, 2-(trimethylsilyl)ethoxymethyl, tert-butyldimethylsilyl and tert-butylcarbonyl.

The amount of compound (20) used will differ depending on the types of compounds and solvents used and the other reaction conditions, but it will usually be from 0.1 to 20 equivalents, and preferably from 0.5 to 5 equivalents, with respect to 1 equivalent of compound (21).

The amount of the base used will differ depending on the types of compounds and solvent used and the other reaction conditions, but it will usually be from 0.1 to 20 equivalents, and preferably from 0.5 to 5 equivalents.

The base used may be any one which allows compound (23) to be produced by reaction between compound (20) and compound (21) in this step, and as examples there may be mentioned cesium carbonate, sodium carbonate, potassium carbonate, potassium phosphate, potassium acetate, potassium tert-butyrate and triethylamine.

The reaction solvent used may be an inert solvent and it is not particularly restricted so long as it does not impede the reaction, but as specific examples there may be mentioned pyridine, toluene, 1,4-dioxane, N,N-dimethylformamide, N,N-dimethylacetamide, dimethylsulfoxide and 1-methyl-2-pyrrolidinone.

Copper (I) oxide, copper (II) oxide or copper (I) chloride may be copresent in the reaction system for this step.

Also, a palladium salt such as palladium (II) acetate or palladium (II) chloride and a ligand such as 2-(di-tert-butylphosphino)biphenyl or triphenylphosphine may be copresent in the reaction system for this step.

In addition, silver carbonate, silver acetate, silver oxide, silver trifluoroacetate or the like may also be copresent in the reaction system for this step.

The reaction temperature in this step will usually be from 0° C. to the reflux temperature of the reaction solvent, and preferably from room temperature to 150° C.

The reaction time in this step will usually be from 0.1 to 72 hours, and preferably from 0.5 to 5 hours.

Compound (23) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification.

(Step 19) In this step, the protective group for the hydroxy group of compound (23) obtained in Step 18 above is removed to produce compound (24).

The removal of the protective group in this step may be accomplished by a method described in the relevant literature (for example, Protective Groups in Organic Synthesis, T. W. Green, 2nd printing, John Wiley & Sons, 1991), a corresponding method, or a combination thereof with an ordinary method, or when $R^4$ is methoxymethyl, removal of the protective group may be accomplished using, for example, trifluoroacetic acid (TFA), hydrochloric acid or the like.

When TFA is used for removal of $R^4$, the amount of TFA will usually be from 0.5 to 1000 equivalents, and preferably from 1 to 100 equivalents.

When hydrochloric acid is used for removal of $R^4$, the amount of hydrochloric acid will usually be from 0.5 to 1000 equivalents, and preferably from 1 to 100 equivalents.

The reaction solvent used in this step is not particularly restricted so long as it does not impede the reaction, and as examples there may be mentioned methylene chloride, chloroform, methanol and 1,4-dioxane.

The reaction temperature will usually be from 0° C. to the reflux temperature of the reaction solvent, and preferably from room temperature to the reflux temperature of the reaction solvent.

The reaction time will usually be from 0.1 to 72 hours, and preferably from 0.5 to 12 hours.

Compound (24) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 20) In this step, compound (24) obtained in the previous step is reacted with compound (25-1) or (25-2) to produce compound (26).

The reaction between compound (24) and compound (25-1) is a Mitsunobu reaction, which may be carried out in the presence of a phosphine compound and an azo compound, according to a method described in the relevant literature (for example, Mitsunobu, O., The use of diethyl azodicarboxylate and triphenylphosphine in synthesis and transformation of natural products, Synthesis, Vol. 1, 1981, p 1-28), a corresponding method, or a combination thereof with an ordinary method.

The amount of the alcohol compound (25-1) used in this step will usually be from 0.5 to 10 equivalents, and preferably from 1 to 3 equivalents, with respect to 1 equivalent of compound (24).

As examples of ordinary phosphine compounds to be used in this step there may be mentioned triphenylphosphine and triethylphosphine.

The amount of the phosphine compound to be used will usually be from 0.5 to 10 equivalents, and preferably from 1 to 3 equivalents, with respect to 1 equivalent of compound (24).

As examples of azo compounds to be used there may be mentioned diethyl azodicarboxylate and diisopropyl azodicarboxylate.

The amount of the azo compound to be used will usually be from 0.5 to 10 equivalents, and preferably from 1 to 3 equivalents, with respect to 1 equivalent of compound (24).

The reaction time in this step will usually be from 1 to 48 hours, and preferably from 4 to 12 hours.

The reaction temperature in this step will usually be from 0° C. to the reflux temperature of the reaction solvent, and preferably from 15 to 30° C.

The reaction solvent to be used in this step is not particularly restricted so long as it does not impede the reaction, and as specific examples there may be mentioned tetrahydrofuran and toluene.

The reaction between compound (24) and compound (25-2) may be carried out by the same method as in Step 2 above.

The number of equivalents of the halogen compound (25-2) with respect to compound (24), and the reaction conditions such as the reaction temperature, reaction time, etc. may be according to the method of Step 2 above, a corresponding method, or a combination thereof with an ordinary method.

Compound (26) may be produced by reaction between compound (24) and a compound represented by formula (25-3):

$$R^{22}\text{—}X^3 \qquad (25\text{-}3)$$

[wherein $R^{22}$ represents $R^2$ optionally having a substituent, and $X^3$ represents a leaving group such as mesylate or tosylate].

The number of equivalents of compound (25-3) with respect to compound (24), and the reaction conditions such as the reaction temperature, reaction time, etc. may be according to the method of Step 2 above, a corresponding method, or a combination thereof with an ordinary method.

Compound (26) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification.

(Step 21) In this step, the protective group R for the carboxyl group of compound (26) obtained in the previous step is removed to produce compound (27).

This step may be carried out under the same reaction conditions as in Step 4 above, or by a method described in the relevant literature (for example, Protective Groups in Organic Synthesis, T. W. Green, 2nd printing, John Wiley & Sons, 1991), a corresponding method, or a combination thereof with an ordinary method.

Compound (27) obtained in this manner may be isolated and purified by publicly known separation and purification means such as, for example, concentration, concentration under reduced pressure, solvent extraction, crystallization, reprecipitation or chromatography, or it may be supplied to the subsequent step without isolation and purification.

(Step 22) In this step, compound (27) obtained in the previous step is reacted with an amino compound (III) to produce compound (28).

This step is an amide bond-forming reaction, and the reaction conditions including the reaction temperature and reaction solvent may be the same as in Steps 5 and 10 above.

Compound (28) of the present invention which is obtained in this manner may be isolated and purified by publicly known separation and purification means such as, for example, concentration, concentration under reduced pressure, solvent extraction, crystallization, reprecipitation or chromatography.

When $R^{22}$ in compound (28) has no protective group, compound (28) will correspond to a compound of the present invention.

Also, when a protective group is present on $R^{22}$ and/or $R^3$ of compound (28), the protective group may be removed to produce compound (I-5) of the present invention. Removal of the protective group may be accomplished by a method described in the relevant literature (for example, Protective Groups in Organic Synthesis, T. W. Green, 2nd printing, John Wiley & Sons, 1991), a corresponding method, or a combination thereof with an ordinary method.

An example where a protective group is necessary is the case where the substituent on $R^2$ is hydroxy, and as an example of a protective group for hydroxy there may be mentioned tert-butyldimethylsilyl, which may be removed using hydrochloric acid, trifluoroacetic acid, sodium hydroxide, tetrabutylammonium fluoride or the like.

As an example of one set of compounds for compound (20) to be used in Step 18 there may be mentioned compounds represented by the following formula (22):

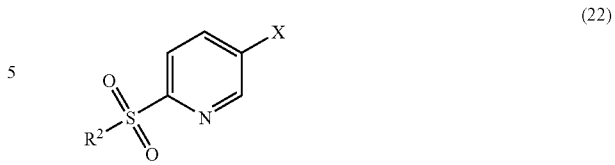

[wherein the symbols have the same definitions specified above], and these compounds may be produced by the scheme illustrated below.

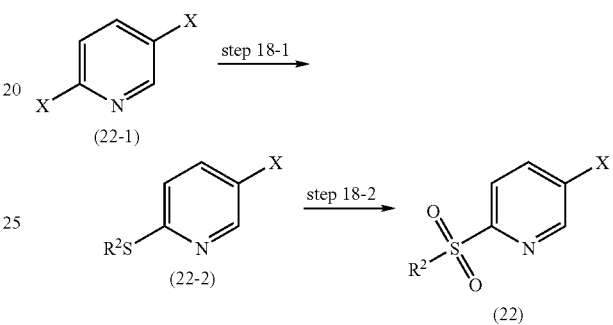

[where the symbols have the same definitions specified above]

(Step 18-1) In this step, a dihalopyridine compound (22-1) is reacted with a sodium thioalkoxide to produce an alkylsulfanylpyridine derivative (22-2).

As specific examples of dihalopyridines to be used in this step there may be mentioned 2,5-dibromopyridine, 2,5-dichloropyridine, 2,5-diiodopyridine, 5-bromo-2-chloropyridine, 2-chloro-5-iodopyridine and 5-bromo-2-fluoropyridine.

The sodium thioalkoxide used in this step will usually be from 0.1 to 3 equivalents, and preferably from 1 to 2 equivalents, with respect to 1 equivalent of compound (22-1).

As specific examples of sodium thioalkoxides to be used there may be mentioned sodium thiomethoxide, sodium thioethoxide, and the like.

The solvent used in this step may be, for example, an inert solvent, with no particular restrictions so long as it does not impede the reaction, and as specific examples there may be mentioned N,N-dimethylformamide, tetrahydrofuran, 1-methyl-2-pyrrolidinone, water, and the like.

The reaction time in this step will usually be from 0.5 to 72 hours, and preferably from 1 to 12 hours.

Compound (22-2) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification.

(Step 18-2) This step is a method of reacting compound (22-2) obtained in Step 18-1 above with mCPBA to produce compound (22).

The oxidation reaction in this step may be carried out by the same method as in Step 3 described above, a corresponding method, or a combination thereof with an ordinary method.

The amount of mCPBA, the reaction temperature, the reaction time and the reaction solvent used in this step may be according to Step 3, or according to a corresponding method.

As oxidizing agents to be used in this step there may be mentioned hydrogen peroxide water, sodium tungstate, sodium hypochlorite and the like.

The amount of oxidizing agent to be used in this step will usually be from 0.1 to 10 equivalents, and preferably from 1 to 5 equivalents, with respect to 1 equivalent of compound (22-2).

The solvent used for this step is not particularly restricted so long as it does not impede the reaction, and specifically there may be mentioned acetonitrile, ethanol, methanol, and the like.

Compound (22) obtained in this manner may be isolated and purified by publicly known separation and purification means such as, for example, concentration, concentration under reduced pressure, crystallization, solvent extraction, reprecipitation or chromatography.

Compound (I-6) of the present invention may be produced by the following scheme.

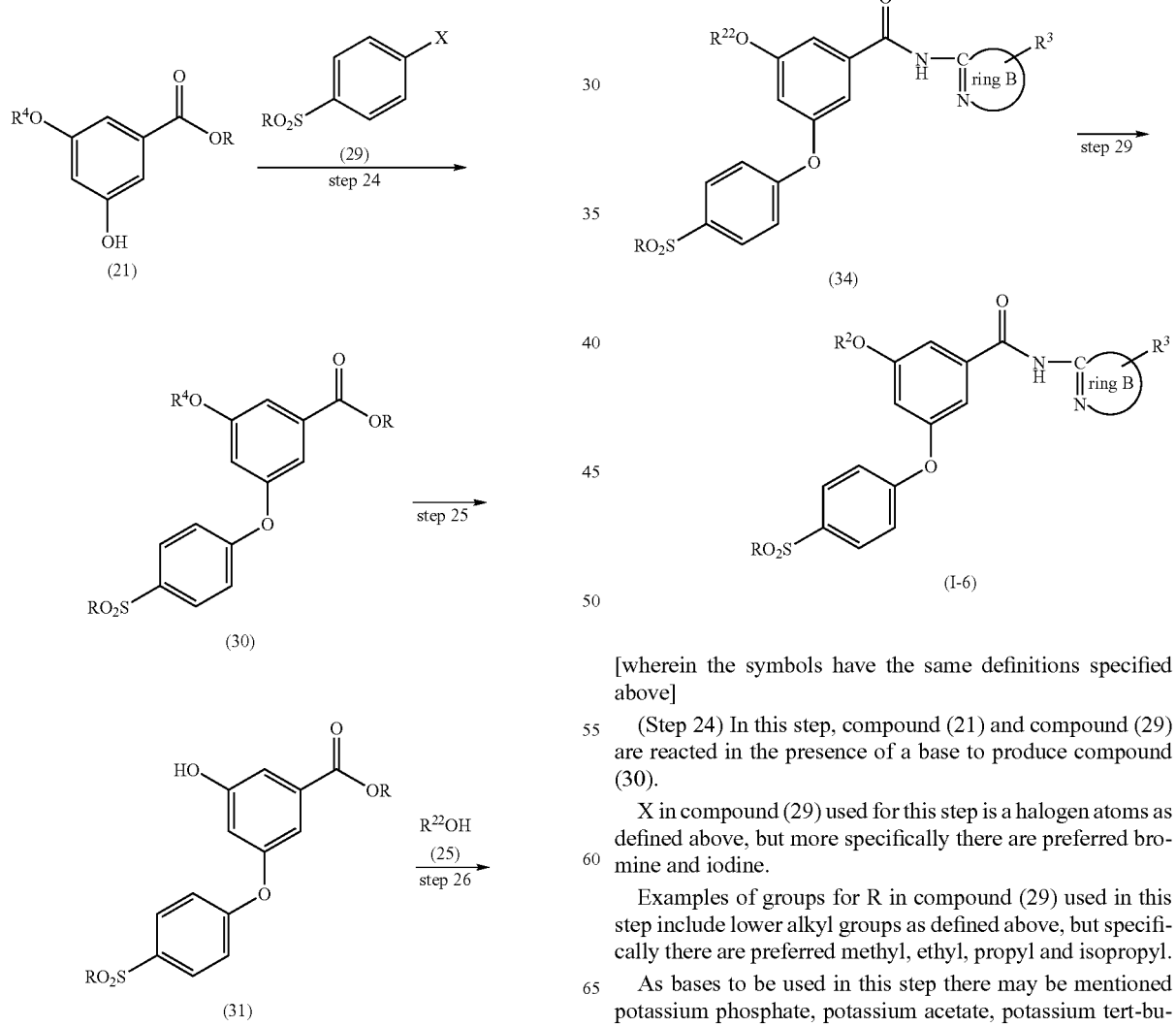

[wherein the symbols have the same definitions specified above]

(Step 24) In this step, compound (21) and compound (29) are reacted in the presence of a base to produce compound (30).

X in compound (29) used for this step is a halogen atoms as defined above, but more specifically there are preferred bromine and iodine.

Examples of groups for R in compound (29) used in this step include lower alkyl groups as defined above, but specifically there are preferred methyl, ethyl, propyl and isopropyl.

As bases to be used in this step there may be mentioned potassium phosphate, potassium acetate, potassium tert-butyrate, triethylamine and the like.

The amount of the base used in this step will usually be from 0.01 to 10 equivalents, and preferably from 0.1 to 2 equivalents, with respect to 1 equivalent of compound (21).

Also, a palladium salt such as palladium (II) acetate or palladium (II) chloride and a ligand such as 2-(di-tert-butylphosphino)biphenyl or triphenylphosphine may be copresent in the reaction system for this step.

The amount of the palladium salt used in this step will usually be from 0.01 to 10 equivalents, and preferably from 0.1 to 2 equivalents, with respect to 1 equivalent of compound (21).

The amount of the ligand used in this step will usually be from 0.1 to 10 equivalents, and preferably from 0.5 to 2 equivalents with respect to compound (21).

The reaction temperature will usually be from room temperature to the reflux temperature of the reaction solvent, and preferably from 50° C. to the reflux temperature of the reaction solvent.

The reaction solvent used may be any one which does not impede the reaction, and there may be mentioned, for example, toluene, 1,4-dioxane, N,N-dimethylformamide, tetrahydrofuran, 1-methyl-2-pyrrolidinone, and the like.

The reaction time will usually be from 0.5 to 72 hours, and preferably from 1 to 12 hours.

Compound (30) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification.

(Step 25) In this step, the protective group $R^4$ for the hydroxy group in compound (30) obtained in Step 24 above is removed to produce compound (31). The reaction for removal of the hydroxy group of compound (30) may be carried out by a method described in the literature (for example, Protective Groups in Organic Synthesis, T. W. Green, 2nd printing, John Wiley & Sons, 1991), a corresponding method, or a combination thereof with an ordinary method, or alternatively the target compound may be produced by the same method as in Step 19 above, a corresponding method, or a combination thereof with an ordinary method.

Compound (31) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification.

(Step 26) In this step, compound (31) obtained in Step 25 above is reacted with $R^{22}OH$ to produce compound (32).

The reaction carried out in this step is a Mitsunobu reaction, which may be conducted in the presence of a phosphine compound and an azo compound according to the aforementioned method described in the literature (for example, Mitsunobu, O., The use of diethyl azodicarboxylate and triphenylphosphine in synthesis and transformation of natural products, Synthesis, Vol. 1, 1981, p 1-28), a corresponding method, or a combination thereof with an ordinary method.

The amount of the alcohol compound (25) used for this step will usually be from 0.5 to 10 equivalents, and preferably from 1 to 3 equivalents, with respect to 1 equivalent of compound (31).

As ordinary examples of phosphine compounds to be used for this step there may be mentioned triphenylphosphine and triethylphosphine.

The amount of the phosphine compound used will usually be from 0.5 to 10 equivalents, and preferably from 1 to 3 equivalents with respect to 1 equivalent of compound (31).

As examples of azo compounds to be used there may be mentioned diethyl azodicarboxylate, diisopropyl azodicarboxylate, and the like.

The amount of the azo compound used will usually be from 0.5 to 10 equivalents, and preferably from 1 to 3 equivalents, with respect to 1 equivalent of compound (31).

The reaction time in this step will usually be from 1 to 48 hours, and preferably from 4 to 12 hours.

The reaction temperature in this step will usually be from 0° C. to the reflux temperature of the reaction solvent, and preferably from 15 to 30° C.

The reaction solvent used in this step is not particularly restricted so long as it does not impede the reaction, and as specific examples there may be mentioned tetrahydrofuran and toluene.

Compound (32) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification.

(Step 27) In this step, the protective group for the carboxyl group of compound (32) above is removed to produce compound (33). This step may be carried out by the same method as in Step 21, etc. described above, a corresponding method, or a combination thereof with an ordinary method.

Compound (33) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification.

(Step 28) In this step, compound (33) obtained in Step 27 above is reacted with a compound represented by formula (III) to produce compound (34).

The reaction in this step is an amide bond-forming reaction, which may be carried out by the same method as in Step 22 above, a corresponding method, or a combination thereof with an ordinary method.

Compound (34) obtained in this manner may be isolated and purified by publicly known separation and purification means such as, for example, concentration, concentration under reduced pressure, crystallization, solvent extraction, reprecipitation or chromatography, or it may be supplied to the subsequent step without isolation and purification. When no protective group is present for $R^3$ and/or $R^{22}$ in compound (34), compound (34) corresponds to a compound of the present invention.

(Step 29) When $R^3$ and/or $R^{22}$ in compound (34) obtained in Step 28 above has a protective group, the protective group is appropriately removed in this step to produce compound (I-5) of the present invention.

The reaction in this step may be conducted according to the aforementioned method described in the literature (for example, Protective Groups in Organic Synthesis, T. W. Green, 2nd printing, John Wiley & Sons, 1991), a corresponding method, or a combination thereof with an ordinary method.

Compound (I-5) obtained in this manner may be isolated and purified by publicly known separation and purification means such as, for example, concentration, concentration under reduced pressure, crystallization, solvent extraction, reprecipitation or chromatography.

The heteroarylcarbamoylbenzene derivatives provided by the invention may be in the form of pharmaceutically acceptable salts, and such salts may be produced according to ordinary methods using compounds of formulas (I-1), (I-2), (I-3), (I-4), (I-5) and (I-6) above which are within the definition of compound (I) of the present invention.

Specifically, when the aforementioned compound (I-1), (I-2), (I-3), (I-4), (I-5) or (I-6) has a basic group derived from amino, pyridyl or the like in the molecule, the compound may be treated with an acid for conversion to a corresponding pharmaceutically acceptable salt.

As examples of such acid addition salts there may be mentioned hydrohalides such as hydrochlorides, hydrofluorides, hydrobromides and hydroiodides; inorganic acid salts such as nitrates, perchlorates, sulfates, phosphates and carbonates; lower alkylsulfonates such as methanesulfonates, trifluoromethanesulfonates and ethanesulfonates; arylsulfonates such as benzenesulfonates, p-toluenesulfonates; organic acid salts such as fumarates, succinates, citrates, tartrates, oxalates and maleates; and acid addition salts with organic acids such as acidic amino acids, including glutamates and aspartates. When the compounds of the invention have acidic groups within such groups, for example, when they have carboxyl groups or the like, the compounds may be treated with bases for conversion to the corresponding pharmaceutically acceptable salts. As examples of such base addition salts there may be mentioned salts of alkali metals such as sodium and potassium, salts of alkaline earth metals such as calcium and magnesium, and salts of organic bases such as ammonium salts, guanidine, triethylamine and dicyclohexylamine. The compounds of the invention may also be in the form of any desired hydrates or solvates of the free compounds or their salts.

For production of a drug for prevention or treatment of type II diabetes or of a condition or symptoms associated therewith, the compound of formula (I) of the present invention may be used in combination with a carrier substance.

Needless to mention, the administered dosage for prevention or treatment of a compound of formula (I) of the present invention will vary depending on the nature of the symptoms to be treated, the specific compound selected, and the route of administration.

The dosage will also vary depending on the age, body weight and sensitivity of each patient. A daily dosage will generally be about 0.001 mg to about 100 mg, preferably about 0.01 mg to about 50 mg and more preferably about 0.1 mg to 10 mg per kilogram of body weight, either as a single dose or as divided doses. Dosages outside of these ranges may sometimes be necessary.

An example of an appropriate oral dosage is at least about 0.01 mg to a maximum of 2.0 g, either as a single dose or divided among 2 to 4 multiple doses per day. The preferred dosage range is between about 1.0 mg and about 200 mg per day, either by one or two administrations. A more preferred dosage range is between about 10 mg and about 100 mg, administered as a single daily dose.

In the case of intravenous administration or oral administration, a typical dosage range is from about 0.001 mg to about 100 mg (preferably from 0.01 mg to about 10 mg) of a compound of formula (I) per day per kilogram of body weight, and more preferably from about 0.1 mg to 10 mg of a compound of formula (I) per day per kilogram of body weight.

As mentioned above, the pharmaceutical composition comprises a compound of formula (I) and a pharmaceutically acceptable carrier. The term "composition" refers to a product obtained by directly or indirectly combining, compounding or aggregating two or more components, a product obtained as a result of dissociation of one or more components, or a product obtained as a result of any other type of action or interaction between components, and the term also includes the active and inactive components (pharmaceutically acceptable excipients) composing the carrier.

Preferred are compositions containing amounts of compounds of formula (I) effective for treating, preventing or delaying the onset of type II diabetes when used in combination with medically acceptable carriers.

An effective amount of a compound of the present invention may be administered by any appropriate route of administration to mammals, and especially humans. Examples of administration routes include oral, intrarectal, local, intravenous, ocular, pulmonary and nasal routes. Examples of dosage forms include tablets, lozenges, powdered agents, suspensions, solutions, capsules, creams and aerosols, among which oral tablets are preferred.

An oral composition may be prepared using any ordinary medicinal media, examples of which include water, glycol, oil, alcohol, aromatic additives, preservatives, coloring agents and the like. Oral liquid compositions may be prepared in the form of, for example, suspensions, elixirs and solutions, using starch, sucrose, microcrystalline cellulose, diluents, granulators, lubricants, binders, disintegrators and the like as carriers, while oral solid compositions may be prepared in the form of, for example, powders, capsules, tablets or the like, among which oral solid compositions are preferred.

Tablets and capsules are the most advantageous oral dosage form because they are easy to administer. If necessary, tablets may be coated by a standard aqueous or non-aqueous technique.

In addition to the ordinary dosage forms mentioned above, the compounds of formula (I) may also be administered by the controlled release means and/or delivery devices described in, for example, U.S. Pat. Nos. 3,845,770, 3,916,899, 3,536,809, 3,598,123, 3,630,200 and 4,008,719.

A pharmaceutical composition of the present invention which is suitable for oral administration may be in the form of granules, tablets, or capsules containing a pre-determined amount of an active ingredient powder or granules, as a water-soluble liquid or non-water-soluble liquid, or as an oil-in-water emulsion or a water-in-oil emulsion. Such compositions may be prepared by any pharmaceutical method, but all methods involve combining an active ingredient with a carrier comprising one or more necessary components.

Generally speaking, a composition may be prepared by uniformly and thoroughly mixing the active ingredient with a liquid carrier, with a completely separated solid carrier, or both, and then shaping the product into an appropriate form if necessary. For example, tablets are prepared by compression and molding, together with one or more secondary ingredients as necessary. Compressed tablets are prepared by using an appropriate machine for admixture of the active ingredient in a powder or granular form with a binder, lubricant, inert excipient, surfactant or dispersing agent as necessary, and compressing the mixture.

Molded tablets are prepared by using an appropriate machine for molding of a mixture of a wetted compound in powder form and an inert liquid diluent.

Each tablet preferably contains from approximately 1 mg to 1 g of the active ingredient, while granules or capsules preferably contain from approximately 1 mg to 500 mg of the active ingredient.

Examples of medicinal dosage forms for the compounds of formula (I) are listed below.

TABLE 1

Suspension for injection (I.M.)

|  | mg/ml |
|---|---|
| Compound of formula (I) | 10 |
| Methyl cellulose | 5.0 |
| Tween80 | 0.5 |
| Benzyl alcohol | 9.0 |
| Benzalkonium chloride | 1.0 |

Water for injection added to 1.0 ml.

TABLE 2

Tablets

|  | mg/tablet |
|---|---|
| Compound of formula (I) | 25 |
| Methyl cellulose | 415 |
| Tween 80 | 14.0 |
| Benzyl alcohol | 43.5 |
| Magnesium stearate | 2.5 |
| Total | 500 mg |

TABLE 3

Capsules

|  | mg/capsule |
|---|---|
| Compound of formula (I) | 25 |
| Lactose powder | 573.5 |
| Magnesium stearate | 1.5 |
| Total | 600 mg |

TABLE 4

Aerosol

|  | Per container |
|---|---|
| Compound of Formula (I) | 24 mg |
| Lecithin, NF Liq. Conc. | 1.2 mg |
| Trichlorofluoromethane, NF | 4.025 g |
| Dichlorodifluoromethane, NF | 12.15 g |

The compounds of formula (I) may be used not only for conditions or symptoms associated with type II diabetes, but also in combination with other drugs applied for treatment, prevention or delay onset of type II diabetes. Such other drugs may be administered either simultaneously or separately from the compound of formula (I), with ordinary routes of administration and dosages.

When the compound of formula (I) is used simultaneously with one or more drugs, it is preferred to use a pharmaceutical composition comprising the compound of formula (I) and the other drugs. Thus, a pharmaceutical composition of the present invention comprises a compound of formula (I) together with one or more other active ingredients. Examples of active ingredients to be used in combination with compounds of formula (I) include, but are not limited to, the following, which may be administered separately or within the same pharmaceutical composition.

(a) Bisguanides (for example, buformin, metformin, phenformin), (b) PPAR agonists (for example, troglitazone, pioglitazone, rosiglitazone), (c) insulin, (d) somatostatin, (e) α-glucosidase inhibitors (for example, voglibose, miglitol, acarbose), and (f) insulin secretagogues (for example, acetohexamide, carbutamide, chlorpropamide, glibomuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide).

The weight ratio of the compound of formula (I) with respect to any second active ingredient may be varied within a wide range, and will depend on the effective amount of each active ingredient. For example, in the case of a combination of a compound of formula (I) with a PPAR agonist, the weight ratio of the compound of formula (I) with respect to the PPAR agonist will generally be from about 1000:1 to 1:1000, and preferably from about 200:1 to 1:200. Combinations of a compound of the formula (I) and other active ingredients will also be within the aforementioned range, but in each case, an effective dose of each active ingredient should be used. The glucokinase activating power of the compounds represented by compound (I) of the present invention, and the test methods used, will now be explained.

The excellent glucokinase activating function of the compounds represented by formula (I) above may be measured by a method described in the relevant literature (for example, Diabetes, Vol. 45, pp. 1671-1677, 1996) or by a corresponding method.

The glucokinase activity is the degree of activation of glucokinase, as determined not by direct measurement of glucose-6-phosphate, but by measurement of the amount of thio-NADH produced upon production of phosphogluconolactone from glucose-6-phosphate by the reporter enzyme glucose-6-phosphate dehydrogenase.

The recombinant human liver GK used in this assay was expressed in *E. coli* as FLAG fusion protein, and it was purified by ANTIFLAG M2 AFFINITY GEL (Sigma).

The assay was carried out using a flat-bottomed 96-well plate at 30° C. A 69 μl portion of assay buffer (25 mM Hepes Buffer: pH=7.2, 2 mM $MgCl_2$, 1 mM ATP, 0.5 mM TNAD, 1 mM dithiothreitol) was dispensed, and either a DMSO solution of the compound or 1 μl of DMSO as a control was added. Next, 20 μl of an enzyme mixture (FLAG-GK, 20 U/ml G6PDH) precooled in ice bath was dispensed, and then 10 μl of 25 mM glucose was added as substrate and reaction was initiated (final glucose concentration=2.5 mM).

After initiation of the reaction, the increase in absorbance at 405 nm was measured every 30 seconds during a 10 minute period, and the increase during the first 5 minutes was used to evaluate the compound. FLAG-GK was added to produce an absorbance increment of from 0.05 to 0.1 after 5 minutes in the presence of 1% DMSO.

The OD values were measured at each concentration of the evaluated compound, using the OD value of the DMSO control as 100%. The Emax (%) and EC50 (μM) values were calculated from the OD value at each concentration, and used as indices of the GK activating power of the compounds.

The GK activating power of the compounds of the invention were measured by this method. The results are shown in Table 1 below.

TABLE 5

(GK activating power of compounds of the invention)

| Compound No. | Emax(%) | EC50(µM) |
|---|---|---|
| Production Example 1 | 957 | 0.25 |
| Production Example 2 | 844 | 0.08 |
| Production Example 59 | 936 | 0.53 |

As shown in Table 1, the compounds of the invention exhibit excellent GK activating power based on the Emax and EC50 values.

BEST MODE FOR CARRYING OUT THE INVENTION

The present invention will now be explained in greater detail through Formulation Examples and Production Examples, with the understanding that the invention is in no way limited to these examples.

Formulation Example 1

Ten parts of the compound of Production Example 1, 15 parts of heavy magnesium oxide and 75 parts of lactose were uniformly mixed to prepare a pulverulent or fine granular powdered medicine with a size of no greater than 350 µm. The powdered medicine was placed in capsule containers to prepare capsules.

Formulation Example 2

Forty-five parts of the compound of Production Example 1, 15 parts of starch, 16 parts of lactose, 21 parts of microcrystalline cellulose, 3 parts of polyvinyl alcohol and 30 parts of distilled water were uniformly mixed, and the mixture was subsequently crushed, granulated and dried and then filtered to prepare granules having sizes with diameters of 1410 to 177 µm.

Formulation Example 3

After preparing granules by the same method as in Formulation Example 2, 3 parts of calcium stearate was added with respect to 96 parts of the granules and the mixture was compression molded to form tablets with diameters of 10 mm.

Formulation Example 4

Ten parts of microcrystalline cellulose and 3 parts of calcium stearate were added with respect to 90 parts of the granules obtained by the method in Formulation Example 2, and the mixture was compression molded to form tablets with diameters of 8 mm, after which a mixed suspension of syrup gelatin and sedimentary calcium carbonate was added to prepare sugar-coated tablets.

The present invention will now be explained in greater detail through Production Examples and Reference Examples, with the understanding that the invention is in no way limited to these examples.

The thin-layer chromatography carried out in the examples employed Silicagel 60F$_{245}$ (Merck) as the plate and a UV detector as the detection method. The column silica gel used was Wakogel™-300 (Wako Pure Chemical Industries), and the reverse-phase column silica gel used was LC-SORB™ SP-B-ODS (Chemco) or YMC-GEL™ ODS-AQ 120-S50 (Yamamura Kagaku Kenkyujo).

The abbreviations in the examples are explained below.

i-Bu: isobutyl n-Bu: n-butyl t-Bu: t-butyl

Me: methyl

Et: ethyl

Ph: phenyl i-Pr: isopropyl n-Pr: n-propyl

CDCl$_3$: heavy chloroform

CD$_3$OD: heavy methanol

DMSO-d$_6$: heavy dimethylsulfoxide

The abbreviations for the nuclear magnetic resonance spectra are explained below.

s: singlet d: doublet dd: double doublet t: triplet m: multiplet br: broad q: quartet J: coupling constant Hz: Hertz

Production Example 1

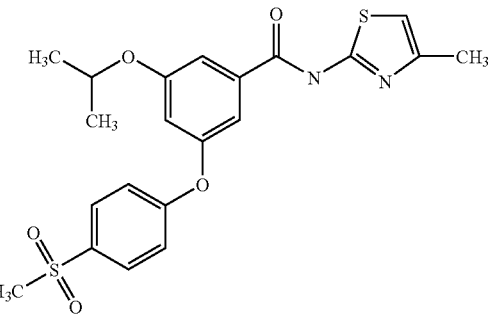

Preparation of 5-isopropoxy-3-(4-methanesulfonylphenoxy)-N-(4-methylthiazol-2-yl)-benzamide After adding 29.0 g of molecular sieves 4A, 22.0 g (0.13 mol) of p-methylthiophenylboric acid, 21.6 g (0.13 mol) of copper (II) acetate and 83.0 ml (0.59 mol) of triethylamine to a solution of 20.0 g (0.12 mol) of 3,5-dihydroxybenzoic acid methyl ester in methylene chloride (1.2 l), the mixture was stirred at room temperature overnight under an oxygen atmosphere. The reaction mixture was filtered and then concentrated under reduced pressure, and the obtained residue was purified by silica gel column chromatography (hexane:acetic acid ethyl ester=2:1) to obtain 12.4 g of 5-hydroxy-3-(4-methylthiophenoxy)benzoic acid methyl ester (yield: 36%) as a yellow solid.

After adding 129 mg (0.94 mmol) of potassium carbonate and 0.053 ml (0.56 mmol) of 2-bromopropane to a solution of 54.4 mg (0.19 mmol) of the obtained phenolic compound in N,N-dimethylformamide (2.5 ml), the reaction mixture was stirred at 80° C. for 4 hours. Water was added to the reaction mixture, extraction was performed with acetic acid ethyl ester, and then the organic layer was washed with brine, dried and concentrated under reduced pressure. The obtained residue was purified by silica gel column chromatography (hexane:acetic acid ethyl ester=2:1) to obtain 55.4 mg of 5-isopropoxy-3-(4-methylthiophenoxy)-benzoic acid methyl ester (yield: 89%) as a colorless oil. After adding 64.0 mg (0.37 mmol) of m-chloroperbenzoic acid to a solution of 41.0 mg (0.12 mmol) of the obtained ester compound in chloroform (2.0 ml) while cooling on ice, the reaction mixture was stirred for 20 minutes while cooling on ice. Aqueous sodium thiosulfate was added to the reaction mixture, and the organic layer was washed with saturated aqueous sodium hydrogencarbonate and brine, dried, and concentrated under reduced pressure. The obtained residue was purified by silica gel column chromatography (hexane:acetic acid ethyl ester=1:1) to obtain 43.9 mg of 5-isopropoxy-3-(4-methanesulfonylphenoxy)-benzoic acid methyl ester (yield: 98%) as a colorless oil.

After adding 0.28 ml (0.56 mmol) of aqueous 2N sodium hydroxide to a solution of 41.0 mg (0.11 mmol) of the obtained sulfone compound in methanol (1.0 ml), the reaction mixture was stirred overnight. Aqueous 2N hydrochloric acid was added to the reaction mixture, extraction was performed with acetic acid ethyl ester, and the organic layer was washed with brine, dried and concentrated under reduced pressure to obtain a crude carboxyl compound. After adding 5.90 mg (0.51 mol) of 2-amino-4-methylthiazole, 9.30 mg (0.068 mmol) of 1-hydroxybenzotriazole hydrate and 13.0 mg (0.068 mol) of 1-(3-dimethylaminopropyl)-3-ethylcarbodiimide hydrochloride to a solution of 12.0 mg (0.034 mmol) of the obtained carboxyl compound in methylene chloride (0.5 ml), the mixture was stirred at room temperature overnight. The reaction mixture was concentrated under reduced pressure, and the obtained residue was purified by silica gel column chromatography (hexane:acetic acid ethyl ester=1:1) to obtain the title compound as a white solid. The analysis data for the compound obtained in Production Example 1 are shown below.

$^1$HNMR (CDCl$_3$) δ: 1.34 (6H, d, J=6.0 Hz), 2.22 (3H, d, J=0.7 Hz), 3.08 (3H, s), 4.53-4.57 (1H, m), 6.57 (1H, d, J=0.7 Hz), 6.80 (1H, t, J=2.0 Hz), 7.11 (1H, d, J=2.0 Hz), 7.12 (2H, d, J=8.8 Hz), 7.27 (1H, d, J=2.0 Hz), 7.92 (2H, d, J=8.8 Hz)

ESI-MS (m/e): 447 [M+H]$^+$

Production Example 2

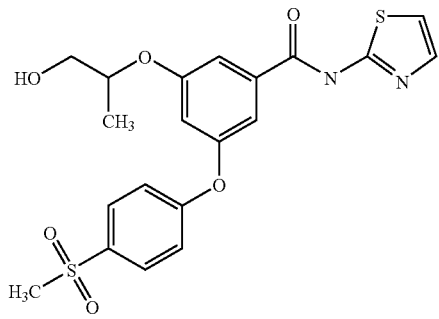

Preparation of 5-(2-hydroxy-1-methyl-ethoxy)-3-(4-methanesulfonylphenoxy)-N-thiazol-2-yl-benzamide After adding 1.40 g (7.40 mmol) of (2R)-1-(t-butyldimethylsiloxy)-2-hydroxypropane and 2.00 g (7.40 mmol) of triphenylphosphine to a solution of 1.20 g (4.13 mmol) of the 5-hydroxy-3-(4-methylthiophenoxy)benzoic acid methyl ester obtained in Production Example 1 in tetrahydrofuran (10 ml), 3.20 ml (7.40 mmol) of diethyl azodicarboxylate was added while cooling on ice, and the mixture was stirred at room temperature for 2 hours. Water was added to the reaction mixture, extraction was performed with acetic acid ethyl ester, and then the organic layer was washed with brine, dried and concentrated under reduced pressure. The obtained residue was purified by silica gel column chromatography (hexane:acetic acid ethyl ester=95:5) to obtain 1.63 g of 5-((1S)-2-(t-butyldimethylsiloxy)-1-methyl-ethoxy)-3-(4-methylthiophenoxy)-benzoic acid methyl ester (yield: 95%) as a colorless oil. After adding 2.06 g (12.0 mmol) of m-chloroperbenzoic acid to a solution of 1.84 g (3.97 mmol) of the obtained ester compound in chloroform (40 ml) while cooling on ice, the reaction mixture was stirred for 0.5 hour while cooling on ice. Aqueous sodium thiosulfate was added to the reaction mixture, and the organic layer was washed with saturated aqueous sodium hydrogencarbonate and brine, dried, and concentrated under reduced pressure to obtain a crude sulfone compound.

After adding 4.00 ml (20.0 mmol) of aqueous 5N sodium hydroxide to a solution of the obtained sulfone compound in methanol (20 ml), the reaction mixture was stirred for 1.5 hours. A 5% aqueous citric acid solution (30 ml) was added to the reaction mixture, extraction was performed with acetic acid ethyl ester, and then the organic layer was washed with brine, dried, and concentrated under reduced pressure to obtain a crude carboxyl compound. After adding 1.20 g (12.0 mmol) of 2-aminothiazole, 1.62 g (12.0 mmol) of 1-hydroxybenzotriazole hydrate and 1.53 g (8.00 mmol) of 1-(3-dimethylaminopropyl)-3-ethylcarbodiimide hydrochloride to a solution of the obtained a crude carboxyl compound in methylene chloride (40 ml), the mixture was stirred at room temperature overnight. The reaction mixture was then stirred for 1.5 hours. Water was added to the reaction mixture, extraction was performed with acetic acid ethyl ester, and the organic layer was washed with a 5% aqueous citric acid, washed with brine, dried and concentrated under reduced pressure to obtain a crude amide compound.

After adding 20 ml of aqueous 4N hydrochloric acid to a solution of the obtained amide compound in 1,4-dioxane (60 ml), the mixture was stirred at room temperature for 15 minutes. The reaction mixture was concentrated under reduced pressure, and then triethylamine was added and the reaction mixture was again concentrated under reduced pressure. The obtained residue was purified by silica gel column chromatography (hexane:acetic acid ethyl ester=1:2) to obtain the title compound as a white solid. The analysis data for the compound obtained in Production Example 2 are shown below.

$^1$HNMR (CDCl$_3$) δ: 1.33 (d, 3H, J=6.2 Hz), 3.10 (s, 3H), 3.80 (m, 2H), 4.56 (m, 1H), 6.88 (m, 1H), 7.03 (d, 1H, J=3.6 Hz), 7.17 (d, 2H, J=8.8 Hz), 7.22 (m, 1H), 7.38 (m, 2H), 7.96 (d, 2H, J=8.8 Hz), 10.8 (br, 1H)

ESI-MS (m/e): 449 [M+H]$^+$

Compounds for the following Production Examples 3 to 58 were obtained by the same method as in Production Example 1 or 2 above. The structures and analysis data for these compounds are shown below.

Production Example 3

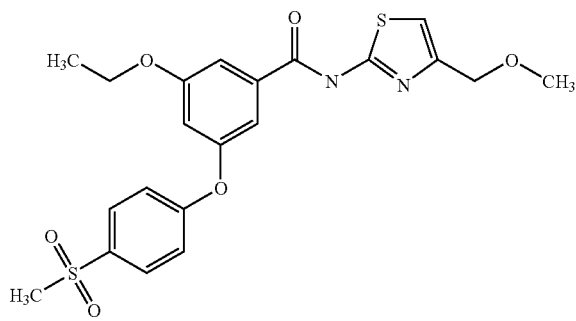

Preparation of 5-ethoxy-3-(4-methanesulfonylphenoxy)-N-(4-methoxymethyl-thiazol-2-yl)benzamide The compound of Production Example 3 was obtained as a colorless oil using the 5-hydroxy-3-(4-methylthiophenoxy)benzoic acid methyl ester obtained in Production Example 1, bromoethane and 2-amino-4-methoxymethyl-thiazole, by the same method as in Production Example 1, a corresponding method, or a combination thereof with an ordinary method.

$^1$HNMR (CDCl$_3$) δ: 1.45 (1H, t, J=7.0 Hz), 3.10 (3H, s), 3.44 (3H, s), 4.10 (2H, q, J=7.0 Hz), 4.45 (2H, s), 6.85 (1H, t, J=2.0 Hz), 6.92 (1H, s), 7.14 (1H, s), 7.15 (2H, d, J=8.8 Hz), 7.29 (1H, s), 7.94 (2H, d, J=8.8 Hz)
ESI-MS (m/e): 463 [M+H]$^+$

Production Example 4

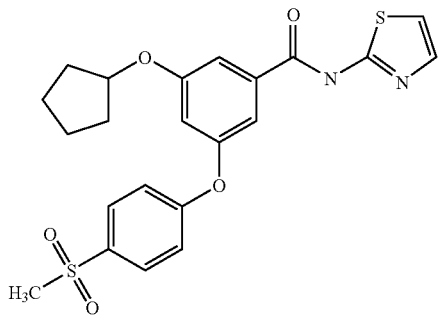

Preparation of 5-cyclopentyloxy-3-(4-methanesulfonylphenoxy)-N-thiazol-2-yl-benzamide The compound of Production Example 4 was obtained as a light yellow oil using the 5-hydroxy-3-(4-methylthiophenoxy)benzoic acid methyl ester obtained in Production Example 1, cyclopentyl bromide and 2-amino-thiazole, by the same method as in Production Example 1, a corresponding method, or a combination thereof with an ordinary method.

$^1$HNMR (CDCl$_3$) δ: 1.61-1.93 (8H, m), 3.07 (3H, s), 4.75-4.79 (1H, m), 6.81 (1H, d, J=2.0 Hz), 6.97 (1H, d, J=3.6 Hz), 7.13 (2H, d, J=8.6 Hz), 7.20 (1H, s), 7.21 (1H, d, J=3.6 Hz), 7.33 (1H, d, J=2.0 Hz), 7.92 (2H, d, J=8.6 Hz)
ESI-MS (m/e): 459 [M+H]$^+$

Production Example 5

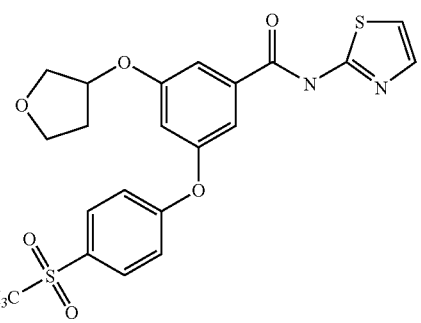

Preparation of 3-(4-methanesulfonylphenoxy)-5-(tetrahydrofuran-3-yloxy)-N-thiazol-2-yl-benzamide The compound of Production Example 5 was obtained as a light yellow oil using the 5-hydroxy-3-(4-methylthiophenoxy)benzoic acid methyl ester obtained in Production Example 1, 3-hydroxytetrahydrofuran and 2-amino-thiazole, by the same method as in Production Example 2, a corresponding method, or a combination thereof with an ordinary method.

$^1$HNMR (CDCl$_3$) δ: 2.14-2.27 (2H, m), 3.08 (3H, s), 3.91-3.99 (4H, m), 4.96-4.97 (1H, m), 6.82 (1H, d, J=1.7 Hz), 6.99 (1H, d, J=3.6 Hz), 7.13 (2H, d, J=8.9 Hz), 7.18 (1H, d, J=3.6 Hz), 7.25 (1H, s), 7.30 (1H, d, J=1.7 Hz), 7.93 (2H, d, J=8.9 Hz)
ESI-MS (m/e): 461 [M+H]$^+$

Production Example 6

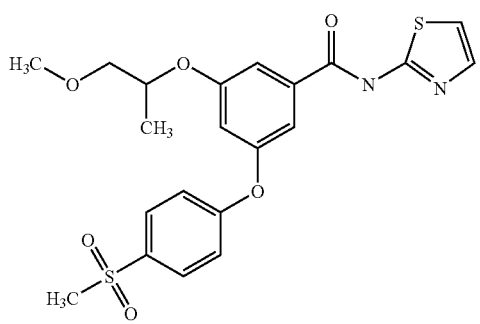

Preparation of 3-(4-methanesulfonylphenoxy)-5-(2-methoxy-1-methyl-ethoxy)-N-thiazol-2-yl-benzamide The compound of Production Example 6 was obtained as a colorless amorphous substance using the 5-hydroxy-3-(4-methylthiophenoxy)benzoic acid methyl ester obtained in Production Example 1, 1-methoxy-2-hydroxy-propane and 2-amino-thiazole, by the same method as in Production Example 2, a corresponding method, or a combination thereof with an ordinary method.

¹HNMR (CDCl₃) δ: 1.31 (d, 3H, J=6.3 Hz), 3.07 (s, 3H), 3.38 (s, 3H), 3.55 (m, 2H), 4.59 (m, 1H), 6.89 (m, 1H), 6.98 (d, 1H, J=3.6 Hz), 7.13 (d, 2H, J=8.8 Hz), 7.22 (m, 1H), 7.25 (d, 1H, J=3.6 Hz), 7.38 (m, 1H), 7.92 (d, 2H, J=8.8 Hz)

ESI-MS (m/e): 463[N+H]⁺

Production Example 7

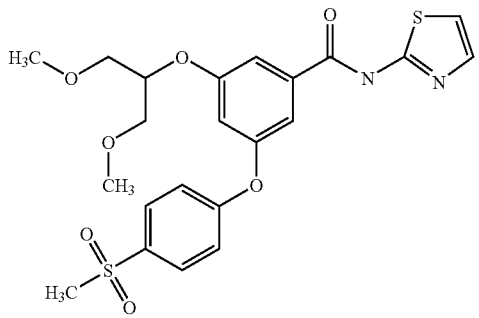

Preparation of 3-(4-methanesulfonylphenoxy)-5-(2-methoxy-1-methoxymethyl-ethoxy)-N-thiazol-2-yl-benzamide The compound of Production Example 7 was obtained as a colorless amorphous substance using the 5-hydroxy-3-(4-methylthiophenoxy)benzoic acid methyl ester obtained in Production Example 1, 1,3-dimethoxy-2-hydroxy-propane and 2-aminothiazole, by the same method as in Production Example 2, a corresponding method, or a combination thereof with an ordinary method.

¹HNMR (CDCl₃) δ: 3.08 (s, 3H), 3.39 (s, 6H), 3.63 (d, 4H, J=4.7 Hz), 4.57 (m, 1H), 6.98 (m, 2H), 7.15 (d, 2H, J=8.9 Hz), 7.27 (m, 2H), 7.45 (m, 1H), 7.93 (d, 2H, J=8.9 Hz)

ESI-MS (m/e): 493 [M+H]⁺

Production Example 8

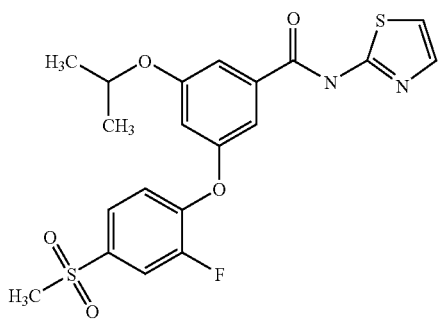

Preparation of 3-(2-fluoro-4-methanesulfonylphenoxy)-5-isopropoxy-N-thiazol-2-yl-benzamide The compound of Production Example 8 was obtained as a light yellow oil using 5-hydroxy-3-(2-fluoro-4-methane-sulfonylphenoxy)benzoic acid methyl ester obtained in the same manner as Production Example 1, 2-bromopropane and 2-amino-thiazole, by the same method as in Production Example 1, a corresponding method, or a combination thereof with an ordinary method.

¹HNMR (CDCl₃) δ: 1.37 (6H, d, J=6.1 Hz), 3.11 (3H, s), 4.60-4.64 (1H, m), 6.81 (1H, t, J=2.2 Hz), 7.02 (1H, d, J=3.6 Hz), 7.15 (1H, t, J=2.2 Hz), 7.21 (1H, dd, J=7.5, 8.5 Hz), 7.31 (1H, t, J=2.2 Hz), 7.40 (1H, d, J=3.6 Hz), 7.72 (1H, ddd, J=1.2, 2.2, 7.5 Hz)

ESI-MS (m/e): 451 [M+H]⁺

Production Example 9

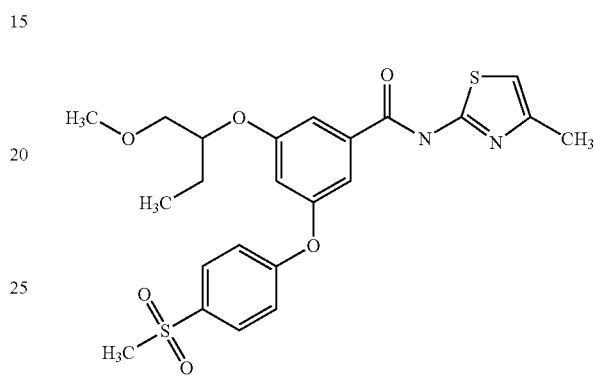

Preparation of 3-(4-methanesulfonylphenoxy)-5-(1-methoxymethyl-propoxy)-N-(4-methyl-thiazol-2-yl)-benzamide The compound of Production Example 9 was obtained as a white amorphous substance using the 5-hydroxy-3-(4-methylthiophenoxy)benzoic acid methyl ester obtained in Production Example 1, 2-hydroxy-1-methoxy-butane and 2-amino-4-methyl-thiazole, by the same method as in Production Example 2, a corresponding method, or a combination thereof with an ordinary method.

¹HNMR (CDCl₃) δ: 0.97 (t, 3H, J=7.3 Hz), 1.71 (quintet, 2H, J=7.3 Hz), 2.23 (s, 3H), 3.08 (s, 3H), 3.36 (s, 3H), 3.54 (m, 2H), 4.32 (m, 1H), 6.56 (s, 1H), 6.90 (m, 1H), 7.13 (d, 2H, J=8.9 Hz), 7.15 (m, 1H), 7.35 (m, 1H), 7.92 (d, 2H, J=8.9 Hz), 10.6 (br, 1H)

ESI-MS (m/e): 491 [M+H]⁺

Production Example 10

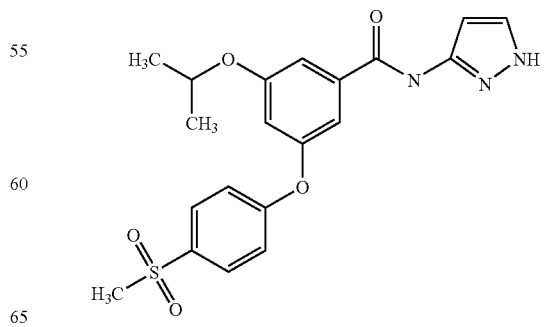

Preparation of 5-isopropoxy-3-(4-methanesulfonylphenoxy)-N-pyrazol-3-yl-benzamide The compound of Production Example 10 was obtained as a light yellow oil using the 5-hydroxy-3-(4-methylthiophenoxy)benzoic acid methyl ester obtained in Production Example 1, 2-bromopropane and 3-aminopyrazole, by the same method as in Production Example 1, a corresponding method, or a combination thereof with an ordinary method.

$^1$HNMR(CDCl$_3$) δ: 1.35 (d, 6H, J=6.0 Hz), 3.06 (s, 3H), 4.58 (septet, 1H, J=6.0 Hz), 6.00 (d, 1H, J=3.0 Hz), 6.78 (m, 1H), 7.15 (d, 2H, J=8.9 Hz), 7.32 (m, 1H), 7.41 (m, 1H), 7.90 (d, 2H, J=8.9 Hz), 8.14 (d, 1H, J=3.0 Hz)

ESI-MS (m/e): 416 [M+H]$^+$

Production Example 11

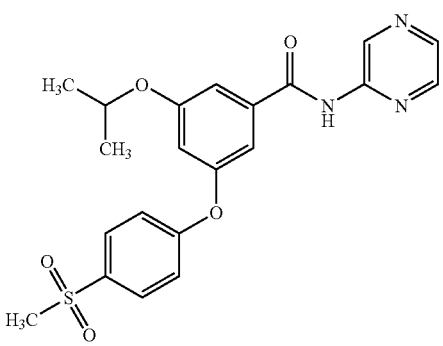

Preparation of 5-isopropoxy-3-(4-methanesulfonylphenoxy)-N-pyrazin-2-yl-benzamide The compound of Production Example 11 was obtained as a white amorphous substance using the 5-hydroxy-3-(4-methylthiophenoxy)benzoic acid methyl ester obtained in Production Example 1, 2-bromopropane and 2-aminopyrazine, by the same method as in Production Example 1, a corresponding method, or a combination thereof with an ordinary method.

$^1$HNMR (CDCl$_3$) δ: 1.39 (d, 6H, J=6.0 Hz), 3.09 (s, 3H), 4.62 (septet, 1H, J=6.0 Hz), 6.82 (m, 1H), 7.14 (m, 1H), 7.17 (d, 2H, J=8.6 Hz), 7.39 (m, 1H), 7.95 (d, 2H, 8.6 Hz), 8.30 (m, 1H), 8.41 (m, 2H), 9.68 (brs, 1H)

ESI-MS (m/e): 428 [M+H]$^+$

Production Example 12

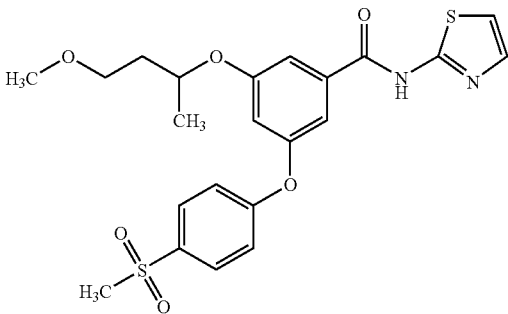

Preparation of 3-(4-methanesulfonylphenoxy)-5-(3-methoxy-1-methyl-propoxy)-N-thiazol-2-yl-benzamide The compound of Production Example 12 was obtained as a white amorphous substance using the 5-hydroxy-3-(4-methylthiophenoxy)benzoic acid methyl ester obtained in Production Example 1, 2-bromo-4-methoxybutane and 2-aminothiazole, by the same method as in Production Example 1, a corresponding method, or a combination thereof with an ordinary method.

$^1$HNMR (CDCl$_3$) δ: 1.34 (d, 3H, J=6.1 Hz), 1.87 (m, 1H), 2.02 (m, 1H), 3.07 (s, 3H), 3.32 (s, 3H), 3.50 (m, 2H), 4.61 (m, 1H), 6.87 (m, 1H), 6.98 (d, 1H, J=3.4 Hz), 7.14 (d, 2H, J=8.8 Hz), 7.21 (m, 1H), 7.25 (d, 1H, J=3.4 Hz), 7.39 (m, 1H), 7.92 (d, 2H, J=8.8 Hz), 11.6 (br, 1H)

ESI-MS (m/e): 477 [M+H]$^+$

Production Example 13

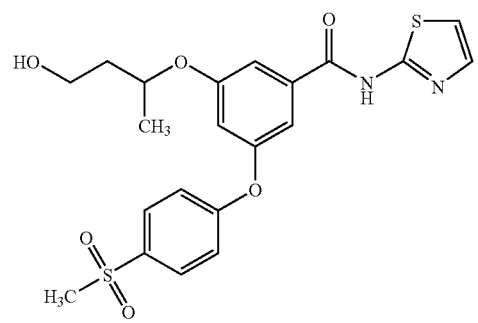

Preparation of 5-(3-hydroxy-1-methyl-propoxy)-3-(4-methanesulfonylphenoxy)-N-thiazol-2-yl-benzamide The compound of Production Example 13 was obtained as a white amorphous substance using the 5-hydroxy-3-(4-methylthiophenoxy)benzoic acid methyl ester obtained in Production Example 1, 1-(tert-butyldimethylsiloxy)-3-hydroxybutane and 2-amino-thiazole, by the same method as in Production Example 2, a corresponding method, or a combination thereof with an ordinary method.

$^1$HNMR (CDCl$_3$) δ: 1.39 (d, 3H, J=6.1 Hz), 1.88 (m, 1H), 2.02 (m, 1H), 3.10 (s, 3H), 3.84 (m, 2H), 4.71 (m, 1H), 6.88 (m, 1H), 7.01 (d, 1H, J=3.5 Hz), 7.17 (d, 2H, J=8.9 Hz), 7.24 (m, 1H), 7.35 (d, 1H, J=3.5 Hz), 7.48 (m, 1H), 7.95 (d, 2H, J=8.9 Hz), 11.0 (br, 1H)

ESI-MS (m/e): 463 [M+H]$^+$

Production Example 14

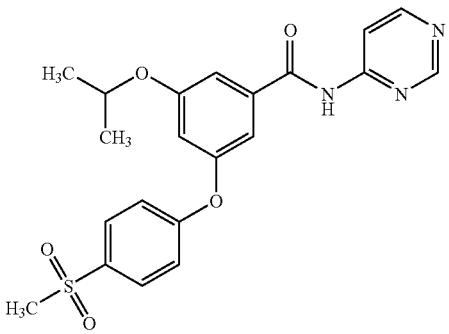

Preparation of 5-isopropoxy-3-(4-methanesulfonylphenoxy)-N-pyrimidin-4-yl-benzamide The compound of Production Example 14 was obtained as a white amorphous substance using the 5-hydroxy-3-(4-methylthiophenoxy)benzoic acid methyl ester obtained in Production Example 1, 2-bromopropane and 4-amino-pyrazine, by the same method as in Production Example 1, a corresponding method, or a combination thereof with an ordinary method.

$^1$HNMR (CDCl$_3$) δ: 1.38 (d, 6H, J=6.0 Hz), 3.90 (s, 3H), 4.63 (septet, 1H, J=6.0 Hz), 6.83 (m, 1H), 7.16 (m, 1H), 7.16 (d, 2H, J=8.9 Hz), 7.29 (m, 1H), 7.95 (d, 2H, J=8.9 Hz), 8.31 (dd, 1H, J=1.2, 5.6 Hz), 8.61 (br, 1H), 8.70 (d, 1H, J=5.6 Hz), 8.90 (d, 1H, J=1.2 Hz)

ESI-MS (m/e): 428 [M+H]$^+$

Production Example 15

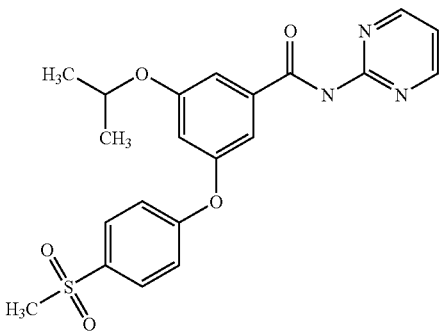

Preparation of 5-isopropoxy-3-(4-methanesulfonylphenoxy)-N-(pyrimidin-2-yl)-benzamide The compound of Production Example 15 was obtained as a white amorphous substance using the 5-hydroxy-3-(4-methylthiophenoxy)benzoic acid methyl ester obtained in Production Example 1, 2-bromopropane and 2-amino-pyrazine, by the same method as in Production Example 1, a corresponding method, or a combination thereof with an ordinary method.

$^1$HNMR (CDCl$_3$) δ: 1.37 (d, 6H, J=6.0 Hz), 3.08 (s, 3H), 4.62 (septet, 1H, J=6.0 Hz), 6.79 (t, 1H, J=2.2 Hz), 7.05-7.20 (m, 4H). 7.31 (t, 1H, J=2.2 Hz), 7.93 (d, 2H, J=8.8 Hz), 8.60 (br, 1H), 8.68 (d, 2H, J=5.9 Hz)

ESI-MS (m/e): 428 [M+H]$^+$

Production Example 16

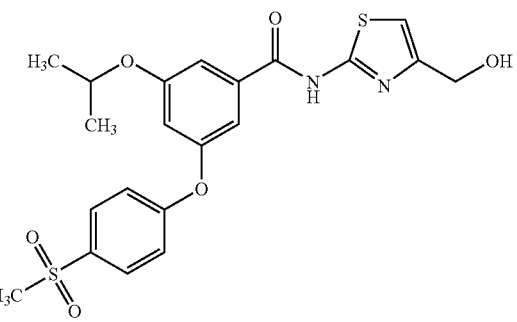

Preparation of N-(4-hydroxymethyl-thiazol-2-yl)-5-isopropoxy-3-(4-methanesulfonylphenoxy)-benzamide The compound of Production Example 16 was obtained as a white amorphous substance using the 5-hydroxy-3-(4-methylthiophenoxy)benzoic acid methyl ester obtained in Production Example 1, 2-bromopropane and 2-amino-4-(tert-butyldimethylsiloxymethyl)-thiazole, by the same method as in Production Example 1, a corresponding method, or a combination thereof with an ordinary method.

$^1$HNMR (CDCl$_3$) δ: 1.38 (6H, d, J=6.0 Hz), 3.08 (3H, s), 4.61-4.65 (3H, m), 6.83 (1H, t, J=2.2 Hz), 6.87 (1H, s), 7.17 (2H, d, J=8.9 Hz), 7.18 (1H, d, J=2.0 Hz), 7.34 (1H, d, J=2.0 Hz), 7.95 (2H, d, J=8.9 Hz)

ESI-MS (m/e): 463 [M+H]$^+$

Production Example 17

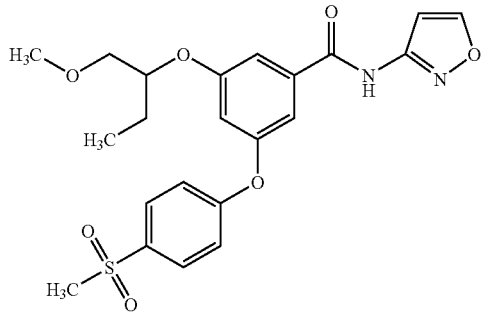

Preparation of N-(isooxazol-3-yl)-3-(4-methanesulfonylphenoxy)-5-(1-methoxymethyl-propoxy)-benzamide The compound of Production Example 17 was obtained as a colorless oil using the 5-hydroxy-3-(4-methylthiophenoxy) benzoic acid methyl ester obtained in Production Example 1, 2-hydroxy-1-methoxy-butane and 3-amino-oxazole, by the same method as in Production Example 2, a corresponding method, or a combination thereof with an ordinary method.

$^1$HNMR (CDCl$_3$) δ: 0.99 (t, 3H, J=7.5 Hz), 1.74 (quintet, 2H, J=7.5 Hz), 3.01 (s, 3H), 3.38 (s, 3H), 3.57 (m, 2H), 4.39 (m, 1H), 6.89 (m, 1H), 7.16-7.12 (m, 2H), 7.14 (d, 2H, J=8.8 Hz), 7.32 (m, 1H), 7.93 (d, 2H, J=8.8 Hz), 8.33 (s, 1H, J=1.9 Hz), 8.64 (br, 1H)

ESI-MS (m/e): 461 [M+H]$^+$

Production Example 18

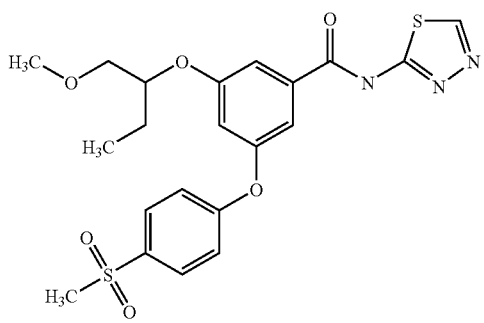

Preparation of 3-(4-methanesulfonylphenoxy)-5-(1-methoxymethyl-propoxy)-N-[1,3,4]thiadiazol-2-yl-benzamide The compound of Production Example 18 was obtained as a colorless oil using the 5-hydroxy-3-(4-methylthiophenoxy)benzoic acid methyl ester obtained in Production Example 1, 2-hydroxy-1-methoxy-butane and 2-amino-1,3,4-thiadiazole, by the same method as in Production Example 2, a corresponding method, or a combination thereof with an ordinary method.

$^1$HNMR(CDCl$_3$) δ: 0.98 (t, 3H, J=7.5 Hz), 1.75 (quintet, 2H, J=7.5 Hz), 3.07 (s, 3H), 3.37 (s, 3H), 3.56 (m, 2H), 4.45 (m, 1H), 6.93 (m, 1H), 7.14 (d, 2H, J=8.9 Hz), 7.44 (m, 1H), 7.53 (m, 1H), 7.91 (d, 2H, J=8.9 Hz), 8.73 (s, 1H), 12.0 (br, 1H)

ESI-MS (m/e): 478 [M+H]$^+$

Production Example 19

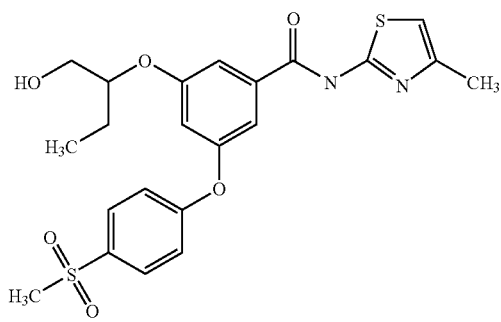

Preparation of 5-(1-hydroxymethyl-propoxy)-3-(4-methanesulfonylphenoxy)-N-(4-methyl-thiazol-2-yl)-benzamide The compound of Production Example 19 was obtained as a colorless amorphous substance using the 5-hydroxy-3-(4-methylthiophenoxy)benzoic acid methyl ester obtained in Production Example 1, 1-(tert-butyldimethylsiloxy)-2-hydroxy-butane and 2-amino-4-methyl-thiazole, by the same method as in Production Example 2, a corresponding method, or a combination thereof with an ordinary method.

$^1$HNMR (CDCl$_3$) δ: 0.99 (t, 3H, J=7.3 Hz), 1.68 (m, 2H), 2.28 (d, 3H, J=1.0 Hz), 3.09 (s, 3H), 3.82 (m, 2H), 4.36 (m, 1H), 6.57 (d, 1H, J=1.0 Hz), 6.75 (m, 1H), 7.11 (m, 1H), 7.13 (d, 2H, J=8.9 Hz), 7.28 (m, 1H), 7.93 (d, 2H, J=8.9 Hz), 10.8 (br, 1H)

ESI-MS (m/e): 477 [M+H]$^+$

Production Example 20

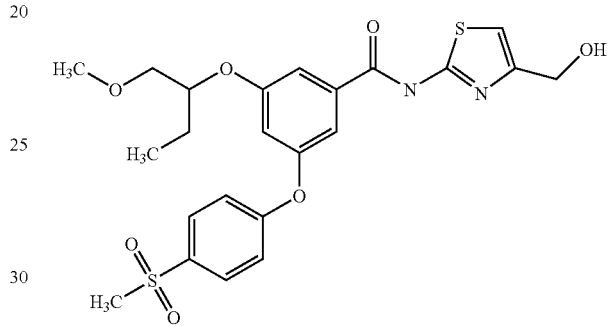

Preparation of N-(4-hydroxymethyl-thiazol-2-yl)-3-(4-methanesulfonylphenoxy)-5-(1-methoxymethyl-propoxy)-benzamide The compound of Production Example 20 was obtained as a white amorphous substance using the 5-hydroxy-3-(4-methylthiophenoxy)benzoic acid methyl ester obtained in Production Example 1, 2-hydroxy-1-methoxy-butane and 2-amino-4-(tert-butyldimethylsiloxymethyl)-thiazole, by the same method as in Production Example 2, a corresponding method, or a combination thereof with an ordinary method.

$^1$HNMR (CDCl$_3$) δ: 1.01 (t, 3H, J=7.5 Hz), 1.76 (quintet, 2H, J=7.5 Hz), 3.10 (s, 3H), 3.40 (s, 3H), 3.59 (m, 2H), 4.43 (m, 1H), 4.64 (s, 2H), 6.89 (s, 1H), 6.94 (m, 1H), 7.18 (d, 2H, J=9.0 Hz), 7.20 (m, 1H), 7.40 (m, 1H), 7.96 (d, 2H, J=9.0 Hz), 10.0 (br, 1H)

ESI-MS (m/e): 507 [M+H]$^+$

Production Example 21

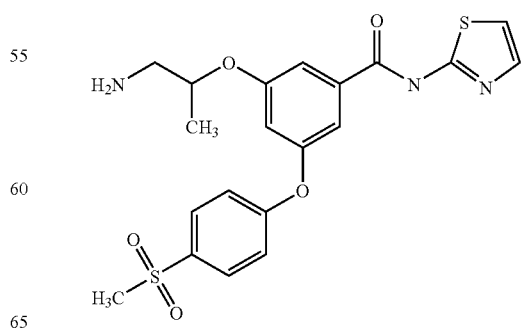

Preparation of 5-(2-amino-1-methyl-ethoxy)-3-(4-methanesulfonylphenoxy)-N-thiazol-2-yl-benzamide The compound of Production Example 21 was obtained as a white amorphous substance using the 5-hydroxy-3-(4-methylthiophenoxy)benzoic acid methyl ester obtained in Production Example 1, 1-(tert-butoxycarbonylamino)-2-hydroxy-propane and 2-aminothiazole, by the same method as in Production Example 2, a corresponding method, or a combination thereof with an ordinary method.

$^1$HNMR (CDCl$_3$) δ: 1.30 (d, 3H, J=6.0 Hz), 2.92 (d, 2H, J=6.0 Hz), 3.09 (s, 3H), 4.41 (sextet, 1H, J=6.0 Hz), 6.86 (m, 1H), 6.98 (d, 1H, J=3.5 Hz), 7.14 (d, 2H, J=8.9 Hz), 7.21 (d, 1H, J=3.5 Hz), 7.25 (m, 1H), 7.42 (m, 1H) 8.87 (d, 2H, J=8.9 Hz)

ESI-MS (m/e): 448 [M+H]$^+$

Production Example 22

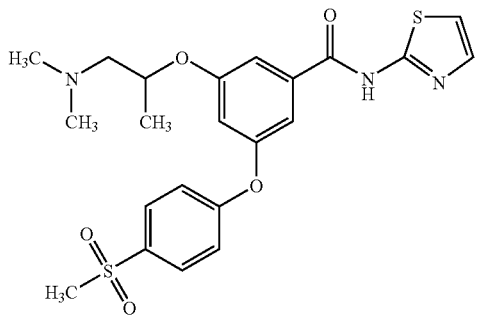

Preparation of 5-(2-dimethylamino-1-methyl-ethoxy-3-(4-methanesulfonylphenoxy)-N-thiazol-2-yl-benzamide The compound of Production Example 22 was obtained as a light yellow oil using the 5-hydroxy-3-(4-methylthiophenoxy)benzoic acid methyl ester obtained in Production Example 1, 1-dimethylamino-2-hydroxypropane and 2-amino-thiazole, by the same method as in Production Example 2, a corresponding method, or a combination thereof with an ordinary method.

$^1$HNMR (CDCl$_3$) δ: 1.28 (d, 3H, J=6.2 Hz), 2.30 (s, 6H), 2.42 (dd, 1H, J=4.4, 13.0 Hz), 2.68 (dd, 1H, J=6.2 Hz, 13.0 Hz), 3.09 (s, 3H), 4.56 (dt, 1H, J=4.5, 6.2 Hz), 6.89 (m, 1H), 7.00 (d, 1H, J=3.6 Hz), 7.15 (d, 2H, J=8.9 Hz), 7.22 (m, 1H), 7.28 (d, 1H, 3.6 Hz), 7.41 (m, 1H), 7.93 (d, 2H, J=8.9 Hz), 11.4 (br, 1H)

ESI-MS (m/e): 476 [M+H]$^+$

Production Example 23

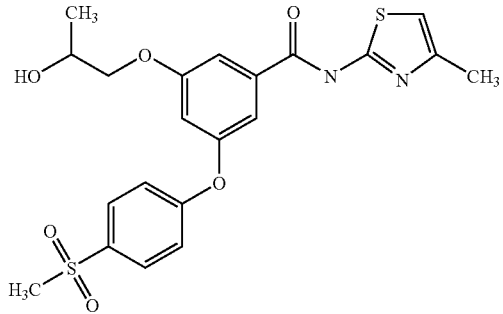

Preparation of 5-(2-hydroxy-propoxy)-3-(4-methanesulfonylphenoxy)-N-(4-methyl-thiazol-2-yl)-benzamide The compound of Production Example 23 was obtained as a white amorphous substance using the 5-hydroxy-3-(4-methylthiophenoxy)benzoic acid methyl ester obtained in Production Example 1, 2-(tert-butyldimethylsiloxy)-1-hydroxy-propane and 2-amino-4-methylthiazole, by the same method as in Production Example 2, a corresponding method, or a combination thereof with an ordinary method.

$^1$HNMR (CDCl$_3$) δ: 1.28 (d, 3H, J=6.4 Hz), 2.20 (d, 3H, J=1.0 Hz), 3.08 (s, 3H), 3.79 (m, 1H), 3.93 (m, 1H), 4.20 (m, 1H), 6.57 (d, 1H, J=1.0 Hz), 6.78 (m, 1H), 7.09 (d, 2H, J=8.9 Hz), 7.16 (m, 1H), 7.25 (m, 1H), 7.92 (d, 2H, J=8.9 Hz), 11.2 (br, 1H)

ESI-MS (m/e): 463 [M+H]$^+$

Production Example 24

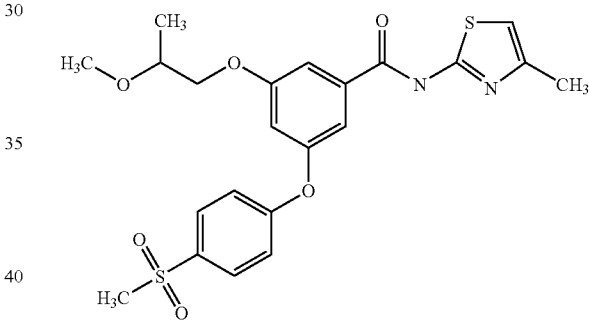

Preparation of 3-(4-methanesulfonylphenoxy)-5-(2-methoxy-propoxy)-N-(4-methyl-thiazol-2-yl)-benzamide The compound of Production Example 24 was obtained as a colorless oil using the 5-hydroxy-3-(4-methylthiophenoxy)benzoic acid methyl ester obtained in Production Example 1, 1-hydroxy-2-methoxy-propane and 2-amino-4-methylthiazole, by the same method as in Production Example 2, a corresponding method, or a combination thereof with an ordinary method.

$^1$NMR (CDCl$_3$) δ: 1.26 (d, 3H, J=6.3 Hz), 2.22 (d, 3H, J=1.1 Hz), 3.08 (s, 3H), 3.43 (s, 3H), 3.72 (m, 1H), 3.93 (m, 2H), 6.57 (d, 1H, J=1.1 Hz), 6.86 (m, 1H), 7.12 (d, 2H, J=8.6 Hz), 7.16 (m, 1H), 7.29 (m, 1H), 7.92 (d, 2H, J=8.6 Hz), 10.6 (br, 1H)

ESI-MS (m/e): 477 [M+H]$^+$

Production Example 25

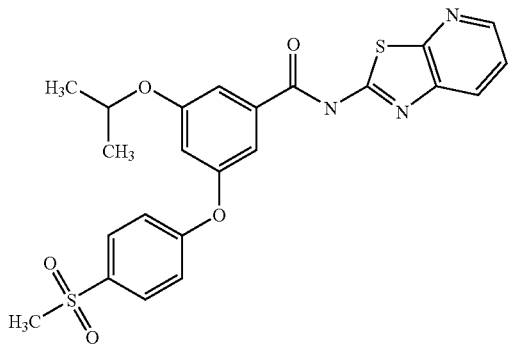

Preparation of 5-isopropoxy-3-(4-methanesulfonylphenoxy)-N-(thiazolo[5,4-b]pyridin-2-yl)-benzamide The compound of Production Example 25 was obtained as a light yellow solid using the 5-hydroxy-3-(4-methylthiophenoxy)benzoic acid methyl ester obtained in Production Example 1, 2-bromopropane and 2-amino-thiazolo[5,4-b]pyridine, by the same method as in Production Example 1, a corresponding method, or a combination thereof with an ordinary method.

$^1$HNMR (CDCl$_3$) δ: 1.37 (6H, d, J=6.0 Hz), 3.09 (3H, s), 4.59-4.63 (1H, m), 6.84 (1H, t, J=1.8 Hz), 7.14 (2H, d, J=8.9 Hz), 7.19 (1H, t, J=1.8 Hz), 7.34 (1H, t, J=1.8 Hz), 7.38 (1H, dd, J=4.7, 8.1 Hz), 7.92 (1H, dd, J=1.5, 8.1 Hz), 7.94 (2H, d, J=8.9 Hz), 8.53 (1H, dd, J=1.5, 4.7 Hz)

ESI-MS (m/e): 484 [M+H]$^+$

Production Example 26

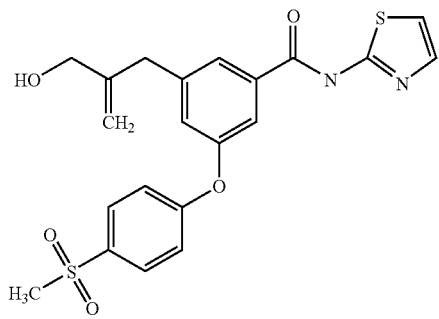

Preparation of 5-(2-hydroxymethyl-allyl)-3-(4-methanesulfonylphenoxy)-N-thiazol-2-yl-benzamide $^1$HNMR (CDCl$_3$) δ: 3.08 (3H, s), 3.49 (2H, s), 4.06 (2H, s), 4.91 (1H, s), 5.19 (1H, s), 7.00 (1H, d, J=3.3 Hz), 7.11 (2H, d, J=9.0 Hz), 7.13 (1H, d, J=3.3 Hz), 7.20 (1H, s), 7.55 (1H, s), 7.67 (1H, s), 7.92 (2H, d, J=9.0 Hz)

ESI-MS (m/e): 445 [M+H]$^+$

Production Example 27

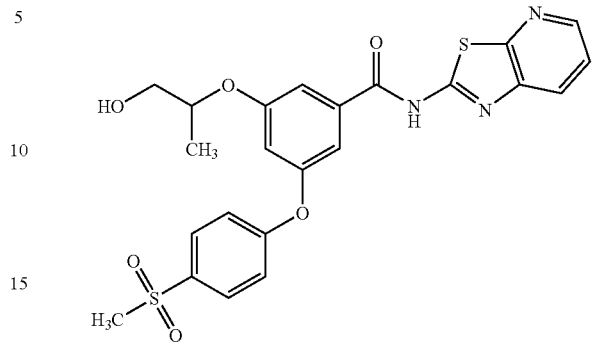

Preparation of 5-(2-hydroxy-1-methyl-ethoxy)-3-(4-methanesulfonylphenoxy)-N-thiazolo[5,4-b]pyridin-2-yl-benzamide The compound of Production Example 27 was obtained as a light yellow solid using the 5-hydroxy-3-(4-methylthiophenoxy)benzoic acid methyl ester obtained in Production Example 1, 1-(tert-butyldimethylsiloxy)-2-hydroxypropane and 2-amino-thiazolo[5,4-b]pyridine, by the same method as in Production Example 2, a corresponding method, or a combination thereof with an ordinary method.

$^1$HNMR (CDCl$_3$) δ: 1.34 (6H, d, J=6.2 Hz), 3.11 (3H, s), 3.74 (2H, d, J=4.6 Hz), 4.57-4.62 (1H, m), 6.92 (1H, t, J=1.8 Hz), 7.19 (2H, d, J=8.9 Hz), 7.36 (1H, t, J=1.8 Hz), 7.43 (1H, dd, J=4.7, 8.2 Hz), 7.49 (1H, t, J=1.8 Hz), 7.94 (2H, d, J=8.9 Hz), 8.03 (1H, dd, J=1.4, 8.2 Hz), 8.49 (1H, dd, J=1.4, 4.7 Hz)

ESI-MS (m/e): 484 [M+H]$^+$

Production Example 28

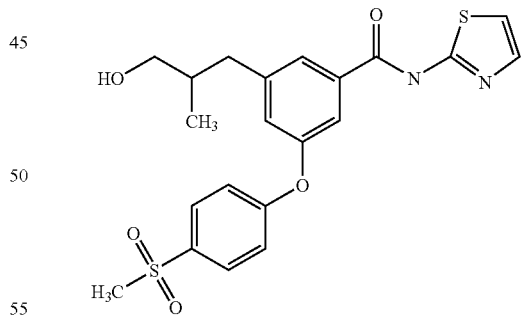

Preparation of 5-(3-hydroxy-2-methyl-propyl)-3-(4-methanesulfonylphenoxy)-N-thiazol-2-yl-benzamide $^1$HNMR (CDCl$_3$) δ: 0.94 (6H, d, J=6.7 Hz), 1.97-2.05 (1H, m), 2.50-2.94 (2H, m), 3.08 (3H, s), 3.50-3.56 (2H, m), 7.03 (1H, d, J=3.5 Hz), 7.13 (2H, d, J=8.8 Hz), 7.17 (1H, s), 7.42 (1H, d, J=3.5 Hz), 7.52 (1H, s), 7.63 (1H, s), 7.93 (2H, d, J=8.8 Hz)

ESI-MS (m/e): 447 [M+H]$^+$

Production Example 29

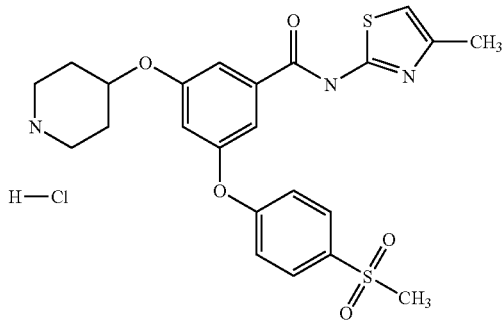

Preparation of 3-(4-methanesulfonylphenoxy)-N-(4-methyl-thiazol-2-yl)-5-(piperidin-4-yl-oxy)-benzamide hydrochloride The compound of Production Example 29 was obtained as white crystals using the 5-hydroxy-3-(4-methylthiophenoxy) benzoic acid methyl ester obtained in Production Example 1, 1-(tert-butoxycarbonyl)-4-hydroxy-piperidine and 2-amino-4-methyl-thiazole, by the same method as in Production Example 2, a corresponding method, or a combination thereof with an ordinary method.

$^1$HNMR (CD$_3$OD) δ: 1.93 (m, 2H), 2.11 (m, 2H), 2.31 (s, 3H), 2.99 (s, 3H), 3.13 (m, 2H), 3.30 (m, 2H), 4.75 (m, 1H), 6.89 (s, 1H), 7.11 (m, 2H, J=8.9 Hz), 7.27 (m, 1H), 7.52 (m, 1H), 7.84 (d, 2H, J=8.9 Hz)

Production Example 30

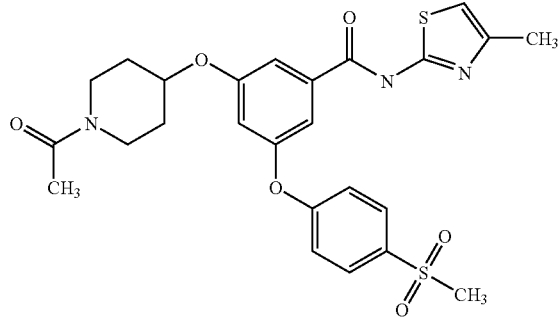

Preparation of 5-(1-acetyl-piperidin-4-yloxy)-3-(4-methanesulfonylphenoxy)-N-(4-methyl-thiazol-2-yl)-benzamide The compound of Production Example 30 was obtained as a white amorphous substance using the 5-hydroxy-3-(4-methylthiophenoxy)benzoic acid methyl ester obtained in Production Example 1, 1-acetyl-4-hydroxy-piperidine and 2-amino-4-thiazole, by the same method as in Production Example 2, a corresponding method, or a combination thereof with an ordinary method.

$^1$HNMR (CDCl$_3$) δ: 1.80 (m, 3H), 2.20-2.00 (m, 2H), 2.14 (s, 3H), 2.51 (s, 3H), 3.10 (s, 3H), 3.50 (m, 1H), 3.75 (m, 1H), 4.01 (m, 1H), 4.84 (m, 1H), 4.84 (m, 1H), 6.71 (s, 1H), 6.92 (m, 1H), 7.18 (d, 2H, J=8.9 Hz), 7.43 (m, 1H), 7.76 (m, 1H), 7.96 (d, 2H, J=8.9 Hz)

ESI-MS (m/e): 530 [M+H]$^+$

Production Example 31

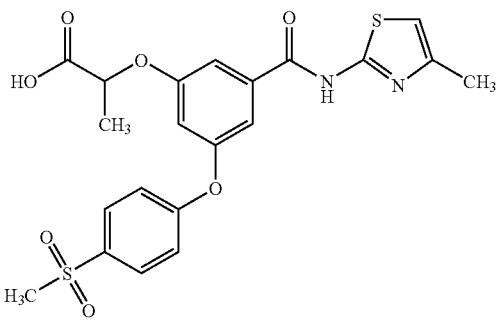

Preparation of 2-[3-(4-methanesulfonylphenoxy)-5-(4-methyl-thiazol-2-yl-carbamoyl)-phenoxy]propionic acid The compound of Production Example 31 was obtained as white crystals using the 5-hydroxy-3-(4-methylthiophenoxy) benzoic acid methyl ester obtained in Production Example 1, 2-bromopropionic acid tert-butyl ester and 2-amino-4-methyl-thiazole, by the same method as in Production Example 1, a corresponding method, or a combination thereof with an ordinary method. The method of removing the tert-butyl group serving as the protective group for the carboxyl group for production of this compound may be a method described in the relevant literature (for example, Protective Groups in Organic Synthesis, T. W. Green, 2nd printing, John Wiley & Sons, 1991), a corresponding method, or a combination thereof with an ordinary method.

$^1$HNMR (DMSO-d$_6$) δ: 1.53 (d, 3H, J=6.8 Hz), 2.28 (s, 3H), 3.27 (s, 3H), 5.03 (septet, 1H, J=6.8 Hz), 6.82 (m, 1H), 6.94 (m, 1H), 7.25 (d, 2H, J=8.8 Hz), 7.42 (m, 1H), 7.50 (m, 1H), 7.95 (d, 2H, J=8.8 Hz)

ESI-MS (m/e): 477 [M+H]$^+$

Production Example 32

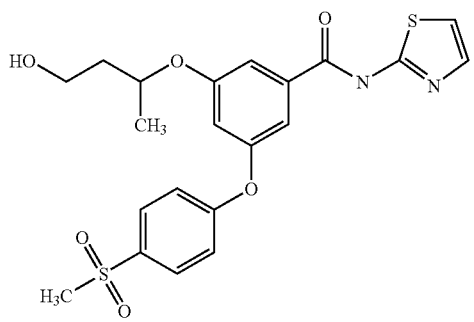

Preparation of 5-(3-hydroxy-1-methyl-propoxy)-3-(4-methanesulfonylphenoxy)-N-thiazol-2-yl-benzamide The compound of Production Example 32 was obtained as a white amorphous substance using the 5-hydroxy-3-(4-methylthiophenoxy)benzoic acid methyl ester obtained in Production Example 1, 1-(tert-butyldimethylsiloxy-3-hydroxybutane and 2-aminothiazole, by the same method as in Production Example 2, a corresponding method, or a combination thereof with an ordinary method.

$^1$HNMR (CDCl$_3$) δ: 1.35 (d, 3H, J=6.0 Hz), 1.83 (m, 1H), 2.00 (m, 1H), 3.08 (s, 3H), 3.78 (m, 2H), 4.65 (m, 1H), 6.86 (m, 1H), 6.98 (m, 1H, J=3.5 Hz), 7.13 (d, 2H, J=8.8 Hz), 7.21 (d, 1H, J=3.5 Hz), 7.23 (m, 1H), 7.45 (m, 1H), 7.91 (d, 2H, J=8.8 Hz), 12.1 (br, 1H)

ESI-MS (m/e): 463 [M+H]$^+$

Production Example 33

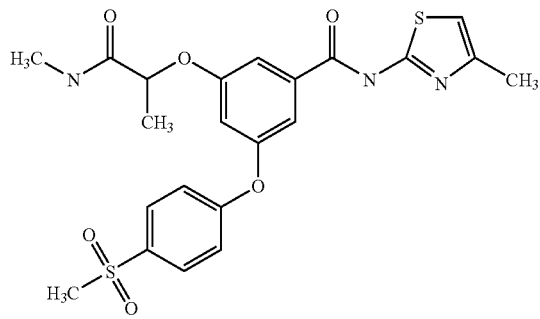

Preparation of 3-(4-methanesulfonylphenoxy)-5-(1-methylcarbamoyl-ethoxy)-N-(4-methyl-thiazol-2-yl)-benzamide The compound of Production Example 33 was obtained as a white amorphous substance by reaction between the 2-[3-(4-methanesulfonylphenoxy)-5-(4-methyl-thiazol-2-yl-carbamoyl)-phenoxy]propionic acid obtained in Production Example 31 and methylamine. The reaction between the compound obtained in Production Example 31 and methylamine is an amide bond-forming reaction, by a method described in the relevant literature (for example, Peptide Gosei no Kiso to Jikken, Izumiya, N. et al., Maruzen Publ., 1983, Comprehensive Organic Synthesis, Vol. 6, Pergamon Press, 1991), a corresponding method, or a combination thereof with an ordinary method.

$^1$HNMR (CDCl$_3$) δ: 1.59 (s, 3H), 2.26 (s, 3H), 2.86 (d, 3H, J=4.7 Hz), 3.10 (s, 3H), 4.73 (q, 1H, J=6.6 Hz), 6.47 (br, 1H), 6.57 (m, 1H), 6.83 (m, 1H), 7.12 (d, 2H, J=8.8 Hz), 7.22 (m, 1H), 7.31 (m, 1H), 7.93 (d, 2H, J=8.8 Hz), 11.0 (br, 1H)

ESI-MS (m/e): 490 [M+H]$^+$

Production Example 34

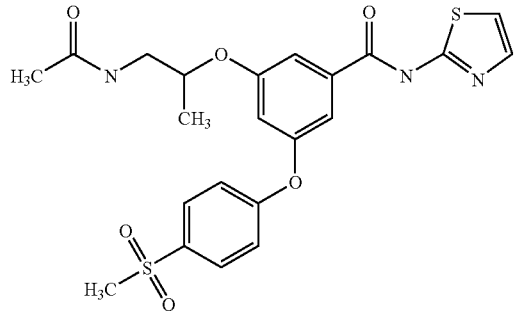

Preparation of 5-(2-acetylamino-1-methyl-ethoxy)-3-(4-methanesulfonylphenoxy)-N-thiazol-2-yl-benzamide The compound of Production Example 34 was obtained as a white amorphous substance by reaction between acetic acid and 5-(2-amino-1-methyl-ethoxy)-3-(4-methanesulfonylphenoxy)-N-thiazol-2-yl-benzamide obtained by converting the hydroxy group of the 5-(2-hydroxy-1-methyl-ethoxy)-3-(4-methanesulfonyl-phenoxy)-N-thiazol-2-yl-benzamide obtained in Production Example 2 to an amino group.

The reaction for conversion from the hydroxy group to an amino group may be accomplished by converting the hydroxy group to a mesyl group, and then reacting the mesyl compound with sodium azide to produce an azide compound, and reducing the azide group with triphenylphosphine or the like. The conversion reaction may be carried out by the method described in Comprehensive Organic Transformations, Richard C. Larock, 2nd printing, John Wiley & Sons, 1999), a corresponding method, or a combination thereof with an ordinary method.

The reaction between the 3-(2-amino-1-methyl-ethoxy)-5-(4-methanesulfonyl-phenoxy)-N-thiazol-2-yl-benzamide and acetic acid is an amide bond-forming reaction, and it may be carried out by the same method as the amide bond-forming reaction used in Step 1 or another step, a corresponding method, or a combination thereof with an ordinary method.

$^1$HNMR (CDCl$_3$) δ: 1.33 (d, 3H, J=6.0 Hz), 2.03 (s, 3H), 3.10 (s, 3H), 3.49 (t, 2H, J=5.8 Hz), 4.56 (sextet, 1H, J=6.0 Hz), 5.98 (t, 1H, J=5.8 Hz), 6.87 (m, 1H), 7.00 (d, 1H, J=3.6 Hz), 7.15 (d, 2H, J=8.7 Hz), 7.28 (m, 2H), 7.54 (m, 1H), 7.94 (d, 2H, J=8.7 Hz), 11.9 (br, 1H)

ESI-MS (m/e): 490 [M+H]$^+$

Production Example 35

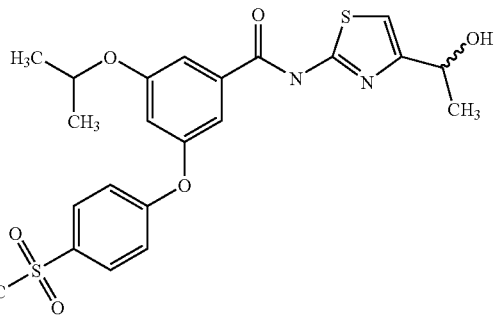

Preparation of N-[4-(1-hydroxy-ethyl)-thiazol-2-yl]-5-isopropoxy-3-(4-methanesulfonylphenoxy)-benzamide The compound of Production Example 35 was obtained as a white solid using the 5-hydroxy-3-(4-methylthiophenoxy)benzoic acid methyl ester obtained in Production Example 1, 2-bromopropane and 2-amino-4-(1-tertbutyldimethylsiloxyethyl)-thiazole, by the same method as in Production Example 1, a corresponding method, or a combination thereof with an ordinary method.

¹HNMR (CDCl₃) δ: 1.38 (6H, d, J=6.0 Hz), 1.55-1.60 (3H, br), 3.08 (3H, s), 4.63 (1H, quint, J=6.0 Hz), 4.90 (1H, q, J=6.6 Hz), 6.79-6.85 (2H, m), 7.16 (2H, d, J=8.8 Hz), 7.20 (1H, br), 7.36 (1H, br), 7.94 (2H, d, J=8.8 Hz)

ESI-MS (m/e): 477 [M+H]⁺

Production Example 36

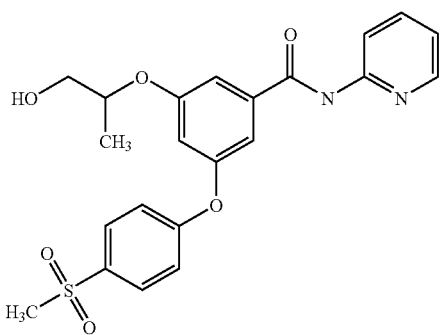

Preparation of 5-(2-hydroxy-1-methyl-ethoxy)-3-(4-methanesulfonylphenoxy)-N-pyridin-2-yl-benzamide The compound of Production Example 36 was obtained as white crystals using the 5-hydroxy-3-(4-methylthiophenoxy) benzoic acid methyl ester obtained in Production Example 1, 1-(tert-butyldimethylsiloxy)-2-hydroxypropane and 2-aminopyridine, by the same method as in Production Example 2, a corresponding method, or a combination thereof with an ordinary method.

¹HNMR (CDCl₃) δ: 1.32 (3H, d, J=3.2 Hz), 3.08 (3H, s), 3.76-3.79 (2H, m), 4.57-4.63 (1H, m), 6.48 (1H, t, J=2.0 Hz), 7.13-7.17 (1H, m), 7.15 (2H, d, J=8.8 Hz), 7.18 (1H, d, J=2.0 Hz), 7.35 (1H, d, J=2.0 Hz), 7.76 (1H, ddd, J=1.6, 5.1, 8.4 Hz), 7.93 (2H, d, J=8.8 Hz), 8.30 (1H, d, J=5.1 Hz), 8.34 (1H, d, J=8.4 Hz)

ESI-MS (m/e): 443 [M+H]⁺

Production Example 37

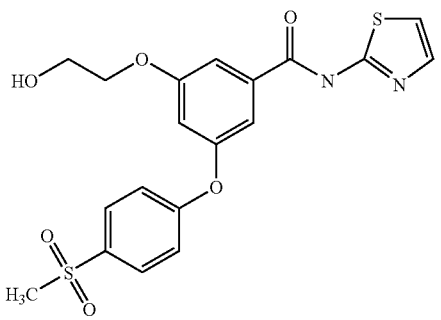

Preparation of 5-(2-hydroxy-ethoxy)-3-(4-methanesulfonylphenoxy)-N-thiazol-2-yl-benzamide The compound of Production Example 37 was obtained as a white amorphous substance using the 5-hydroxy-3-(4-methylthiophenoxy)benzoic acid methyl ester obtained in Production Example 1, 1-(tert-dimethylbutylsiloxy)-2-hydroxyethane and 2-aminothiazole, by the same method as in Production Example 2, a corresponding method, or a combination thereof with an ordinary method.

¹HNMR (CDCl₃) δ: 3.10 (s, 3H), 4.01 (t, 2H, J=4.5 Hz), 4.14 (t, 2H, J=4.5 Hz), 6.87 (m, 1H), 7.02 (d, 1H, J=3.0 Hz), 7.16 (d, 2H, J=8.4 Hz), 7.30 (m, 2H), 7.38 (m, 1H), 7.95 (d, 2H, J=8.4 Hz), 11.3 (br, 1H)

ESI-MS (m/e): 435 [M+H]⁺

Production Example 38

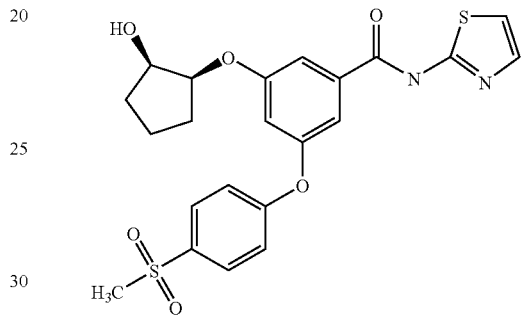

Preparation of 5-(2-hydroxy-cyclopentyloxy)-3-(4-methanesulfonylphenoxy)-N-thiazol-2-yl-benzamide The compound of Production Example 38 was obtained as a light yellow oil using the 5-hydroxy-3-(4-methylthiophenoxy)benzoic acid methyl ester obtained in Production Example 1, 1-(tert-butyldiphenylsiloxy)-2-hydroxycyclopentane and 2-aminothiazole, by the same method as in Production Example 2, a corresponding method, or a combination thereof with an ordinary method.

¹HNMR (CDCl₃) δ: 1.62-2.08 (6H, m), 3.08 (3H, s), 4.24-4.30 (1H, m), 4.55-4.60 (1H, m), 6.87 (1H, t, J=2.0 Hz), 7.00 (1H, d, J=3.6 Hz), 7.14 (2H, d, J=8.8 Hz), 7.25 (1H, t, J=2.0 Hz), 7.25 (1H, d, J=3.6 Hz), 7.40 (1H, t, J=2.0 Hz), 7.93 (2H, d, J=8.8 Hz)

ESI-MS (m/e): 475 [M+H]⁺

Production Example 39

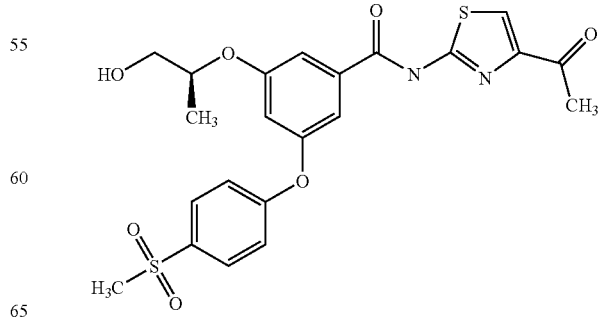

Preparation of N-(4-acetyl-thiazol-2-yl)-5-(2-hydroxy-1-methyl-ethoxy)-3-(4-methanesulfonylphenoxy)-benzamide The compound of Production Example 39 was obtained as a white amorphous substance using the 5-hydroxy-3-(4-methylthiophenoxy)benzoic acid methyl ester obtained in Production Example 1, 1-(tert-butyldimethylsiloxy)-2-hydroxypropane and 4-acetyl-2-amino-thiazole, by the same method as in Production Example 2, a corresponding method, or a combination thereof with an ordinary method.

$^1$HNMR (CDCl$_3$) δ: 1.32 (3H, d, J=6.2 Hz), 2.58 (3H, s), 3.10 (3H, s), 3.80 (2H, d, J=5.2 Hz), 4.63 (1H, q, J=5.6 Hz), 6.81-6.89 (1H, m), 7.12-7.19 (3H, m), 7.38 (1H, br), 7.83 (1H, d, J=2.0 Hz), 7.95 (2H, dd, J=8.9 Hz)

ESI-MS (m/e): 491 [M+H]$^+$

Production Example 40

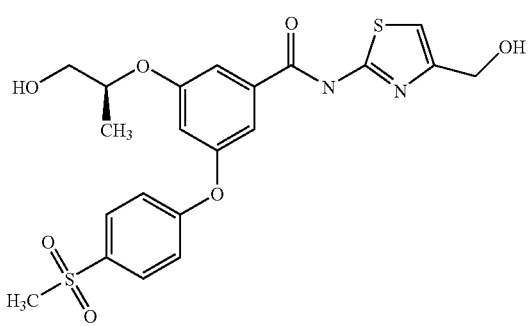

Preparation of 5-(2-hydroxy-1-methyl-ethoxy)-N-(4-hydroxymethyl-thiazol-2-yl)-3-(4-methanesulfonylphenoxy)-benzamide The compound of Production Example 40 was obtained as a white solid using the 5-hydroxy-3-(4-methylthiophenoxy)benzoic acid methyl ester obtained in Production Example 1, 1-(tert-butyldimethylsiloxy)-2-hydroxypropane and 2-amino-4-tert-butyldimethylsiloxymethylthiazole, by the same method as in Production Example 2, a corresponding method, or a combination thereof with an ordinary method.

$^1$HNMR (CDCl$_3$) δ: 1.31 (3H, d, J=6.2 Hz), 3.09 (3H, s), 3.75-3.80 (2H, m), 4.55-4.66 (3H, m), 6.83-6.86 (1H, m), 6.88 (1H, s), 7.12-7.20 (3H, m), 7.33-7.36 (1H, m), 7.94 (2H, d, J=8.6 Hz)

ESI-MS (m/e): 479 [M+H]$^+$

Production Example 41

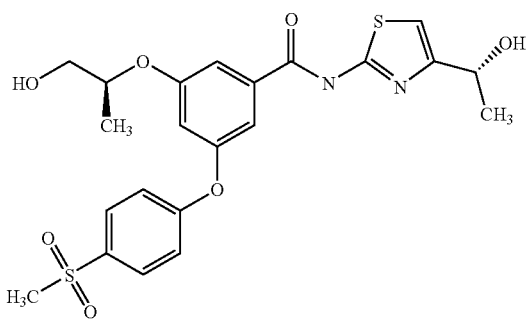

Preparation of N-[4-(1-hydroxy-ethyl)-thiazol-2-yl]-5-(2-hydroxy-1-methyl-ethoxy)-3-(4-methanesulfonylphenoxy)-benzamide The compound of Production Example 41 was obtained as a light yellow oil using the 5-hydroxy-3-(4-methylthiophenoxy)benzoic acid methyl ester obtained in Production Example 1, 1-(tert-butyldimethylsiloxy)-2-hydroxypropane and 2-amino-4-(1-tertbutyldimethylsiloxy-ethyl)thiazole, by the same method as in Production Example 2, a corresponding method, or a combination thereof with an ordinary method.

$^1$HNMR (CDCl$_3$) δ: 1.31 (3H, d, J=6.2 Hz), 1.49 (3H, d, J=6.5 Hz), 3.12 (3H, s), 3.68 (2H, d, J=5.0 Hz), 4.60 (1H, q, J=6.2 Hz), 4.80-4.90 (1H, m), 6.94 (1H, s), 6.96-6.99 (1H, m), 7.23 (2H, d, J=8.9 Hz), 7.29-7.32 (1H, m), 7.47-7.50 (1H, m), 7.89 (1H, s), 7.96 (2H, d, J=8.9 Hz)

ESI-MS (m/e): 493 [M+H]$^+$

Production Example 42

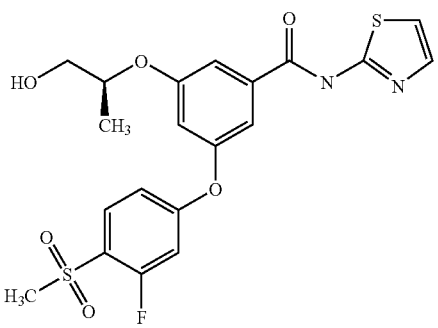

Preparation of 3-(3-fluoro-4-methanesulfonylphenoxy)-5-(2-hydroxy-1-methyl-ethoxy)-N-thiazol-2-yl-benzamide After adding 20.4 g (0.68 mol) of 1-bromo-2-fluoro-4-iodobenzene, 20.8 g (0.64 mol) of cesium carbonate and 5.07 g (0.64 mol) of copper (II) oxide to a solution of 9.00 g (0.43 mol) of 5-hydroxy-3-methoxymethoxybenzoic acid methyl ester in pyridine (50.0 ml), the mixture was stirred at 130° C. for 8 hours under a nitrogen atmosphere. The reaction mixture was filtered and then concentrated under reduced pressure, acetic acid ethyl ester and saturated aqueous ammonium chloride were added to the obtained residue, and the organic layer was washed with brine, dried and concentrated under reduced pressure. The obtained residue was purified by silica gel column chromatography (hexane:acetic acid ethyl ester=9:1) to obtain 10.6 g of 3-(4-bromo-3-fluoro-phenoxy)-5-methoxymethoxybenzoic acid methyl ester (yield: 65%) as a yellow oil.

After adding 757 mg (7.41 mmol) of sodium methanesulfinate and 1.41 g (7.41 mmol) of copper iodide to a solution of 357 mg (0.93 mmol) of the obtained ester compound in dimethylsulfoxide (6.0 ml), the reaction mixture was stirred at 120° C. for 6 hours. Sodium chloride water-ammonia water (9:1) was added to the reaction mixture and extraction was performed with acetic acid ethyl ester, and then the organic layer was washed with brine, dried and concentrated under reduced pressure. The obtained residue was purified by silica gel column chromatography (hexane:acetic acid ethyl ester=2:1) to obtain 170 mg of 3-(3-fluoro-4-methanesulfonyl-phenoxy)-5-methoxymethoxybenzoic acid methyl ester (yield: 48%) as a colorless oil.

After adding 30.0 ml of trifluoroacetic acid to a solution of 3.34 g (8.69 mmol) of the obtained ester compound in methylene chloride (60.0 ml), the reaction mixture was stirred at room temperature for 2 hours. The reaction mixture was concentrated under reduced pressure, and the obtained residue was purified by silica gel column chromatography (hexane:acetic acid ethyl ester=3:7) to obtain 2.59 g of 3-(3-fluoro-4-methanesulfonyl-phenoxy)-5-hydroxybenzoic acid methyl ester (yield: 88%) as a colorless oil.

After adding 87.0 mg (0.46 mmol) of (2R)-1-(t-butyldimethylsiloxy)-2-hydroxypropane and 119 mg (0.46 mmol) of triphenylphosphine to a solution of 77.5 mg (0.23 mmol) of the obtained phenol compound in tetrahydrofuran (1.0 ml), a solution of 0.25 ml (0.57 mmol) of diethyl azodicarboxylate in 40% toluene was added, and the mixture was stirred at room temperature overnight. The reaction mixture was concentrated under reduced pressure, and the obtained residue was purified by silica gel column chromatography (hexane:acetic acid ethyl ester=2:1) to obtain 80.0 mg of 5-((1S)-2-(t-butyldimethylsiloxy)-1-methyl-ethoxy)-3-(3-fluoro-4-methanesulfonyl-phenoxy)-benzoic acid methyl ester (yield: 69%) as a colorless oil.

The compound of Production Example 42 was obtained as a colorless oil using the obtained 5-((1S)-2-(t-butyldimethylsiloxy)-1-methyl-ethoxy)-3-(3-fluoro-4-methanesulfonyl-phenoxy)-benzoic acid methyl ester and 2-amino-thiazole, by the same method as in Production Example 2, a corresponding method, or a combination thereof with an ordinary method.

$^1$HNMR (CDCl$_3$) δ: 1.32 (3H, d, J=6.3 Hz), 3.23 (3H, s), 3.78-3.80 (2H, m), 4.56-4.61 (1H, m), 6.83-6.94 (3H, m), 7.01 (1H, d, J=3.5 Hz), 7.23 (1H, t, J=1.8 Hz), 7.37 (1H, d, J=3.5 Hz), 7.41 (1H, t, J=1.8 Hz), 7.94 (1H, t, J=8.2 Hz)

ESI-MS (m/e): 467 [M+H]$^+$

Production Example 43

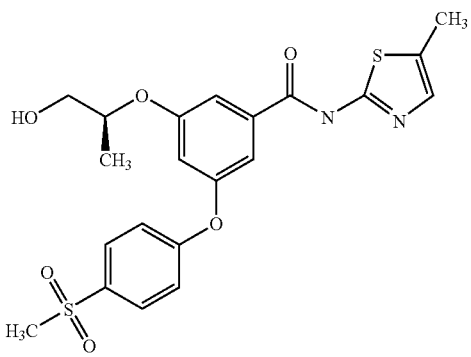

Preparation of 5-(2-hydroxy-1-methyl-ethoxy)-3-(4-methanesulfonylphenoxy)-N-(5-methyl-thiazol-2-yl)benzamide The compound of Production Example 43 was obtained as a light yellow oil using the 5-hydroxy-3-(4-methylthiophenoxy)benzoic acid methyl ester obtained in Production Example 1, 1-(tert-butyldimethylsiloxy)-2-hydroxypropane and 2-amino-5-methylthiazole, by the same method as in Production Example 2, a corresponding method, or a combination thereof with an ordinary method.

$^1$HNMR (CDCl$_3$) δ: 1.29 (3H, d, J=6.2 Hz), 2.37 (3H, s), 3.08 (2H, s), 3.69-3.76 (2H, m), 4.52-4.57 (1H, m), 6.82 (1H, t, J=2.0 Hz), 6.88 (1H, s), 7.12 (2H, d, J=8.8 Hz), 7.20 (1H, d, J=2.0 Hz), 7.35 (1H, d, J=2.0 Hz), 7.92 (2H, d, J=8.8 Hz)

ESI-MS (m/e): 463 [M+H]$^+$

Production Example 44

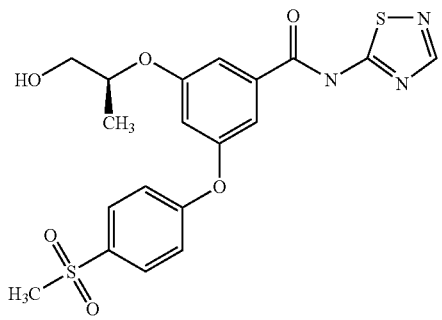

Preparation of 5-(2-hydroxy-1-methyl-ethoxy)-3-(4-methanesulfonylphenoxy)-N-([1,2,4]thiadiazol-5-yl)-benzamide The compound of Production Example 44 was obtained as a light yellow oil using the 5-hydroxy-3-(4-methylthiophenoxy)benzoic acid methyl ester obtained in Production Example 1, 1-(tert-butyldimethylsiloxy)-2-hydroxypropane and 5-amino-1,2,4-thiadiazole, by the same method as in Production Example 2, a corresponding method, or a combination thereof with an ordinary method.

$^1$HNMR (CDCl$_3$) δ: 1.30 (3H, d, J=6.2 Hz), 3.12 (3H, s), 3.68 (2H, d, J=5.1 Hz), 4.58-4.85 (1H, m), 7.00 (1H, s), 7.23 (2H, d, J=8.9 Hz), 7.37 (1H, s), 7.56 (1H, s), 7.95 (2H, d, J=8.9 Hz), 8.37 (1H, s)

ESI-MS (m/e): 450 [M+H]$^+$

Production Example 45

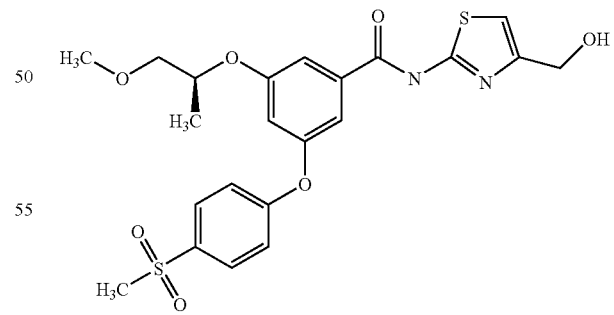

Preparation of N-(4-hydroxymethyl-thiazol-2-yl)-3-(4-methanesulfonylphenoxy)-5-(2-methoxy-1-methyl-ethoxy)-benzamide The compound of Production Example 45 was obtained as a colorless amorphous substance using the 5-hydroxy-3-(4- methylthiophenoxy)benzoic acid methyl ester obtained in Production Example 1, 2-hydroxy-1-methoxypropane and 2-amino-4-tertbutyldimethylsiloxymethylthiazole, by the same method as in Production Example 2, a corresponding method, or a combination thereof with an ordinary method.

¹HNMR (CDCl₃) δ: 1.35 (3H, d, J=6.3 Hz), 3.09 (3H, s), 3.41 (3H, s), 3.49-3.64 (2H, m), 4.58-4.67 (3H, m), 6.87-6.92 (2H, m), 7.13-7.20 (3H, m), 7.35-7.38 (1H, br), 7.94 (2H, d, J=8.8 Hz)

ESI-MS (m/e): 493 [M+H]⁺

Production Example 46

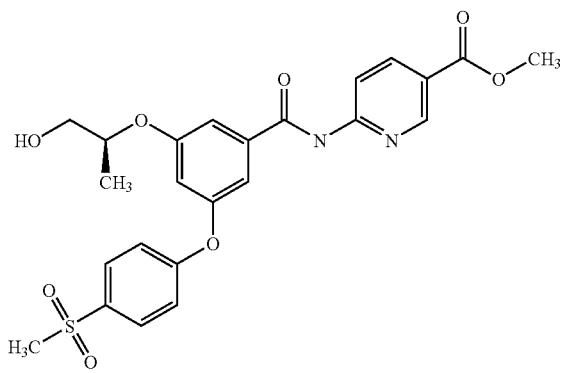

Preparation of 5-(2-hydroxy-1-methyl-ethoxy)-3-(4-methanesulfonylphenoxy)-N-(5-methoxycarbonyl-pyridin-2-yl)-benzamide The compound of Production Example 46 was obtained as a white amorphous substance using the 5-hydroxy-3-(4-methylthiophenoxy)benzoic acid methyl ester obtained in Production Example 1, 1-(tert-butyldimethylsiloxy)-2-hydroxypropane and 2-amino-5-methoxycarbonyl-pyridine, by the same
method as in Production Example 2, a corresponding method, or a combination thereof with an ordinary method.

¹HNMR (CDCl₃) δ: 1.34 (d, 3H, J=6.0 Hz), 3.10 (s, 3H), 3.80 (m, 2H), 3.96 (s, 3H), 4.61 (m, 1H), 6.80 (m, 1H), 7.16 (d, 2H, J=8.8 Hz), 7.20 (m, 1H), 7.37 (m, 1H), 7.94 (d, 2H, J=8.8 Hz), 8.33-8.46 (m, 2H), 8.80 (br, 1H), 8.93 (m, 1H)

ESI-MS (m/e): 501 [M+H]⁺

Production Example 47

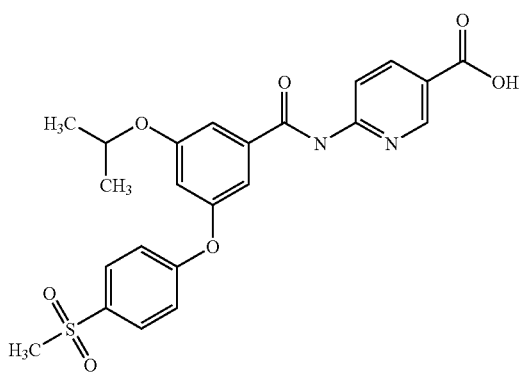

Preparation of 6-[5-isopropoxy-3-(4-methanesulfonylphenoxy)-benzoylamino]nicotinic acid The compound of Production Example 47 was obtained as a white solid using the 5-hydroxy-3-(4-methylthiophenoxy) benzoic acid methyl ester obtained in Production Example 1, 1-(tert-butyldimethylsiloxy)-2-hydroxypropane and 6-amino-nicotinic acid, by the same method as in Production Example 2, a corresponding method, or a combination thereof with an ordinary method.

¹HNMR (DMSO-d₆) δ: 1.29 (d, 6H, J=6.0 Hz), 3.20 (s, 3H), 4.76 (septet, 1H, J=6.0 Hz), 6.94 (m, 1H), 7.23 (d, 2H, J=8.8 Hz), 7.33 (m, 1H), 7.49 (m, 1H), 7.94 (d, 2H, J=8.8 Hz), 8.29 (m, 2H), 8.87 (m, 1H), 11.2 (s, 1H)

ESI-MS (m/e): 471 [M+H]⁺

Production Example 48

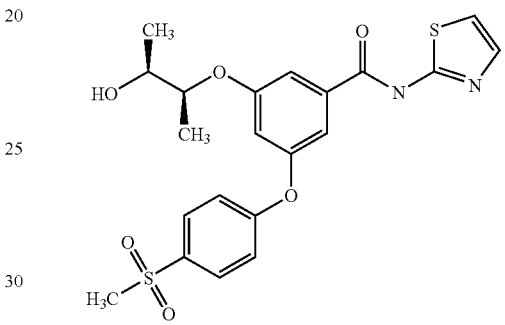

Preparation of 5-(2-hydroxy-1-methyl-propoxy)-3-(4-methanesulfonylphenoxy)-N-thiazol-2-yl-benzamide The compound of Production Example 48 was obtained as a light yellow oil using the 5-hydroxy-3-(4-methylthiophenoxy)benzoic acid methyl ester obtained in Production Example 1, 2-(tert-butyldimethylsiloxy-3-hydroxy)butane and 2-aminothiazole, by the same method as in Production Example 2, a corresponding method, or a combination thereof with an ordinary method.

¹HNMR (CDCl₃) δ: 1.25 (s, 3H, J=6.2 Hz), 1.28 (s, 3H, J=6.2 Hz), 3.08 (s, 3H), 3.87 (m, 1H), 4.22 (m, 1H), 6.85 (m, 1H), 6.99 (m, 1H), 7.13 (d, 2H, J=8.8 Hz), 7.23 (m, 2H), 7.38 (m, 1H), 7.92 (d, 2H, J=8.8 Hz), 12.0 (br, 1H)

ESI-MS (m/e): 463 [M+H]⁺

Production Example 49

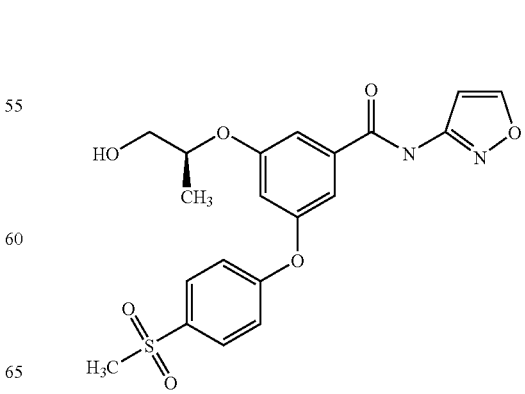

Preparation of 5-(2-hydroxy-1-methyl-ethoxy)-N-(isoxazol-3-yl)-3-(4-methanesulfonylphenoxy)-benzamide The compound of Production Example 49 was obtained as a white amorphous substance using the 5-hydroxy-3-(4-methylthiophenoxy)benzoic acid methyl ester obtained in Production Example 1, 1-(tert-butyldimethylsiloxy)-2-hydroxypropane and 3-aminooxazole, by the same method as in Production Example 2, a corresponding method, or a combination thereof with an ordinary method.

$^1$HNMR (CDCl$_3$) δ: 1.32 (d, 3H, J=6.0 Hz), 2.04 (br, 1H), 3.08 (s, 3H), 3.77 (m, 2H), 4.60 (m, 1H), 6.87 (m, 1H), 7.15 (d, 2H, J=8.8 Hz), 7.19 (m, 2H), 7.35 (m, 1H), 7.94 (d, 2H, J=8.8 Hz), 8.30 (d, 1H, J=1.6 Hz), 9.24 (br, 1H)

ESI-MS (m/e): 433 [M+H]$^+$

Production Example 50

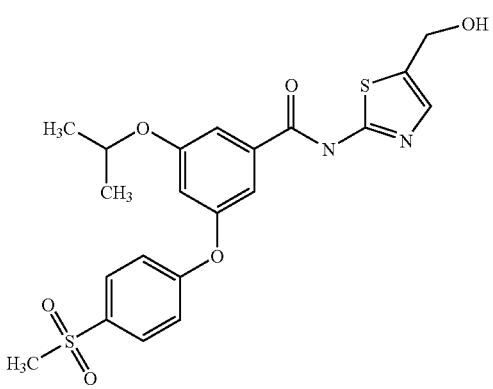

Preparation of N-(5-hydroxymethyl-thiazol-2-yl)-5-isopropoxy-3-(4-methanesulfonylphenoxy)-benzamide The compound of Production Example 50 was obtained as a light yellow oil using the 5-hydroxy-3-(4-methylthiophenoxy)benzoic acid methyl ester obtained in Production Example 1, 2-bromopropane and 2-amino-5-formylthiazole, by the same method as in Production Example 1, a corresponding method, or a combination thereof with an ordinary method.

$^1$HNMR (CDCl$_3$) δ: 1.36 (d, 6H, J=6.0 Hz), 3.08 (s, 3H), 4.59 (septet, 1H, J=6.0 Hz), 4.79 (s, 2H), 6.82 (s, 1H), 7.14 (d, 2H, J=8.4 Hz), 7.13-1.18 (m, 2H), 7.31 (s, 1H), 7.92 (d, 2H, J=8.4 Hz), 11.2 (br, 1H)

ESI-MS (m/e): 463 [M+H]$^+$

Production Example 51

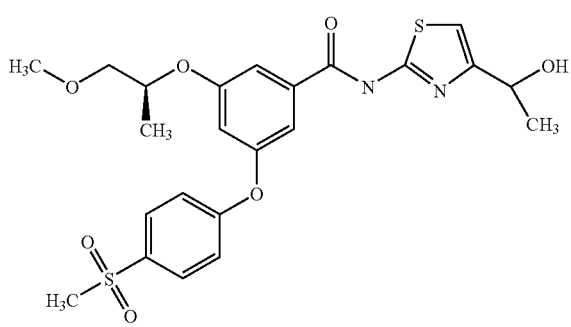

Preparation of N-[4-(1-hydroxy-ethyl)-thiazol-2-yl]-3-(4-methanesulfonylphenoxy)-5-(2-methoxy-1-methyl-ethoxy)-benzamide The compound of Production Example 51 was obtained as a colorless amorphous substance using the 5-hydroxy-3-(4-methylthiophenoxy)benzoic acid methyl ester obtained in Production Example 1, 1-methoxy-2-hydroxy-propane and 2-amino-4-(1-tertbutyldimethylsiloxyethyl)thiazole, by the same method as in Production Example 2, a corresponding method, or a combination thereof with an ordinary method.

$^1$HNMR (CDCl$_3$) δ: 1.35 (3H, d, J=6.3 Hz), 1.55 (3H, d, J=6.3 Hz), 3.08 (3H, s), 3.41 (3H, s), 3.49-3.64 (2H, m), 4.59-4.70 (1H, m), 4.90 (1H, q, J=6.3 Hz), 6.80 (1H, brs), 6.90 (1H, br), 7.16 (2H, d, J=8.9 Hz), 7.23-7.26 (1H, br), 7.42 (1H, brs), 7.94 (2H, d, J=8.9 Hz)

ESI-MS (m/e): 507 [M+H]$^+$

Production Example 52

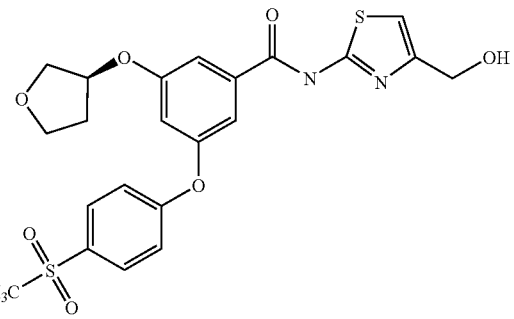

Preparation of N-(4-hydroxymethyl-thiazol-2-yl)-3-(4-methanesulfonylphenoxy)-5-(tetrahydrofuran-3-yl-oxy)-benzamide The compound of Production Example 52 was obtained as a colorless amorphous substance using the 5-hydroxy-3-(4-methylthiophenoxy)benzoic acid methyl ester obtained in Production Example 1, 3-hydroxy-tetrahydrofuran and 2-amino-4-tertbutyldimethylsiloxymethylthiazole, by the same method as in Production Example 2, a corresponding method, or a combination thereof with an ordinary method.

$^1$HNMR (CDCl$_3$) δ: 2.10-2.36 (2H, m), 3.09 (3H, s), 3.39-4.07 (4H, m), 4.66 (2H, s), 4.96-5.05 (1H, m), 6.84 (1H, t. J=2.0 Hz), 7.15-7.20 (3H, m), 7.30 (1H, br), 7.96 (2H, d, J=8.8 Hz)

ESI-MS (m/e): 491 [M+H]$^+$

Production Example 53

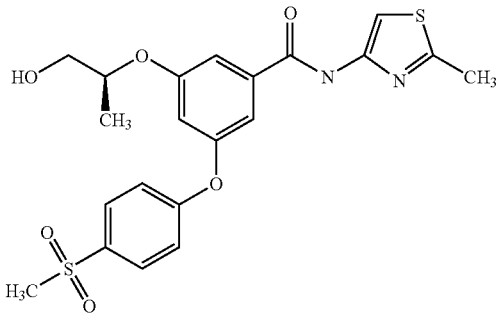

Preparation of 5-(2-hydroxy-1-methyl-ethoxy)-3-(4-methanesulfonylphenoxy)-N-(2-methylthiazol-4-yl)-benzamide The compound of Production Example 53 was obtained as a white amorphous substance using the 5-hydroxy-3-(4-methylthiophenoxy)benzoic acid methyl ester obtained in Production Example 1, 1-(tert-butyldimethylsiloxy)-2-hydroxypropane and 4-amino-2-methylthiazole, by the same method as in Production Example 2, a corresponding method, or a combination thereof with an ordinary method.

$^1$HNMR (CDCl$_3$) δ: 1.32 (d, 3H, J=6.0 Hz), 2.31 (br, 1H), 2.66 (s, 3H), 3.09 (s, 3H), 3.78 (m, 2H), 4.59 (m, 1H), 7.13-7.16 (m, 1H), 7.15 (d, 2H, J=8.8 Hz), 7.32 (m, 1H), 7.60 (s, 1H), 7.94 (d, 2H, J=8.8 Hz), 8.90 (br, 1H)

ESI-MS (m/e): 463 [M+H]$^+$

Production Example 54

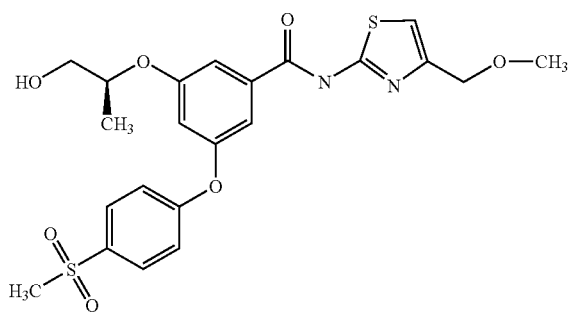

Preparation of 5-(2-hydroxy-1-methyl-ethoxy)-3-(4-methanesulfonylphenoxy)-N-(4-methoxymethyl-thiazol-2-yl)-benzamide The compound of Production Example 54 was obtained as a white amorphous substance using the 5-hydroxy-3-(4-methylthiophenoxy)benzoic acid methyl ester obtained in Production Example 1, 1-(tert-butyldimethylsiloxy)-2-hydroxypropane and 2-amino-4-methoxymethylthiazole, by the same method as in Production Example 2, a corresponding method, or a combination thereof with an ordinary method.

$^1$HNMR (CDCl$_3$) δ: 1.31 (d, 3H, J=6.0 Hz), 3.09 (s, 3H), 3.42 (s, 3H), 3.78 (m, 2H), 4.44 (m, 2H), 4.57 (m, 1H), 6.86 (m, 1H), 6.91 (s, 1H), 7.10-7.26 (m, 3H), 7.31 (m, 1H), 7.97 (d, 2H, J=8.9 Hz), 9.67 (br, 1H)

ESI-MS (m/e): 493 [M+H]$^+$

Production Example 55

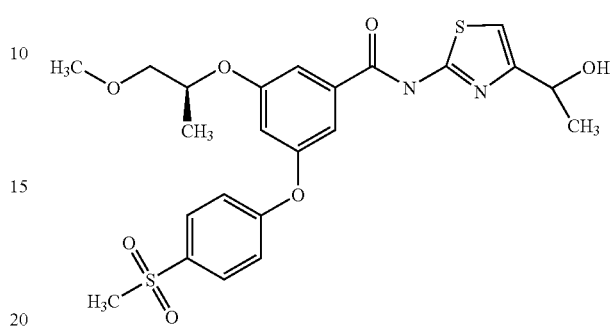

Preparation of N-[4-(1-hydroxy-ethyl-thiazol-2-yl]-3-(4-methanesulfonylphenoxy)-5-(2-methoxy-1-methyl-ethoxy)-benzamide (diastereoisomer of Production Example 51)

The compound of Production Example 55 was obtained as a colorless amorphous substance using the 5-hydroxy-3-(4-methylthiophenoxy)benzoic acid methyl ester obtained in Production Example 1, 2-hydroxy-1-methoxypropane and 2-amino-4-(1-tertbutyldimethylsiloxyethyl)thiazole, by the same method as in Production Example 2, a corresponding method, or a combination thereof with an ordinary method.

$^1$HNMR (CDCl$_3$) δ: 1.35 (3H, d, J=6.3 Hz), 1.55 (3H, d, J=6.3 Hz), 3.08 (3H, s), 3.41 (3H, s), 3.49-3.64 (2H, m), 4.59-4.70 (1H, m), 4.90 (1H, q, J=6.3 Hz), 6.80 (1H, brs), 6.90 (1H, br), 7.16 (2H, d, J=8.9 Hz), 7.23-7.26 (1H, br), 7.42 (1H, brs), 7.94 (2H, d, J=8.9 Hz)

ESI-MS (m/e): 507-[M+H]$^+$

Production Example 56

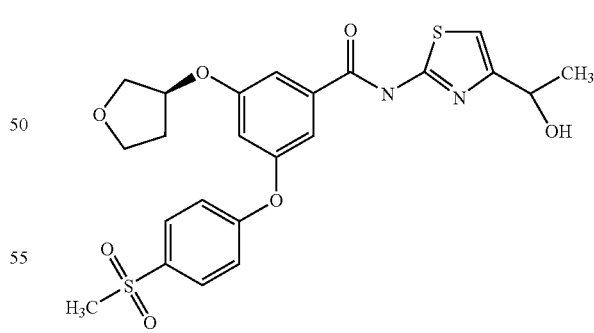

Preparation of N-[4-(1-hydroxy-ethyl)-thiazol-2-yl]-3-(4-methanesulfonylphenoxy)-5-(tetrahydrofuran-3-yl-oxy)-benzamide The compound of Production Example 56 was obtained as a white solid using the 5-hydroxy-3-(4-methylthiophenoxy) benzoic acid methyl ester obtained in Production Example 1, 3-hydroxytetrahydrofuran and 2-amino-4-(1-tertbutyldimethylsiloxyethyl)thiazole, by the same method as in Production Example 2, a corresponding method, or a combination thereof with an ordinary method.

¹HNMR (CDCl₃) δ: 2.10-2.36 (2H, m), 0.39 (3H, s), 3.89-4.07 (4H, m), 4.85-4.95 (1H, m), 4.97-5.04 (1H, m), 6.81-6.85 (2H, m), 7.16 (2H, d, J=8.7 Hz), 7.23 (1H, brs), 7.34 (1H, brs), 7.96 (2H, d, J=8.7 Hz)

ESI-MS (m/e): 505 [M+H]⁺

Production Example 57

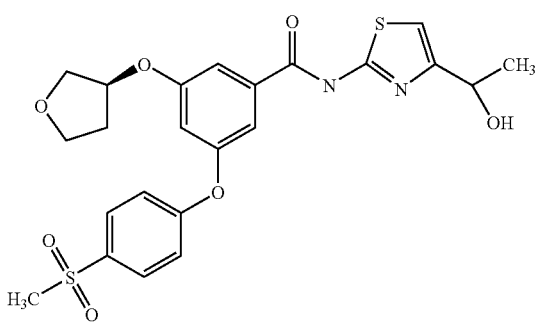

Preparation of N-[4-(1-hydroxy-ethyl)-thiazol-2-yl]-3-(4-methanesulfonylphenoxy)-5-(tetrahydrofuran-3-yl-oxy)-benzamide (diastereoisomer of Production Example 56)

The compound of Production Example 57 was obtained as a white solid, by the same method as in Production Example 56, a corresponding method, or a combination thereof with an ordinary method.

¹HNMR (CDCl₃) δ: 2.10-2.35 (2H, m), 3.09 (3H, s), 3.89-4.06 (4H, m), 4.86-4.95 (1H, m), 4.97-5.05 (1H, m), 6.81-6.85 (2H, m), 7.16 (2H, d, J=8.7 Hz), 7.22 (1H, brs), 7.34 (1H, brs), 7.96 (2H, d, J=8.7 Hz)

ESI-MS (m/e): 505 [M+H]⁺

Production Example 58

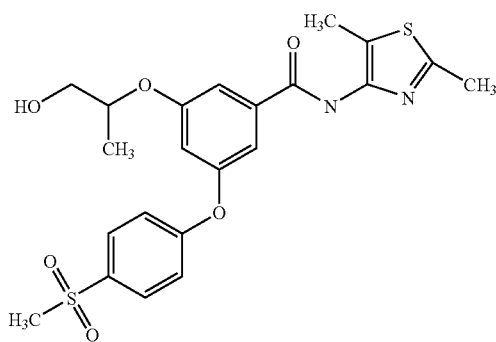

Preparation of N-(2,5-dimethylthiazol-4-yl)-5-(2-hydroxy-1-methyl-ethoxy)-3-(4-methanesulfonylphenoxy)-benzamide The compound of Production Example 58 was obtained as a light yellow oil using the 5-hydroxy-3-(4-methylthiophenoxy)benzoic acid methyl ester obtained in Production Example 1, 1-(tert-butyldimethylsiloxy)-2-hydroxypropane and 4-amino-2,5-dimethylthiazole, by the same method as in Production Example 2, a corresponding method, or a combination thereof with an ordinary method.

¹HNMR (CDCl₃) δ: 1.28 (d, 3H, J=6.0 Hz), 2.32 (s, 3H), 2.56 (s, 3H), 3.07 (s, 3H), 3.72 (m, 2H), 4.53 (m, 1H), 6.79 (t, 1H, J=2.0 Hz), 7.08 (dd, 2H, J=2.0, 6.8 Hz), 7.18 (s, 1H), 7.32 (s, 1H), 7.89 (dd, 2H, J=2.0, 6.8 Hz), 8.67 (br, 1H)

ESI-MS (m/e): 477 [M+H]⁺

Production Example 59

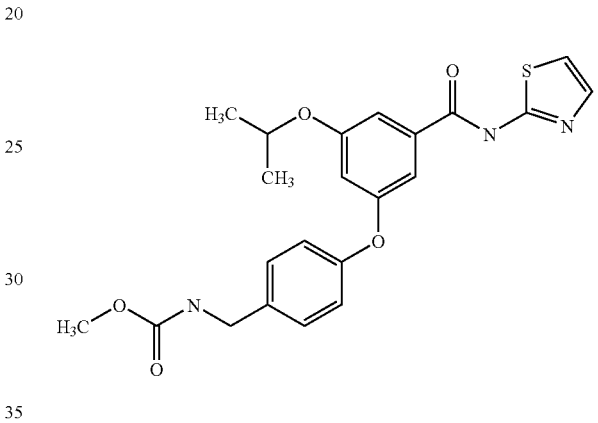

Preparation of 5-isopropoxy-3-(4-methoxycarbonylaminomethylphenoxy)-N-thiazol-2-yl-benzamide After adding 41.0 g (0.30 mmol) of potassium carbonate and 23.8 g (0.19 mmol) of 2-bromopropane to a solution of 25.0 g (0.15 mol) of 3,5-dihydroxybenzoic acid methyl ester in N,N-dimethylformamide (250 ml), the reaction mixture was stirred at 80° C. for 4 hours. Water was added to the reaction mixture, extraction was performed with acetic acid ethyl ester, and then the organic layer was washed with brine, dried and concentrated under reduced pressure. The obtained residue was purified by silica gel column chromatography (hexane:acetic acid ethyl ester=5:1) to obtain 12.0 g of 5-hydroxy-3-isopropoxybenzoic acid methyl ester (yield: 38%) as a colorless oil.

After adding 1.05 g of molecular sieves 4A, 1.00 g (6.70 mol) of p-formylphenylboric acid, 605 mg (3.30 mol) of copper (II) acetate and 2.32 ml (16.6 mol) of triethylamine to a solution of 700 mg (3.30 mmol) of the obtained phenol compound in methylene chloride (30 ml), the mixture was stirred at room temperature overnight under a oxygen atmosphere. The reaction mixture was filtered and then concentrated under reduced pressure, and the obtained residue was purified by silica gel column chromatography (hexane:acetic acid ethyl ester=5:1) to obtain 593 mg of 3-(4-formylphenoxy)-5-isopropoxybenzoic acid methyl ester (yield: 57%) as a colorless oil.

After adding 85.0 mg (2.25 mmol) of sodium borohydride to a solution of 590 mg (1.88 mmol) of the obtained formyl compound in methanol (20 ml), the reaction mixture was stirred at room temperature for 16 hours. The reaction mixture was concentrated, and then saturated aqueous sodium hydrogencarbonate was added, extraction was performed with chloroform, and the organic layer was dried and concentrated under reduced pressure. The obtained residue was purified by silica gel column chromatography (hexane:acetic acid ethyl ester=2:1) to obtain 567 mg of 3-(4-hydroxymethylphenoxy)-5-isopropoxybenzoic acid methyl ester (yield: 95%) as a colorless oil.

After adding 0.18 ml (1.26 mmol) of triethylamine and 0.073 ml (0.95 mmol) of methanesulfonyl chloride to a solution of 200 mg (0.63 mmol) of the obtained alcohol compound in chloroform (10 ml), the reaction mixture was stirred at 50° C. for 15 minutes. Saturated aqueous sodium hydrogencarbonate was added to the reaction mixture, extraction was performed with chloroform, and the organic layer was dried and then concentrated under reduced pressure. After adding 5.0 ml of DMF to the obtained residue and dissolving it therein, 123 mg (1.90 mmol) of sodium azide was added and the mixture was stirred at 80° C. for 1 hour. Water was added to the reaction mixture, extraction was performed with acetic acid ethyl ester, and the organic layer was dried and then concentrated under reduced pressure to obtain a crude azide compound.

After adding 247 mg (1.26 mmol) of triphenylphosphine to a solution of 11 ml of the obtained azide compound in tetrahydrofuran-water (10:1), the reaction mixture was stirred at 90° C. for 14 hours. A 2N aqueous hydrochloric acid solution was added to the reaction mixture to produce an acidic aqueous solution. The mixture was washed with acetic acid ethyl ester, and then a 4N aqueous sodium hydroxide solution was added to the aqueous layer to produce a basic aqueous solution, after which extraction was performed with chloroform and the organic layer was dried and concentrated under reduced pressure to obtain 67.8 mg of a crude amine compound (yield: 34%).

After adding 0.057 ml (0.41 mmol) of triethylamine and 0.024 ml (0.31 mmol) of chloroformic acid methyl ester to a solution of the obtained amine compound in chloroform (5.0 ml), the mixture was stirred at room temperature for 1 hour. Saturated aqueous sodium hydrogencarbonate was added to the reaction mixture, and then extraction was performed with chloroform and the organic layer was dried and concentrated under reduced pressure to obtain a crude methoxycarbonylaminomethyl compound.

After adding 1.0 ml (4.00 mmol) of a 4N aqueous sodium hydroxide solution to a 5:3 solution of the obtained methoxycarbonylaminomethyl compound in tetrahydrofuran-methanol (8.0 ml), the reaction mixture was stirred at 50° C. overnight. Saturated aqueous ammonium chloride was added to the reaction mixture, extraction was performed with chloroform, the organic layer was dried and then concentrated under reduced pressure, and the obtained residue was purified by silica gel column chromatography (chloroform:methanol=30:1) to obtain 63.1 mg of 5-isopropoxy-3-(4-methoxycarbonylaminomethylphenoxy)-benzoic acid (yield: 85%) as a white solid.

After adding 33.0 mg (0.33 mol) of 2-aminothiazole, 76.0 mg (0.49 mmol) of 1-hydroxybenzotriazole hydrate and 63.0 mg (0.33 mol) of 1-(3-dimethylaminopropyl)-3-ethylcarbodiimide hydrochloride to a solution of the obtained carboxyl compound in N,N-dimethylformamide (3.0 ml), the mixture was stirred at room temperature overnight. Water was added to the reaction mixture, extraction was performed with acetic acid ethyl ester, the reaction mixture was concentrated under reduced pressure, and the obtained residue was purified by silica gel column chromatography (chloroform:methanol=100:1) to obtain the title compound as a white solid. The analysis data for the compound obtained in Production Example 59 are shown below.

¹HNMR (CDCl₃) δ: 1.34 (6H, d, J=6.0 Hz), 3.71 (3H, s), 4.36 (2H, d, J=5.5 Hz), 4.57 (1H, m), 4.99-5.10 (1H, br), 6.75 (1H, brs), 6.96-7.05 (4H, m), 7.20 (1H, br), 7.27-7.34 (3H, m), 10.70-10.88 (1H, br)

ESI-MS (m/e): 442 [M+H]⁺

Compounds for Production Examples 60 to 64 were obtained by the same method as in Production Example 59 above. The structures and analysis data for these compounds are shown below.

Production Example 60

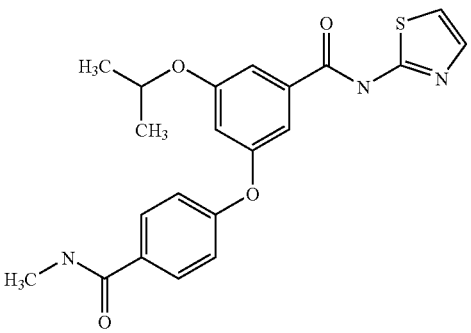

Preparation of 5-isopropoxy-3-(4-methylcarbamoyl-phenoxy)-N-thiazol-2-yl-benzamide The compound of Production Example 60 was obtained as a colorless amorphous substance using 2-aminothiazole and 3-(4-methylcarbamoyl-phenoxy)-5-isopropoxybenzoic acid methyl ester obtained by condensation reaction between methylamine and 3-(4-carboxyphenoxy)-5-isopropoxybenzoic acid methyl ester obtained by oxidizing the formyl group of the 3-(4-formylphenoxy)-5-isopropoxybenzoic acid methyl ester obtained in Production Example 59, by the same method as in Production Example 2, a corresponding method, or by a similar method.

¹HNMR (CDCl₃) δ: 1.36 (6H, d, J=6.1 Hz), 3.00 (3H, d, J=4.8 Hz), 4.58 (1H, m), 6.12-6.21 (1H, br), 6.79 (1H, t. J=2.2 Hz), 6.99-7.06 (4H, m), 7.24-7.27 (1H, m), 7.34 (1H, d, J=3.6 Hz), 7.72 (2H, m)

ESI-MS (m/e): 412 [M+H]⁺

Production Example 61

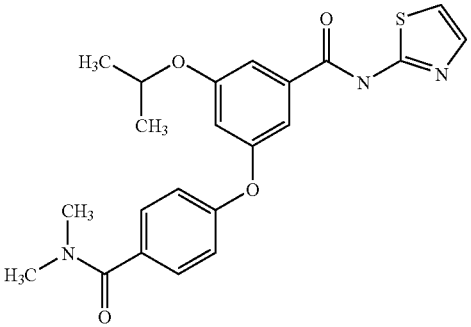

Preparation of 3-(4-dimethylcarbamoyl-phenoxy)-5-isopropoxy-N-thiazol-2-yl-benzamide The compound of Production Example 61 was obtained as a colorless amorphous substance using the 3-(4-carboxylphenoxy)-5-isopropoxybenzoic acid methyl ester obtained in Production Example 60, dimethylamine and 2-aminothiazole, by the same method as in Production Example 60, a corresponding method, or a similar method.

$^1$HNMR (CDCl$_3$) δ: 1.34 (6H, d, J=6.0 Hz), 2.98-3.15 (6H, br), 4.56 (1H, m), 6.78 (1H, t, J=2.3 Hz), 6.98 (1H, d, J=3.6 Hz), 7.00-7.06 (2H, m), 7.14-7.17 (1H, m), 7.24-7.28 (2H, m), 7.40-7.47 (2H, m)

ESI-MS (m/e): 426 [M+H]$^+$

Production Example 62

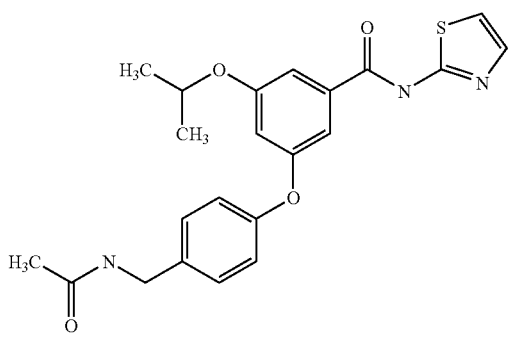

Preparation of 5-isopropoxy-3-(4-methylcarbonylaminomethyl-phenoxy)-N-thiazol-2-yl-benzamide The compound of Production Example 62 was obtained as a colorless amorphous substance using the 3-(4-aminomethylphenoxy)-5-isopropoxybenzoic acid methyl ester obtained in Production Example 59, acetyl chloride and 2-aminothiazole, by the same method as in Production Example 59, a corresponding method, or a combination thereof with an ordinary method.

$^1$HNMR (CDCl$_3$) δ: 1.35 (6H, d, J=6.0 Hz), 2.05 (3H, s), 4.40 (2H, d, J=5.6 Hz), 4.57 (1H, m), 5.95-6.07 (1H, br), 6.78 (1H, t, J=2.2 Hz), 6.93-7.02 (4H, m), 7.20-7.32 (4H, m)

ESI-MS (m/e): 426 [M+H]$^+$

Production Example 63

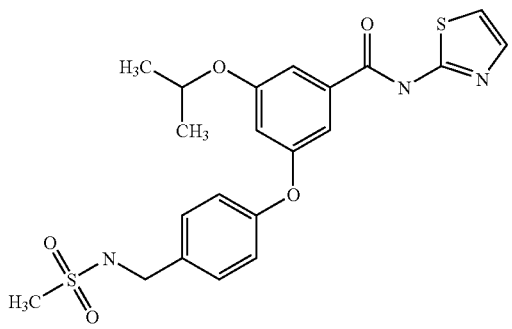

Preparation of 5-isopropoxy-3-(4-methanesulfonylaminomethyl-phenoxy)-N-thiazol-2-yl-benzamide The compound of Production Example 63 was obtained as a colorless amorphous substance using the 3-(4-aminomethylphenoxy)-5-isopropoxybenzoic acid methyl ester obtained in Production Example 59, methanesulfonyl chloride and 2-aminothiazole, by the same method as in Production Example 59, a corresponding method, or a combination thereof with an ordinary method.

$^1$HNMR (CDCl$_3$) δ: 1.36 (6H, d, J=6.0 Hz), 2.94 (3H, s), 4.32 (2H, d, J=6.1 Hz), 4.60 (1H, m), 4.79-4.88 (1H, m), 6.77 (1H, m), 6.98-7.38 (8H, m)

ESI-MS (m/e): 462 [M+H]$^+$

Production Example 64

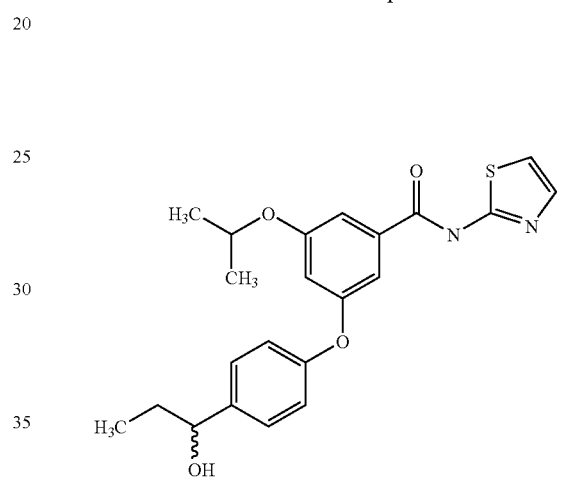

Preparation of 3-[4-(1-hydroxy-propyl)-phenoxy]-5-isopropoxy-N-thiazol-2-yl-benzamide The compound of Production Example 64 was obtained as a colorless amorphous substance using the 3-(4-formylphenoxy)-5-isopropoxybenzoic acid methyl ester obtained in Production Example 59, ethylmagnesium bromide and 2-aminothiazole, by the same method as in Production Example 59, a corresponding method, or a combination thereof with an ordinary method.

The reaction between the 3-(4-formylphenoxy)-5-isopropoxybenzoic acid methyl ester and ethylmagnesium bromide is a Grignard reaction, and it may be conducted by a method described in the relevant literature (for example, Comprehensive Organic Transformations, Richard L. et al., VCH Publishers, 1988), a corresponding method, or a combination thereof with an ordinary method.

$^1$HNMR (CDCl$_3$) δ: 0.92 (3H, t, J=7.4 Hz), 1.34 (6H, d, J=6.1 Hz), 1.67-1.88 (2H, m), 4.51-4.63 (2H, m), 6.76 (1H, t, J=2.3 Hz), 6.95-7.07 (3H, m), 7.04-7.07 (1H, m), 7.20-7.24 (2H, m), 7.32 (2H, d, J=8.5 Hz)

ESI-MS (m/e): 413 [M+H]$^+$

Production Example 65

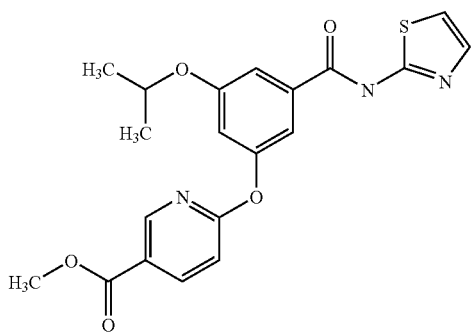

Preparation of 6-[3-isopropoxy-5-(thiazol-2-ylcarbamoyl)-phenoxy]-nicotinic acid methyl ester After adding 10 ml of 4N aqueous sodium hydroxide solution to a solution of the 3.0 g (14.3 mmol) of 5-hydroxy-3-isopropoxybenzoic acid methyl ester obtained in Production Example 59 in methanol (50 ml), the mixture was stirred at room temperature for 12 hours. The reaction mixture was concentrated under reduced pressure, and then saturated aqueous ammonium chloride was added, extraction was performed with chloroform, and the organic layer was dried and then concentrated under reduced pressure. The obtained residue was purified by silica gel chromatography (chloroform: methanol=50:1) to obtain 2.44 g of 5-hydroxy-3-isopropoxybenzoic acid (yield: 87%) as a white solid.

After adding 2.45 g (24.5 mmol) of 2-aminothiazole, 3.40 ml (24.5 mmol) of triethylamine and 4.14 g (24.5 mmol) of 2-chloro-1,3-dimethylimidazolinium chloride to a solution of 2.40 g (12.2 mmol) of the obtained carboxylic acid in chloroform (50 ml) while cooling on ice, the mixture was stirred at room temperature for 13 hours. Saturated aqueous ammonium chloride was added to the reaction mixture, extraction was performed with chloroform, and the organic layer was dried and then concentrated under reduced pressure. After adding 10 ml of 4N aqueous sodium hydroxide to a solution of the obtained residue in methanol (40 ml), the mixture was stirred at room temperature for 1 hour. The reaction mixture was concentrated under reduced pressure, and then saturated aqueous ammonium chloride was added, extraction was performed with chloroform, and the organic layer was dried and then concentrated under reduced pressure. The obtained residue was purified by silica gel chromatography (chloroform: methanol=100:1) to obtain 1.81 g of 5-hydroxy-3-isopropoxy-N-thiazol-2-yl-benzamide (yield: 53%) as a white solid.

After adding 123 mg (0.72 mmol) of 6-chloronicotinic acid methyl ester and 199 mg (1.44 mmol) of potassium carbonate to a solution of 100 mg (0.36 mmol) of the obtained amide compound in N,N-dimethylfommamide (10.0 ml), the mixture was stirred at 80° C. for 18 hours under a nitrogen atmosphere. Water was added to the reaction mixture, extraction was performed with ethyl acetate, and the organic layer was dried and then concentrated under reduced pressure. The obtained residue was purified by silica gel chromatography (hexane:ethyl acetate=3:1) to obtain the title compound as a white solid. The analysis data for the compound obtained in Production Example 65 are shown below.

$^1$HNMR (CDCl$_3$) δ: 1.36 (6H, d, J=6.0 Hz), 3.93 (3H, s), 4.60 (1H, m), 6.91-7.02 (3H, m), 7.29-7.40 (3H, m), 8.31 (1H, dd, J=8.6, 2.4 Hz), 8.81 (1H, d, J=2.4 Hz)

ESI-MS (m/e): 414 [M+H]$^+$

Production Example 66

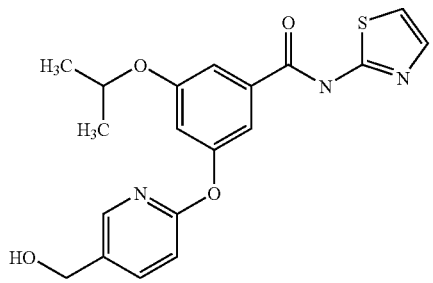

Preparation of 3-(5-hydroxymethyl-pyridin-2-yloxy)-5-isopropoxy-N-thiazol-2-yl-benzamide After adding 6.0 mg (0.16 mmol) of lithium aluminum hydride to a solution of 60.0 mg (0.15 mmol) of the 6-[3-isopropoxy-5-(thiazol-2-ylcarbamoyl)-phenoxy]-nicotinic acid methyl ester obtained in Production Example 65 in tetrahydrofuran (5.0 ml) while cooling on ice, the mixture was stirred at 0° C. for 1 hour. Saturated aqueous sodium hydrogencarbonate was added to the reaction mixture, extraction was performed with ethyl acetate, and the organic layer was dried and then concentrated under reduced pressure. The obtained residue was purified by silica gel chromatography (chloroform:methanol=30:1) to obtain the title compound as a white solid. The analysis data for the compound obtained in Production Example 66 are shown below.

$^1$HNMR (CDCl$_3$) δ: 1.36 (6H, d, J=6.0 Hz), 4.54-4.64 (1H, m), 4.68 (2H, s), 6.90 (1H, t, J=2.1 Hz), 6.92-6.98 (2H, m), 7.22 (1H, t, J=1.7 Hz), 7.31-7.37 (2H, m), 7.77 (1H, dd, J=2.8, 8.3 Hz), 8.14 (1H, br)

ESI-MS (m/e): 386 [M+H]$^+$

Compounds for Production Examples 67 to 73 were obtained by the same method as in Production Example 65 or 66 above. The analysis data for these compounds are shown below.

Production Example 67

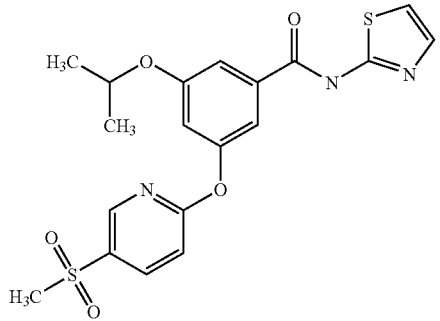

Preparation of 5-isopropoxy-3-(5-methanesulfonylpyridin-2-yl)-N-thiazol-2-yl-benzamide The compound of Production Example 67 was obtained as a light yellow oil using the 5-hydroxy-3-isopropoxy-N-thiazol-2-yl-benzamide obtained in Production Example 65 and 2,5-bismethanesulfonylpyridine, by the same method as in Production Example 65, a corresponding method, or a combination thereof with an ordinary method.

The 2,5-bismethanesulfonylpyridine was obtained by reacting 2,5-dibromopyridine with sodium thiomethoxide to obtain 2,5-bis-methylthiopyridine, and then oxidizing it with metachloroperbenzoic acid. The reaction between 2,5-dibromopyridine and sodium methoxide and the oxidation of 2,5-bis-methylthiopyridine with metachloroperbenzoic acid may be carried out according to ordinary methods.

$^1$HNMR (CDCl$_3$) δ: 1.37 (6H, d, J=6.1 Hz), 3.11 (3H, s), 4.58-4.66 (1H, m), 6.93 (1H, t, J=1.8 Hz), 6.99 (1H, d, J=3.6 Hz), 7.12 (1H, d, J=8.7 Hz), 7.29 (1H, d, J=1.8 Hz), 7.36 (1H, d, J=3.6 Hz), 7.40 (1H, d, J=1.8 Hz), 8.21 (1H, dd, J=2.6, 8.7 Hz), 8.71 (1H, d, J=2.6 Hz)

ESI-MS (m/e): 434 [M+H]$^+$

Production Example 68

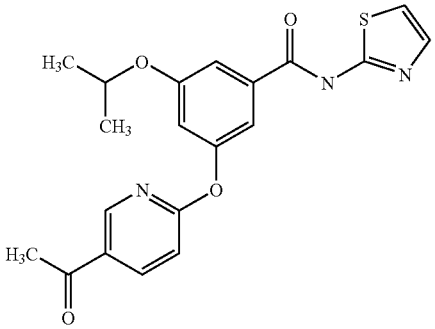

Preparation of 3-(5-acetyl-pyridin-2-yl-oxy)-5-isopropoxy-N-thiazol-2-yl-benzamide The compound of Production Example 68 was obtained as a white solid using 5-hydroxy-3-isopropoxy-N-thiazol-2-yl-benzamide obtained in the same manner as Production Example 65 and 2-chloro-5-acetylpyridine, by the same method as in Production Example 65, a corresponding method, or a combination thereof with an ordinary method.

$^1$HNMR (CDCl$_3$) δ: 1.37 (6H, d, J=6.0 Hz), 2.59 (3H, s), 4.61 (1H, m), 6.93 (1H, t, J=2.1 Hz), 6.98 (1H, d, J=3.6 Hz), 7.04 (1H, d, J=8.6 Hz), 7.29 (1H, t, J=2.1 Hz), 7.38 (2H, m), 8.30 (1H, dd, J=2.5, 8.6 Hz), 8.75 (1H, d, J=2.5 Hz)

ESI-MS (m/e): 398 [M+H]$^+$

Production Example 69

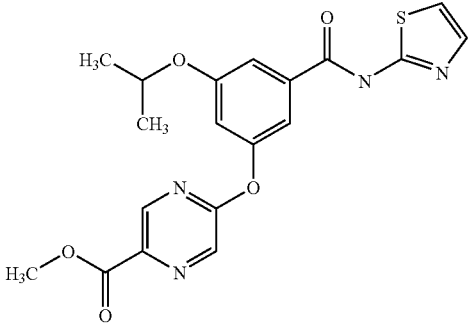

Preparation of 5-isopropoxy-3-(5-methoxycarbonylpyrazin-2-yl-oxy)-N-thiazol-2-yl-benzamide The compound of Production Example 69 was obtained as a colorless amorphous substance using 5-hydroxy-3-isopropoxy-N-thiazol-2-yl-benzamide obtained in the same manner as Production Example 65 and 2-chloro-5-methoxycarbonylpyrazine, by the same method as in Production Example 65, a corresponding method, or a combination thereof with an ordinary method.

$^1$HNMR (CDCl$_3$) δ: 1.38 (6H, d, J=6.0 Hz), 4.03 (3H, s), 4.57-4.65 (1H, m), 6.95 (1H, t, J=2.1 Hz), 7.00 (1H, d, J=3.6 Hz), 7.33-7.35 (1H, m), 7.37-7.42 (2H, m), 8.54 (1H, d, J=1.2 Hz), 8.85 (1H, d, J=1.2 Hz)

ESI-MS (m/e): 415 [M+H]$^+$

Production Example 70

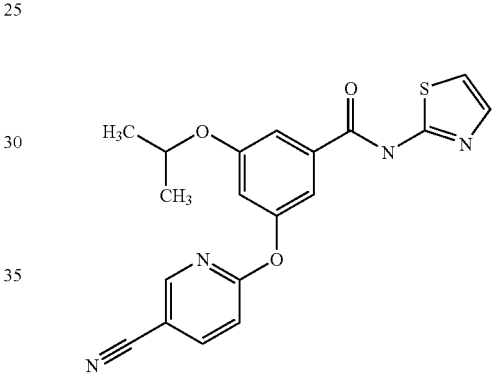

Preparation of 3-(5-cyano-pyridin-2-yl-oxy)-5-isopropoxy-N-thiazol-2-yl-benzamide The compound of Production Example 70 was obtained as a colorless amorphous substance using 5-hydroxy-3-isopropoxy-N-thiazol-2-yl-benzamide obtained in the same manner as Production Example 65 and 2,5-dibromopyridine, by reaction between 3-(5-bromo-pyridin-2-yl-oxy)-5-isopropoxy-N-thiazol-2-yl-benzamide obtained in the same manner as Production Example 65 and copper (I) cyanide.

The reaction between 3-(5-bromo-pyridin-2-yl-oxy)-5-isopropyl-N-thiazol-2-yl-benzamide and copper cyanide may be carried out by a method described in the relevant literature (for example, Comprehensive Organic Transformations, Richard L. et al., VCH Publishers, 1988), a corresponding method, or a combination thereof with an ordinary method.

$^1$HNMR (CDCl$_3$) δ: 1.37 (6H, d, J=6.0 Hz), 4.61 (1H, m), 6.89-6.92 (1H, m), 6.97-7.01 (1H, m), 7.06-7.09 (1H, m), 7.26-7.29 (1H, m), 7.35-7.40 (1H, m), 7.93-7.98 (1H, m), 8.47-8.49 (1H, m)

ESI-MS (m/e): 381 [M+H]$^+$

Production Example 71

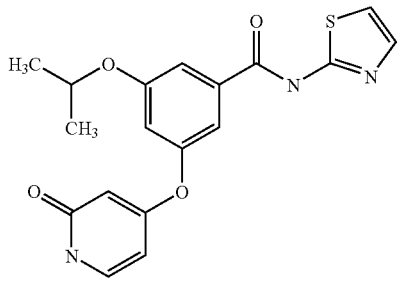

Preparation of 5-isopropoxy-3-(2-oxo-1,2-dihydro-pyridin-4-yl-oxy)-N-thiazol-2-yl-benzamide The compound of Production Example 71 was obtained as a white solid using 5-hydroxy-3-isopropoxybenzoic acid methyl ester obtained in the same manner as Production Example 59, 4-bromo-pyridine hydrochloride and 2-aminothiazole, by the same method as in Production Example 65, a corresponding method, or a combination thereof with an ordinary method.

$^1$HNMR (CDCl$_3$) δ: 1.31 (6H, d, J=6.0 Hz), 4.73-4.83 (1H, m), 5.51 (1H, d, J=2.6 Hz), 6.03 (1H, dd, J=2.5, 7.4 Hz), 6.99 (1H, t, J=2.2 Hz), 7.30 (1H, d, J=3.6 Hz), 7.38-7.44 (2H, m), 7.55-7.59 (2H, m)

ESI-MS (m/e): 372 [M+H]$^+$

Production Example 72

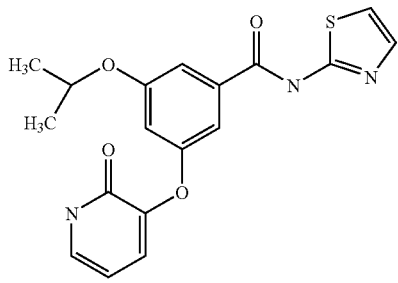

Preparation of 5-isopropoxy-3-(2-oxo-1,2-dihydro-pyridin-3-yl-oxy)-N-thiazol-2-yl-benzamide The compound of Production Example 72 was obtained as white crystals using 5-hydroxy-3-isopropoxybenzoic acid methyl ester obtained in the same manner as Production Example 59, 3-bromo-2-hydroxy-pyridine and 2-aminothiazole, by the same method as in Production Example 65, a corresponding method, or a combination thereof with an ordinary method.

$^1$HNMR (CDCl$_3$) δ: 1.34 (6H, d, J=6.0 Hz), 4.62-4.72 (1H, m), 6.41 (1H, dd, J=6.7, 7.2 Hz), 6.76 (1H, t, J=2.3 Hz), 7.10-7.13 (1H, dd, J=1.5, 2.2 Hz), 7.14 (1H, d, J=3.6 Hz), 7.27-7.29 (1H, m), 7.30-7.37 (2H, m), 7.48 (2H, d, J=3.6 Hz)

ESI-MS (m/e): 372 [M+H]$^+$

Production Example 73

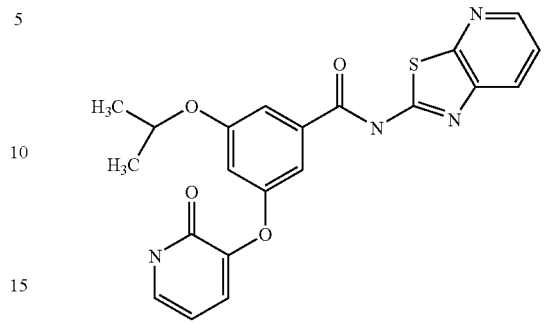

Preparation of 5-isopropoxy-3-(2-oxo-1,2-dihydro-pyridin-3-yl-oxy)-N-thiazolo[54-b]pyridin-2-yl-benzamide The compound of Production Example 73 was obtained as a white solid using 5-hydroxy-3-isopropoxybenzoic acid methyl ester obtained in the same manner as Production Example 59, 3-bromo-2-hydroxy-pyridine and 2-amino-thiazolo[5,4-b]pyridine, by the same method as in Production Example 65, a corresponding method, or a combination thereof with an ordinary method.

$^1$HNMR (CDCl$_3$) δ: 1.31 (6H, d, J=6.0 Hz), 4.68-4.81 (1H, m), 6.25 (1H, t, J=6.9 Hz), 6.68-6.72 (1H, m), 7.13-7.16 (1H, m), 7.31-7.40 (2H, m), 7.44-7.54 (2H, m), 8.12 (1H, d, J=7.8 Hz), 8.46-8.52 (1H, m)

ESI-MS (m/e): 423 [M+H]$^+$

Production Example 74

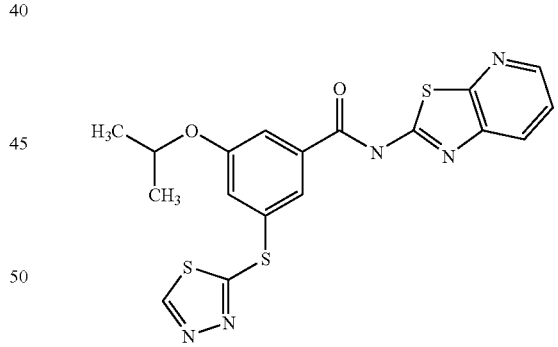

Preparation of 5-isopropoxy-3-([1,3,4]thiadiazol-2-ylsulfanyl)-N-thiazolo[5,4-b]-pyridine-2-yl-benzamide After adding 298 mg (2.16 mmol) of potassium carbonate and 0.12 ml (1.29 mmol) of 2-bromopropane to a solution of 120 mg (0.43 mol) of 3-hydroxy-5-iodobenzoic acid methyl ester in N,N-dimethylformamide (4.0 ml), the reaction mixture was stirred at 80° C. overnight. Water was added to the reaction mixture, extraction was performed with acetic acid ethyl ester, and then the organic layer was washed with brine, dried and concentrated under reduced pressure. The obtained residue was purified by silica gel column chromatography (hexane:acetic acid ethyl ester=5:1) to obtain 133 mg of 5-iodo-3-isopropoxybenzoic acid methyl ester (yield: 96%) as a colorless oil.

After adding 292 mg (2.47 mol) of 2-mercapto-1,3,4-thiadiazole, 456 mg (3.30 mol) of potassium carbonate, 27.0 mg (0.25 mmol) of hydroquinone and 35.0 mg (0.25 mmol) of copper (1) bromide to a solution of 132 mg (0.41 mmol) of the obtained iodo compound in N,N-dimethylformamide (10 ml), the mixture was stirred at 130° C. for 40 minutes under a nitrogen atmosphere. Water was added to the reaction mixture, extraction was performed with acetic acid ethyl ester, and then the organic layer was washed with brine, dried and concentrated under reduced pressure. The obtained residue was purified by silica gel column chromatography (hexane:acetic acid ethyl ester=1:1) to obtain 8.90 mg of 5-isopropoxy-3-(1,3,4-thiadiazol-2-yl-thio)benzoic acid methyl ester (yield: 7%) as a colorless oil.

After adding 0.14 ml (0.29 mmol) of a 2N aqueous sodium hydroxide solution to a solution of the obtained ester compound in methanol (1.0 ml), the reaction mixture was stirred at room temperature for 5 hours. A 2N aqueous hydrochloric acid solution was added to the reaction mixture, extraction was performed with acetic acid ethyl ester, and then the organic layer was washed with brine, dried and concentrated under reduced pressure to obtain a crude carboxyl compound.

After adding 8.20 mg (0.054 mol) of 2-amino-thiazolo[5,4-b]-pyridine, 5.00 mg (0.037 mmol) of 1-hydroxybenzotriazole hydrate and 7.10 mg (0.037 mol) of 1-(3-dimethylaminopropyl)-3-ethylcarbodiimide hydrochloride to a solution of the obtained carboxyl compound in N,N-dimethylformamide (1.2 ml), the mixture was stirred at room temperature overnight. The reaction mixture was concentrated under reduced pressure, and the obtained residue was purified by silica gel column chromatography (hexane:acetic acid ethyl ester=1:1) to obtain the title compound as a white solid. The analysis data for the compound obtained in Production Example 74 are shown below.

$^1$HNMR (CDCl$_3$) δ: 1.32 (6H, d, J=6.0 Hz), 4.54-4.62 (1H, m), 7.32 (1H, dd, J=4.6, 8.2 Hz), 7.37 (1H, t, J=1.8 Hz), 7.56 (1H, t, J=1.8 Hz), 7.74 (1H, dd, J=1.4, 8.2 Hz), 7.79 (1H, t, J=1.8 Hz), 8.52 (1H, dd, J=1.4, 4.6 Hz), 9.07 (1H, s)

ESI-MS (m/e): 430 [M+H]$^+$

Compounds for Production Example 75 to Production Example 88 were obtained by the same method as in Production Example 74 above. The analysis data for representative compounds among these are shown below.

Production Example 75

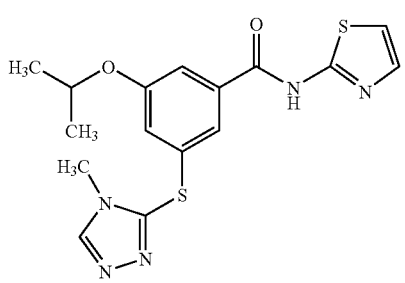

Preparation of 5-isopropoxy-3-(4-methyl-[1,2,4]triazol-3-ylsulfanyl)-N-thiazol-2-yl-benzamide The compound of Production Example 75 was obtained as a colorless amorphous substance using the 5-iodo-3-isopropoxybenzoic acid methyl ester obtained in Production Example 74, 2-aminothiazole and 3-mercapto-4-methyl-[1,2,4]triazole, by the same method as in Production Example 74, a corresponding method, or a combination thereof with an ordinary method.

$^1$HNMR (CDCl$_3$) δ: 1.31 (6H, d, J=5.9 Hz), 3.65 (3H, s), 4.53-4.57 (1H, m), 6.98 (1H, q, J=3.5 Hz), 7.06 (1H, s), 7.20 (1H, d, J=3.5 Hz), 7.41 (1H, s), 7.53 (1H, s), 8.29 (1H, s)

ESI-MS (m/e): 374[M−H]$^−$

Production Example 76

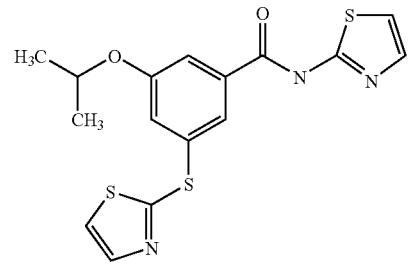

Preparation of 5-isopropoxy-3-thiazol-2-ylsulfanyl-N-thiazol-2-yl-benzamide

The compound of Production Example 76 was obtained as a colorless amorphous substance using the 5-iodo-3-isopropoxybenzoic acid methyl ester obtained in Production Example 75, 2-aminothiazole and 2-mercapto-thiazole, by the same method as in Production Example 74, a corresponding method, or a combination thereof with an ordinary method.

$^1$HNMR (CDCl$_3$) δ: 1.33 (6H, d, J=6.0 Hz), 4.54-4.62 (1H, m), 6.95 (1H, d, J=3.6 Hz), 7.15 (1H, d, J=3.6 Hz), 7.29-7.32 (2H, m), 7.50 (1H, dd, J=1.5, 2.2 Hz), 7.69 (1H, d, J=1.5 Hz), 7.77 (1H, d, J=3.4 Hz)

Production Example 77

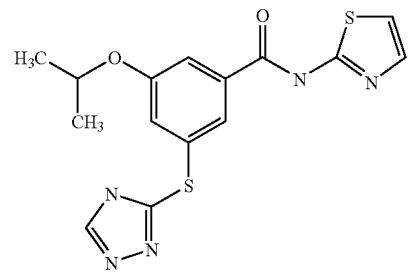

Preparation of 5-isopropoxy-3-(4H-[1,2,4]triazol-3-ylsulfanyl)-N-thiazol-2-yl-benzamide The compound of Production Example 77 was obtained as a colorless amorphous substance using the 5-iodo-3-isopropoxybenzoic acid methyl ester obtained in Production Example 74, 2-aminothiazole and 3-mercapto-[1,2,4]triazole, by the same method as in Production Example 74, a corresponding method, or a combination thereof with an ordinary method.

$^1$HNMR (CDCl$_3$) δ: 1.34 (6H, d, J=6.0 Hz), 4.59-4.63 (1H, m), 7.04 (1H, d, J=2.51 Hz), 7.44 (1H, dd, J=1.0 Hz), 7.49 (1H, t, J=1.0 Hz), 7.49 (1H, d, J=2.5 Hz), 7.67 (1H, t, J=1.0 Hz), 8.24 (1H, s)

ESI-MS (m/e): 362 [M+H]$^+$

Production Example 78

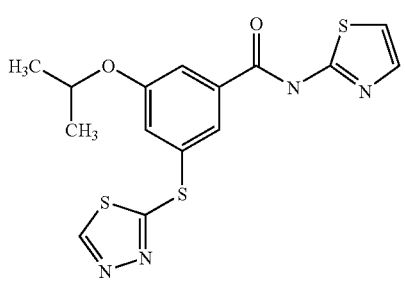

Preparation of 5-isopropoxy-3-([1,3,4]thiadiazol-2-ylsulfanyl)-N-thiazol-2-yl-benzamide The compound of Production Example 78 was obtained as a colorless amorphous substance using the 5-iodo-3-isopropoxybenzoic acid methyl ester obtained in Production Example 74, 2-aminothiazole and 2-mercapto-[1,3,4]thiadiazole, by the same method as in Production Example 74, a corresponding method, or a combination thereof with an ordinary method.

$^1$HNMR (CD$_3$OD) δ: 1.37 (6H, d, J=6.0 Hz), 4.71-4.81 (1H, m), 7.14 (1H, d, J=3.7 Hz), 7.45 (1H, t, J=1.8 Hz), 7.50 (1H, d, J=3.7 Hz), 7.68 (1H, t, J=1.8 Hz), 7.89 (1H, t, J=1.8 Hz), 9.32 (1H, s)

ESI-MS (m/e): 379 [M+H]$^+$

Production Example 79

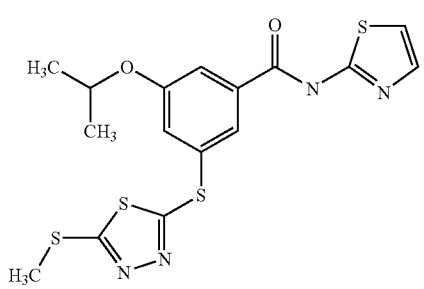

Preparation of 5-isopropoxy-3-(5-methylsulfanyl-[1,3,4]thiadiazol-2-ylsulfanyl)-N-thiazol-2-yl-benzamide The compound of Production Example 79 was obtained as a colorless oil using the 5-iodo-3-isopropoxybenzoic acid methyl ester obtained in Production Example 74, 2-aminothiazole and 2-mercapto-5-methylsulfanyl-[1,3,4]thiadiazole, by the same method as in Production Example 74, a corresponding method, or a combination thereof with an ordinary method.

$^1$HNMR (CDCl$_3$) δ: 1.34 (6H, d, J=6.0 Hz), 2.75 (3H, s), 4.55-4.63 (1H, m), 6.97 (1H, d, J=3.6 Hz), 7.13 (1H, d, J=3.6 Hz), 7.32 (1H, t, J=1.8 Hz), 7.53 (1H, t, J=1.8 Hz), 7.72 (1H, t, J=1.8 Hz)

ESI-MS (m/e): 425-[N+H]$^+$

Production Example 80

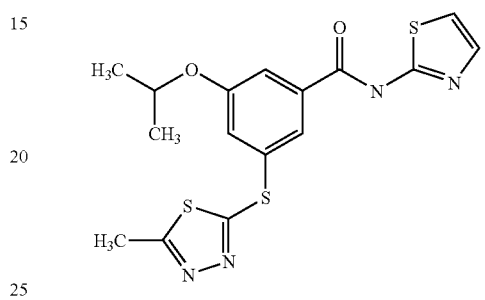

Preparation of 5-isopropoxy-3-(5-methyl-[1,3,4]thiadiazol-2-ylsulfanyl)-N-thiazol-2-yl-benzamide The compound of Production Example 80 was obtained as a colorless amorphous substance using the 5-iodo-3-isopropoxybenzoic acid methyl ester obtained in Production Example 74, 2-aminothiazole and 2-mercapto-5-methyl-[1,3,4]thiadiazole, by the same method as in Production Example 74, a corresponding method, or a combination thereof with an ordinary method.

$^1$HNMR (CDCl$_3$) δ: 1.35 (6H, d, J=6.0 Hz), 2.72 (3H, s), 4.56-4.64 (1H, m), 6.97 (1H, d, J=3.6 Hz), 7.17 (1H, d, J=3.6 Hz), 7.35 (1H, t, J=1.8 Hz), 7.54 (1H, t, J=1.8 Hz), 7.73 (1H, t, J=1.8 Hz)

ESI-MS (m/e): 393 [M+H]$^+$

Production Example 81

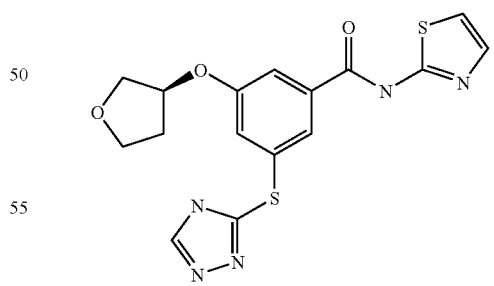

Preparation of 5-(tetrahydrofuran-3-yl-oxy)-N-thiazol-2-yl-3-(4H-[1,2,4]triazol-3-ylsulfanyl)-benzamide The compound of Production Example 81 was obtained as a colorless oil by the same method as in Production Example 74, a corresponding method, or a combination thereof with an ordinary method, using (3R)-3-bromopropane instead of 2-bromopropane, and using 5-iodo-3-(tetrahydrofuran-3-yloxy)benzoic acid methyl ester produced by the same method as in Production Example 74, 2-aminothiazole and 3-mercapto-[1,2,4]triazole.

$^1$HNMR (CDCl$_3$) δ: 2.05-2.24 (2H, m), 3.89-4.02 (4H, m), 4.94-4.98 (1H, m), 7.06 (1H, d, J=3.6 Hz), 7.23 (1H, t, J=1.8 Hz), 7.40 (1H, d, J=1.8 Hz), 7.48 (1H, d, J=3.6 Hz), 7.68 (1H, d, J=1.8 Hz), 8.32 (1H, s)

ESI-MS (m/e): 390 [M+H]$^+$

Production Example 82

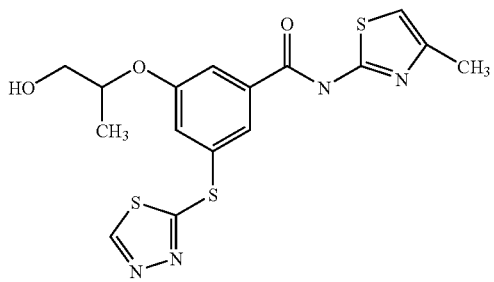

Preparation of 5-(2-hydroxy-1-methyl-ethoxy)-N-(4-methyl-thiazol-2-yl)-3-([1,3,4]thiadiazol-2-ylsulfanyl)-benzamide The compound of Production Example 82 was obtained as a colorless oil using 3-hydroxy-5-iodo-benzoic acid methyl ester, 1-tert-dimethylsiloxy-2-hydroxypropane and 2-amino-4-methyl-thiazole, and using 3-(2-tert-butyl-dimethylsiloxy-1-methyl-ethoxy)-5-iodo-N-(4-methyl-thiazol-2-yl)-benzamide obtained in the same manner as Production Example 65 and 2-mercapto-[1,3,4]thiadiazole, by the same method as in Production Example 74, a corresponding method, or a combination thereof with an ordinary method. Removal of the tert-butyldimethylsiloxy group serving as the protective group for the hydroxy group may be accomplished by the same method as in Production Example 2, a corresponding method, or a combination thereof with an ordinary method.

$^1$HNMR (CDCl$_3$) δ: 1.32 (d, 3H, J=6.2 Hz), 2.38 (s, 3H), 4.79 (m, 2H), 4.65 (m, 1H), 6.63 (s, 1H), 7.38 (m, 1H), 7.72 (m, 1H), 7.82 (m, 1H), 9.08 (s, 1H)

ESI-MS (m/e): 409 [M+H]$^+$

Production Example 83

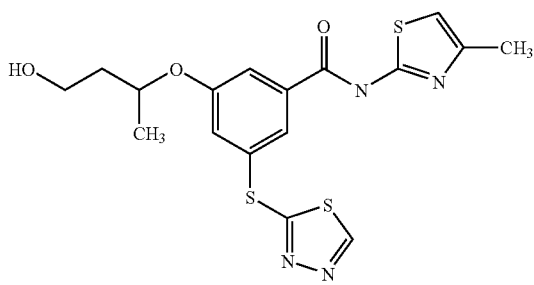

Preparation of 5-(3-hydroxy-1-methyl-propoxy)-N-(4-methyl-thiazol-2-yl)-3-([1,3,4]thiadiazol-2-ylsulfanyl)-benzamide The compound of Production Example 83 was obtained as a white amorphous substance using 3-hydroxy-5-iodo-benzoic acid methyl ester, 5-tert-butyldimethylsiloxy-pentan-2-ol and 2-amino-4-methyl-thiazole, and using 3-(3-tert-butyldimethylsiloxy-1-methyl-propoxy)-5-iodo-N-(4-methyl-thiazol-2-yl)-benzamide obtained in the same manner as Production Example 65 and 2-mercapto-[1,3,4]thiadiazole, by the same method as in Production Example 74, a corresponding method, or a combination thereof with an ordinary method. Removal of the tert-butyldimethylsiloxy group serving as the protective group for the hydroxy group may be accomplished by the same method as in Production Example 2, a corresponding method, or a combination thereof with an ordinary method.

$^1$HNMR (CDCl$_3$) δ: 1.33 (d, 3H, J=6.1 Hz), 2.10-1.75 (m, 4H), 2.18 (d, 1H, J=1.0 Hz), 3.78 (m, 2H), 4.63 (m, 1H), 6.56 (d, 1H, J=1.0 Hz), 7.38 (m, 1H), 7.61 (m, 1H), 7.73 (m, 1H), 9.05 (s, 1H), 11.1 (br, 1H)

ESI-MS (m/e): 423 [M+H]$^+$

Production Example 84

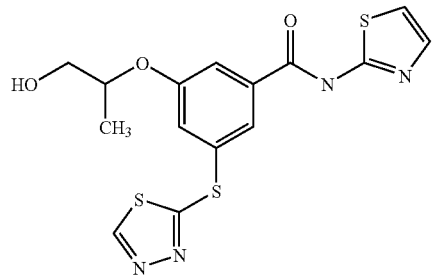

Preparation of 5-(2-hydroxy-1-methyl-ethoxy)-3-([1,3,4]thiadiazol-2-ylsulfanyl)-N-thiazol-2-yl-benzamide The compound of Production Example 84 was obtained as a colorless oil using 3-hydroxy-5-iodo-benzoic acid methyl ester, 1-tert-butoxy-2-ol and 2-aminothiazole, and using 3-(2-tert-butyldimethylsiloxy-1-methyl-propoxy)-5-iodo-N-(thiazol-2-yl)-benzamide obtained in the same manner as Production Example 65 and 2-mercapto-[1,3,4]thiadiazole, by the same method as in Production Example 74, a corresponding method, or a combination thereof with an ordinary method. Removal of the tert-butyldimethylsiloxy group serving as the protective group for the hydroxyl group may be accomplished by the same method as in Production Example 2, a corresponding method, or a combination thereof with an ordinary method.

$^1$HNMR (CDCl$_3$) δ: 1.30 (d, 3H, J=6.0 Hz), 3.80 (m, 2H), 4.62 (sextet, 1H, J=6.0 Hz), 7.00 (d, 1H, J=3.6 Hz), 7.27 (d, 1H, J=3.6 Hz), 7.40 (m, 1H), 7.62 (m, 1H), 7.81 (m, 1H), 9.09 (s, 1H)

ESI-MS (m/e): 395 [M+H]$^+$

Production Example 85

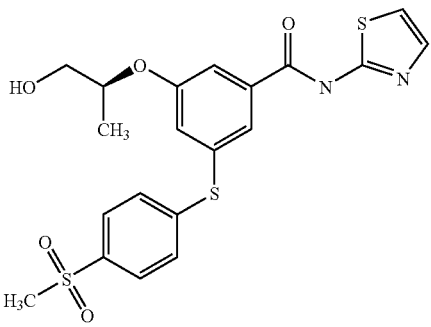

Preparation of 5-(2-hydroxy-1-methyl-ethoxy)-3-(4-methanesulfonylphenylsulfanyl)-N-thiazol-2-yl-benzamide The compound of Production Example 85 was obtained as a colorless oil using 3-hydroxy-5-iodo-benzoic acid methyl ester, 1-tert-butyldimethylsiloxy-butan-2-ol and 2-aminothiazole, and using 3-(2-tert-butyldimethylsiloxy-1-methyl-propoxy)-5-iodo-N-(thiazol-2-yl)-benzamide obtained in the same manner as Production Example 65 and 2-mercapto-[1,3,4]thiadiazole, by the same method as in Production Example 74, a corresponding method, or a combination thereof with an ordinary method. Removal of the tert-butyldimethylsiloxy group serving as the protective group for the hydroxyl group may be accomplished by the same method as in Production Example 2, a corresponding method, or a combination thereof with an ordinary method.

$^1$HNMR (CDCl$_3$) δ: 1.31 (d, 3H, J=6.2 Hz), 3.07 (s, 3H), 3.78 (m, 2H), 4.58 (m, 1H), 7.01 (d, 1H, J=3.6 Hz), 7.24 (m, 2H), 7.37 (d, 2H, J=8.6 Hz), 7.55 (m, 1H), 7.61 (m, 1H), 7.84 (d, 2H, J=8.6 Hz), 11.3 (br, 1H)

ESI-MS (m/e): 465 [M+H]$^+$

Production Example 86

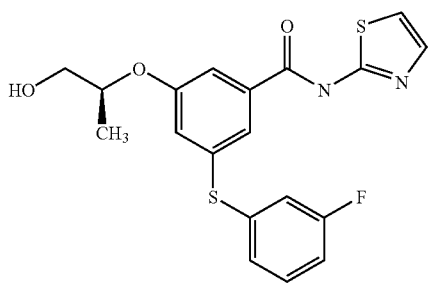

Preparation of 3-(3-fluoro-phenylthio)-5-(2-hydroxy-1-methyl-ethoxy)-N-thiazol-2-yl-benzamide The compound of Production Example 86 was obtained as a white amorphous substance using 3-hydroxy-5-iodo-benzoic acid methyl ester, 1-(tert-dimethylsiloxy)-2-hydroxypropane and 2-aminothiazole, and using 3-(2-tert-butyldimethylsiloxy-1-methyl-ethoxy)-5-iodo-N-(thiazol-2-yl)-benzamide obtained in the same manner as Production Example 65 and 3-fluorothiophenol, by the same method as in Production Example 74, a corresponding method, or a combination thereof with an ordinary method. Removal of the tert-butyldimethylsiloxy group serving as the protective group for the hydroxy group may be accomplished by the same method as in Production Example 2, a corresponding method, or a combination thereof with an ordinary method.

$^1$HNMR (CDCl$_3$) δ: 1.27 (d, 3H, J=6.2 Hz), 3.75 (m, 2H), 4.54 (m, 1H), 7.18-6.95 (m, 4H), 7.21 (m, 1H), 7.30 (m, 1H), 7.52-7.40 (m, 2H)

ESI-MS (m/e): 405 [M+H]$^+$

Production Example 87

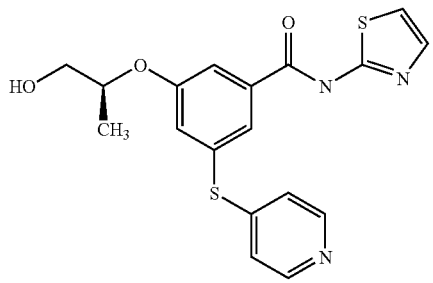

Preparation of 5-(2-hydroxy-1-methyl-ethoxy)-3-(pyridin-4-ylsulfanyl)-N-thiazol-2-yl-benzamide The compound of Production Example 87 was obtained as a yellow oil using 3-hydroxy-5-iodo-benzoic acid methyl ester, 1-(tert-butyldimethylsiloxy)-2-hydroxypropane and 2-aminothiazole, and using 3-(2-tert-butyldimethylsiloxy-1-methyl-ethoxy)-5-iodo-N-(thiazol-2-yl)-benzamide
obtained in the same manner as Production Example 65 and 4-mercaptopyridine, by the same method as in Production Example 74, a corresponding method, or a combination thereof with an ordinary method. Removal of the tert-butyldimethylsiloxy group serving as the protective group for the hydroxy group may be accomplished by the same method as in Production Example 2, a corresponding method, or a combination thereof with an ordinary method.

$^1$HNMR (CDCl$_3$) δ: 1.36 (d, 3H, J=6.1 Hz), 3.72 (d, 2H, J=6.1 Hz), 4.68 (sextet, 1H, J=6.1 Hz), 7.20 (m, 3H), 7.45 (m, 1H), 7.54 (m, 1H), 7.75 (m, 1H), 7.85 (m, 1H), 8.36 (m, 2H)

ESI-MS (m/e): 388 [M+H]$^+$

Production Example 88

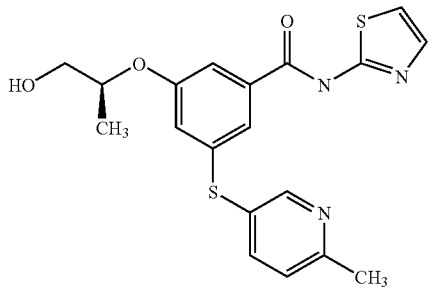

Preparation of 5-(2-hydroxy-1-methyl-ethoxy)-3-(6-methyl-pyridin-3-ylsulfanyl)-N-thiazol-2-yl-benzamide The compound of Production Example 88 was obtained as a white amorphous substance using 3-hydroxy-5-iodo-benzoic acid methyl ester, 1-(tert-dimethylsiloxy)-2-hydroxypropane and 2-aminothiazole, and using 3-(2-tert-butyldimethylsiloxy-1-methyl-ethoxy)-5-iodo-N-(thiazol-2-yl)-benzamide obtained in the same manner as Production Example 65 and 3-mercapto-6-methyl-pyridine, by the same method as in Production Example 74, a corresponding method, or a combination thereof with an ordinary method. Removal of the tert-butyldimethylsiloxy group serving as the protective group for the hydroxy group may be accomplished by the same method as in Production Example 2, a corresponding method, or a combination thereof with an ordinary method.

$^1$HNMR (CDCl$_3$) δ: 1.24 (d, 3H, J=6.2 Hz), 2.54 (s, 3H), 3.72 (m, 2H), 4.52 (m, 1H), 6.97 (m, 2H), 7.16 (m, 2H), 7.33 (m, 1H), 7.59 (m, 1H), 8.52 (m, 1H), 12.0 (br, 1H)

ESI-MS (m/e): 402 [M+H]$^+$

Production Example 89

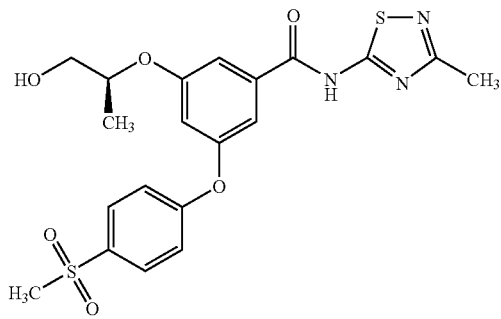

Preparation of 5-(2-hydroxy-1-methyl-ethoxy)-3-(4-methanesulfonylphenoxy)-N-(3-methyl-[1,2,4]-thiadiazol-5-yl)-benzamide After adding 33.4 g (142 mmol) of 4-methanesulfonyl-bromobenzene, 2.67 g (11.9 mmol) of palladium acetate, 5.31 g (17.8 mmol) of 2-(di-tert-butylphosphino)biphenyl and 50.3 g (237 mmol) of potassium phosphate to a solution of 25.0 g (119 mmol) of 5-hydroxy-3-methoxymethoxybenzoic acid methyl ester in toluene (375 ml), the reactor was sealed and the mixture was subsequently stirred at 130° C. for 6 hours. Acetic acid ethyl ester was added to the reaction mixture, which was then filtered and concentrated under reduced pressure. The obtained residue was purified by silica gel column chromatography (hexane:acetic acid ethyl ester=2:1) to obtain 31.0 g of 3-(4-methanesulfonyl-phenoxy)-5-methoxymethoxy-benzoic acid methyl ester (yield: 69%) as a white solid.

After adding 60 ml of trifluoroacetic acid to a solution of 30.9 g (84.3 mmol) of the obtained 3-(4-methanesulfonyl-phenoxy)-5-methoxymethoxy-benzoic acid methyl ester in methylene chloride (100 ml) while cooling on ice, the reaction mixture was stirred at room temperature for 4 hours. The reaction mixture was concentrated under reduced pressure, and the obtained residue was purified by silica gel column chromatography (hexane:acetic acid ethyl ester=1:1) to obtain 15.2 g of 5-hydroxy-3-(4-methanesulfonyl-phenoxy)benzoic acid methyl ester (yield: 56%) as a white solid.

After then adding 11.8 g (62.1 mmol) of (2R)-1-(t-butyldimethylsiloxy)-2-hydroxypropane and 16.3 g (62.1 mmol) of triphenylphosphine to a solution of 10.0 g (31.0 mmol) of the obtained 5-hydroxy-3-(4-methanesulfonyl-phenoxy)benzoic acid methyl ester in tetrahydrofuran (200 ml), 33.8 ml (77.6 mmol) of a solution of diethyl azodicarboxylate in 40% toluene was added while cooling on ice, and the mixture was stirred at room temperature for 12 hours. The reaction mixture was concentrated under reduced pressure, and the obtained residue was purified by silica gel column chromatography (hexane:acetic acid ethyl ester=8:2) to obtain 5-((1S)-2-(tert-butyldimethylsiloxy)-1-methyl-ethoxy)-3-(4-methanesulfonyl-phenoxy)-benzoic acid methyl ester as a yellow oil.

The compound of Production Example 89 was obtained as a colorless amorphous substance using 200 mg (0.40 mmol) of the obtained 5-((1S)-2-(t-butyldimethylsiloxy)-1-methyl-ethoxy)-3-(4-methanesulfonyl-phenoxy)-benzoic acid methyl ester and 5-amino-3-methyl-[1,2,4]thiadiazole, by the same method as in Production Example 2, a corresponding method, or a combination thereof with an ordinary method.

$^1$HNMR (CD$_3$OD) δ: 1.30 (d, 6H, J=6.2 Hz), 2.50 (s, 3H), 3.12 (s, 3H), 3.68 (d, 2H, J=5.0 Hz), 4.58-4.63 (m, 1H), 7.01 (s, 1H), 7.23 (d, 2H, J=8.8 Hz), 7.36 (s, 1H), 7.54 (s, 1H), 7.97 (d, 2H, J=8.8 Hz)

ESI-MS (m/e): 464 [M+H]$^+$

Production Example 90

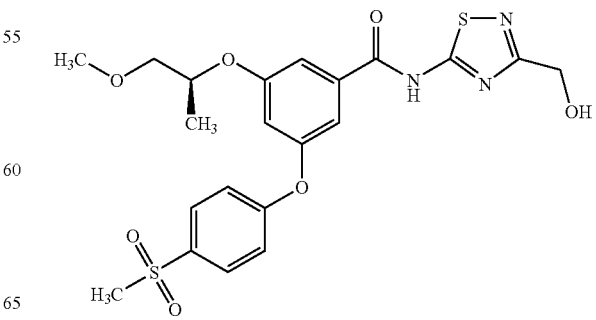

Preparation of N-[3-hydroxymethyl-1,2,4-thiadiazol-5-yl]-3-(4-methanesulfonylphenoxy)-5-(2-methoxy-1-methyl-ethoxy)benzamide The compound of Production Example 90 was obtained as a colorless amorphous substance using the 3-(4-methanesulfonyl-phenoxy)-5-methoxymethoxy-benzoic acid methyl ester obtained in Production Example 89, (2R)-1-methoxy-2-propanol and 5-amino-3-(t-butyldimethylsiloxymethyl)-[1,2,4]thiadiazole, by the same method as in Production Example 89, a corresponding method, or a combination thereof with an ordinary method.

$^1$HNMR (CDCl$_3$) δ: 1.34 (3H, d, J=6.3 Hz), 3.09 (3H, s), 3.41 (3H, s), 3.49-3.64 (2H, m), 4.60-4.72 (1H, m), 4.79 (2H, s), 6.92 (1H, t, J=2.0 Hz), 7.16 (2H, d, J=8.7 Hz), 7.43 (1H, br), 7.93 (2H, d, J=8.7 Hz)

ESI-MS (m/e): 494 [M+H]$^+$

Production Example 91

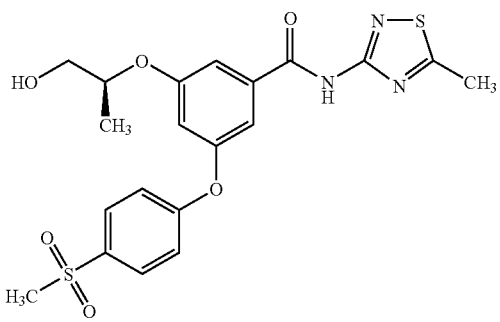

Preparation of 5-(3-hydroxy-1-methylethoxy)-3-(4-methanesulfonylphenoxy)-N-[5-methyl-1,2,4-thiadiazol-3-yl]benzamide The compound of Production Example 91 was obtained as a white solid using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 3-amino-5-methyl-[1,2,4]thiadiazole, by the same method as in Production Example 89, a corresponding method, or a combination thereof with an ordinary method.

$^1$HNMR (CDCl$_3$) δ: 1.29 (d, 3H, J=6.3 Hz), 2.76 (s, 3H), 3.07 (s, 3H), 3.79 (m, 2H), 4.57 (m, 1H), 6.81 (m, 1H), 7.12 (d, 2H, J=8.8 Hz), 7.17 (m, 1H), 7.33 (m 1H), 7.91 (d, 2H, J=8.8 Hz), 9.27 (br, 1H)

ESI-MS (m/e): 464 [M+H]$^+$

Production Example 92

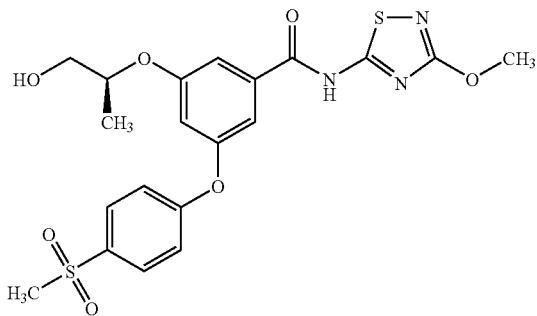

Preparation of 5-(hydroxy-1-methylethoxy)-3-(4-methanesulfonylphenoxy)-N-(3-methoxy-1,2,4-thiadiazol-5-yl)benzamide The compound of Production Example 92 was obtained as a white amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 5-amino-3-methoxy-[1,2,4]thiadiazole, by the same method as in Production Example 89, a corresponding method, or a combination thereof with an ordinary method.

$^1$HNMR (CDCl$_3$) δ: 1.32 (d, 3H, J=6.3 Hz), 3.12 (s, 3H), 3.80 (d, 2H, J=5.5 Hz), 3.99 (s, 3H), 4.61 (m, 1H), 6.87 (m, 1H), 7.17 (d, 2H, J=8.8 Hz), 7.23 (m, 1H), 7.35 (m, 1H), 7.96 (d, 2H, J=8.8 Hz), 11.2 (br, 1H)

ESI-MS (m/e): 480 [M+H]$^+$

Production Example 93

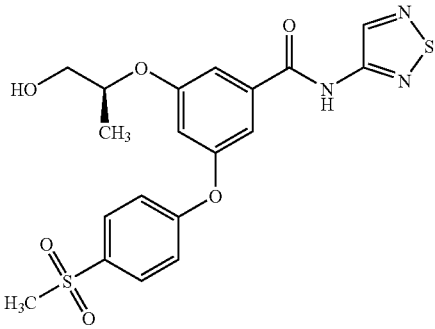

Preparation of 5-(2-hydroxy-1-methyl-ethoxy)-3-(4-methanesulfonylphenoxy)-N-(1,2,5-thiadiazol-3-yl)benzamide The compound of Production Example 93 was obtained as a light yellow amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 3-amino-[1,2,5]thiadiazole, by the same method as in Production Example 89, a corresponding method, or a combination thereof with an ordinary method.

$^1$HNMR (CDCl$_3$) δ: 1.34 (d, 3H, J=6.3 Hz), 1.91 (t, 1H, J=5.7 Hz), 3.09 (s, 3H), 3.80 (m, 2H), 4.60 (m, 1H), 6.89 (m, 1H), 7.17 (d, 2H), 7.18 (m, 1H), 7.35 (m, 1H), 7.96 (d, 2H, J=8.8 Hz), 8.92 (br, 1H), 9.32 (s, 1H)

ESI-MS (m/e): 450 [M+H]$^+$

Production Example 94

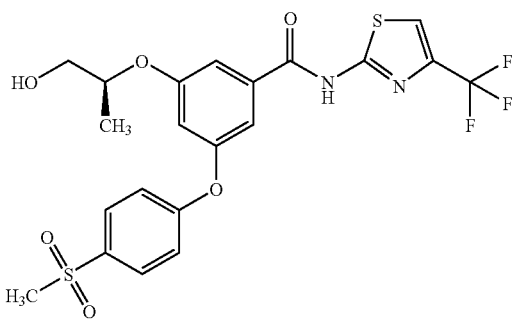

Preparation of 5-(2-hydroxy-1-methyl-ethoxy)-3-(4-methanesulfonylphenoxy)-N-(4-trifluoromethyl thiazol-2-yl)benzamide The compound of Production Example 94 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 2-amino-4-trifluoromethyl-thiazole, by the same method as in Production Example 89, a corresponding method, or a combination thereof with an ordinary method.

$^1$HNMR (CDCl$_3$) δ: 1.32 (d, 3H, J=6.2 Hz), 3.11 (s, 3H), 3.78 (d, 2H, J=5.1 Hz), 4.57-4.63 (m, 1H), 6.91 (s, 1H), 7.16-7.17 (m, 1H), 7.17 (d, 2H, J=8.8 Hz), 7.34-7.36 (m, 1H), 7.44-7.46 (m, 1H), 7.96 (d, 2H, J=8.8 Hz)

ESI-MS (m/e): 517 [M+H]$^+$

Production Example 95

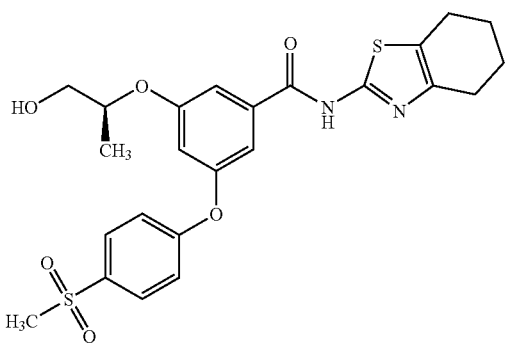

Preparation of 5-(2-hydroxy-1-methyl-ethoxy)-3-(4-methanesulfonylphenoxy)-N-(4,5,6,7-tetrahydrobenzothiazol-2-yl)benzamide The compound of Production Example 95 was obtained as a colorless oil using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 2-amino-4,5,6,7-tetrahydrobenzothiazole, by the same method as in Production Example 89, a corresponding method, or a combination thereof with an ordinary method.

$^1$HNMR (CDCl$_3$) δ: 1.26-1.29 (m, 3H), 1.82-1.86 (m, 4H), 2.57-2.72 (m, 4H), 3.09 (s, 3H), 3.73-3.78 (m, 2H), 4.54-4.56 (m, 1H), 6.78-6.81 (m, 1H), 7.09-7.14 (m, 3H), 7.22-7.29 (m, 1H), 7.90-7.95 (m, 2H)

ESI-MS (m/e): 503 [M+H]$^+$

Production Example 96

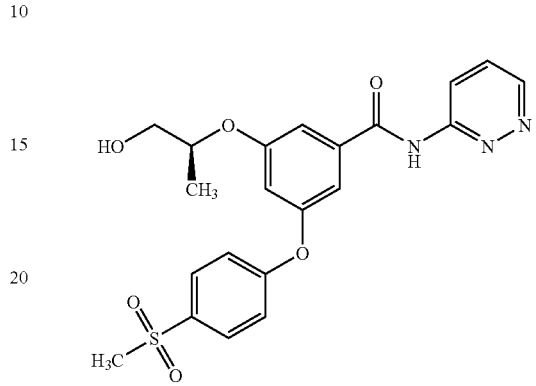

Preparation of 5-(2-hydroxy-1-methyl-ethoxy)-3-(4-methanesulfonylphenoxy)-N-(pyridazin-3-yl)-benzamide The compound of Production Example 96 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 3-amino-pyridazine, by the same method as in Production Example 89, a corresponding method, or a combination thereof with an ordinary method.

$^1$HNMR (CDCl$_3$) δ: 1.30 (d, 3H, J=5.9 Hz), 2.55 (brs, 1H), 3.07 (s, 3H), 3.76 (m, 2H), 4.59 (qt, 1H, J=5.9, 5.5 Hz), 6.83 (s, 1H), 7.11 (d, 2H, J=8.4 Hz), 7.24 (s, 1H), 7.39 (s, 1H), 7.52 (dd, 1H, 9.2, J=4.8 Hz), 7.90 (d, 2H, J=8.4 Hz), 8.55 (d, 1H, J=9.2 Hz), 8.93 (m, 1H), 9.54 (brs, 1H)

ESI-MS (m/e): 444 [M+H]$^+$, 442[M−H]$^−$

Production Example 97

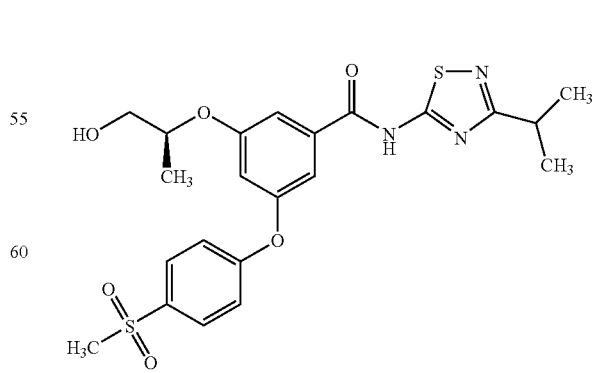

121

Preparation of 5-(2-hydroxy-1-methyl-ethoxy)-N-(3-isopropyl-[1,2,4]-triazol-5-yl)-3-(4-methanesulfonylphenoxy)benzamide The compound of Production Example 97 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 5-amino-3-isopropyl-[1,2,4]triazole, by the same method as in Production Example 89, a corresponding method, or a combination thereof with an ordinary method.

$^1$HNMR (CDCl$_3$) δ: 1.33 (d, 6H, J=7.3 Hz), 1.35 (d, 6H, J=7.0 Hz), 3.10 (s, 3H), 3.16-3.21 (m, 1H), 3.77-3.79 (m, 2H), 4.57-4.62 (m, 1H), 6.91 (s, 1H), 7.16 (d, 2H, J=8.9 Hz), 7.17 (d, 1H, J=1.7 Hz), 7.35 (d, 1H, J=1.7 Hz), 7.95 (d, 2H, J=8.9 Hz)

ESI-MS (m/e): 492 [M+H]$^+$

Production Example 98

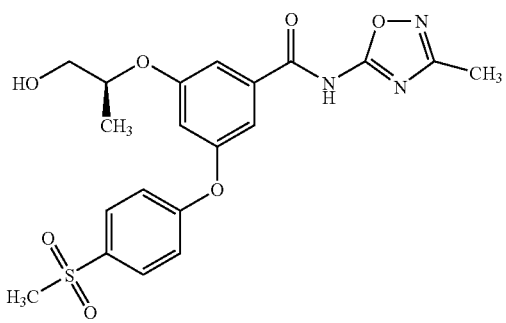

Preparation of 5-(2-hydroxy-1-methyl-ethoxy)-3-(4-methanesulfonylphenoxy)-N-(3-methyl-[1,2,4]-oxadiazol-5-yl)benzamide The compound of Production Example 98 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 5-amino-3-methyl-[1,2,4]oxadiazole, by the same method as in Production Example 89, a corresponding method, or a combination thereof with an ordinary method.

$^1$HNMR (CDCl$_3$) δ: 1.28 (d, 3H, J=5.9 Hz), 2.31 (s, 3H), 3.08 (s, 3H), 3.75-3.76 (m, 2H), 4.57-4.58 (m, 1H), 5.60 (brs, 1H), 6.84 (s, 1H), 7.09 (d, 2H, J=8.6 Hz), 7.24 (s, 1H), 7.35 (s, 1H), 7.87 (d, 2H, J=8.6 Hz), 10.52 (brs, 1H)

ESI-MS (m/e): 448 [M+H]$^+$, 446[M−H]$^−$

122

Production Example 99

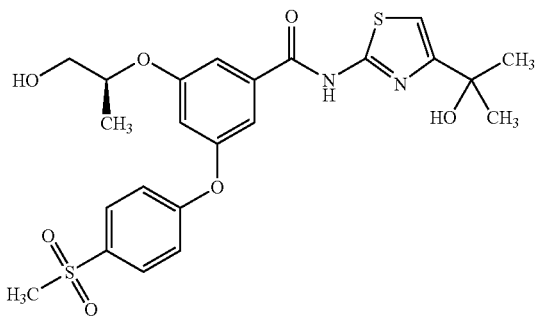

Preparation of 5-(2-hydroxy-1-methyl-ethoxy)-N-[4-(1-hydroxy-1-methyl-ethyl)-thiazol-2-yl]-3-(4-methanesulfonylphenoxy)benzamide The compound of Production Example 99 was obtained as a white solid using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 2-amino-4-(1-hydroxy-1-methyl-ethyl)-thiazole, by the same method as in Production Example 89, a corresponding method, or a combination thereof with an ordinary method.

$^1$HNMR (CDCl$_3$) δ: 1.33 (3H, d, J=6.2 Hz), 1.61 (6H, s), 3.08 (3H, s), 3.75-3.84 (2H, m), 4.55-4.65 (1H, m), 6.77 (1H, s), 6.88 (1H, t, J=2.0 Hz), 7.16 (2H, d, J=8.7 Hz), 7.28 (1H, br), 7.45 (1H, br), 7.95 (2H, d, J=8.7 Hz)

ESI-MS (m/e): 507 [M+H]$^+$

Production Example 100

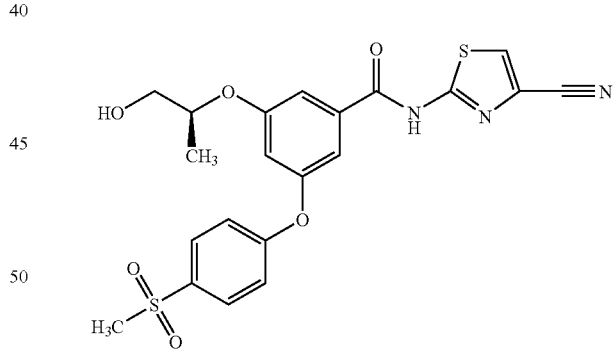

Preparation of N-(4-cyano-thiazol-2-yl)-5-(2-hydroxy-1-methyl-ethoxy)-3-(4-methanesulfonylphenoxy)benzamide The compound of Production Example 100 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 2-amino-4-cyano-thiazole, by the same method as in Production Example 89, a corresponding method, or a combination thereof with an ordinary method.

¹HNMR (CDCl₃) δ: 1.32 (d, 3H, J=6.2 Hz), 2.48 (brs, 1H), 3.12 (s, 3H), 3.75-3.85 (m, 2H), 4.59-4.62 (m, 1H), 6.88 (s, 1H), 7.15 (d, 2H, J=8.8 Hz), 7.22 (s, 1H), 7.38 (s, 1H), 7.70 (s, 1H), 7.94 (d, 2H, J=8.8 Hz), 10.52 (brs, 1H)

ESI-MS (m/e): 474 [M+H]⁺, 472[M−H]⁻

Production Example 101

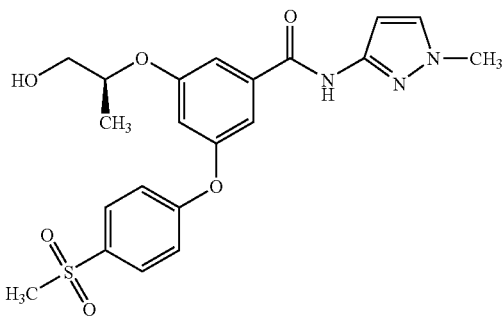

Preparation of 5-(2-hydroxy-1-methyl-ethoxy)-3-(4-methanesulfonylphenoxy)-N-(1-methyl-1H-pyrazol-3-yl)benzamide The compound of Production Example 101 was obtained as white crystals using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 3-amino-1-methyl-1H-pyrazole, by the same method as in Production Example 89, a corresponding method, or a combination thereof with an ordinary method.

¹HNMR (CDCl₃) δ: 1.31 (d, 3H, J=6.3 Hz), 3.08 (s, 3H), 3.77 (m, 2H), 3.81 (s, 3H), 4.57 (m, 1H), 6.78 (m, 1H), 6.82 (m, 1H), 7.11 (m, 1H), 7.15 (d, 2H, J=8.9 Hz), 7.30 (m, 2H), 7.93 (d, 2H, J=8.9 Hz), 8.45 (br, 1H)

ESI-MS (m/e): 466 [M+H]⁺

Production Example 102

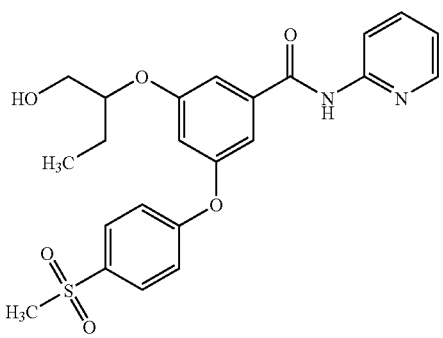

Preparation of 5-(1-hydroxymethyl-propoxy)-3-(4-methanesulfonylphenoxy)-N-(pyridin-2-yl)benzamide The compound of Production Example 102 was obtained as a colorless amorphous substance using the 3-(4-methanesulfonyl-phenoxy)-5-methoxymethoxy-benzoic acid methyl ester obtained in production Example 89, (2R)-1-(tert-butyldimethylsiloxy)-2-hydroxybutane instead of (2R)-1-(tert-butyldimethylsiloxy)-2-hydroxypropane, and 2-amino-pyridine, by the same method as in Production Example 89, a corresponding method, or a combination thereof with an ordinary method.

¹HNMR (CDCl₃) δ: 1.01 (t, 3H, J=7.7 Hz), 1.76 (qd, 2H, J=7.7, 6.2 Hz), 2.10 (brs, 1H), 3.09 (s, 3H), 3.78-3.88 (m, 2H), 4.38-4.44 (m, 1H), 6.86 (s, 1H), 7.10 (dd, 1H, J=4.0, 8.4 Hz), 7.15 (d, 2H, J=9.2 Hz), 7.17 (s, 1H), 7.37 (s, 1H), 7.77 (dd, 1H, J=8.4, 8.4 Hz), 7.93 (d, 2H, J=9.2 Hz), 8.29 (d, 1H, J=4.0 Hz), 8.34 (d, 1H, J=8.4 Hz), 8.62 (brs, 1H)

ESI-MS (m/e): 457 [M+H]⁺

Production Example 103

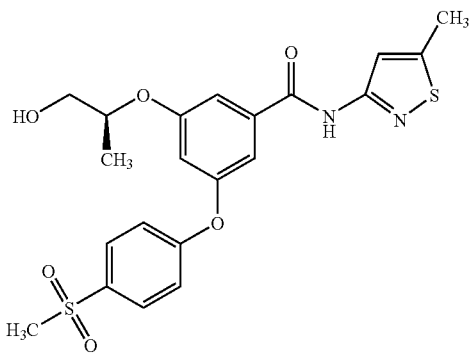

Preparation of 5-(2-hydroxy-1-methyl-ethoxy)-3-(4-methanesulfonylphenoxy)-N-(5-methyl-isothiazol-3-yl)benzamide The compound of Production Example 103 was obtained as a white amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 3-amino-5-methyl-isothiazole, by the same method as in Production Example 89, a corresponding method, or a combination thereof with an ordinary method.

¹HNMR (CDCl₃) δ: 1.30 (d, 3H, J=6.2 Hz), 2.58 (s, 3H), 3.07 (s, 3H), 3.75 (m, 2H), 4.57 (m, 1H), 6.82 (m, 1H), 7.13 (d, 2H, J=8.9 Hz), 7.15 (m, 1H), 7.31 (m, 1H), 7.73 (m, 1H), 7.92 (d, 2H, J=8.9 Hz), 9.12 (br, 1H)

ESI-MS (m/e): 463 [M+H]⁺

Production Example 104

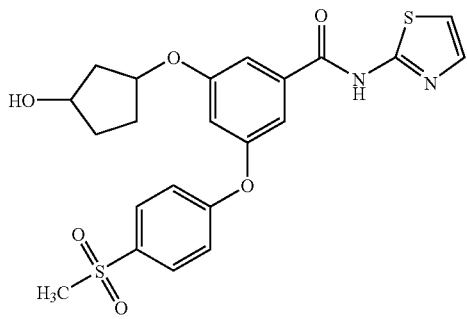

Preparation of 5-(3-hydroxy-cyclopentyloxy)-3-(4-methanesulfonylphenoxy)-N-(thiazol-2-yl)benzamide The compound of Production Example 104 was obtained as a colorless amorphous substance using the 3-(4-methanesulfonyl-phenoxy)-5-methoxymethoxy-benzoic acid methyl ester obtained in production Example 89, 3-(tert-butyldiphenylsiloxy)cyclopentanol instead of (2R)-1-(t-butyldimethylsiloxy)-2-hydroxypropane, and 2-amino-thiazole, by the same method as in Production Example 89, a corresponding method, or a combination thereof with an ordinary method.

$^1$HNMR (CDCl$_3$) δ: 1.92 (m, 6H), 3.08 (s, 3H), 4.39 (s, 1H), 4.82-4.84 (s, 1H), 6.82 (t, 1H, J=1.9 Hz), 7.00 (d, 1H, J=3.6 Hz), 7.13 (d, 2H, J=8.6 Hz), 7.16 (d, 1H, J=1.9 Hz), 7.23 (d, 1H, J=3.6 Hz), 7.34 (d, 1H, J=1.9 Hz), 7.92 (d, 2H, J=8.6 Hz)

ESI-MS (m/e): 475 [M+H]$^+$

Production Example 105

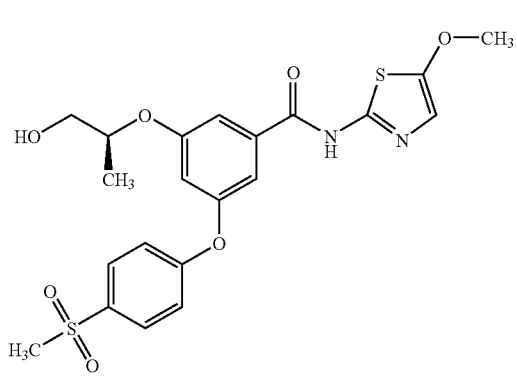

Preparation of 5-(2-hydroxy-1-methyl-ethoxy)-3-(4-methanesulfonylphenoxy)-N-(5-methoxy-thiazol-2-yl)benzamide The compound of Production Example 105 was obtained as a white solid using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 2-amino-5-methoxy-thiazole, by the same method as in Production Example 89, a corresponding method, or a combination thereof with an ordinary method.

$^1$HNMR (CDCl$_3$) δ: 1.28 (d, 3H, J=6.2 Hz), 3.07 (s, 3H), 3.75 (d, 2H, J=5.6 Hz), 3.87 (s, 3H), 4.57 (m, 1H), 6.52 (s, 1H), 6.81 (m, 1H), 7.12 (d, 2H, J=8.8 Hz), 7.17 (m, 1H), 7.31 (m, 1H), 7.90 (d, 2H, J=8.8 Hz), 11.5 (br, 1H)

ESI-MS (m/e): 479 [M+H]$^+$

Production Example 106

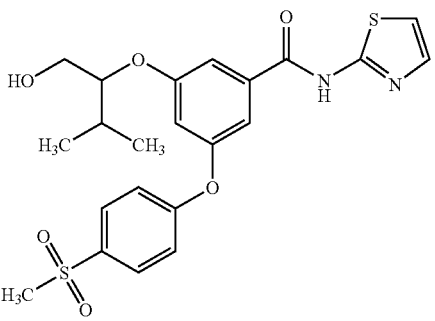

Preparation of 5-(1-hydroxymethyl-2-methyl-propoxy)-3-(4-methanesulfonylphenoxy)-N-(thiazol-2-yl)benzamide The compound of Production Example 106 was obtained as a white amorphous substance using the 3-(4-methanesulfonyl-phenoxy)-5-methoxymethoxy-benzoic acid methyl ester obtained in production Example 89, 1-(tert-butyldimethylsiloxy)-3-methyl-butan-2-ol instead of (2R)-1-(t-butyldimethylsiloxy)-2-hydroxypropane, and 2-amino-thiazole, by the same method as in Production Example 89, a corresponding method, or a combination thereof with an ordinary method.

$^1$HNMR (CDCl$_3$) δ: 0.97 (m, 6H), 2.05 (m, 1H), 3.07 (s, 3H), 3.83 (m, 2H), 4.22 (m, 1H), 6.84 (m, 1H), 6.96 (d, 1H, J=3.7 Hz), 7.11 (d, 2H, J=8.9 Hz), 7.18 (m, 1H), 7.23 (d, 1H, J=3.7 Hz), 7.39 (m, 1H), 7.91 (d, 2H, J=8.8 Hz), 12.0 (br, 1H)

ESI-MS (m/e): 477 [M+H]$^+$

Production Example 107

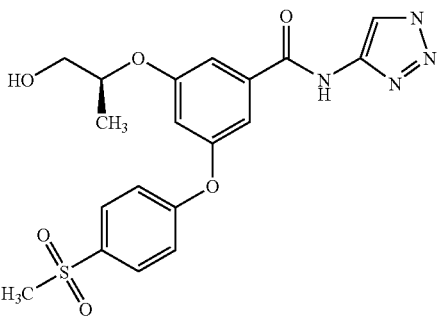

Preparation of 5-(2-hydroxy-1-methyl-ethoxy)-3-(4-methanesulfonylphenoxy)-N-(1H-[1,2,3]triazol-4-yl)benzamide The compound of Production Example 107 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 4-amino-1H-[1,2,3]triazole, by the same method as in Production Example 89, a corresponding method, or a combination thereof with an ordinary method.

$^1$HNMR (CDCl$_3$) δ: 1.31 (d, 3H, J=6.2 Hz), 3.11 (s, 3H), 3.34 (s, 1H), 3.67-3.68 (m, 2H), 4.56-4.60 (m, 2H), 6.93 (s, 1H), 7.21 (d, 2H, J=8.8 Hz), 7.25 (s, 1H), 7.43 (s, 1H), 7.94 (d, 2H, J=8.8 Hz), 8.08 (brs, 1H)

ESI-MS (m/e): 433 [M+H]$^+$, 431 [M−H]$^−$

Production Example 108

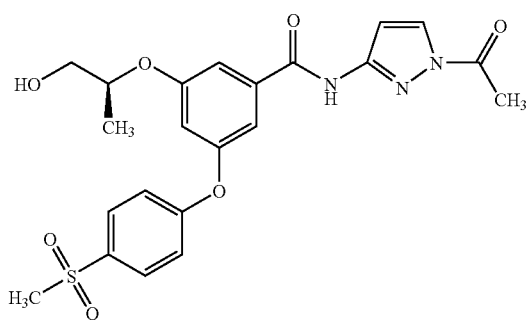

Preparation of N-(1-acetyl-1H-pyrazol-3-yl)-5-(2-hydroxy-1-methyl-ethoxy)-3-(4-methanesulfonylphenoxy)benzamide The compound of Production Example 108 was obtained as a white amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 3-amino-1-acetyl-1H-pyrazole, by the same method as in Production Example 89, a corresponding method, or a combination thereof with an ordinary method.

$^1$HNMR (CDCl$_3$) δ: 1.36 (d, 3H, J=6.3 Hz), 2.65 (s, 3H), 3.12 (s, 3H), 3.82 (m, 2H), 4.61 (m, 1H), 6.89 (m, 1H), 7.16-7.22 (m, 4H), 7.35 (m, 1H), 7.98 (d, 2H, J=8.8 Hz), 8.22 (d, 1H, J=3.0 Hz), 8.46 (br, 1H)

ESI-MS (m/e): 474 [M+H]$^+$

Production Example 109

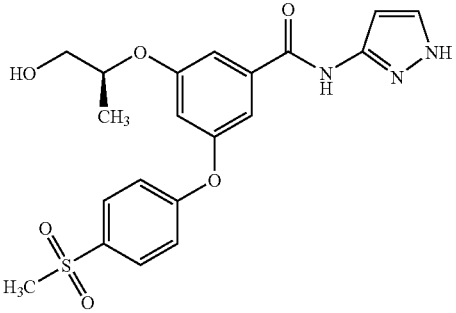

Preparation of 5-(2-hydroxy-1-methyl-ethoxy)-3-(4-methanesulfonylphenoxy)-N-(pyrazol-3-yl)benzamide The compound of Production Example 109 was obtained as a white amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 3-amino-pyrazole, by the same method as in Production Example 89, a corresponding method, or a combination thereof with an ordinary method.

$^1$HNMR (CDCl$_3$) δ: 1.26 (d, 3H, J=6.3 Hz), 3.05 (s, 3H), 3.73 (m, 2H), 4.52 (m, 1H), 6.75 (m, 2H), 7.06 (d, 2H, J=8.8 Hz), 7.14 (m, 1H), 7.32 (m, 1H), 7.46 (m, 1H), 7.85 (d, 2H, J=8.8 Hz), 9.72 (br, 1H)

ESI-MS (m/e): 432 [M+H]$^+$

Production Example 110

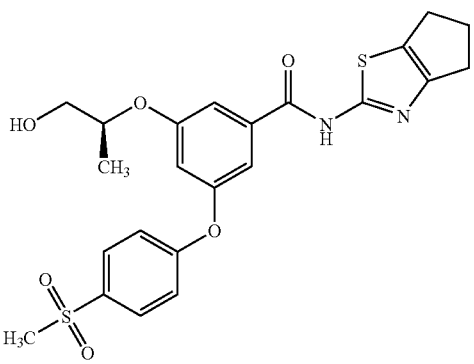

Preparation of N-(5,6-dihydro-4H-cyclopentathiazol-2-yl)-5-(2-hydroxy-1-methyl-ethoxy)-3-(4-methanesulfonylphenoxy)benzamide The compound of Production Example 110 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 2-amino-5,6-dihydro-4H-cyclopentanethiazole, by the same method as in Production Example 89, a corresponding method, or a combination thereof with an ordinary method.

¹HNMR (CDCl₃) δ: 1.28 (d, 3H, J=6.2 Hz), 2.44 (tt, 2H, J=7.0, 7.0 Hz), 2.61 (t, 2H, J=7.0 Hz), 2.90 (t, 2H, J=7.0 Hz), 3.08 (s, 3H), 3.70-3.76 (m, 2H), 4.51-4.55 (m, 1H), 6.76 (s, 1H), 7.10 (d, 2H, J=8.8 Hz), 7.12 (s, 1H), 7.28 (s, 1H), 7.90 (d, 2H, J=9.2 Hz)

ESI-MS (m/e): 489 [M+H]⁺, 487[M−H]⁻

Production Example 111

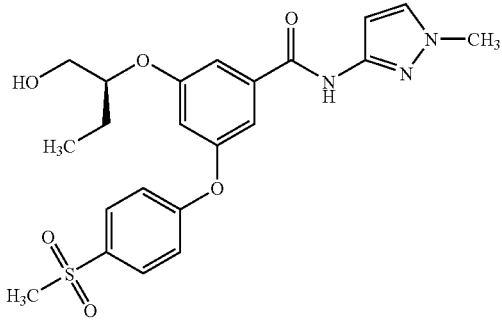

Preparation of 5-(1-hydroxymethyl-propoxy)-3-(4-methanesulfonylphenoxy)-N-(1-methyl-1H-pyrazol-3-yl)benzamide The compound of Production Example 111 was obtained as a white amorphous substance using the 3-(4-methanesulfonyl-phenoxy)-5-methoxymethoxy-benzoic acid methyl ester obtained in production Example 89 and (2R)-1-(tert-butyldimethylsiloxy)-butan-2-ol instead of (2R)-1-(tert-butyldimethylsiloxy)-2-hydroxypropane, and 3-amino-1-methyl-1H-pyrazole, by the same method as in Production Example 89, a corresponding method, or a combination thereof with an ordinary method.

¹HNMR (CDCl₃) δ: 0.93 (t, 3H, J=7.5 Hz), 1.69 (quintet, 1H, J=7.5 Hz), 2.75 (t, 1H, J=6.2 Hz), 3.06 (s, 3H), 3.74 (s, 3H), 3.70-3.80 (m, 2H), 4.33 (m, 1H), 6.77 (m, 2H), 7.09 (d, 2H, J=8.8 Hz), 7.11 (m, 1H), 7.27 (m, 2H), 7.99 (d, 2H, J=8.8 Hz), 9.03 (br, 1H)

ESI-MS (m/e): 460 [M+H]⁺

Production Example 112

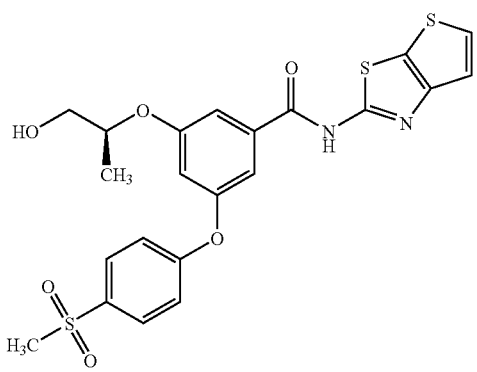

Preparation of 5-(2-hydroxy-1-methyl-ethoxy)-3-(4-methanesulfonylphenoxy)-N-(thieno[3,2-d]thiazol-2-yl)benzamide The compound of Production Example 112 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 2-amino-thieno[3,2-d]thiazole, by the same method as in Production Example 89, a corresponding method, or a combination thereof with an ordinary method.

¹HNMR (CDCl₃) δ: 1.30 (d, 3H, J=6.2 Hz), 2.05 (brs, 1H), 3.09 (s, 3H), 3.76-3.78 (m, 2H), 4.55-4.57 (m, 1H), 6.84 (s, 1H), 7.11 (d, 2H, J=8.8 Hz), 7.11 (s, 1H), 7.19 (s, 1H), 7.36 (s, 1H), 7.38 (s, 1H), 7.92 (d, 2H, J=8.8 Hz), 10.42 (brs, 1H)

ESI-MS (m/e): 505 [M+H]⁺, 503[M−H]⁻

Production Example 113

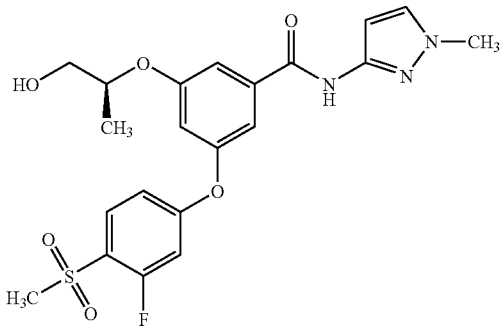

Preparation of 3-(3-fluoro-4-methanesulfonylphenoxy)-5-(2-hydroxy-1-methyl-ethoxy)-N-(1-methyl-1H-pyrazol-3-yl)benzamide The compound of Production Example 113 was obtained as white crystals using 3-(3-fluoro-4-methanesulfonylphenoxy)-5-hydroxy-benzoic acid methyl ester obtained in the same manner as Production Example 42, (2R)-1-(t-butyldimethylsiloxy)-2-hydroxypropane and 3-amino-1-methyl-1H-pyrazole, by the same method as in Production Example 2, a corresponding method, or a combination thereof with an ordinary method.

¹HNMR (CDCl₃) δ: 1.31 (d, 3H, J=6.3 Hz), 2.20 (t, 1H, J=6.5 Hz), 3.23 (s, 3H), 3.77 (m, 2H), 3.80 (s, 3H), 4.57 (sextet, 1H, J=4.5 Hz), 6.79-6.93 (m, 4H), 7.14 (m, 1H), 7.30 (m, 1H), 7.33 (m, 1H), 7.92 (t, 1H, J=8.4 Hz), 8.57 (br, 1H)

ESI-MS (m/e): 464 [M+H]⁺

Production Example 114

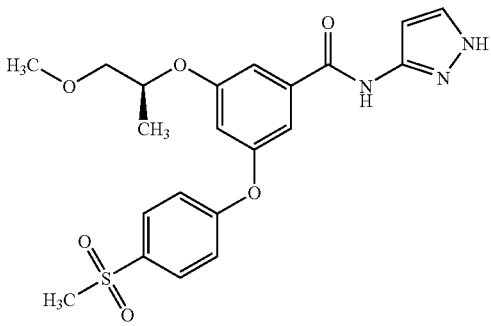

Preparation of 3-(4-methanesulfonylphenoxy)-5-(2-methoxy-1-methyl-ethoxy)-N-(pyrazol-3-yl)benzamide The compound of Production Example 114 was obtained as a white amorphous substance using the 3-(4-methanesulfonyl-phenoxy)-5-methoxymethoxy-benzoic acid methyl ester obtained in Production Example 89, (2R)-1-methoxy-2-propanol and 3-amino-pyrazole, by the same method as in Production Example 89, a corresponding method, or a combination thereof with an ordinary method.

$^1$HNMR (CDCl$_3$) δ: 1.32 (d, 3H, J=6.2 Hz), 3.05 (s, 3H), 3.39 (s, 3H), 3.50-3.60 (m, 2H), 4.60 (m, 1H), 6.80 (t, 1H, J=2.2 Hz), 6.85 (d, 1H, J=2.2 Hz), 7.09 (d, 2H, J=8.8 Hz), 7.16 (t, 1H, J=2.2 Hz), 7.39 (t, 1H, J=2.2 Hz), 7.47 (d, 1H, J=2.2 Hz), 7.87 (d, 2H, J=8.8 Hz), 9.80 (br, 1H)

ESI-MS (m/e): 446 [M+H]$^+$

Production Example 115

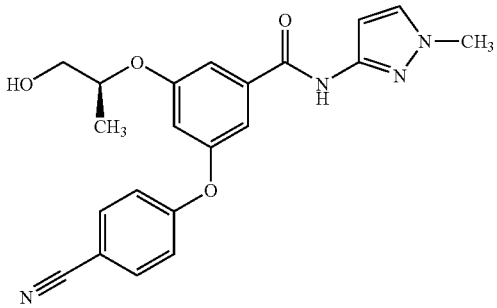

Preparation of 3-(4-cyano-phenoxy)-5-(2-hydroxy-1-methyl-ethoxy)-N-(1-methyl-1H-pyrazol-3-yl)benzamide The compound of Production Example 115 was obtained as a colorless amorphous substance using 5-hydroxy-3-methoxymethoxybenzoic acid methyl ester and p-cyanophenylboric acid, and using 3-(4-cyano-phenoxy)-5-methoxymethoxy-benzoic acid methyl ester obtained in the same manner as Production Example 1, (2R)-1-(t-butyldimethylsiloxy)-2-hydroxypropane and 3-amino-1-methyl-1H-pyrazole, by the same method as in Production Example 89, a corresponding method, or a combination thereof with an ordinary method.

$^1$HNMR (CDCl$_3$) δ: 1.30 (d, 3H, J=6.2 Hz), 2.31 (brs, 1H), 3.76-3.79 (m, 2H), 3.79 (s, 3H), 4.54 (qt, 1H, J=6.2 Hz, 4.0 Hz), 6.77 (d, 1H, J=2.2 Hz), 6.78 (s, 1H), 7.07 (d, 2H, J=8.8 Hz), 7.09 (s, 1H), 7.27 (s, 1H), 7.28 (d, 1H, J=2.2 Hz), 7.63 (d, 2H, 8.8 Hz), 8.64 (brs, 1H)

ESI-MS (m/e): 393 [M+H]$^+$

Production Example 116

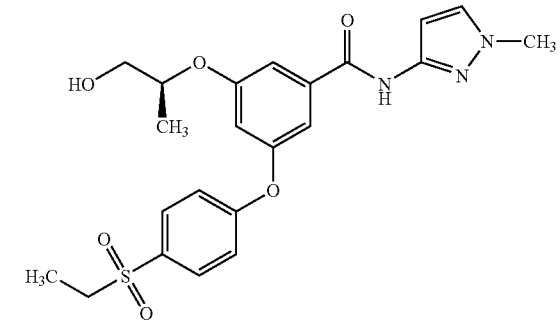

Preparation of 3-(4-ethylsulfonylphenoxy)-5-(2-hydroxy-1-methyl-ethoxy)-N-(1-methyl-1H-pyrazol-3-yl)benzamide The compound of Production Example 116 was obtained as a colorless amorphous substance using 3-(4-ethylthio-phenoxy)-5-hydroxy-benzoic acid methyl ester obtained by deprotection of the methoxymethyl group of 3-(4-ethylthio-phenoxy)-5-methoxymethoxy-benzoic acid methyl ester obtained using 5-hydroxy-3-methoxymethoxybenzoic acid methyl ester and p-ethylthiophenylboric acid according to the same method as in Production Example 1, (2R)-1-(t-butyldimethylsiloxy)-2-hydroxypropane and 3-amino-1-methyl-1H-pyrazole, by the same method as in Production Example 2, a corresponding method, or a combination thereof with an ordinary method.

$^1$HNMR (CDCl$_3$) δ: 1.32 (d, 3H, J=6.2 Hz), 1.33 (t, 3H, J=7.7 Hz), 2.05 (brs, 1H), 3.14 (q, 2H, J=7.7 Hz), 3.75-3.79 (m, 2H), 3.81 (s, 3H), 4.56 (qt, 1H, J=6.2, 3.7 Hz), 6.78 (s, 1H), 6.81 (d, 1H, J=2.2 Hz), 7.11 (s, 1H), 7.12 (d, 2H, J=8.8 Hz), 7.28 (d, 1H, J=2.2 Hz), 7.28 (s, 1H), 7.87 (d, 2H, J=8.8 Hz), 8.41 (brs, 1H)

ESI-MS (m/e): 460 [M+H]$^+$, 458[M−H]$^−$

Production Example 117

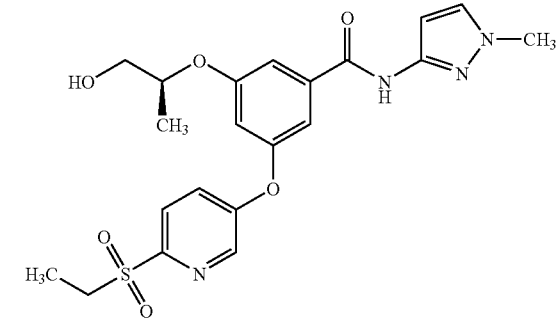

Preparation of 3-(6-ethanesulfonylpyridin-3-yloxy)-5-(2-hydroxy-1-methyl-ethoxy)-N-(1-methyl-1H-pyrazol-3-yl)benzamide After adding 178 mg (0.71 mmol) of 5-bromo-2-ethanesulfonylpyridine and 232 mg (0.71 mmol) of cesium carbonate to a solution of 100 mg (0.47 mmol) of 5-hydroxy-3- methoxymethoxybenzoic acid methyl ester in N,N-dimethylformamide (1.0 ml), the mixture was stirred at 100° C. for 2.5 hours under a nitrogen atmosphere. Acetic acid ethyl ester and aqueous ammonium chloride were added to the reaction mixture, the aqueous layer was extracted with acetic acid ethyl ester, and then the organic layer was washed with brine, dried and concentrated under reduced pressure. The obtained residue was purified by silica gel column chromatography (hexane:acetic acid ethyl ester=1:1) to obtain 165 mg of 3-(6-ethanesulfonyl-pyridin-3-yloxy)-5-methoxymethoxybenzoic acid methyl ester (yield: 91%) as a colorless oil.

After adding 30.0 ml of trifluoroacetic acid to a solution of 11.8 g (30.9 mmol) of the obtained ester compound in methylene chloride (50.0 ml), the reaction mixture was stirred at room temperature for 5 hours. The reaction mixture was concentrated under reduced pressure, and the obtained residue was purified by silica gel column chromatography (hexane:acetic acid ethyl ester=2:1) to obtain 8.86 g of 3-(6-ethanesulfonyl-pyridin-3-yloxy)-5-hydroxybenzoic acid methyl ester (yield: 85%) as a colorless oil.

After adding 1.02 g (5.34 mmol) of (2R)-1-(t-butyldimethylsiloxy)-2-hydroxypropane and 1.40 g (5.34 mmol) of triphenylphosphine to a solution of 1.00 g (2.97 mmol) of the obtained phenol compound in tetrahydrofuran (30.0 ml), 2.42 ml (5.34 mmol) of a solution of diethyl azodicarboxylate in 40% toluene was added while cooling on ice, and the mixture was stirred at room temperature for 1 hour. The reaction mixture was concentrated under reduced pressure, and the obtained residue was purified by silica gel column chromatography (hexane:acetic acid ethyl ester=3:2) to obtain 1.31 g of 3-((1S)-2-(t-butyldimethylsiloxy)-1-methyl-ethoxy)-5-(6-ethanesulfonyl-pyridin-3-yloxy)-benzoic acid methyl ester (yield: 87%) as a colorless oil.

The compound of Production Example 117 was obtained as a colorless amorphous substance using the obtained 3-((1S)-2-(t-butyldimethylsiloxy)-1-methyl-ethoxy)-5-(6-ethanesulfonyl-pyridin-3-yloxy)-benzoic acid methyl ester and 3-amino-1-methylpyrazole, by the same method as in Production Example 2, a corresponding method, or a combination thereof with an ordinary method.

$^1$HNMR (CDCl$_3$) δ: 1.32 (d, 3H, J=6.2 Hz), 1.33 (t, 3H, J=7.3 Hz), 3.40 (q, 2H, J=7.3 Hz), 3.75-3.77 (m, 2H), 3.81 (s, 3H), 4.54-4.59 (m, 1H, J=6.2, -Hz), 6.76 (d, 1H, J=2.2 Hz), 6.81 (dd, 1H, J=2.2, 2.2 Hz), 7.14 (dd, 1H, J=2.2, 1.7 Hz), 7.28 (d, 1H, J=2.2 Hz), 7.32 (d, 1H, J=2.2, 1.7 Hz), 7.43 (dd, 1H, J=8.8, 2.6 Hz), 8.05 (d, 1H, J=8.8 Hz), 8.45 (brs, 1H), 8.47 (d, 1H, J=2.6 Hz)

ESI-MS (m/e): 461 [M+H]$^+$, 459[M−H]$^-$

Production Example 118

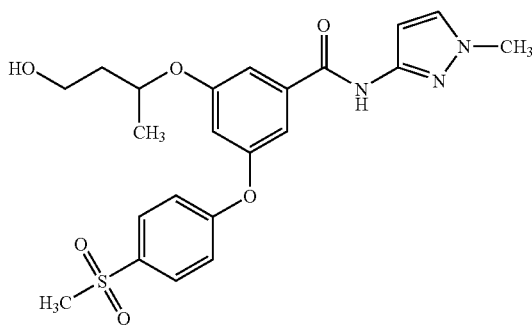

Preparation of 5-(3-hydroxy-1-methyl-propoxy)-3-(4-methanesulfonylphenoxy)-N-(1-methyl-1H-pyrazol-3-yl)benzamide The compound of Production Example 118 was obtained as a colorless amorphous substance using the 3-(4-methanesulfonyl-phenoxy)-5-methoxymethoxy-benzoic acid methyl ester obtained in Production Example 89, 4-(tert-butyldimethylsiloxy)-butan-2-ol and 3-amino-1-methyl-1H-pyrazole, by the same method as in Production Example 89, a corresponding method, or a combination thereof with an ordinary method.

$^1$HNMR (CDCl$_3$) δ: 1.37 (3H, d, J=6.2 Hz), 1.88-1.93 (2H, m), 1.96-2.09 (1H, m), 3.08 (3H, s), 3.78-3.87 (2H, m), 3.81 (3H, s), 6.78 (1H, d, J=2.0 Hz), 6.81 (1H, t, J=2.1 Hz), 7.11-7.18 (3H, m), 7.29 (1H, d, J=2.2 Hz), 7.35 (1H, br), 7.92 (2H, d, J=9.0 Hz), 8.51 (1H, br)

ESI-MS (m/e): 460 [M+H]$^+$

Production Example 119

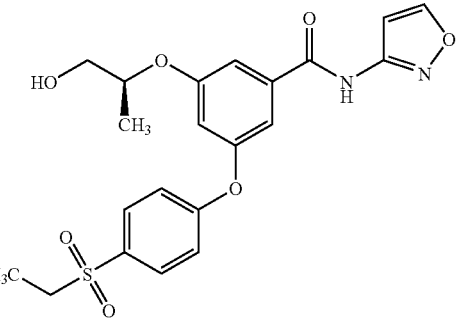

Preparation of 3-(4-ethanesulfonylphenoxy)-5-(2-hydroxy-1-methyl-ethoxy)-N-(isoxazol-3-yl)benzamide The compound of Production Example 119 was obtained as a colorless amorphous substance using 3-(4-ethylthio-phenoxy)-5-hydroxy-benzoic acid methyl ester obtained by deprotection of the methoxymethyl group of 3-(4-ethylthio-phenoxy)-5-methoxymethoxy-benzoic acid methyl ester obtained using 5-hydroxy-3-methoxymethoxybenzoic acid methyl ester and p-ethylthiophenylboric acid according to the same method as in Production Example 1, (2R)-1-(t-butyldimethylsiloxy)-2-hydroxypropane and 3-amino-isoxazole, by the same method as in Production Example 2, a corresponding method, or a combination thereof with an ordinary method.

$^1$HNMR (CDCl$_3$) δ: 1.32 (t, 3H, J=7.4 Hz), 1.32 (d, 3H, J=6.3 Hz), 3.13 (q, 2H, J=7.4 Hz), 3.76-3.79 (m, 2H), 4.56-4.62 (m, 1H), 6.87 (t, 1H, J=1.8 Hz), 7.14 (d, 2H, J=8.7 Hz), 7.16 (d, 1H, J=1.8 Hz), 7.26 (d, 1H, J=1.8 Hz), 7.31 (s, 1H), 7.93 (d, 2H, J=8.7 Hz), 8.34 (s, 1H),

ESI-MS (m/e): 477 [M+H]$^+$

Production Example 120

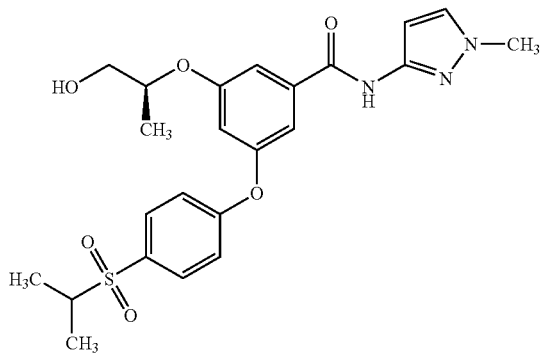

Preparation of 5-(2-hydroxy-1-methyl-ethoxy)-3-(4-isopropylsulfonylphenoxy)-N-(1-methyl-1H-pyrazol-3-yl)benzamide The compound of Production Example 120 was obtained as a colorless amorphous substance using 3-(4-isopropylthio-phenoxy)-5-hydroxy-benzoic acid methyl ester obtained by deprotection of the methoxymethyl group of 3-(4-isopropylthio-phenoxy)-5-methoxymethoxy-benzoic acid methyl ester obtained using 5-hydroxy-3-methoxymethoxybenzoic acid methyl ester and p-isopropylthiophenylboric acid according to the same method as in Production Example 1, (2R)-1-(t-butyldimethylsiloxy)-2-hydroxypropane and 3-amino-1-methyl-1H-pyrazole, by the same method as in Production Example 2, a corresponding method, or a combination thereof with an ordinary method.

$^1$HNMR (CDCl$_3$) δ: 1.32 (d, 3H, J=6.2 Hz), 1.32 (d, 6H, J=7.0 Hz), 3.20 (septet, 1H, J=7.0 Hz), 3.76-3.77 (m, 2H), 3.79 (s, 3H), 4.55 (qt, 1H, J=6.2, 4.0 Hz), 6.79 (d, 1H, J=2.2 Hz), 6.80 (s, 1H), 7.10 (d, 2H, J=8.8 Hz), 7.13 (s, 1H), 7.29 (d, 1H, J=2.2 Hz), 7.29 (s, 1H), 7.83 (d, 2H, J=8.8 Hz), 8.61 (brs, 1H)

ESI-MS (m/e): 474 [M+H]$^+$, 472 [M−H]$^-$

Production Example 121

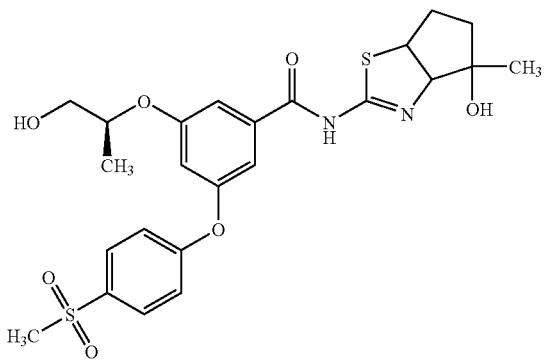

Preparation of 5-(2-hydroxy-1-methyl-ethoxy)-N-(4-hydroxy-4-methyl-4,5,6,6a-tetrahydro-3aH-cyclopentathiazol-2-yl)-3-(4-methanesulfonylphenoxy)benzamide The compound of Production Example 121 was obtained as a colorless amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 2-amino-4-hydroxy-4-methyl-4,5,6,6a-tetrahydro-3aH-cyclopentathiazole, by the same method as in Production Example 89, a corresponding method, or a combination thereof with an ordinary method.

$^1$HNMR (CDCl$_3$) δ: 1.27-1.33 (3H, m), 1.60 (3H, s), 2.56 (2H, m), 2.75-3.07 (2H, m), 3.08 (3H, s), 3.74-3.82 (2H, m), 4.53-4.65 (1H, m), 6.75-6.83 (1H, m), 7.11-7.20 (3H, m), 7.29-7.35 (1H, m), 7.93 (2H, d, J=8.9 Hz)

ESI-MS (m/e): 519 [M+H]$^+$

Production Example 122

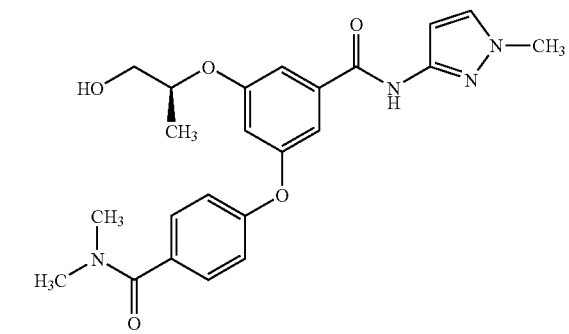

Preparation of 3-(4-dimethylcarbamoyl-phenoxy)-5-(2-hydroxy-1-methyl-ethoxy)-N-(1-methyl-1H-pyrazol-3-yl)benzamide The compound of Production Example 122 was obtained as a colorless amorphous substance by the same method as in Production Example 2, a corresponding method, or a combination thereof with an ordinary method, using (2R)-1-(t-butyldimethylsiloxy)-2-hydroxypropane, 3-amino-1-methyl-1H-pyrazole and 3-(4-dimethylcarbamoyl-phenoxy)-5-hydroxy-benzoic acid methyl ester obtained by deprotection of the methoxymethyl group of 3-(4-dimethylcarbamoyl-phenoxy)-5-methoxymethoxy-benzoic acid methyl ester obtained by converting the formyl group of 3-(4-formyl-phenoxy)-5-methoxymethoxy-benzoic acid methyl ester obtained in the same manner as Production Example 1, using 5-hydroxy-3-methoxymethoxybenzoic acid methyl ester and p-formylphenylboric acid, to carboxyl, followed by condensation with dimethylamine.

$^1$HNMR (CDCl$_3$) δ: 1.33 (d, 3H, J=6.2 Hz), 2.11 (brs, 1H), 3.08 (s, 3H), 3.13 (s, 3H), 3.74-3.81 (m, 2H), 3.83 (s, 3H), 4.54-4.58 (m, 1H), 6.77 (s, 1H), 6.80 (s, 1H), 7.06 (d, 2H, J=7.7 Hz), 7.10 (s, 1H), 7.26 (s, 1H), 7.30 (s, 1H), 7.46 (d, 2H, J=7.7 Hz), 8.49 (brs, 1H)

ESI-MS (m/e): 439 [M+H]$^+$, 437[M−H]$^-$

Production Example 123

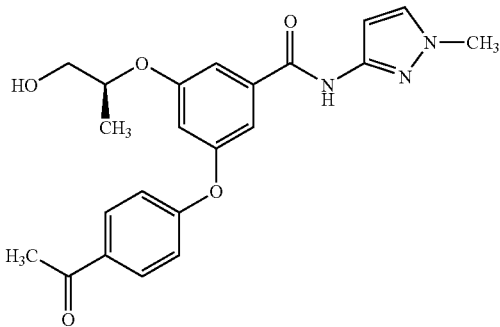

Preparation of 3-(4-acetylphenoxy)-5-(2-hydroxy-1-methyl-ethoxy)-N-(1-methyl-1H-pyrazol-3-yl)benzamide The compound of Production Example 123 was obtained as a colorless amorphous substance by the same method as in Production Example 2, a corresponding method, or a combination thereof with an ordinary method, using (2R)-1-(t-butyldimethylsiloxy)-2-hydroxypropane, 3-amino-1-methyl-1H-pyrazole and 3-(4-acetyl-phenoxy)-5-hydroxy-benzoic acid methyl ester obtained by deprotection of the methoxymethyl group of 3-(4-acetyl-phenoxy)-5-methoxymethoxy-benzoic acid methyl ester obtained by reaction of the formyl group of 3-(4-formyl-phenoxy)-5-methoxymethoxy-benzoic acid methyl ester obtained by the same method as in Production Example 122 with methylmagnesium bromide, followed by oxidation.

$^1$HNMR (CDCl$_3$) δ: 1.30 (d, 3H, J=6.2 Hz), 2.59 (s, 3H), 3.75-3.76 (m, 2H), 3.79 (s, 3H), 4.52-4.56 (m, 1H, J=6.2, -Hz), 6.78 (d, 1H, J=2.2 Hz, dd, 1H, J=2.2, 1.8 Hz), 7.04 (d, 2H, J=8.8 Hz), 7.07 (dd, 1H, J=1.8, 1.8 Hz), 7.25 (dd, 1H, J=2.2, 1.8 Hz), 7.26 (d, 1H, J=2.2 Hz), 7.95 (d, 2H, J=8.8 Hz), 8.52 (brs, 1H)

ESI-MS (m/e): 410 [M+H]$^+$, 408[M−H]$^-$

Production Example 124

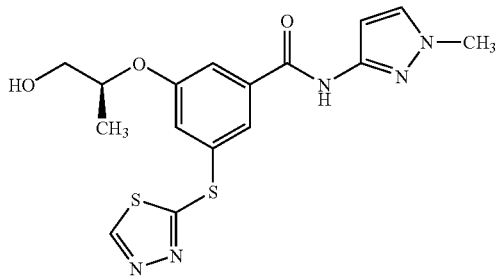

Preparation of 5-(2-hydroxy-1-methyl-ethoxy)-N-(1-methyl-1H-pyrazol-3-yl)-3-(1,3,4-thiadiazol-2-ylsulfanyl)benzamide The compound of Production Example 124 was obtained as a colorless amorphous substance using 3-hydroxy-5-iodo-benzoic acid methyl ester, 1-tert-dimethylsiloxy-2-hydroxypropane, 2-mercapto-[1,3,4]thiadiazole and 3-amino-1-methyl-1H-pyrazole, by the same method as in Production Example 74 or 82, a corresponding method, or a combination thereof with an ordinary method.

$^1$HNMR (CDCl$_3$) δ: 1.31 (3H, d, J=6.2 Hz), 3.74-3.79 (2H, m), 3.82 (3H, s), 4.54-4.63 (1H, m), 6.78 (1H, d, J=2.2 Hz), 7.30 (1H, d, J=2.3 Hz), 7.39 (1H, m), 7.54 (1H, m), 7.69 (1H, m), 8.55 (1H, br), 9.05 (1H, s)

ESI-MS (m/e): 392 [M+H]$^+$

Production Example 125

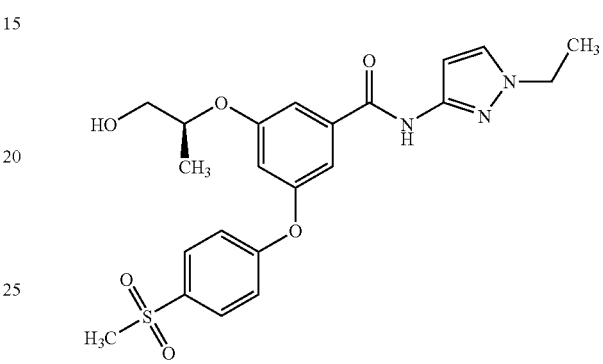

Preparation of N-(1-ethyl-1H-pyrazol-3-yl)-5-(2-hydroxy-1-methyl-ethoxy)-3-(4-methanesulfonylphenoxy)benzamide The compound of Production Example 125 was obtained as a white amorphous substance using the 3-(4-methanesulfonyl-phenoxy)-5-methoxymethoxy-benzoic acid methyl ester obtained in Production Example 89, (2R)-1-(t-butyldimethylsiloxy)-2-hydroxypropane and 3-amino-1-ethyl-1H-pyrazole, by the same method as in Production Example 89, a corresponding method, or a combination thereof with an ordinary method.

$^1$HNMR (CDCl$_3$) δ: 1.30 (d, 3H, J=6.2 Hz), 1.43 (t, 3H, J=7.3 Hz), 3.07 (s, 3H), 3.76 (m, 2H), 4.05 (q, 2H, J=7.3 Hz), 4.56 (m, 1H), 6.79 (m, 2H), 7.12 (d, 2H, J=8.8 Hz), 7.14 (m, 1H), 7.30 (m, 1H), 7.33 (m, 1H), 7.92 (d, 2H, J=8.8 Hz), 8.70 (br, 1H)

ESI-MS (m/e): 460 [M+H]$^+$

Production Example 126

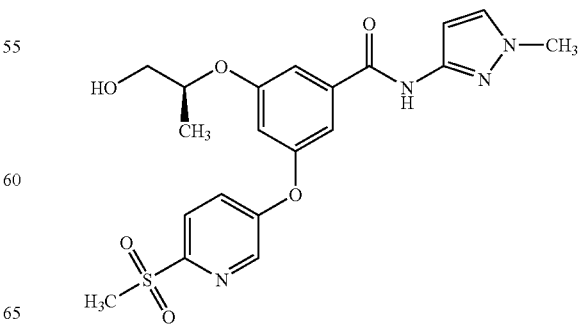

Preparation of 5-(2-hydroxy-1-methyl-ethoxy)-3-(6-methanesulfonylpyridin-3-yloxy)-N-(1-methyl-1H-pyrazol-3-yl)benzamide The compound of Production Example 126 was obtained as a white amorphous substance using 5-hydroxy-3-methoxymethoxybenzoic acid methyl ester, 5-bromo-2-methanesulfonylpyridine, (2R)-1-(t-butyldimethylsiloxy)-2-hydroxypropane and 3-amino-1-methyl-1H-pyrazole, by the same method as in Production Example 117, a corresponding method, or a combination thereof with an ordinary method.

$^1$HNMR (CDCl$_3$) δ: 1.29 (d, 3H, J=6.3 Hz), 3.22 (s, 3H), 3.75 (m, 2H), 3.78 (s, 3H), 4.55 (m, 1H), 6.75 (m, 1H), 6.78 (m, 1H), 7.11 (m, 1H), 7.26 (m, 1H), 7.29 (m, 1H), 7.42 (dd, 1H, J=2.9, 8.5 Hz), 8.03 (d, 1H, J=8.5 Hz), 8.44 (d, 1H, J=2.9 Hz), 8.65 (br, 1H)

ESI-MS (m/e): 447 [M+H]$^+$

Production Example 127

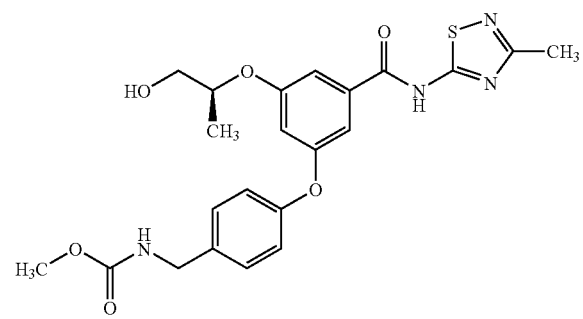

Preparation of 5-(2-hydroxy-1-methyl-ethoxy)-3-(4-methoxycarbonylaminomethyl-phenoxy)-N-(3-methyl-1,2,4-thiadiazol-5-yl)benzamide The compound of Production Example 127 was obtained as a colorless amorphous substance by the same method as in Production Example 2, a corresponding method, or a combination thereof with an ordinary method, using (2R)-1-(t-butyldimethylsiloxy)-2-hydroxypropane, 5-amino-3-methyl-[1,2,4]-thiadiazole and 3-(4-methoxycarbonylaminomethylphenoxy)-5-hydroxy-benzoic acid methyl ester obtained by deprotection of the methoxymethyl group of 3-(4-methoxycarbonylaminomethylphenoxy)-5-methoxymethoxy-benzoic acid methyl ester obtained by the same method as in Production Example 59, using 5-hydroxy-3-methoxymethoxybenzoic acid methyl ester instead of 5-hydroxy-3-isopropoxybenzoic acid methyl ester.

$^1$HNMR (CDCl$_3$) δ: 1.29 (d, 3H, J=6.2 Hz), 2.45 (s, 3H), 3.71 (s, 3H), 3.73-3.78 (m, 2H), 4.35 (d, 2H, J=6.2 Hz), 4.50-4.57 (m, 1H, J=6.2 Hz, -), 5.08 (brs, 1H), 6.76 (s, 1H), 6.97 (d, 2H, J=8.3 Hz), 7.01 (s, 1H), 7.16 (s, 1H), 7.27 (d, 2H, J=8.3 Hz), 10.8 (brs, 1H)

ESI-MS (m/e): 495 [M+Na]$^+$, 473 [M+H]$^+$, 471 [M−H]$^-$

Production Example 128

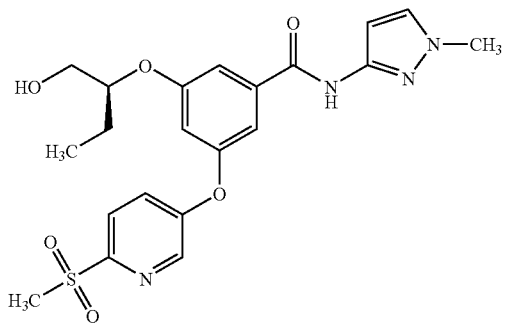

Preparation of 5-(1-hydroxymethyl-propoxy)-3-(6-methanesulfonylpyridin-3-yloxy)-N-(1-methyl-1H-pyrazol-3-yl)benzamide The compound of Production Example 128 was obtained as a colorless amorphous substance using 5-hydroxy-3-methoxymethoxybenzoic acid methyl ester, 5-bromo-2-methanesulfonylpyridine, (2S)-1-(tert-butyldimethylsiloxy)-2-hydroxybutane and 3-amino-1-methyl-1H-pyrazole, by the same method as in Production Example 117, a corresponding method, or a combination thereof with an ordinary method.

$^1$HNMR (CDCl$_3$) δ: 0.99 (t, 3H, J=7.5 Hz), 1.70-1.77 (m, 2H), 3.24 (s, 3H), 3.79-3.82 (m, 5H), 4.36-4.40 (m, 1H), 6.78 (d, 1H, J=1.8 Hz), 6.85 (d, 1H, J=1.8 Hz), 7.13 (s, 1H), 7.29 (d, 1H, J=2.3 Hz), 7.34 (d, 1H, J=2.3 Hz), 7.46 (dd, 1H, J=2.6, 8.9 Hz), 8.08 (d, 1H, J=8.9 Hz), 8.48 (d, 1H, J=2.6 Hz)

ESI-MS (m/e): 461 [M+H]$^+$

Production Example 129

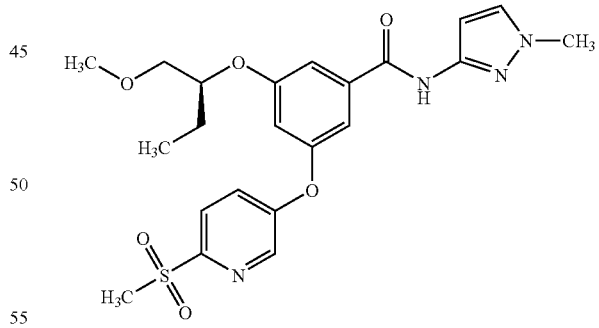

Preparation of 3-(6-methanesulfonylpyridin-3-yloxy)-5-(1-methoxymethyl-propoxy)-N-(1-methyl-1H-pyrazol-3-yl)benzamide The compound of Production Example 129 was obtained as a colorless amorphous substance using 5-hydroxy-3-methoxymethoxybenzoic acid methyl ester, 5-bromo-2-methanesulfonylpyridine, (2S)-1-methoxy-2-hydroxybutane and 3-amino-1-methyl-1H-pyrazole, by the same method as in Production Example 117, a corresponding method, or a combination thereof with an ordinary method.

¹HNMR (CDCl₃) δ: 0.99 (t, 3H, J=7.4 Hz), 1.74-1.79 (m, 2H), 3.24 (s, 3H), 3.37 (s, 3H), 3.56-3.57 (m, 2H), 3.79 (s, 3H), 4.37-4.40 (m, 1H), 6.79 (s, 1H), 6.87 (t, 1H, J=1.2 Hz), 7.14 (s, 1H), 7.29 (d, 1H, J=1.2 Hz), 7.34 (d, 1H, J=1.2 Hz), 7.45 (dd, 1H, J=2.0, 8.6 Hz), 8.06 (d, 1H, J=8.6 Hz), 8.48 (d, 1H, J=2.0 Hz)

ESI-MS (m/e): 475 [M+H]⁺

Production Example 130

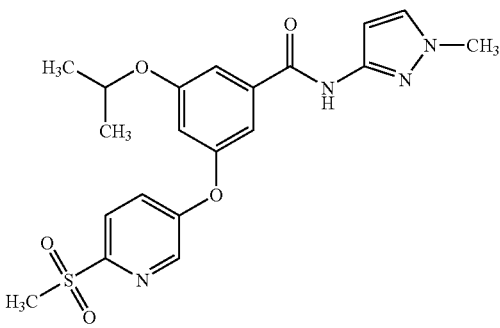

Preparation of 5-isopropoxy-3-(6-methanesulfonylpyridin-3-yloxy)-N-(1-methyl-1H-pyrazol-3-yl)benzamide The compound of Production Example 130 was obtained as a white amorphous substance using 5-hydroxy-3-methoxymethoxybenzoic acid methyl ester, 5-bromo-2-methanesulfonylpyridine, 2-hydroxypropane and 3-amino-1-methyl-1H-pyrazole, by the same method as in Production Example 117, a corresponding method, or a combination thereof with an ordinary method.

¹HNMR (CDCl₃) δ: 1.35 (d, 6H, J=6.2 Hz), 3.22 (s, 3H), 3.77 (s, 3H), 6.75 (septe, 1H, J=6.2 Hz), 6.74 (m, 1H), 6.76 (m, 1H), 7.08 (m, 1H), 7.24 (m, 1H), 7.26 (m, 1H), 7.41 (dd, 1H, J=2.9, 8.8 Hz), 8.03 (d, 1H, J=8.8 Hz), 8.44 (d, 1H, J=2.9 Hz), 8.64 (br, 1H)

ESI-MS (m/e): 431 [M+H]⁺

Production Example 131

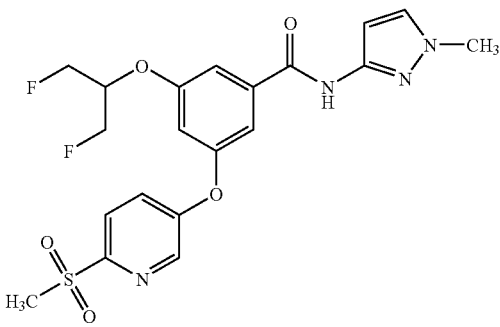

Preparation of 5-(2-fluoro-1-fluoromethyl-ethoxy)-3-(6-methanesulfonylpyridin-3-yloxy)-N-(1-methyl-1H-pyrazol-3-yl)benzamide The compound of Production Example 131 was obtained as a white amorphous substance using 5-hydroxy-3-methoxymethoxybenzoic acid methyl ester, 5-bromo-2-methanesulfonylpyridine, 1,3-difluoro-2-propanol and 3-amino-1-methyl-1H-pyrazole, by the same method as in Production Example 117, a corresponding method, or a combination thereof with an ordinary method.

¹HNMR (CDCl₃) δ: 3.23 (s, 3H), 3.75 (s, 3H), 4.55-4.61 (m, 2H), 4.61-4.80 (m, 3H), 6.75 (m, 1H), 6.88 (m, 1H), 7.18 (m, 1H), 7.27 (m, 1H), 7.34 (m, 1H), 7.43 (dd, 1H, J=2.4, 8.4 Hz), 8.04 (d, 1H), 8.44 (d, 1H, J=2.4 Hz), 8.84 (br, 1H)

ESI-MS (m/e): 467 [M+H]⁺

Production Example 132

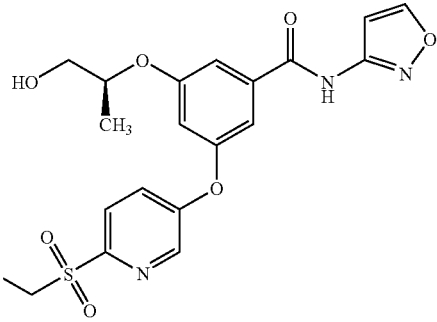

Preparation of 3-(6-ethanesulfonylpyridin-3-yloxy)-5-(2-hydroxy-1-methyl-ethoxy)-N-(isoxazol-3-yl)benzamide The compound of Production Example 132 was obtained as a colorless amorphous substance using 5-hydroxy-3-methoxymethoxybenzoic acid methyl ester, 5-bromo-2-ethanesulfonylpyridine, (2R)-1-(tert-butyldimethylsiloxy)-2-hydroxypropane and 3-amino-isoxazole, by the same method as in Production Example 117, a corresponding method, or a combination thereof with an ordinary method.

¹HNMR (CDCl₃) δ: 1.31 (d, 3H, J=6.2 Hz), 1.32 (t, 3H, J=7.3 Hz), 2.22 (brs, 1H), 3.40 (q, 2H, J=7.3 Hz), 3.75-3.77 (m, 2H), 4.56-4.61 (m, 1H, J=6.2, -Hz), 6.86 (d, 1H, J=2.2 Hz), 7.17 (d, 1H, J=2.2 Hz), 7.26 (d, 1H, 0.7 Hz), 7.40 (d, 1H, J=2.2 Hz), 7.43 (dd, 1H, J=8.8, 2.9 Hz), 8.04 (d, 1H, J=8.8 Hz), 8.26 (d, 1H, J=0.7 Hz), 8.46 (d, 1H, J=2.9 Hz), 9.83 (brs, 1H)

ESI-MS (m/e): 448 [M+H]⁺, 446 [M−H]⁻

Production Example 133

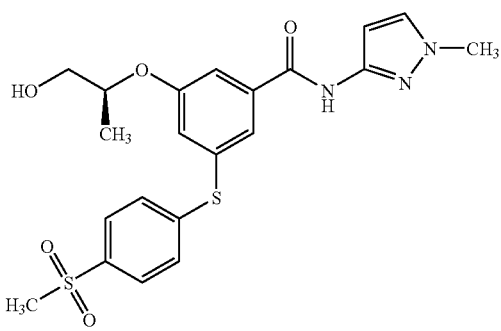

Preparation of 5-(2-hydroxy-1-methyl-ethoxy)-3-(4-methanesulfonylphenylsulfanyl)-N-(1-methyl-1H-pyrazol-3-yl)benzamide The compound of Production Example 133 was obtained as a colorless amorphous substance using 3-hydroxy-5-iodobenzoic acid methyl ester, (2R)-1-(tert-butyldimethylsiloxy)-2-hydroxypropane, 4-methanesulfonylbenzenethiol and 3-amino-1-methyl-1H-pyrazole, by the same method as in Production Example 74 or 82, a corresponding method, or a combination thereof with an ordinary method.

$^1$HNMR (CDCl$_3$) δ: 1.30 (3H, d, J=6.2 Hz), 3.05 (3H, s), 3.74-3.79 (2H, m), 3.81 (3H, s), 4.52-4.63 (1H, m), 6.78 (1H, d, J=2.3 Hz), 7.21 (1H, m), 7.30 (1H, d, J=2.2 Hz), 7.34 (2H, d, J=8.6 Hz), 7.47-7.50 (1H, m), 7.51-7.54 (1H, m), 7.82 (2H, d, J=8.6 Hz), 8.53 (1H, br)

ESI-MS (m/e): 392 [M+H]$^+$

Production Example 134

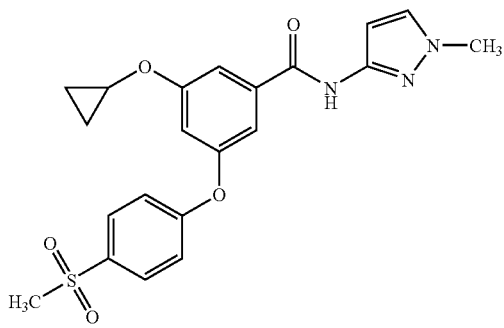

Preparation of 5-cyclopropyloxy-3-(4-methanesulfonylphenoxy)-N-(1-methyl-1H-pyrazol-3-yl)benzamide The compound of Production Example 134 was obtained as a colorless oil by the same method as in Production Example 1, a corresponding method, or a combination thereof with an ordinary method, using 5-methoxymethoxy-3-vinyloxy-benzoic acid methyl ester obtained by reacting 5-hydroxy-3-methoxymethoxybenzoic acid methyl ester, tetravinyltin and copper acetate, and then using p-methylthiophenylboric acid, 3-amino-1-methyl-1H-pyrazole, and 3-cyclopropyloxy-5-methoxymethoxy-benzoic acid methyl ester obtained by reaction between diethylzinc and diiodomethane.

$^1$HNMR (CDCl$_3$) δ: 0.70-0.85 (m, 4H), 3.08 (s, 3H), 3.78 (m, 1H), 3.79 (s, 3H), 6.78 (m, 1H), 6.91 (m, 1H), 7.10-7.14 (m, 3H), 7.27 (m, 1H), 7.41 (m, 1H), 7.90 (d, 2H, J=8.8 Hz), 8.52 (br, 1H)

ESI-MS (m/e): 428 [M+H]$^+$

Production Example 135

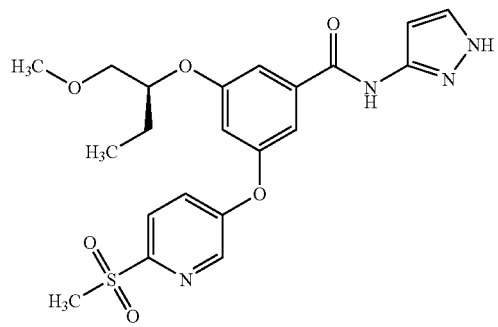

Preparation of 3-(6-methanesulfonylpyridin-3-yloxy)-5-(1-methoxymethyl-propoxy)-N-(pyrazol-3-yl)benzamide The compound of Production Example 135 was obtained as a colorless amorphous substance using 5-hydroxy-3-methoxymethoxybenzoic acid methyl ester, 5-bromo-2-methanesulfonylpyridine, (2R)-1-methoxy-2-hydroxybutane and 3-amino-pyrazole, by the same method as in Production Example 117, a corresponding method, or a combination thereof with an ordinary method.

$^1$HNMR (CDCl$_3$) δ: 0.98 (t, 3H, J=7.4 Hz), 1.69-1.78 (m, 2H), 3.22 (s, 3H), 3.38 (s, 3H), 3.58-3.59 (m, 2H), 4.37-4.43 (m, 1H), 6.84-6.85 (m, 2H), 7.20 (s, 1H), 7.41-7.49 (m, 3H), 8.04 (d, 1H, J=8.6 Hz), 8.45 (d, 1H, J=2.6 Hz), 9.92 (brs, 1H)

ESI-MS (m/e): 461 [M+H]$^+$

Production Example 136

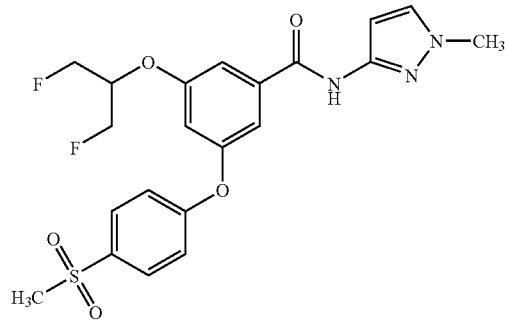

Preparation of 5-(2-fluoro-1-fluoromethyl-ethoxy)-3-(4-methanesulfonylphenoxy)-N-(1-methyl-1H-pyrazol-3-yl)benzamide The compound of Production Example 136 was obtained as a colorless amorphous substance using the 3-(4-methanesulfonyl-phenoxy)-5-methoxymethoxy-benzoic acid methyl ester obtained in Production Example 89, 1,3-difluoro-2-propanol and 3-amino-1-methyl-1H-pyrazole, by the same method as in Production Example 89, a corresponding method, or a combination thereof with an ordinary method.

$^1$HNMR (CDCl$_3$) δ: 3.09 (s, 3H), 3.77 (s, 3H), 4.59-4.76 (m, 5H), 6.78 (s, 1H), 6.89 (t, 1H, J=2.0 Hz), 7.13 (d, 2H, J=8.6 Hz), 7.18 (s, 1H), 7.29 (d, 1H, J=2.0 Hz), 7.33 (d, 1H, J=2.0 Hz), 7.93 (d, 2H, J=8.6 Hz), 8.76 (brs, 1H)

ESI-MS (m/e): 466 [M+H]$^+$

Production Example 137

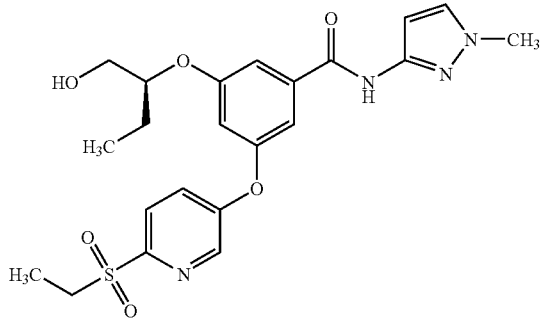

Preparation of 3-(6-ethanesulfonylpyridin-3-yloxy)-5-(1-hydroxymethyl-propoxy)-N-(1-methyl-1H-pyrazol-3-yl)benzamide The compound of Production Example 137 was obtained as a colorless amorphous substance using 5-hydroxy-3-methoxymethoxybenzoic acid methyl ester, 5-bromo-2-ethanesulfonylpyridine, (2R)-1-(tert-butyldimethylsiloxy)-2-hydroxybutane and 3-amino-1-methyl-1H-pyrazole, by the same method as in Production Example 117, a corresponding method, or a combination thereof with an ordinary method.

$^1$HNMR (CDCl$_3$) δ: 0.97 (t, 3H, J=7.4 Hz), 1.32 (t, 3H, J=7.4 Hz), 1.67-1.84 (m, 2H), 3.40 (q, 2H, J=7.4 Hz), 3.74-3.84 (m, 5H), 4.33-4.40 (m, 1H), 6.77 (s, 1H), 6.79 (s, 1H), 7.15 (s, 1H), 7.28 (s, 1H), 7.33 (s, 1H), 7.43 (dd, 1H, J=2.6, 8.8 Hz), 8.05 (d, 1H, J=8.8 Hz), 8.47 (d, 1H, J=2.6 Hz)

ESI-MS (m/e): 475 [M+H]$^+$

Production Example 138

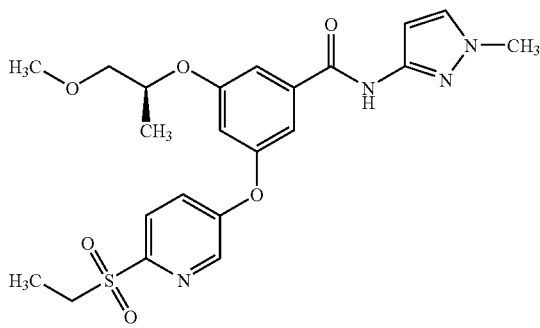

Preparation of 5-(6-ethanesulfonylpyridin-3-yloxy)-3-(2-methoxy-1-methyl-ethoxy)-N-(1-methyl-1H-pyrazol-3-yl)benzamide The compound of Production Example 138 was obtained as a colorless amorphous substance using 5-hydroxy-3-methoxymethoxybenzoic acid methyl ester, 5-bromo-2-ethanesulfonylpyridine, (2R)-2-hydroxy-1-methoxypropane and 3-amino-1-methyl-1H-pyrazole, by the same method as in Production Example 117, a corresponding method, or a combination thereof with an ordinary method.

$^1$HNMR (CDCl$_3$) δ: 1.34 (t, 3H, J=7.3 Hz), 1.34 (d, 3H, J=4.0 Hz), 3.40 (s, 3H), 3.41 (q, 2H, J=7.3 Hz), 3.49-3.60 (m, 2H), 3.80 (s, 3H), 4.60 (qt, 1H, J=4.0, 6.2 Hz), 6.78 (s, 1H), 6.83 (d, 1H, J=2.2 Hz), 7.14 (s, 1H), 7.28 (d, 1H, J=2.2 Hz), 7.31 (s, 1H), 7.42 (dd, 1H, J=8.4, 2.6 Hz), 8.05 (d, 1H, J=8.4 Hz), 8.48 (d, 1H, J=2.6 Hz), 8.49 (brs, 1H)

ESI-MS (m/e): 475 [M+H]$^+$, 473[M−H]$^−$

Production Example 139

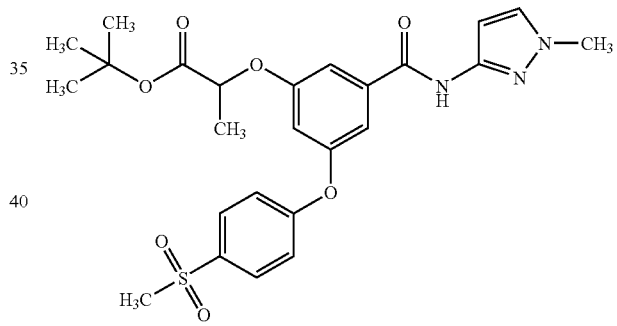

Preparation of 2-[3-(4-methanesulfonylphenoxy)-5-(1-methyl-1H-pyrazol-3-ylcarbamoyl)-phenoxy]propionic acid-tert-butyl ester The compound of Production Example 139 was obtained as a colorless amorphous substance using the 5-hydroxy-3-(4-methylthiophenoxy)benzoic acid methyl ester obtained in Production Example 1, 2-bromopropionic acid tert-butyl ester and 3-amino-1-methyl-1H-pyrazole, by the same method as in Production Example 1, a corresponding method, or a combination thereof with an ordinary method.

$^1$HNMR (CDCl$_3$) δ: 1.44 (9H, s), 1.60 (3H, d, J=6.8 Hz), 3.07 (3H, s), 3.81 (3H, s), 4.69 (1H, q, J=6.8 Hz), 6.77 (1H, br), 7.10-7.16 (3H, m), 7.24 (1H, br), 7.29 (1H, d, J=2.2 Hz), 7.92 (2H, d, J=8.9 Hz), 8.38 (1H, br)

ESI-MS (m/e): 516 [M+H]$^+$

Production Example 140

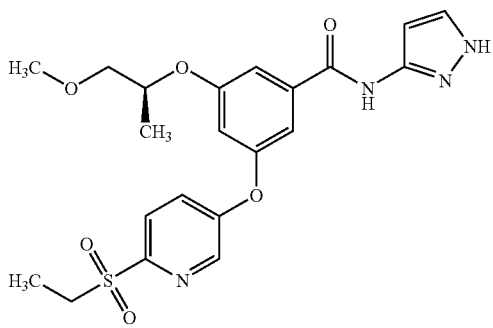

Preparation of 3-(6-ethanesulfonylpyridin-3-yloxy)-5-(2-methoxy-1-methyl-ethoxy)-N-(pyrazol-3-yl)-benzamide The compound of Production Example 140 was obtained as a colorless amorphous substance using 5-hydroxy-3-methoxymethoxybenzoic acid methyl ester, 5-bromo-2-ethanesulfonylpyridine, (2R)-2-hydroxy-1-methoxypropane and 3-amino-pyrazole, by the same method as in Production Example 117, a corresponding method, or a combination thereof with an ordinary method.

$^1$HNMR (CDCl$_3$) δ: 1.33 (t, 3H, J=7.3 Hz), 1.34 (d, 3H, J=6.2 Hz), 3.40 (q, 2H, J=7.3 Hz), 3.41 (s, 3H), 3.52-3.62 (m, 2H), 4.60-4.65 (m, 1H, J=6.2 Hz, -Hz), 6.83 (d, 1H, J=2.2 Hz), 6.86 (s, 1H), 7.20 (s, 1H), 7.42 (d, 1H, J=2.2 Hz), 7.42 (dd, 1H, J=8.8, 2.6 Hz), 7.49 (s, 1H), 7.04 (d, 1H, J=8.8 Hz), 8.47 (d, 1H, J=2.6 Hz), 9.47 (brs, 1H)

ESI-MS (m/e): 461 [M+H]$^+$, 459[M−H]$^−$

Production Example 141

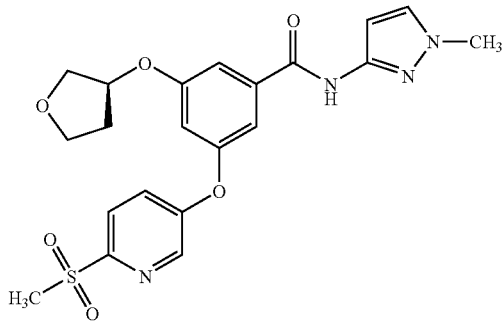

Preparation of 3-(6-methanesulfonylpyridin-3-yloxy)-N-(1-methyl-1H-pyrazol-3-yl)-5-(tetrahydrofuran-3-yl)benzamide The compound of Production Example 141 was obtained as a colorless oil using 5-hydroxy-3-methoxymethoxybenzoic acid methyl ester, 5-bromo-2-methanesulfonylpyridine, (S)-(+)-3-hydroxytetrahydrofuran and 3-amino-1-methyl-1H-pyrazole, by the same method as in Production Example 117, a corresponding method, or a combination thereof with an ordinary method.

$^1$HNMR (CDCl$_3$) δ: 2.15-2.26 (m, 1H), 2.26-2.30 (m, 1H), 3.24 (s, 3H), 3.80 (s, 3H), 3.88-4.03 (m, 4H), 4.97 (m, 1H), 6.76 (m, 2H), 7.11 (t, 1H, J=2.2 Hz), 7.24 (d, 1H, J=2.2 Hz) 7.28 (d, 1H, J=2.2 Hz), 7.44 (dd, 1H, J=2.9, 8.4 Hz), 8.05 (d, 1H, J=8.4 Hz), 8.44 (br, 1H), 8.45 (d, 1H, J=2.9 Hz)

ESI-MS (m/e): 459 [M+H]$^+$

Production Example 142

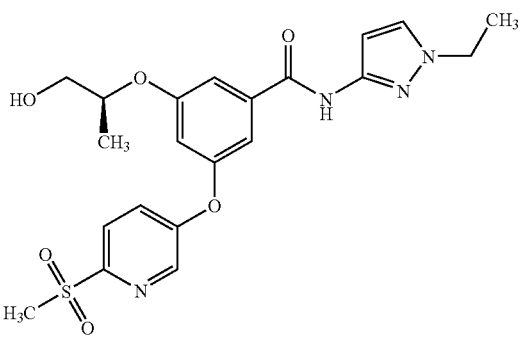

Preparation of N-(1-ethyl-1H-pyrazol-3-yl)-5-(2-hydroxy-1-methyl-ethoxy)-3-(6-methanesulfonylpyridin-3-yloxy)benzamide The compound of Production Example 142 was obtained as a white amorphous substance using 5-hydroxy-3-methoxymethoxybenzoic acid methyl ester, 5-bromo-2-methanesulfonylpyridine, (2R)-1-(tert-butyldimethylsiloxy)-2-hydroxypropane and 3-amino-1-ethyl-1H-pyrazole, by the same method as in Production Example 117, a corresponding method, or a combination thereof with an ordinary method.

$^1$HNMR (CDCl$_3$) δ: 1.33 (d, 3H, J=6.2 Hz), 1.47 (t, 3H, J=7.3 Hz), 1.98 (m, 1H), 3.24 (s, 3H) 3.77 (m, 2H), 4.07 (q, 2H, J=7.3 Hz), 4.58 (m, 1H), 6.77 (d, 1H, J=2.6 Hz), 6.82 (t, 1H, J=2.6 Hz), 7.13 (m, 1H), 7.32 (m, 2H), 7.45 (dd, 1H, J=2.6, 8.4 Hz), 8.06 (d, 1H, J=8.4 Hz), 8.34 (br, 1H), 8.47 (d, 1H, J=2.6 Hz)

ESI-MS (m/e): 461 [M+H]$^+$

Production Example 143

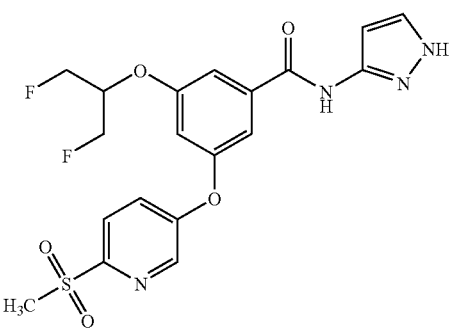

Preparation of 5-(2-fluoro-1-fluoromethyl-ethoxy)-3-(6-methanesulfonylpyridin-3-yloxy)-N-(pyrazol-3-yl)benzamide The compound of Production Example 143 was obtained as a white amorphous substance using 5-hydroxy-3-methoxymethoxybenzoic acid methyl ester, 5-bromo-2-methanesulfonylpyridine, 1,3-difluoro-2-propanol and 3-amino-pyrazole, by the same method as in Production Example 117, a corresponding method, or a combination thereof with an ordinary method.

$^1$HNMR (CDCl$_3$) δ: 3.23 (s, 3H), 4.55-4.70 (m, 2H), 4.70-4.90 (m, 3H), 6.79 (m, 1H), 6.91 (m, 1H), 7.28 (m, 1H), 7.42-7.51 (m, 3H), 8.04 (d, 1H, J=8.9 Hz), 8.44 (d, 1H, J=2.6 Hz), 9.60 (br, 1H)

ESI-MS (m/e): 453 [M+H]$^+$

Production Example 144

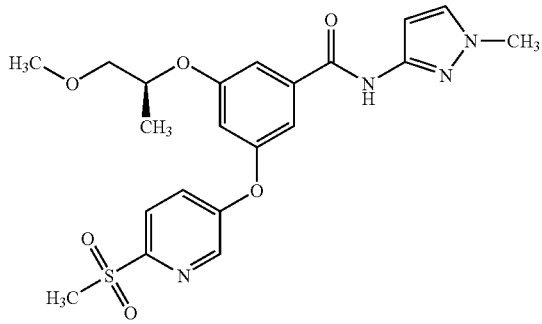

Preparation of 3-(6-methanesulfonylpyridin-3-yloxy)-5-(2-methoxy-1-methyl-ethoxy)-N-(1-methyl-1H-pyrazol-3-yl benzamide The compound of Production Example 144 was obtained as a colorless oil using 5-hydroxy-3-methoxymethoxybenzoic acid methyl ester, 5-bromo-2-methanesulfonylpyridine, (2R)-2-hydroxy-1-methoxypropane and 3-amino-1-methyl-1H-pyrazole, by the same method as in Production Example 117, a corresponding method, or a combination thereof with an ordinary method.

$^1$HNMR (CDCl$_3$) δ: 1.32 (d, 3H, J=6.4 Hz), 3.23 (s, 3H), 3.40 (s, 3H), 3.54 (m, 2H), 3.78 (s, 3H), 4.59 (m, 1H), 6.78 (m, 1H), 6.84 (m, 1H), 7.14 (m, 1H), 7.29 (m, 1H), 7.32 (m, 1H), 7.44 (dd, 1H, J=2.6, 8.6 Hz), 8.05 (d, 1H, J=8.6 Hz), 8.47 (d, 1H, J=2.6 Hz), 8.66 (br, 1H)

ESI-MS (m/e): 461 [M+H]$^+$

Production Example 145

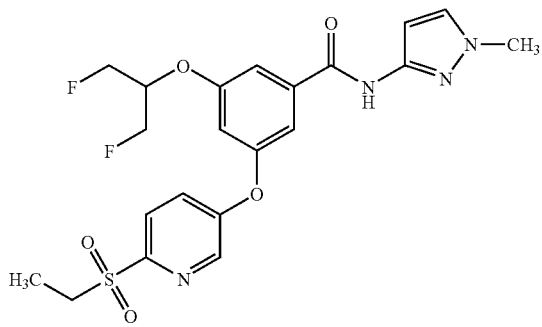

Preparation of 3-(6-ethanesulfonylpyridin-3-yloxy)-5-(2-fluoro-1-fluoromethyl-ethoxy)-N-(1-methyl-1H-pyrazol-3-yl)benzamide The compound of Production Example 145 was obtained as a colorless amorphous substance using 5-hydroxy-3-methoxymethoxybenzoic acid methyl ester, 5-bromo-2-ethanesulfonylpyridine, 1,3-difluoro-2-propanol and 3-amino-1-methyl-1H-pyrazole, by the same method as in Production Example 117, a corresponding method, or a combination thereof with an ordinary method.

$^1$HNMR (CDCl$_3$) δ: 1.33 (t, 3H, J=7.42 Hz), 3.41 (q, 2H, J=7.4 Hz), 3.80 (s, 3H), 4.61-4.65 (m, 2H), 4.73-4.78 (m, 3H), 6.78 (dd, 1H, J=2.0, 1.8 Hz), 6.91 (d, 1H, J=2.3 Hz), 7.23 (dd, 1H, J=1.8, 1.6 Hz), 7.30 (d, 1H, J=2.3 Hz), 7.38 (dd, 1H, J=2.0, 1.6 Hz), 7.16 (dd, 1H, J=8.6, 2.7 Hz), 8.08 (d, 1H, J=8.6 Hz), 8.50 (d, 1H, J=2.7 Hz), 8.63 (brs, 1H)

ESI-MS (m/e): 481 [M+H]$^+$, 479[M−H]$^-$

Production Example 146

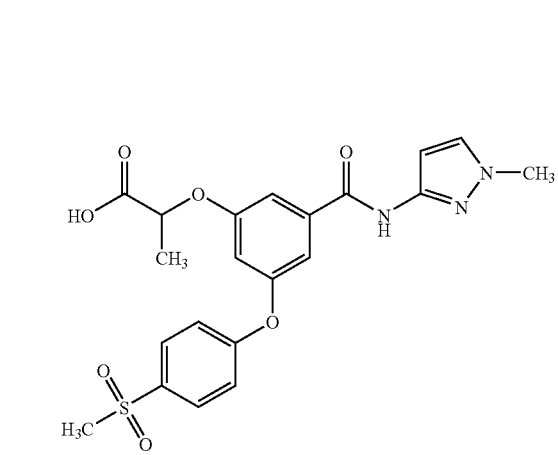

Preparation of 2-[3-(4-methanesulfonylphenoxy)-5-(1-methyl-1H-pyrazol-3-ylcarbamoyl)-phenoxy] propionic acid The compound of Production Example 146 was obtained as a white solid by conversion of the tert-butyl ester portion of the 2-[3-(4-methanesulfonylphenoxy)-5-(1-methyl-1H-pyrazol-3-ylcarbamoyl)-phenoxy]propionic acid-tert-butyl ester obtained in Production Example 139 to a carboxyl group. The conversion of the ester portion to a carboxyl group was accomplished by the method described in Comprehensive Organic Transformations, Richard L. et al., VCH Publishers, 1988, a corresponding method, or a combination thereof with an ordinary method.

$^1$HNMR (CD$_3$OD) δ: 1.60 (3H, d, J=6.8 Hz), 3.11 (3H, s), 3.82 (3H, s), 6.54-6.58 (1H, br), 6.84 (1H, br), 7.16-7.28 (3H, m), 7.34 (1H, br), 7.49 (1H, d, J=2.1 Hz), 7.95 (2H, d, J=8.9 Hz)

ESI-MS (m/e): 460 [M+H]$^+$

Production Example 147

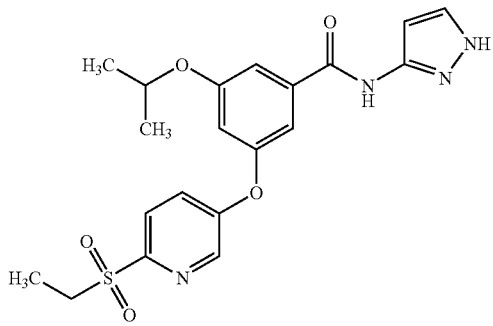

Preparation of 3-(6-ethanesulfonylpyridin-3-yloxy)-5-isopropoxy-N-(pyrazol-3-yl)benzamide The compound of Production Example 147 was obtained as a colorless amorphous substance using 5-hydroxy-3-methoxymethoxybenzoic acid methyl ester, 5-bromo-2-ethanesulfonylpyridine, 2-hydroxypropane and 3-amino-pyrazole, by the same method as in Production Example 117, a corresponding method, or a combination thereof with an ordinary method.

$^1$HNMR (CDCl$_3$) δ: 1.32 (t, 3H, J=7.3 Hz), 1.37 (d, 6H, J=5.9 Hz), 3.39 (q, 2H, J=7.3 Hz), 4.60 (septet, 1H, J=5.9 Hz), 6.76 (dd, 1H, J=2.2, 2.2 Hz), 6.84 (s, 1H), 7.16 (s, 1H), 7.33 (s, 1H), 7.40 (dd, 1H, J=8.8, 2.6 Hz), 7.51 (dd, 1H, J=2.2, 2.6 Hz), 8.03 (dd, 1H, J=8.8, 2.6 Hz), 8.46 (dd, 1H, J=2.6, 2.6 Hz), 9.03 (brs, 1H)

ESI-MS (m/e): 431 [M+H]$^+$, 429[M−H]$^-$

Production Example 148

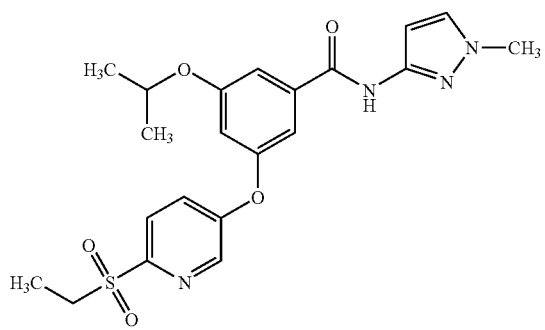

Preparation of 3-(6-ethanesulfonylpyridin-3-yloxy)-5-isopropoxy-N-(1-methyl-1H-pyrazol-3-yl)benzamide The compound of Production Example 148 was obtained as a colorless amorphous substance using 5-hydroxy-3-methoxymethoxybenzoic acid methyl ester, 5-bromo-2-ethanesulfonylpyridine, 2-hydroxypropane and 3-amino-1-methyl-1H-pyrazole, by the same method as in Production Example 117, a corresponding method, or a combination thereof with an ordinary method.

$^1$HNMR (CDCl$_3$) δ: 1.34 (t, 3H, J=7.3 Hz), 1.37 (d, 6H, J=5.9 Hz), 3.41 (q, 2H, J=7.3 Hz), 3.81 (s, 3H), 4.60 (septet, 1H, J=5.9 Hz), 6.75-6.78 (m, 2H), 7.11 (s, 1H), 7.26 (s, 1H), 7.28 (d, 1H, J=2.2 Hz), 7.42 (dd, 1H, J=8.8, 2.9 Hz), 8.05 (d, 1H, J=8.8 Hz), 8.36 (brs, 1H), 8.48 (d, 1H, J=2.9 Hz)

ESI-MS (m/e): 445 [M+H]$^+$, 443 [M−H]$^-$

Production Example 149

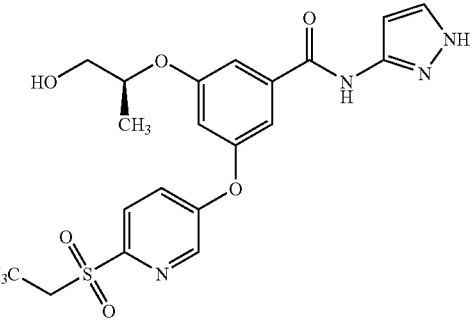

Preparation of 3-(6-ethanesulfonylpyridin-3-yloxy)-5-(2-hydroxy-1-methyl-ethoxy)-N-(pyrazol-3-yl)benzamide The compound of Production Example 149 was obtained as a colorless amorphous substance using 5-hydroxy-3-methoxymethoxybenzoic acid methyl ester, 5-bromo-2-ethanesulfonylpyridine, (2R)-1-(tert-butyldimethylsiloxy)-2-hydroxypropane and 3-amino-pyrazole, by the same method as in Production Example 117, a corresponding method, or a combination thereof with an ordinary method.

$^1$HNMR (CDCl$_3$ (one drop of CD$_3$OD)) δ: 1.29 (d, 3H, J=6.3 Hz), 1.31 (t, 3H, J=7.4 Hz), 3.39 (q, 2H, J=7.4 Hz), 3.70-3.76 (m, 2H), 4.55 (septet, 1H, J=6.3 Hz), 6.77 (s, 1H), 6.79 (d, 1H, J=2.3 Hz), 7.20 (s, 1H), 7.37 (s, 1H), 7.41 (dd, 1H, J=8.6, 2.7 Hz), 7.49 (d, 1H, J=2.3 Hz), 8.02 (d, 1H, J=8.6 Hz), 8.44 (d, 1H, J=2.7 Hz), 9.55 (brs, 1H)

ESI-MS (m/e): 447 [M+H]$^+$, 445[M−H]$^-$

Production Example 150

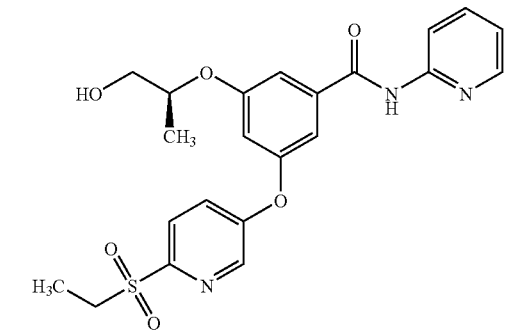

153

Preparation of 3-(6-ethanesulfonylpyridin-3-yloxy)-5-(2-hydroxy-1-methyl-ethoxy)-N-(pyridin-2-yl)benzamide The compound of Production Example 150 was obtained as a colorless amorphous substance using 5-hydroxy-3-methoxymethoxybenzoic acid methyl ester, 5-bromo-2-ethanesulfonylpyridine, (2R)-1-(tert-butyldimethylsiloxy)-2-hydroxypropane and 2-aminopyridine, by the same method as in Production Example 117, a corresponding method, or a combination thereof with an ordinary method.

¹HNMR (CDCl₃) δ: 1.33 (d, 3H, J=6.1 Hz), 1.33 (t, 3H, J=7.4 Hz), 3.41 (q, 2H, J=7.4 Hz), 3.78-3.80 (m, 2H), 4.62 (dq, 1H, J=4.5, 6.1 Hz), 6.84 (s, 1H), 7.11 (dd, 1H, J=6.6, 5.1 Hz), 7.22 (s, 1H), 7.38 (s, 1H), 7.45 (dd, 1H, J=8.8, 2.5 Hz), 7.78 (dd, 1H, J=8.4, 6.6 Hz), 8.08 (d, 1H, J=8.8 Hz), 8.30 (d, 1H, J=5.1 Hz), 8.34 (d, 1H, J=8.4 Hz), 8.50 (d, 1H, J=2.5 Hz), 8.63 (brs, 1H)

ESI-MS (m/e): 481 [M+H]⁺

Production Example 151

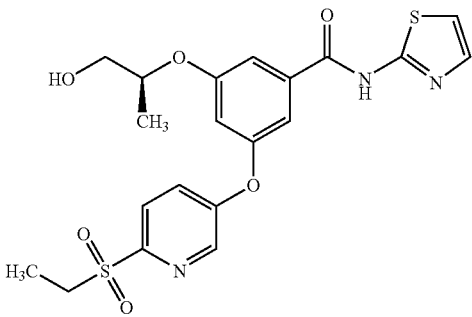

Preparation of 3-(6-ethanesulfonylpyridin-3-yloxy)-5-(2-hydroxy-1-methyl-ethoxy)-N-thiazol-2-yl-benzamide The compound of Production Example 151 was obtained as a colorless amorphous substance using 5-hydroxy-3-methoxymethoxybenzoic acid methyl ester, 5-bromo-2-ethanesulfonylpyridine, (2R)-1-(tert-butyldimethylsiloxy)-2-hydroxypropane and 2-aminothiazole, by the same method as in Production Example 117, a corresponding method, or a combination thereof with an ordinary method.

¹HNMR (CDCl₃) δ: 1.31 (d, 3H, J=6.3 Hz), 1.33 (t, 3H, J=7.4 Hz), 3.41 (q, 2H, J=7.4 Hz), 3.76-3.78 (m, 2H), 4.55-4.60 (m, 1H), 6.86 (m, 1H), 7.02 (d, 1H, J=3.5 Hz), 7.26 (m, 1H), 7.29 (d, 1H, J=3.5 Hz), 7.42 (m, 1H), 7.46 (dd, 1H, J=8.6, 2.7 Hz), 8.08 (d, 1H, J=8.6 Hz), 8.49 (d, 1H, J=2.7 Hz)

ESI-MS (m/e): 464 [M+H]+, 462[M−H]−

Production Example 152

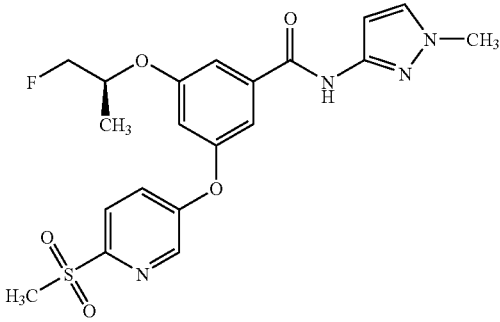

154

Preparation of 5-(2-fluoro-1-methyl-ethoxy)-3-(6-methanesulfonylpyridin-3-yloxy)-N-(1-methyl-1H-pyrazol-3-yl)benzamide The compound of Production Example 152 was obtained as a colorless amorphous substance by conversion of the hydroxyl group of the 5-(2-hydroxy-1-methyl-ethoxy)-3-(6-methanesulfonylpyridin-3-yloxy)-N-(1-methyl-1H-pyrazol-3-yl)benzamide obtained in Production Example 126 to mesylate with triethylamine and methanesulfonyl chloride, followed by reaction with tetrabutylammonium chloride.

¹HNMR (CDCl₃) δ: 1.35 (dd, 3H, J=1.6, 6.2 Hz), 3.24 (s, 3H), 3.77 (s, 3H), 4.45 (m, 1H), 4.57 (m, 1H), 4.67 (m, 1H), 6.79 (d, 1H, J=2.3 Hz), 6.84 (t, 1H, J=2.3 Hz), 7.16 (t, 1H, J=2.3 Hz), 7.30 (d, 1H, J2.3 Hz), 7.32 (m, 1H), 7.45 (d, 1H, J=2.3, 8.6 Hz), 8.06 (d, 1H, J=8.6 Hz), 8.47 (d, 1H, J=2.3 Hz), 8.79 (br, 1H)

ESI-MS (M/E): 449 [M+H]⁺

Production Example 153

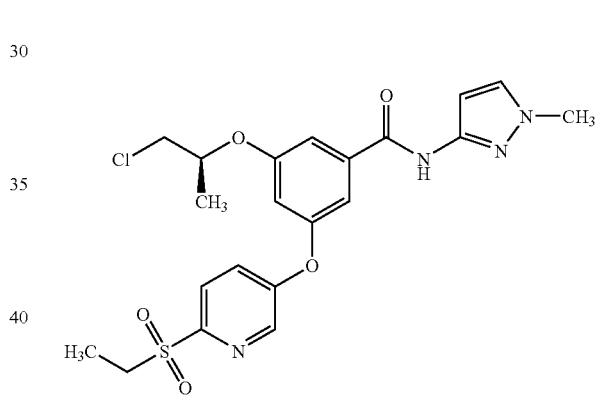

Preparation of 5-(2-chloro-1-methyl-ethoxy)-3-(6-ethanesulfonylpyridin-3-yloxy)-N-(1-methyl-1H-pyrazol-3-yl)benzamide The compound of Production Example 153 was obtained as a colorless amorphous substance during conversion of the hydroxyl group of the 3-(6-ethanesulfonylpyridin-3-yloxy)-5-(2-hydroxy-1-methyl-ethoxy)-N-(1-methyl-1H-pyrazol-3-yl)benzamide obtained in Production Example 117 to mesylate with triethylamine and methanesulfonyl chloride.

¹HNMR (CDCl₃) δ: 1.33 (t, 3H, J=7.4 Hz), 1.45 (d, 3H, J=6.2 Hz), 3.41 (q, 2H, J=7.4 Hz), 3.63 (dd, 1H, J=5.0, 11.5 hz), 3.69 (dd, 1H, J=5.0, 11.5 Hz), 3.79 (s, 3H), 4.62 (m, 1H), 6.79 (d, 1H, J=2.2 Hz), 6.83 (t, 1H, J=2.2 Hz), 7.18 (m, 1H), 7.29-7.35 (m, 2H), 7.45 (dd, 1H, J=2.7, 8.6 Hz), 8.07 (d, 1H, J=8.6 Hz), 8.49 (d, 1H, J=2.7 Hz), 8.67 (br, 1H)

ESI-MS (M/E): 479 [M+H]⁺

Production Example 154

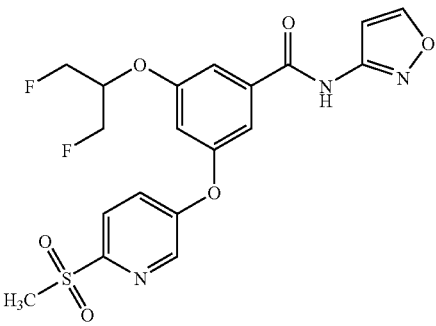

Preparation of 5-(2-fluoro-1-fluoromethyl-ethoxy)-N-(isoxazol-3-yl)-3-(6-methanesulfonylpyridin-3-yloxy)benzamide The compound of Production Example 154 was obtained as a white amorphous substance using 5-hydroxy-3-methoxymethoxybenzoic acid methyl ester, 5-bromo-2-methanesulfonylpyridine, 1,3-difluoro-2-propanol and 3-aminooxazole, by the same method as in Production Example 117, a corresponding method, or a combination thereof with an ordinary method.

$^1$HNMR (CDCl$_3$) δ: 3.24 (s, 3H), 4.59-4.70 (m, 2H), 4.70-4.90 (m, 3H), 6.96 (t, 1H, J=2.3 Hz), 7.19 (m, 1H), 7.32 (m, 1H), 7.45 (m, 1H), 7.48 (dd, 1H, J=2.7, 8.5 Hz), 8.09 (d, 1H, J=8.5 Hz), 8.29 (m, 1H), 8.49 (d, 1H, J=2.7 Hz), 9.60 (br, 1H)

ESI-MS (M/E): 454 [M+H]$^+$

Production Example 155

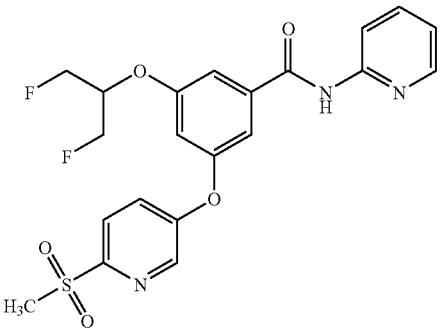

Preparation of 5-(2-fluoro-1-fluoromethyl-ethoxy)-3-(6-methanesulfonylpyridin-3-yloxy)-N-(pyridin-2-yl)benzamide The compound of Production Example 155 was obtained as a white amorphous substance using 5-hydroxy-3-methoxymethoxybenzoic acid methyl ester, 5-bromo-2-methanesulfonylpyridine, 1,3-difluoro-2-propanol and 2-aminopyridine, by the same method as in Production Example 117, a corresponding method, or a combination thereof with an ordinary method.

$^1$HNMR (CDCl$_3$) δ: 3.24 (s, 3H), 4.60-4.70 (m, 2H), 4.70-4.90 (m, 3H), 6.93 (t, 1H, J=2.1 Hz), 7.10 (m, 1H), 7.26 (m, 1H), 7.42 (m1H), 7.48 (dd, 1H, J=2.1, 8.2 Hz), 7.78 (dt, 1H, J=), 8.09 (d, 1H, J=8.4 Hz), 8.30 (m, 1H), 8.32 (d, 1H, J=8.4 Hz), 8.49 (d, 1H, J=2.1 Hz), 8.59 (br, 1H)

ESI-MS (M/E): 464 [M+H]$^+$

Production Example 156

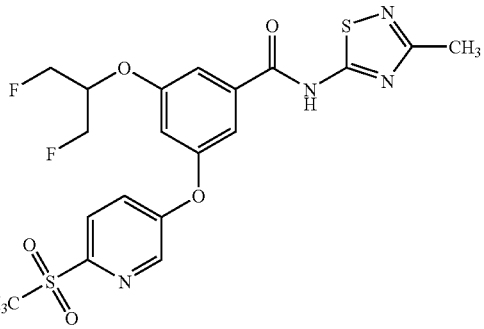

Preparation of 5-(2-fluoro-1-fluoromethyl-ethoxy)-3-(6-methanesulfonylpyridin-3-yloxy)-N-(3-methyl-[1,2,4]-thiadiazol-5-yl)benzamide The compound of Production Example 156 was obtained as a white amorphous substance using 5-hydroxy-3-methoxymethoxybenzoic acid methyl ester, 5-bromo-2-methanesulfonylpyridine, 1,3-difluoro-2-propanol and 5-amino-3-methyl-[1,2,4]thiadiazole, by the same method as in Production Example 117, a corresponding method, or a combination thereof with an ordinary method.

$^1$HNMR (CDCl$_3$) δ: 2.50 (s, 3H), 3.27 (s, 3H), 4.57-4.67 (m, 2H), 4.67-4.90 (m, 3H), 7.01 (t, 1H, J=2.3 Hz), 7.29 (m, 1H), 7.45 (m, 1H), 7.49 (dd, 1H, J=2.3, 8.7 Hz), 8.09 (d, 1H, J=8.7 Hz), 8.47 (d, 1H, J=2.3 Hz)

ESI-MS (M/E): 485 [M+H]$^+$

Production Example 157

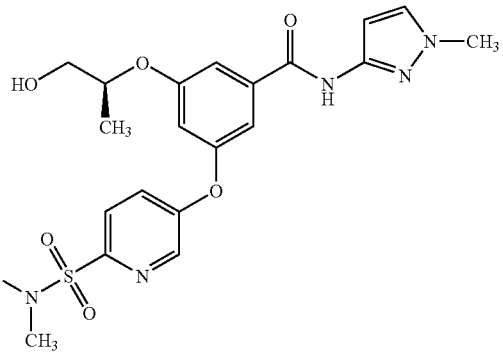

Preparation of 3-(4-dimethylsulfamoylphenoxy)-5-(2-hydroxy-1-methyl-ethoxy)-N-(1-methyl-1H-pyrazol-3-yl)benzamide The compound of Production Example 157 was obtained as a white amorphous substance using 5-hydroxy-3-methoxymethoxybenzoic acid methyl ester, 4-bromo-dimethylsulfamoylbenzene, (2R)-1-(t-butyldimethylsiloxy)-2-hydroxypropane and 3-amino-1-methyl-1H-pyrazole, by the same method as in Production Example 42, a corresponding method, or a combination thereof with an ordinary method.

$^1$HNMR (CDCl$_3$) δ: 1.31 (d, 3H, J=6.3 Hz), 2.19 (brs, 1H), 2.74 (s, 6H), 3.76-3.80 (m, 2H), 3.81 (s, 3H), 4.54-4.59 (m, 1H, J=6.3 Hz, -Hz), 6.79 (m, 1H), 6.81 (m, 1H), 7.11 (d, 2H, J=9.0 Hz), 7.13 (s, 1H), 7.29-7.30 (m, 2H), 7.77 (d, 2H, J=9.0 Hz), 8.55 (br, 1H)

ESI-MS (m/e): 475 [M+H]+, 473[M−H]−

Production Example 158

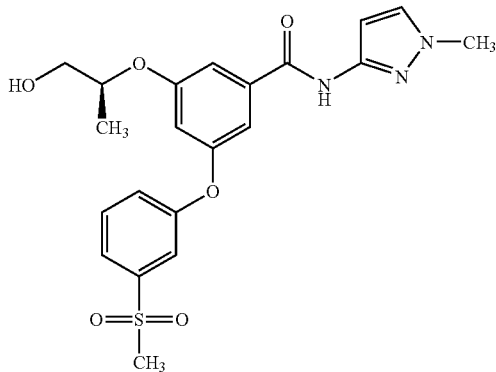

Preparation of 5-(2-hydroxy-1-methyl-ethoxy)-3-(3-methanesulfonylphenoxy)-N-(1-methyl-1H-pyrazol-3-yl)benzamide The compound of Production Example 158 was obtained as a white amorphous substance using 5-hydroxy-3-methoxymethoxybenzoic acid methyl ester, 3-methylthio-phenylboric acid, (2R)-1-(t-butyldimethylsiloxy)-2-hydroxypropane and 3-amino-1-methyl-1H-pyrazole, by the same method as in Production Example 1 or Production Example 89, a corresponding method, or a combination thereof with an ordinary method.

$^1$HNMR (CDCl$_3$) δ: 1.30 (d, 3H, J=6.2 Hz), 2.08 (t, 1H, J=6.5 Hz), 3.07 (s, 3H), 3.73-3.78 (m, 5H), 4.52-4.57 (m, 1H), 6.77-6.78 (m, 2H), 7.08 (d, 1H, J=2.1 Hz), 7.25-7.31 (m, 3H), 7.54 (t, 1H, J=7.6 Hz), 7.59 (d, 1H, J=2.1 Hz), 7.70 (d, 1H, J=7.6 Hz), 8.49 (brs, 1H)

ESI-MS (m/e): 446 [M+H]$^+$

Production Example 159

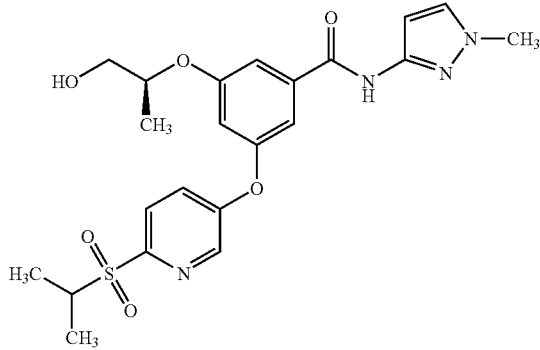

Preparation of 5-(2-hydroxy-1-methyl-ethoxy)-3-(6-isopropylsulfonylpyridin-3-yloxy)-N-(1-methyl-1H-pyrazol-3-yl)benzamide The compound of Production Example 159 was obtained as a white amorphous substance using 5-hydroxy-3-methoxymethoxybenzoic acid methyl ester, 5-bromo-2-isopropylsulfonylpyridine, (2R)-1-(t-butyldimethylsiloxy)-2-hydroxypropane and 3-amino-1-methyl-1H-pyrazole, by the same method as in Production Example 117, a corresponding method, or a combination thereof with an ordinary method.

$^1$HNMR (CDCl$_3$) δ: 1.31 (d, 3H, J=5.9 Hz), 1.35 (d, 6H, J=6.7 Hz), 2.25 (brs, 1H), 3.72 (septet, 1H, J=6.7 Hz), 3.70-3.81 (m, 2H), 3.81 (s, 3H), 4.53-4.59 (m, 1H), 6.78-6.79 (m, 1H), 6.80-6.82 (m, 1H), 7.17 (m, 1H), 7.29-7.31 (m, 1H), 7.32 (m, 1H), 7.43 (dd, 1H, J=8.6, 2.7 Hz), 8.06 (d, 1H, J=8.6 Hz), 8.50 (d, 1H, J=2.7 Hz), 8.60 (brs, 1H)

ESI-MS (m/e): 475 [M+H]+, 473[M−H]−

Production Example 160

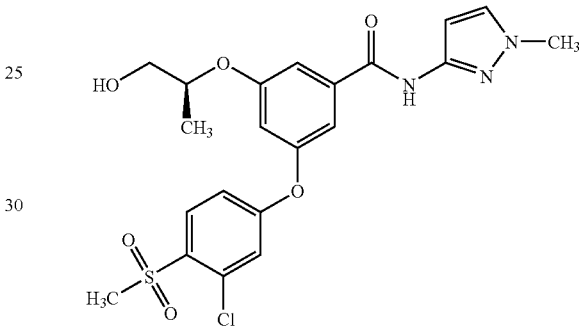

Preparation of 3-(3-chloro-4-methanesulfonylphenoxy)-5-(2-hydroxy-1-methyl-ethoxy)-N-(1-methyl-1H-pyrazol-3-yl)benzamide The compound of Production Example 160 was obtained as a white amorphous substance using 5-hydroxy-3-methoxymethoxybenzoic acid methyl ester, 4-bromo-2-chloromethanesulfonylbenzene, (2R)-1-(t-butyldimethylsiloxy)-2-hydroxypropane and 3-amino-1-methyl-1H-pyrazole, by the same method as in Production Example 42, a corresponding method, or a combination thereof with an ordinary method.

$^1$HNMR (CDCl$_3$) δ: 1.31 (d, 3H, J=6.1 Hz), 3.28 (s, 3H), 3.76-3.80 (m, 5H), 4.54-4.59 (m, 1H), 6.80-6.81 (m, 2H), 7.02 (dd, 1H, J=2.3, 8.8 Hz), 7.14-7.15 (m, 2H), 7.30 (d, 1H, J=2.3 Hz), 7.33 (s, 1H), 8.11 (d, 1H, J=8.8 Hz), 8.75 (brs, 1H)

ESI-MS (m/e): 480 [M+H]$^+$

Production Example 161

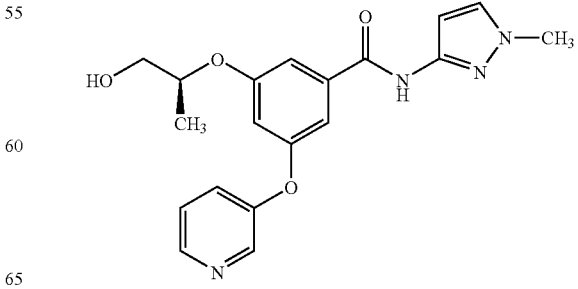

Preparation of 5-(2-hydroxy-1-methyl-ethoxy)-N-(1-methyl-1H-pyrazol-3-yl)-3-(pyridin-3-yloxy)benzamide The compound of Production Example 161 was obtained as a white amorphous substance using 5-hydroxy-3-methoxymethoxybenzoic acid methyl ester, 3-iodopyridine, (2R)-1-(t-butyldimethylsiloxy)-2-hydroxypropane and 3-amino-1-methyl-1H-pyrazole, by the same method as in Production Example 117, a corresponding method, or a combination thereof with an ordinary method.

$^1$HNMR (CDCl$_3$) δ: 1.30 (d, 3H, J=6.3 Hz), 2.27 (br, 1H), 3.72-3.80 (m, 2H), 3.80 (s, 3H), 4.55 (m, 1H), 6.75 (t, 1H, J=2.3 Hz), 6.79 (d, 1H, J=2.3 Hz), 7.05 (m, 1H), 7.22 (m, 1H), 7.29 (d, 1H, J=2.3 Hz), 7.31-7.38 (m, 2H), 8.44 (m, 2H), 8.62 (br, 1H)

ESI-MS (M/E): 369 [M+H]$^+$

Production Example 162

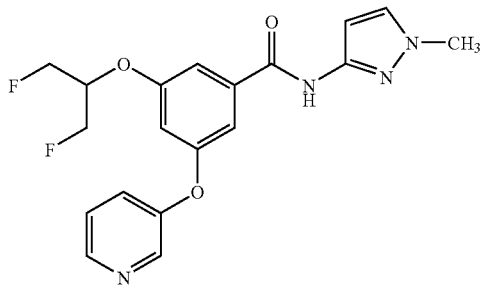

Preparation of 5-(2-fluoro-1-fluoromethyl-ethoxy)-N-(1-methyl-1H-pyrazol-3-yl)-3-(pyridin-3-yloxy)benzamide The compound of Production Example 162 was obtained as a white amorphous substance using 5-hydroxy-3-methoxymethoxybenzoic acid methyl ester, 3-iodopyridine, 1,3-difluoro-2-propanol and 3-amino-1-methyl-1H-pyrazole, by the same method as in Production Example 117, a corresponding method, or a combination thereof with an ordinary method.

$^1$HNMR (CDCl$_3$) δ: 3.77 (s, 3H), 4.55-4.67 (m, 2H), 4.67 (m, 3H), 6.79 (d, 1H, J=2.3 Hz), 6.82 (t, 1H, J=2.3 Hz), 7.11 (m, 1H), 7.26 (m, 1H), 7.29 (d, 1H, J=2.3 Hz), 7.30-7.38 (m, 2H), 8.45 (m, 2H), 8.70 (br, 1H)

ESI-MS (M/E): 389 [M+H]$^+$

Production Example 163

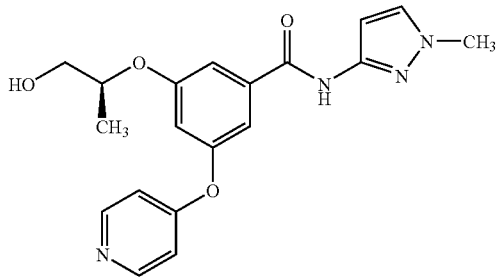

Preparation of 5-(2-hydroxy-1-methyl-ethoxy)-N-(1-methyl-1H-pyrazol-3-yl)-3-(pyridin-4-yloxy)benzamide The compound of Production Example 163 was obtained as a white amorphous substance using 5-hydroxy-3-methoxymethoxybenzoic acid methyl ester, 4-chloropyridine hydrochloride, (2R)-1-(t-butyldimethylsiloxy)-2-hydroxypropane and 3-amino-1-methyl-1H-pyrazole, by the same method as in Production Example 117, a corresponding method, or a combination thereof with an ordinary method.

$^1$HNMR (CDCl$_3$) δ: 1.31 (d, 3H, J=6.3 Hz), 2.05 (br, 1H), 3.77 (m, 2H), 3.82 (s, 3H), 4.56 (m, 1H), 6.79 (d, 1H, J=2.3 Hz), 6.83 (t, 1H, J=2.3 Hz), 6.88 (dd, 2H, J=1.6, 4.7 Hz), 7.15 (m, 1H), 7.30 (d, 1H, J=2.2 Hz), 7.33 (m, 1H), 8.42 (br, 1H), 8.51 (dd, 2H, J=1.6, 4.7 Hz)

ESI-MS (M/E): 369 [M+H]$^+$

Production Example 164

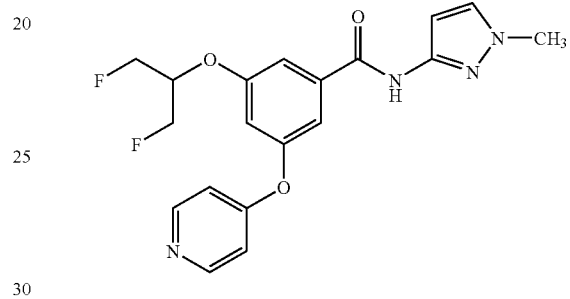

Preparation of 5-(2-fluoro-1-fluoromethyl-ethoxy)-N-(1-methyl-1H-pyrazol-3-yl)-3-(pyridin-4-yloxy)benzamide The compound of Production Example 164 was obtained as a white amorphous substance using 5-hydroxy-3-methoxymethoxybenzoic acid methyl ester, 4-chloropyridine hydrochloride, 1,3-difluoro-2-propanol and 3-amino-1-methyl-1H-pyrazole, by the same method as in Production Example 117, a corresponding method, or a combination thereof with an ordinary method.

$^1$HNMR (CDCl$_3$) δ: 3.81 (s, 3H), 4.58-4.67 (m, 2H), 4.67-4.82 (m, 3H), 6.79 (d, 1H, J=2.0 Hz), 6.89 (dd, 2H, J=1.6, 4.7 Hz), 6.91 (t, 1H, J2.3 Hz), 7.21 (t, 1H, J=2.3 Hz), 7.30 (d, 1H, J=2.0 Hz), 7.38 (t, 1H, J=2.3 Hz), 8.52 (br, 1H), 8.52 (dd, 2H, J=1.6, 4.7 Hz)

ESI-MS (M/E): 389 [M+H]$^+$

Production Example 165

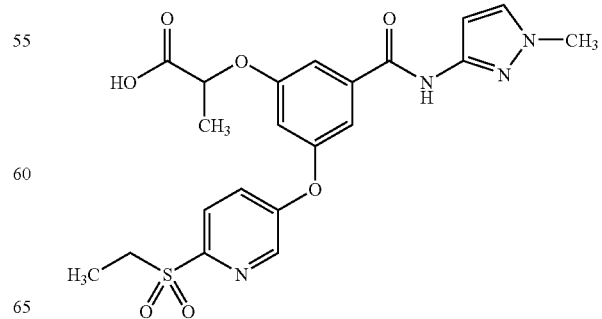

Preparation of 2-[3-(6-ethanesulfonylpyridin-3-yloxy)-5-(1-methyl-1H-pyrazol-3-ylcarbamoyl)-phenoxy]propionic acid The compound of Production Example 165 was obtained as a white solid by conversion of the tert-butyl ester portion of 2-[3-(6-ethanesulfonylpyridin-3-yloxy)-5-(1-methyl-1H-pyrazol-3-ylcarbamoyl)-phenoxy]propionic acid-tert-butyl ester obtained in the same manner as Production Example 1 to a carboxyl group, using the 3-(6-ethanesulfonylpyridin-3-yloxy)-5-hydroxy-benzoic acid methyl ester obtained in Production Example 117, 2-bromopropionic acid tert-butyl ester and 3-amino-1-methyl-1H-pyrazole. The conversion of the ester portion to a carboxyl group was accomplished by the method described in Comprehensive Organic Transformations, Richard L. et al., VCH Publishers, 1988, a corresponding method, or a combination thereof with an ordinary method.

$^1$HNMR (CDCl$_3$) δ: 1.24 (3H, t, J=7.4 Hz), 1.59 (3H, d, J=6.8 Hz), 3.39 (2H, q, J=7.4 Hz), 3.81 (3H, s), 4.69-4.80 (1H, m), 6.56 (1H, d, J=2.3 Hz), 6.90 (1H, t, J=2.2 Hz), 7.25 (1H, br), 7.37 (1H, br), 7.48 (1H, d, J=2.3 Hz), 7.62 (1H, dd, J=8.7 Hz, 2.7 Hz), 8.07 (1H, d, J=6.4 Hz), 8.52 (1H, d, J=2.7 Hz)

ESI-MS (MIE): 475 [M+H]$^+$

Production Example 166

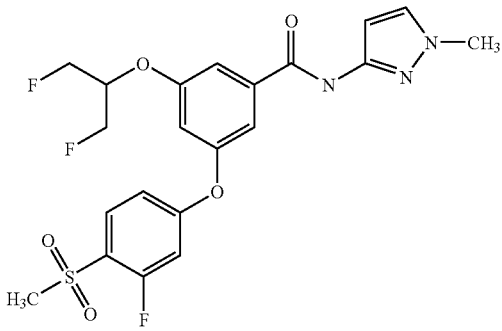

Preparation of 5-(2-fluoro-1-fluoromethyl-ethoxy)-3-(3-fluoro-4-methanesulfonylphenoxy)-N-(1-methyl-1H-pyrazol-3-yl)benzamide The compound of Production Example 166 was obtained as a colorless amorphous substance using 3-(3-fluoro-4-methanesulfonylphenoxy)-5-hydroxy-benzoic acid methyl ester, 1,3-difluoro-2-propanol and 3-amino-1-methyl-1H-pyrazole obtained in the same manner as Production Example 42, by the same method as in Production Example 2, a corresponding method, or a combination thereof with an ordinary method.

$^1$HNMR (CDCl$_3$) δ: 3.23 (3H, s), 3.82 (3H, s), 4.61-4.78 (5H, m), 6.78 (1H, d, J=2.3 Hz), 6.83-6.94 (3H, m), 7.19 (1H, t, J=1.8 Hz), 7.30 (1H, d, J=2.3 Hz), 7.38 (1H, t, J=1.8 Hz), 7.94 (1H, t, J=8.4 Hz), 8.37 (1H, brs)

ESI-MS (M/E): 484 [M+H]$^+$

INDUSTRIAL APPLICABILITY

The heteroarylcarbamoylbenzene derivatives of the present invention represented by formula (I) exhibit excellent glucokinase activity, and are therefore useful for treatment and/or prevention of diabetes, diabetes complications or obesity in the field of medicine.

What is claimed is:

1. A compound represented by the following formula (I):

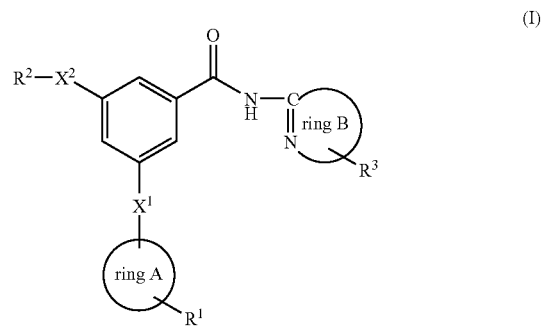

or a pharmaceutically acceptable salt thereof, wherein:
X$^1$ represents oxygen, sulfur or NH,
X$^2$ represents oxygen, sulfur or CH$_2$,
R$^1$ represents 1 or 2 substituents optionally present on Ring A which are selected from the group consisting of alkylsulfonyl, alkanoyl, lower alkyl, hydroxyalkyl, hydroxy, alkylcarbamoyl, alkylsulfamoyl, dialkylsulfamoyl, alkylthio, alkoxy, dialkylcarbamoyl, alkoxycarbonylamino, alkoxycarbonyl, halogen atoms, alkanoylaminoalkyl, alkoxycarbonylaminoalkyl, alkylsulfonylaminoalkyl, cyano and trifluoromethyl,
R$^2$ represents: a C3-7 cyclic alkyl group, wherein one of the constituent carbon atoms of the ring, except for the carbon atom that is bonded to X$^2$, is optionally replaced with oxygen, NH, N-alkanoyl or CONH);
or a straight-chain or branched lower alkyl group or a lower alkenyl group, optionally having a substituent selected from the group consisting of halo, carboxyl, alkoxycarbonyl, hydroxyl; amino which may be further substituted with 1 or 2 alkanoyl or lower alkyl groups, alkoxy and N-alkylcarbamoyl,
R$^3$ represents 1 or 2 substituents optionally present on Ring B which are selected from the group consisting of lower alkyl; alkoxy; alkylamino; lower dialkylamino; halo; trifluoromethyl; hydroxyalkyl, wherein the hydrogen of the hydroxy in the hydroxyalkyl group may be substituted with lower alkyl; aminoalkyl; alkanoyl; carboxyl; alkoxycarbonyl and cyano;

formula (II):

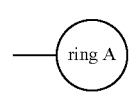

represents a pyridyl ring optionally having 1 or 2 substituents represented by R$^1$ above, and formula (III):

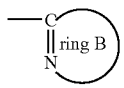

represents thiazolyl.

2. A compound according to claim 1 or a pharmaceutically acceptable salt thereof, wherein $X^1$ is O or S, and $X^2$ is O or $CH_2$.

3. A compound according to claim 1 or a pharmaceutically acceptable salt thereof, wherein $R^1$ is alkylsulfonyl, alkanoyl, hydroxyalkyl, alkylcarbamoyl, alkylsulfamoyl, dialkylsulfamoyl, dialkylcarbamoyl, alkoxycarbonylamino, halogen atoms, alkanoylaminoalkyl, alkylsulfonylaminoalkyl or alkoxycarbonylaminoalkyl.

4. A compound according to claim 3 or a pharmaceutically acceptable salt thereof, wherein $R^1$ is alkylsulfonyl, alkanoyl, hydroxyalkyl, alkanoylaminoalkyl, alkylsulfonylaminoalkyl or alkoxycarbonylaminoalkyl.

5. A compound according to claim 4 or a pharmaceutically acceptable salt thereof, wherein $R^1$ is alkylsulfonyl, alkanoyl or hydroxyalkyl.

6. A compound according to claim 1 or a pharmaceutically acceptable salt thereof, wherein $R^2$ is
  a C3-7 cyclic alkyl group in which one of the carbon atoms of the ring is optionally replaced with oxygen, NH or N-alkanoyl, or
  a straight-chain or branched lower alkyl group or a lower alkenyl group, optionally substituted with a halo, carboxyl, alkoxycarbonyl, hydroxy, amino optionally substituted with 1 or 2 lower alkyl groups, alkoxy, N-alkylcarbamoyl or alkanoylamino.

7. A compound according to claim 1 or a pharmaceutically acceptable salt thereof, wherein $R^3$ is lower alkyl; alkoxy; halo; hydroxyalkyl in which the hydrogen of the hydroxy in the hydroxyalkyl group may be substituted with lower alkyl; aminoalkyl or alkanoyl.

8. A compound according to claim 2 or a pharmaceutically acceptable salt thereof, wherein $R^3$ is lower alkyl or hydroxyalkyl in which the hydrogen of the hydroxy in the hydroxyalkyl group may be substituted with lower alkyl.

9. A compound in accordance with claim 1, or a pharmaceutically acceptable salt thereof, selected from the group consisting of:
  3-(5-hydroxymethyl-pyridin-2-yl-oxy)-5-isopropoxy-N-thiazol-2-yl-benzamide, 5-isopropoxy-3-(5-methanesulfonylpyridin-2-yl)-N-thiazol-2-yl-benzamide, 3-(5-acetyl-pyridin-2-yl-oxy)-5-isopropoxy-N-thiazol-2-yl-benzamide, 3-(5-cyano-pyridin-2-yl-oxy)-5-isopropoxy-N-thiazol-2-yl-benzamide, 5-isopropoxy-3-(2-oxo-1,2-dihydro-pyridin-4-yl-oxy)-N-thiazol-2-yl-benzamide, 5-isopropoxy-3-(2-oxo-1,2-dihydro-pyridin-3-yl-oxy)-N-thiazol-2-yl-benzamide, 5-isopropoxy-3-(2-oxo-1,2-dihydro-pyridin-3-yl-oxy)-N-thiazolo[5,4-b]pyridin-2-yl-benzamide, 5-isopropoxy-3-([1,3,4]thiadiazol-2-ylsulfanyl)-N-thiazolo[5,4-b]-pyridine-2-yl-benzamide, 5-(2-hydroxy-1-methyl-ethoxy)-3-(pyridin-4-ylsulfanyl)-N-thiazol-2-yl-benzamide, 5-(2-hydroxy-1-methyl-ethoxy)-3-(6-methyl-pyridin-3-ylsulfanyl)-N-thiazol-2-yl-benzamide.

10. A pharmaceutical composition comprising a compound in accordance with claim 1, or a pharmaceutically acceptable salt thereof, in combination with a pharmaceutically acceptable carrier.

11. A pharmaceutical composition comprising a compound in accordance with claim 9, or a pharmaceutically acceptable salt thereof, in combination with a pharmaceutically acceptable carrier.

12. A pharmaceutical composition in accordance with claim 11 further comprising a compound selected from the group consisting of:
  (a) other glucokinase activators
  (b) bisguanides
  (c) PPAR agonists
  (d) insulin
  (e) somatostatin
  (f) α-glucosidase inhibitors, and
  (g) insulin secretagogues.

13. A method of treating type 2 diabetes in a mammalian patient in need of such treatment comprising administering to the patient a compound in accordance with claim 1, or a pharmaceutically acceptable salt thereof, in an amount effective to treat type 2 diabetes.

14. A method of treating type 2 diabetes in a mammalian patient in need of such treatment comprising administering to the patient a compound in accordance with claim 9, or a pharmaceutically acceptable salt thereof, in an amount effective to treat type 2 diabetes.

15. A method of treating obesity in a mammalian patient in need of such treatment comprising administering to the patient a compound in accordance with claim 1 in an amount that is effective to treat diabetes.

* * * * *